(12) United States Patent
Tomatsu et al.

(10) Patent No.: US 12,247,213 B2
(45) Date of Patent: Mar. 11, 2025

(54) TREATMENT OF MUCOPOLYSACCHARIDOSIS IVA

(71) Applicants: REGENXBIO INC., Rockville, MD (US); THE NEMOURS FOUNDATION, Wilmington, DE (US)

(72) Inventors: Shunji Tomatsu, Wilmington, DE (US); Kazuki Sawamoto, Tokyo (JP); Subha Karumuthil-Melethil, Germantown, MD (US); Olivier Danos, Princeton, NJ (US)

(73) Assignees: THE NEMOURS FOUNDATION, Wilmington, DE (US); REGENXBIO INC., Rockville, MD (US)

( * ) Notice: Subject to any disclaimer, the term of this patent is extended or adjusted under 35 U.S.C. 154(b) by 968 days.

(21) Appl. No.: 17/263,049

(22) PCT Filed: Jul. 26, 2019

(86) PCT No.: PCT/US2019/043631
§ 371 (c)(1),
(2) Date: Jan. 25, 2021

(87) PCT Pub. No.: WO2020/023857
PCT Pub. Date: Jan. 30, 2020

(65) Prior Publication Data
US 2021/0292789 A1    Sep. 23, 2021

(51) Int. Cl.
*C12N 15/86* (2006.01)
*A61K 48/00* (2006.01)

(52) U.S. Cl.
CPC ......... *C12N 15/86* (2013.01); *A61K 48/0058* (2013.01); *C12N 2750/14143* (2013.01); *C12N 2830/008* (2013.01); *C12Y 301/06004* (2013.01)

(58) Field of Classification Search
CPC ......... C12N 15/86; C12N 2750/14143; C12N 2830/008; C12N 9/16; C12Y 301/06004; A61K 48/0058
See application file for complete search history.

(56) References Cited

U.S. PATENT DOCUMENTS 7,972,593 B2 * 7/2011 Tomatsu ........ C12Y 301/03001
435/235.1
2010/0158889 A1    6/2010 Tomatsu et al.
2011/0311487 A1    12/2011 Tomatsu et al.
2014/0271550 A1    9/2014 Rabinowitz et al.
2021/0214695 A1 *  7/2021 Bosch Tubert ........ C12N 15/86

FOREIGN PATENT DOCUMENTS

| WO | WO 2010/087709 | 8/2010 |
| WO | WO 2017/040524 | 3/2017 |
| WO | WO 2019/228950 | 12/2019 |
| WO | WO 2020/023857 | 1/2020 |
| WO | WO 2021/154956 | 8/2021 |

OTHER PUBLICATIONS

Almeciga-Díaz et al. The FEBS Journal, First published: Aug. 13, 2010, vol. 277, Issue 17, pp. 3608-3619.*
Stapleton et al. (Int. J. Mol. Sci. Jul. 2017, 187 (7), pp. 1-15.*
Tomatsu et al. (2). Res. Rep. Endocr. Disord, published on 2012(2): 65-77.*
Chen et al., 2019, "Enzyme replacement therapy for mucopolysaccharidoses; past, present, and future," Journal of Human Genetics, 64(11):1153-1171.
International Search Report and Written Opinion dated Dec. 18, 2019 for PCT/US2019/043631 (16 pages).
International Search Report and Written Opinion dated Jul. 13, 2021 for PCT/US2021/015436 (21 pages).
Lee et al., 2012, "An acidic oligopeptide displayed on AAV2 improves axial muscle tropism after systemic delivery", Genetic Vaccines and Therapy, 10(3).
Sawamoto et al., 2018, "Gene therapy for Mucopolysaccharidoses," Molecular Genetics and Metabolism, 123(2):59-68.
Tomatsu et al., 2019, "Development of AAV gene therapy for Morqui A syndrome," FEBS Open Bio, 9(1):31, XP009527355, abstract, Retrieved from the Internet: URL: https://2019.febscongress.org/abstract_preview.aspx?idAbstractEnc=442417009409 7099091098424170.

* cited by examiner

*Primary Examiner* — Bao Q Li
(74) *Attorney, Agent, or Firm* — Faegre Drinker Biddle & Reath LLP

(57) ABSTRACT

Provided herein are gene therapy methods for the treatment of mucopolysaccharidosis type IVA (MPS IVA) involving the use of recombinant adeno-associated viruses (rAAVs) to deliver human N-acetylgalactosamine-6-sulfate sulfatase (hGALNS) to the bone of a human subject diagnosed with MPS IVA. Also provided herein are rAAVs that can be used in the gene therapy methods and methods of making such rAAVs.

16 Claims, 80 Drawing Sheets
Specification includes a Sequence Listing.

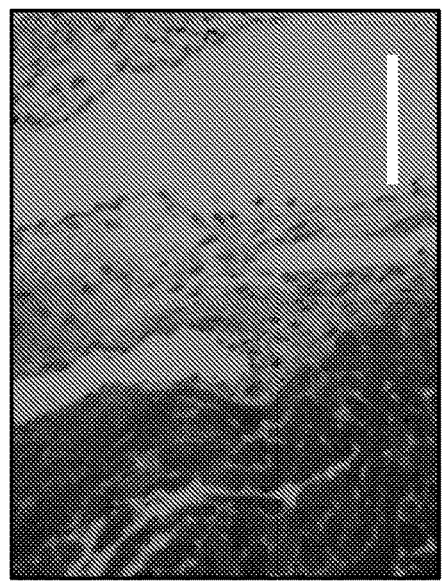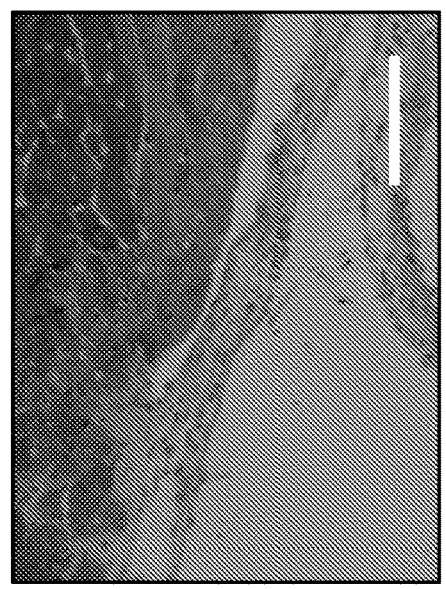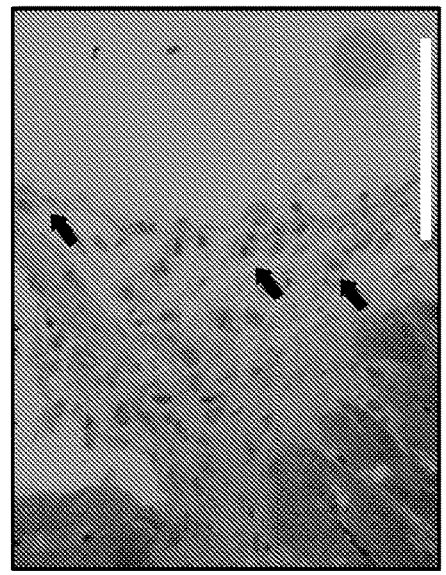
FIG. 11M

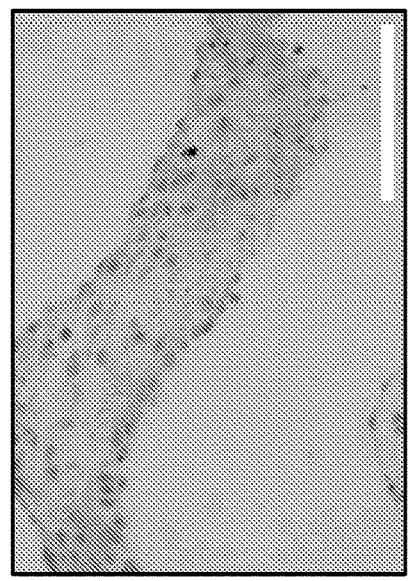
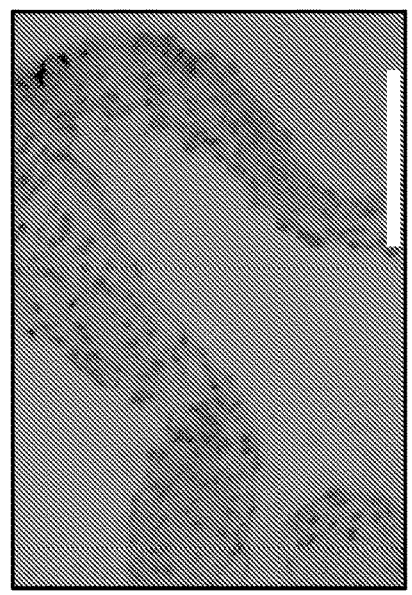
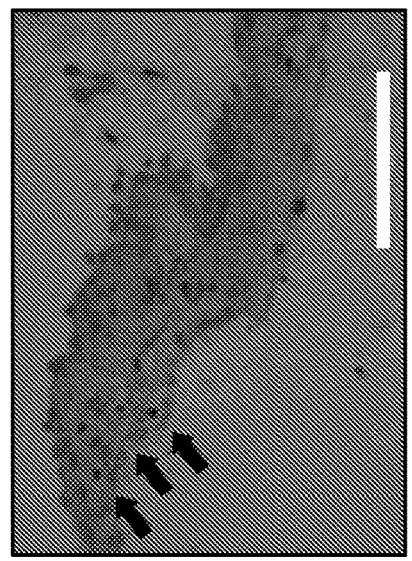
FIG. 11O

Untreated

WT

Figure 17B:
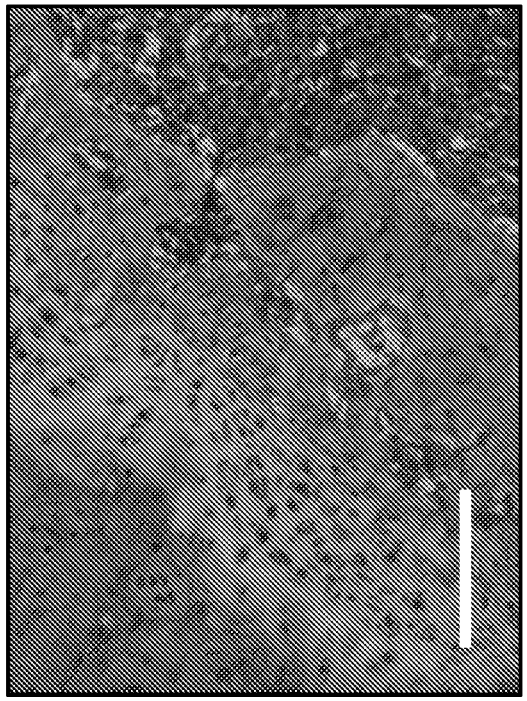
Figure 17A:
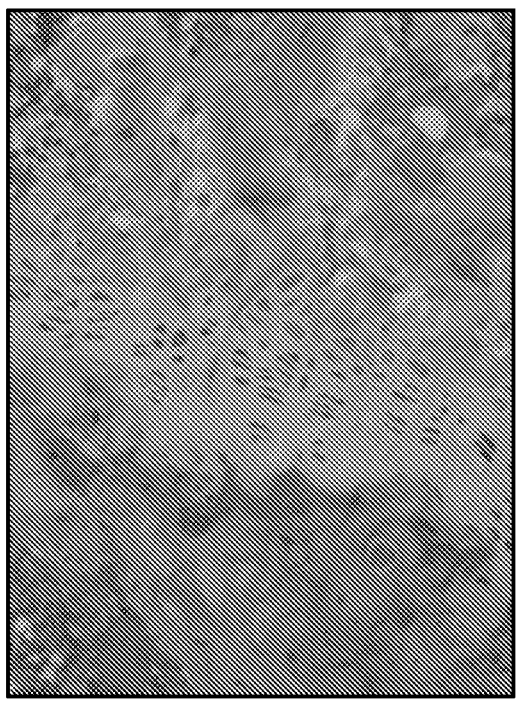

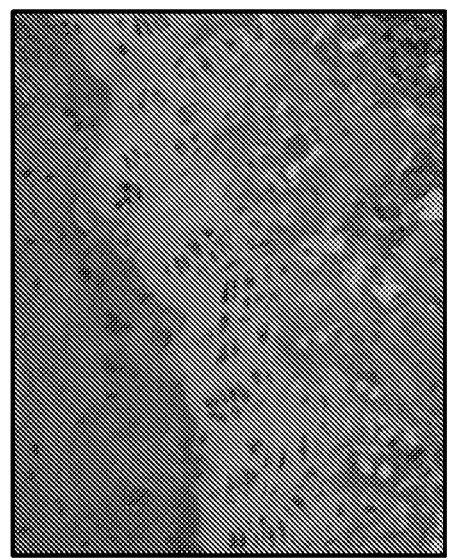
FIG. 17E AAV8-D8-GALNS
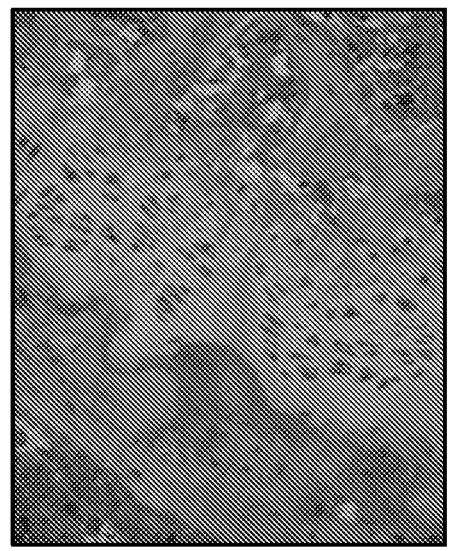
FIG. 17D AAV8-hGALNS
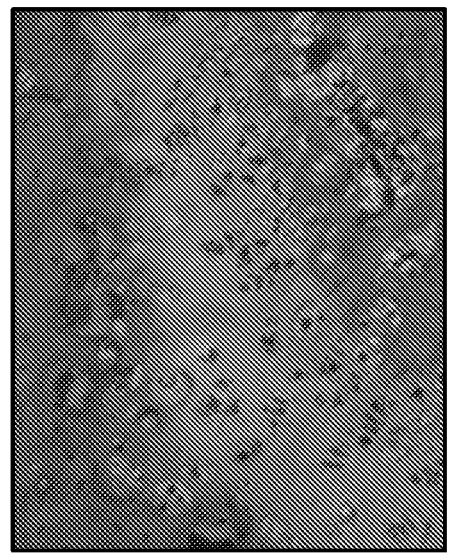
FIG. 17C Untreated

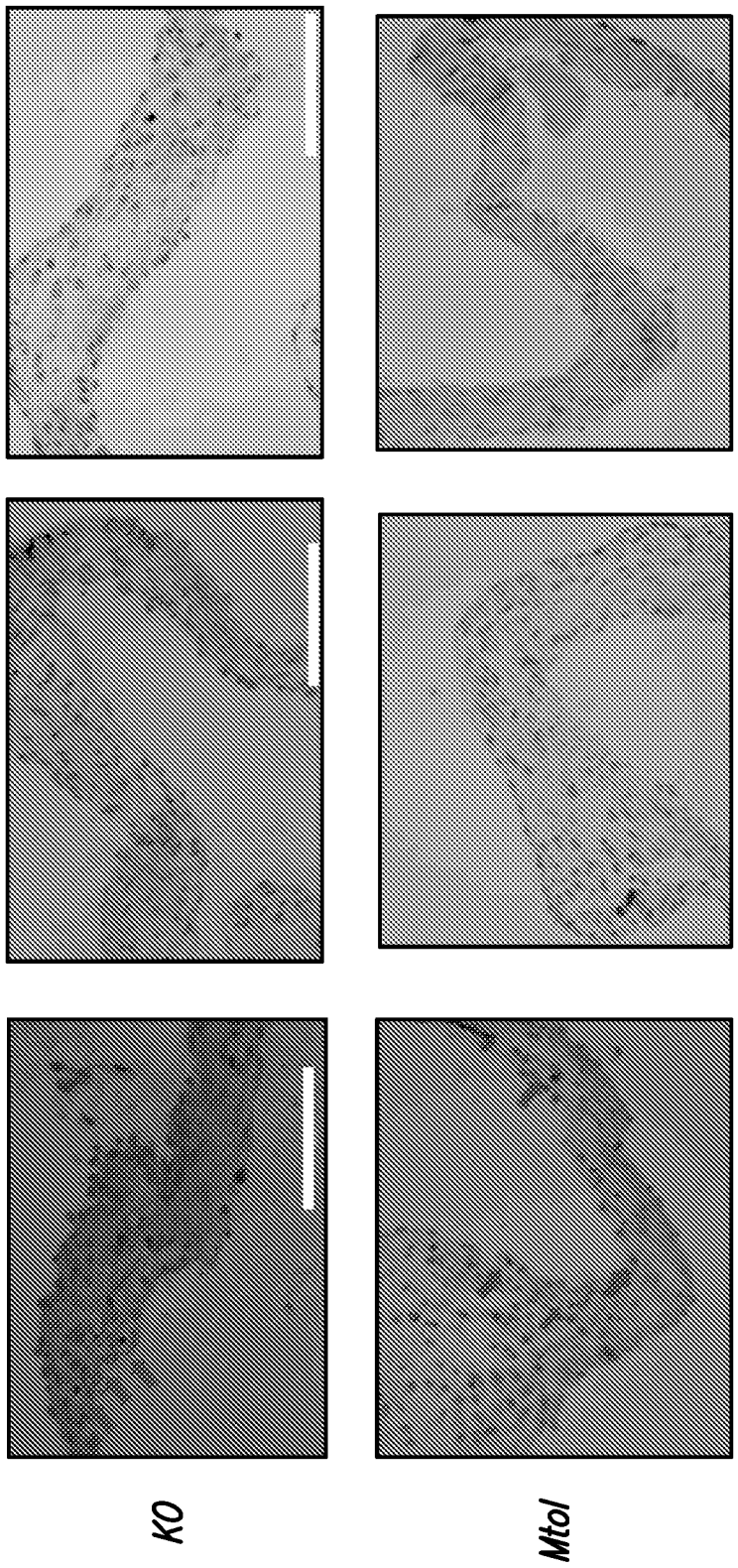

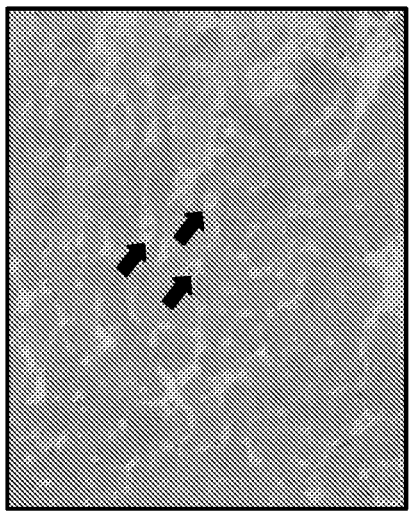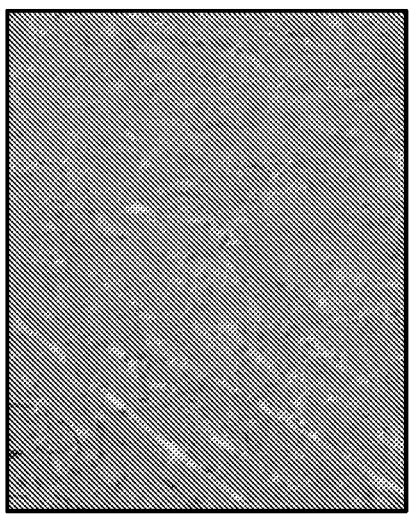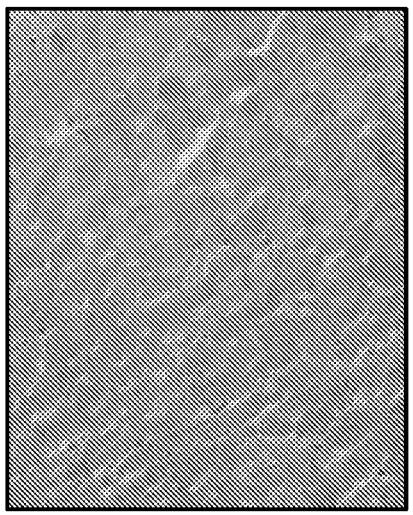
FIG. 20

Figures 24D, 24E:
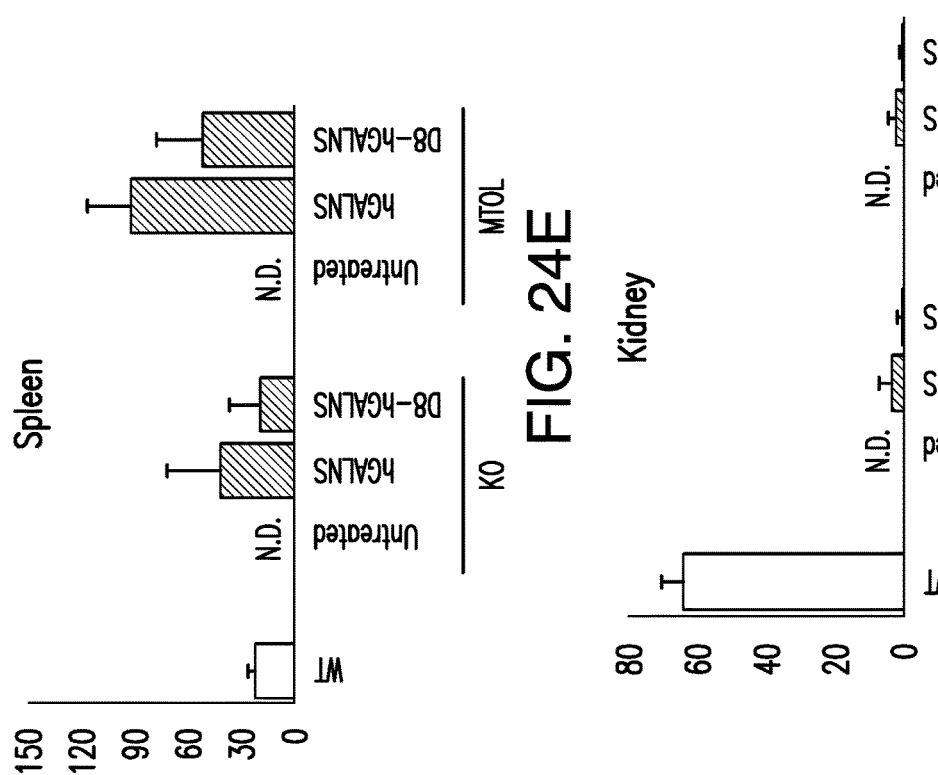
Figures 24F, 24G:
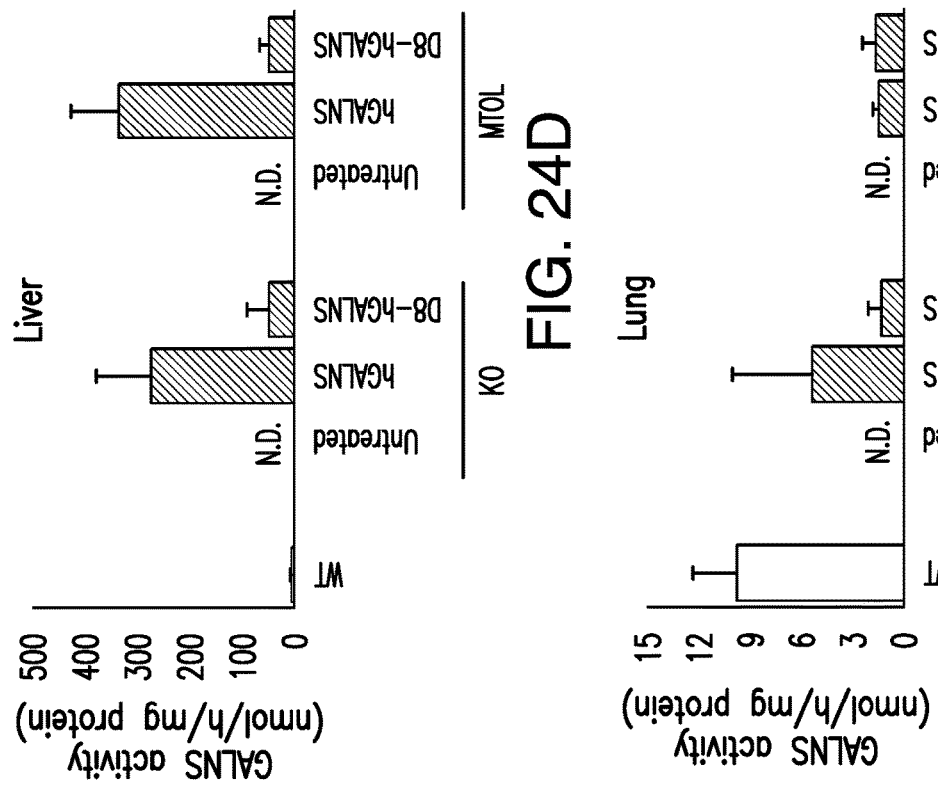

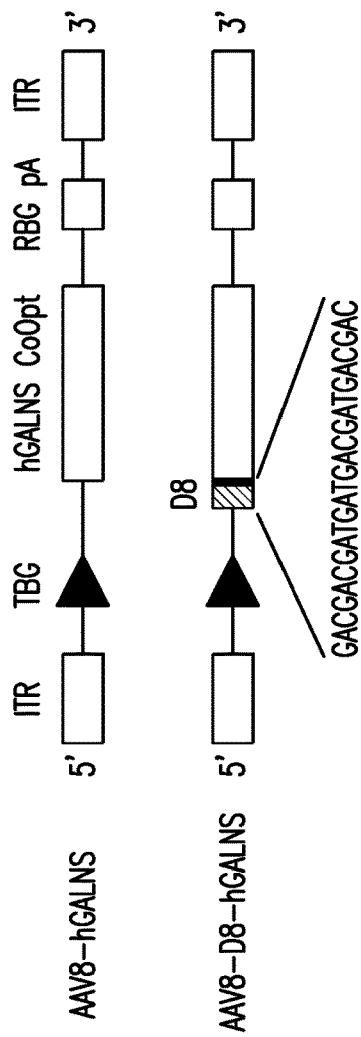
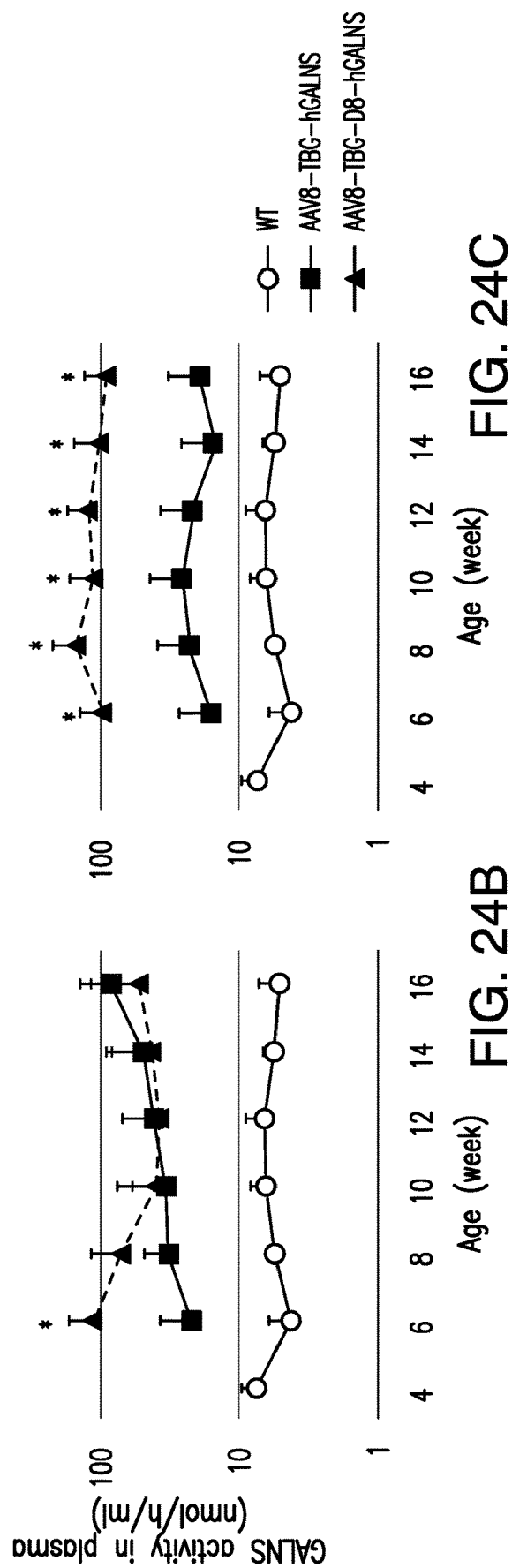
FIG. 24A
FIG. 24B
FIG. 24C

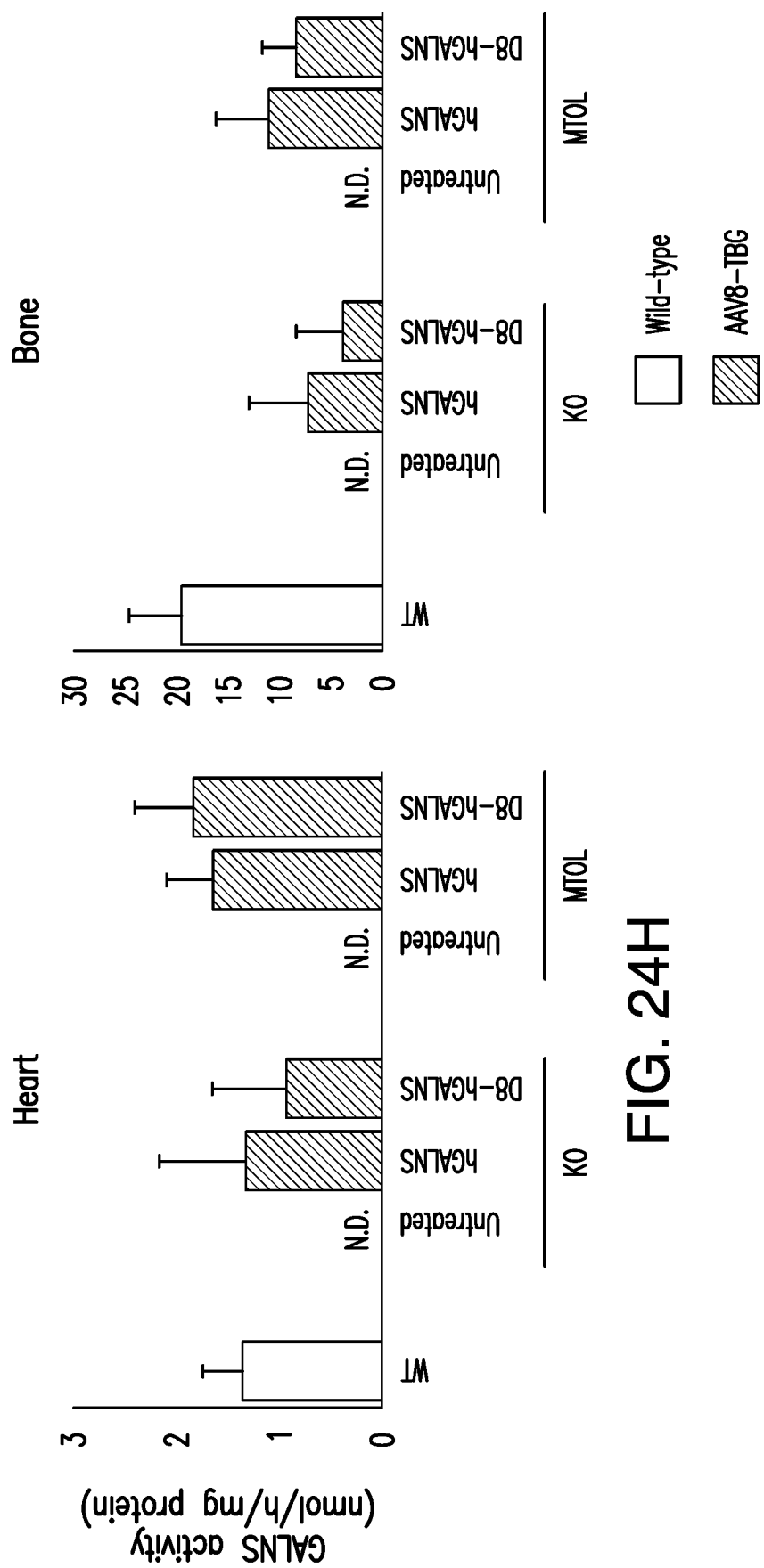

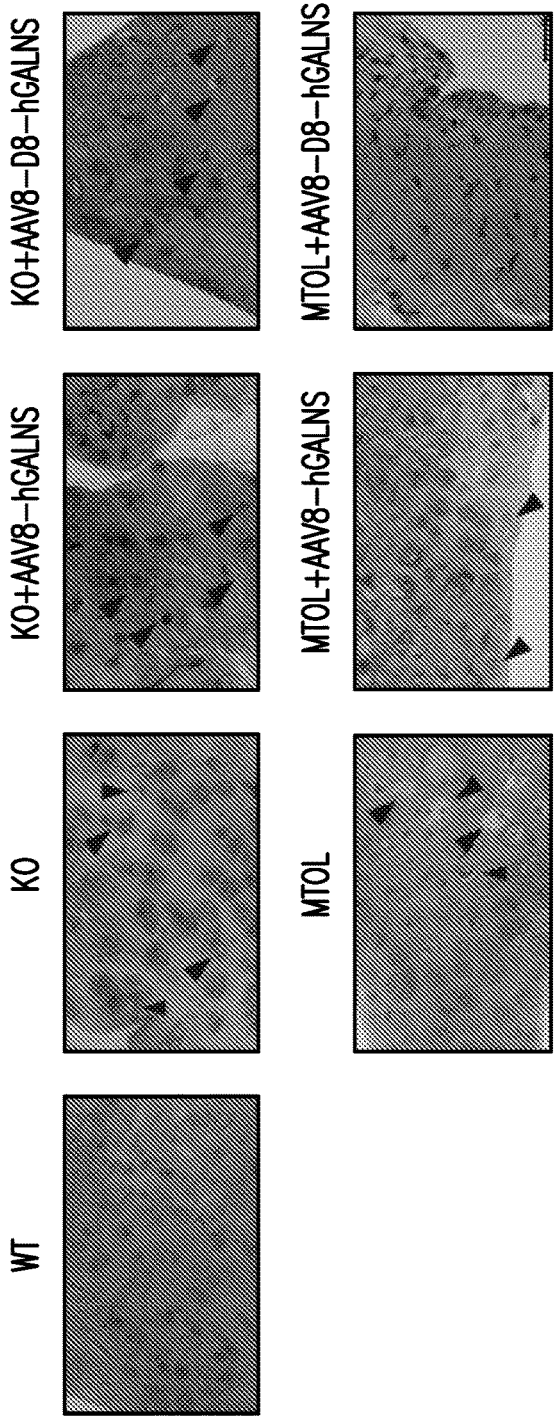
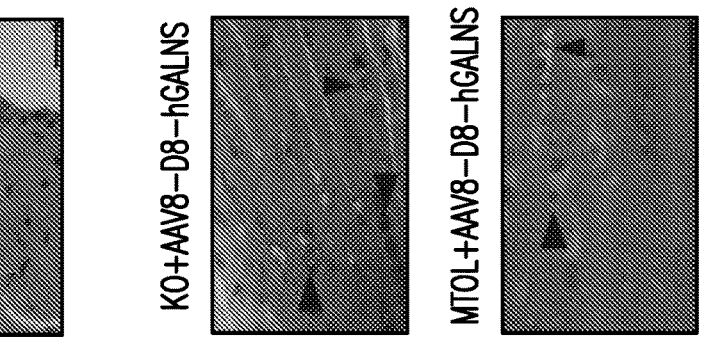

SEQUENCE LISTING

<160> NUMBER OF SEQ ID NOS: 16

<210> SEQ ID NO 1
<211> LENGTH: 738
<212> TYPE: PRT
<213> ORGANISM: Adeno-associated Virus (AAV)
<220> FEATURE:
<223> OTHER INFORMATION: AAV8 capsid protein

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
```

355                 360                 365
Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 2
<211> LENGTH: 1569
<212> TYPE: DNA
<213> ORGANISM: homo sapiens
<220> FEATURE:

<223> OTHER INFORMATION: Human GALNS (hGALNS)

<400> SEQUENCE: 2

```
atggcggcgg ttgtcgcggc gacgaggtgg tggcagctgt tgctggtgct cagcgccgcg    60
gggatggggg cctcgggcgc cccgcagccc cccaacatcc tgctcctgct catggacgac   120
atgggatggg gtgacctcgg ggtgtatgga gagccctcca gagaccccc gaatttggac    180
cggatggctg cagaagggct gcttttccca aacttctatt ctgccaaccc tctgtgctcg   240
ccatcgaggg cggcactgct cacaggacgg ctacccatcc gcaatggctt ctacaccacc   300
aacgcccatg ccagaaacgc ctacacaccg caggagattg gggcggcat cccagactcg    360
gagcagctcc tgccggagct tctgaagaag gccggctacg tcagcaagat tgtcggcaag   420
tggcatctgg gtcacaggcc ccagttccac cccctgaagc acggatttga tgagtggttt   480
ggatccccca actgccactt tggacccttat gacaacaagg ccaggcccaa catccctgtg   540
tacagggact gggagatggt tggcagatat tatgaagaat ttcctattaa tctgaagacg   600
ggggaagcca acctcaccca gatctacctg caggaagccc tggacttcat taagagacag   660
gcacggcacc acccttttt cctctactgg gctgtcgacg ccacgcacgc acccgtctat   720
gcctccaaac ccttcttggg caccagtcag cgagggcgt atggagacgc cgtccgggag   780
attgatgaca gcattgggaa gatactggag ctcctccaag acctgcacgt cgcggacaac   840
accttcgtct tcttcacgtc ggacaacggc gctgccctca tttccgcccc cgaacaaggt   900
ggcagcaacg gcccctttct gtgtgggaag cagaccacgt ttgaaggagg gatgagggag   960
cctgccctcg catggtggcc agggcacgtc actgcaggcc aggtgagcca ccagctgggc  1020
agcatcatgg acctcttcac caccagcctg gcccttgcgg gcctgacgcc gcccagcgac  1080
agggccattg atggcctcaa cctcctcccc acctcctgc agggccggct gatggacagg  1140
cctatcttct attaccgtgg cgacacgctg atggcggcca ccctcgggca gcacaaggct  1200
cacttctgga cctggaccaa ctcctgggag aacttcagac agggcattga tttctgccct  1260
gggcagaacg tttcaggggt cacaactcac aatctggaag accacacgaa gctgcccctg  1320
atcttccacc tggacggag cccaggggag aggttcccc tcagctttgc cagcgccgag  1380
taccaggagg ccctcagcag gatcacctcg gtcgtccagc agcaccagga ggccttggtc  1440
cccgcgcagc cccagctcaa cgtgtgcaac tgggcggtca tgaactgggc acctccgggc  1500
tgtgaaaagt tagggaagtg tctgacacct ccagaatcca ttcccaagaa gtgcctctgg  1560
tcccactag                                                          1569
```

<210> SEQ ID NO 3
<211> LENGTH: 1569
<212> TYPE: DNA
<213> ORGANISM: Artificial Sequence
<220> FEATURE:
<223> OTHER INFORMATION: hGLANSco (Codon Optimized)

<400> SEQUENCE: 3

```
atggctgctg ttgttgccgc taccagatgg tggcagctgc tgctggttct gtctgccgct    60
ggaatgggag cttctggtgc tccccagcct cctaacattc tgctgctgct catggacgac   120
atgggctggg gcgatctggg agtgtatggc gagcctagca gagagacacc caacctggat   180
agaatggccg ccgagggcct gctgttcccc aatttctaca gcgccaatcc tctgtgcagc   240
ccctctagag ctgctctgct gacaggcaga ctgcccatca gaaacggctt ctacaccacc   300
aacgctcacg cccggaatgc ctacacaccc caagagatcg ttggcggcat ccccgattct   360
```

```
gagcagctcc tgcctgagct gctgaagaag gccggctacg tcagcaagat cgtcggcaaa    420
tggcacctgg gccacagacc tcagtttcac cctctgaagc acggcttcga cgagtggttc    480
ggcagcccca attgtcactt cggccctac gacaacaagg ccagacctaa catccccgtg    540
tacagagact gggagatggt cggacggtac tacgaggaat cccccatcaa cctgaaaacc    600
ggcgaggcca atctgaccca gatctacctg caagaggccc tggacttcat caagcggcag    660
gccagacacc atcctttctt tctgtactgg gccgtcgacg ccacacacgc ccctgtgtat    720
gccagcaagc cttttctggg caccagccag cgtggcagat atggcgacgc cgtgcgggaa    780
atcgatgaca gcatcggcaa gatcctggaa ctgctgcagg atctgcacgt ggccgacaac    840
accttcgtgt cttcaccag cgacaacggc gctgccctga tttctgctcc tgagcaaggc    900
ggcagcaacg cccatttct gtgtggcaag cagaccacct ttgaaggcgg catgagagag    960
cctgctctgg cttggtggcc tggacatgtg acagccggac aagtgtctca ccagctgggc   1020
agcatcatgg acctgtttac cacctctctg gccctggccg gactgacacc tccatctgat   1080
agagccatcg acggcctgaa cctgctgcct acactgcttc agggcagact gatggacaga   1140
cccatcttct actaccgggg cgacaccctg atggccgcta cactgggaca gcacaaggcc   1200
cacttttgga cctggaccaa cagctgggag aacttccggc agggcatcga cttttgccct   1260
ggccagaatg tgtccggcgt gaccacacac aatctggaag atcacaccaa gctgcccctg   1320
atctttcacc tgggcagaga tcccggcgag agattccctc tgtcttttgc cagcgccgag   1380
taccaagaag ccctgagcag aatcacctcc gtggtcagc agcaccaaga ggctctggtt   1440
ccagctcagc cccagctgaa cgtgtgtaat tgggccgtga tgaactgggc ccctcctgga   1500
tgtgaaaagc tgggcaagtg tctgaccct cctgagagca tccccaagaa atgcctgtgg   1560
tcccactga                                                            1569

<210> SEQ ID NO 4
<211> LENGTH: 1604
<212> TYPE: DNA
<213> ORGANISM: Artificial Sequence
<220> FEATURE:
<223> OTHER INFORMATION: D8-hGALNS

<400> SEQUENCE: 4
accgccatgc ggggtccgag cggggctctg tggctgctcc tggctctgcg caccgtgctc     60
ggatcagatg atgatgatga tgatgatgat gccgaggcag aaaccggtgc ccgcagccc    120 cccaacatcc tgctcctgct catggacgac atgggatggg gtgacctcgg ggtgtatgga    180
gagccctcca gagaccccg gaatttggac cggatggctg cagaagggct gcttttccca    240
aacttctatt ctgccaaccc tctgtgctcg ccatcgaggg cggcactgct cacaggacgg    300
ctacccatcc gcaatggctt ctacaccacc aacgcccatg ccagaaacgc ctacacaccg    360
caggagattg tgggcggcat cccagactcg agcagctcc tgccggagct tctgaagaag    420
gccggctacg tcagcaagat tgtcggcaag tgcatctgg tcacaggcc cagttccac    480 cccctgaagc acggatttga tgagtggttt ggatccccca actgccactt tggaccttat    540
gacaacaagg ccaggcccaa catccctgtg tacagggact gggagatggt tggcagatat    600
tatgaagaat tcctattaa tctgaagacg ggggaagcca acctcaccca gatctacctg    660
caggaagccc tggacttcat taagagacag gcacggcacc acccttttt cctctactgg    720 gctgtcgacg ccacgcacgc accgtctat gcctccaaac ccttcttggg caccagtcag    780
```

```
cgagggcggt atggagacgc cgtccgggag attgatgaca gcattgggaa gatactggag    840
ctcctccaag acctgcacgt cgcggacaac accttcgtct tcttcacgtc ggacaacggc    900
gctgccctca tttccgcccc cgaacaaggt ggcagcaacg ccccttttct gtgtgggaag    960
cagaccacgt tgaaggagg gatgaggag cctgccctcg catggtggcc agggcacgtc     1020
actgcaggcc aggtgagcca ccagctgggc agcatcatgg acctcttcac caccagcctg    1080
gcccttgcgg gcctgacgcc gcccagcgac agggccattg atggcctcaa cctcctcccc    1140
accctcctgc agggccggct gatggacagg cctatcttct attaccgtgg cgacacgctg    1200
atggcggcca ccctcgggca gcacaaggct cacttctgga cctggaccaa ctcctgggag    1260
aacttcagac agggcattga tttctgccct gggcagaacg tttcaggggt cacaactcac    1320
aatctggaag accacacgaa gctgcccctg atcttccacc tgggacggga cccaggggag    1380
aggttccccc tcagctttgc cagcgccgag taccaggagg ccctcagcag gatcacctcg    1440
gtcgtccagc agcaccagga ggccttggtc cccgcgcagc cccagctcaa cgtgtgcaac    1500
tgggcggtca tgaactgggc acctccgggc tgtgaaaagt tagggaagtg tctgacacct    1560
ccagaatcca ttcccaagaa gtgcctctgg tcccactagc tcga                    1604

<210> SEQ ID NO 5
<211> LENGTH: 1593
<212> TYPE: DNA
<213> ORGANISM: Artificial Sequence
<220> FEATURE:
<223> OTHER INFORMATION: D8-GALNSco (codon optimized)

<400> SEQUENCE: 5
atgagaggac catctggtgc tctgtggctg ctgctggctc tgagaacagt gctgggcagc    60
gacgacgatg atgacgatga cgacgccgag gctgaaacag gtgctcccca gcctcctaac    120
atcctgctgc tgctcatgga cgatatgggc tggggcgatc tgggagtgta tggcgagcct    180
agcagagaga caccccaacct ggatagaatg gcgccgaggg cctgctgtt ccccaatttc    240
tacagcgcca atcctctgtg cagcccctct agagctgctc tgctgacagg cagactgccc    300
atcagaaacg gcttctacac caccaacgct cacgcccgga tgcctacac accccaagag    360
atcgttggcg gcatccccga ttctgaacag ctgctgcctg agctgctgaa gaaggccggc    420
tacgtcagca agatcgtcgg caaatggcac ctgggccaca gacctcagtt tcaccctctg    480
aagcacggct cgacgagtg gttcggcagc cccaattgtc acttcggccc ctacgacaac    540
aaggccagac caaacatccc cgtgtacaga gactgggaga tggtcggacg gtactacgag    600
gaattcccca tcaacctgaa aaccggcgag gccaatctga cccagatcta cctgcaagag    660
gccctggact tcatcaagcg gcaggccaga caccatcctt tctttctgta ctgggccgtc    720
gacgccacac acgcccctgt gtatgccagc aagccttttc tgggcaccag ccagcgtggc    780
agatatggcg acgccgtgcg ggaaatcgat gacagcatcg gcaagatcct ggaactgctg    840
caggatctgc acgtggccga caacaccttc gtgttcttca ccagcgacaa cggcgctgcc    900
ctgatttctg ctcctgagca aggcggcagc aacgcccat ttctgtgtgg caagcagacc    960
acctttgaag gcggcatgag agagcctgct ctggcttggt ggcctggaca tgtgacagcc    1020
ggacaagtgt ctcaccagct gggctccatc atggacctgt ttaccacctc tctggcctg    1080
gccggactga cacctccatc tgatagagcc atcgacggcc tgaacctgct gcctacactg    1140
cttcagggca gactgatgga cagacccatc ttctactacc ggggcgacac cctgatggcc    1200
gctacactgg gacagcacaa ggcccacttt tggacctgga ccaacagctg ggagaacttc    1260
```

-continued

```
cggcagggca tcgacttttg ccctggccag aatgtgtccg gcgtgaccac acacaatctg    1320
gaagatcaca ccaagctgcc cctgatcttt cacctgggca gagatcccgg cgagagattc    1380
cctctgtctt ttgccagcgc cgagtaccaa gaagccctga gcagaatcac cagcgtggtg    1440
cagcagcacc aagaggctct ggttccagct cagccccagc tgaacgtgtg taattgggcc    1500
gtgatgaact gggcccctcc tggatgtgaa aagctgggca agtgtctgac ccctcctgag    1560
agcatcccca agaaatgcct gtggtcccac tga                                 1593
```

<210> SEQ ID NO 6
<211> LENGTH: 460
<212> TYPE: DNA
<213> ORGANISM: Artificial Sequence
<220> FEATURE:
<223> OTHER INFORMATION: TBG promoter

<400> SEQUENCE: 6

```
gggctggaag ctacctttga catcatttcc tctgcgaatg catgtataat ttctacagaa     60
cctattagaa aggatcaccc agcctctgct tttgtacaac tttcccttaa aaaactgcca    120
attccactgc tgtttggccc aatagtgaga acttttttcct gctgcctctt ggtgcttttg    180
cctatggccc ctattctgcc tgctgaagac actcttgcca gcatggactt aaaccccctcc    240 agctctgaca atcctctttc tcttttgttt tacatgaagg gtctggcagc caaagcaatc    300
actcaaagtt caaaccttat catttttttgc tttgttcctc ttggccttgg ttttgtacat    360
cagctttgaa ataccatcc cagggttaat gctggggtta atttataact aagagtgctc    420
tagttttgca atacaggaca tgctataaaa atggaaagat                          460
```

<210> SEQ ID NO 7
<211> LENGTH: 130
<212> TYPE: DNA
<213> ORGANISM: Artificial Sequence
<220> FEATURE:
<223> OTHER INFORMATION: 5-prime ITR

<400> SEQUENCE: 7

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct                                                           130
```

<210> SEQ ID NO 8
<211> LENGTH: 130
<212> TYPE: DNA
<213> ORGANISM: Artificial Sequence
<220> FEATURE:
<223> OTHER INFORMATION: 3-prime ITR

<400> SEQUENCE: 8

```
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc    120 gagcgcgcag                                                           130
```

<210> SEQ ID NO 9
<211> LENGTH: 127
<212> TYPE: DNA
<213> ORGANISM: Rabbit
<220> FEATURE:
<223> OTHER INFORMATION: Rabbit globin poly A

<400> SEQUENCE: 9

```
gatcttttc cctctgccaa aaattatggg gacatcatga agcccttga gcatctgact      60
tctggctaat aaaggaaatt tatttcatt gcaatagtgt gttggaattt tttgtgtctc     120
tcactcg                                                              127
```

<210> SEQ ID NO 10
<211> LENGTH: 133
<212> TYPE: DNA
<213> ORGANISM: Artificial Sequence
<220> FEATURE:
<223> OTHER INFORMATION: Intron_1

<400> SEQUENCE: 10

```
gtaagtatca aggttacaag acaggtttaa ggagaccaat agaaactggg cttgtcgaga     60
cagagaagac tcttgcgttt ctgataggca cctattggtc ttactgacat ccactttgcc    120
tttctctcca cag                                                       133
```

<210> SEQ ID NO 11
<211> LENGTH: 100
<212> TYPE: DNA
<213> ORGANISM: Artificial Sequence
<220> FEATURE:
<223> OTHER INFORMATION: Alpha mic/bik enhancer

<400> SEQUENCE: 11

```
aggttaattt ttaaaaagca gtcaaaagtc caagtggccc ttggcagcat ttactctctc     60
tgtttgctct ggttaataat ctcaggagca caaacattcc                          100
```

<210> SEQ ID NO 12
<211> LENGTH: 1569
<212> TYPE: DNA
<213> ORGANISM: Artificial Sequence
<220> FEATURE:
<223> OTHER INFORMATION: GALNS (codon optimized and CpG depleted)

<400> SEQUENCE: 12

```
atggctgctg tggtggctgc tacaagatgg tggcaactgc tgctggtgct gtctgcagct     60
ggaatgggag cttctggtgc ccctcagcct cctaatatcc tgctgctgct gatggatgac    120
atgggctggg gagatctggg agtgtatggg gagcctagca gagagacacc caacctggat    180
agaatggctg cagagggcct gctgttcccc aacttctact ctgccaatcc tctgtgcagc    240
ccctctagag ctgcactgct acaggcaga ctgcccatca gaaatggctt ctacaccaca     300
aatgcccatg ccagaaatgc ctacacaccc aagagatag ttggaggcat ccctgactct    360
gaacagctgc tgcctgagct gctgaagaaa gctggctatg tgtccaagat agttggcaag    420
tggcacctgg ccacagacc tcagtttcac cctctgaaac atggctttga tgagtggttt    480
ggcagcccca actgccactt tggccctat gataacaagg ccagacctaa catccctgtg    540
tacagagact gggagatggt tggaaggtac tatgaagagt tccccatcaa cctgaaaaca    600
ggggaagcca atctgaccca gatctacctg caagaggccc tggacttcat caagagacag    660
gccagacacc atccttttt tctgtactgg gctgttgatg ccacacatgc ccctgtgtat    720
gccagcaagc cttttctggg caccagccag aggggcagat atgggatgc tgtcagagaa    780
attgatgaca gcattggcaa gatcctggaa ctgctgcagg acctgcatgt ggctgacaac    840
accttgtgt tcttcaccct tgacaatggg gcagccctga tctctgcccc tgagcaaggt    900
ggcagcaatg gcccatttct gtgtggcaag cagaccacct ttgaaggtgg catgagagag    960
```

```
cctgctctgg cctggtggcc tggacatgtt acagctggac aagtgtctca ccagctgggc    1020
agcatcatgg acctgtttac cacatctctg gccctggctg gactgacccc tccatctgat    1080
agagccattg atggcctgaa cctgctgcct acacttctgc agggcagact gatggacaga    1140
cccatcttct actacagagg tgacaccctg atggctgcca cactgggaca gcacaaggcc    1200
cacttttgga cctggaccaa cagctgggag aacttcagac agggcattga tttctgccct    1260
ggccagaatg tgtctggggt caccactcac aacctggaag atcacaccaa gctgcccctc    1320
atcttccacc tgggaagaga tcctggggag agattccctc tgagctttgc ctctgctgag    1380
taccaagaag ccctgagcag aatcacatct gtggtgcagc agcatcaaga ggctctggtt    1440
ccagctcagc cccagctgaa tgtgtgcaac tgggcagtga tgaattgggc cccacctggc    1500
tgtgaaaagc tgggcaaatg tctgaccccc cctgagagca tccctaaaaa gtgcctgtgg    1560
tcccactga                                                            1569

<210> SEQ ID NO 13
<211> LENGTH: 969
<212> TYPE: DNA
<213> ORGANISM: Artificial Sequence
<220> FEATURE:
<223> OTHER INFORMATION: LSPX1 Promoter

<400> SEQUENCE: 13
aggttaattt ttaaaaagca gtcaaaagtc caagtggccc ttggcagcat ttactctctc      60
tgtttgctct ggttaataat ctcaggagca caaacattcc agatccaggt taatttttaa     120
aaagcagtca aaagtccaag tggcccttgg cagcatttac tctctctgtt tgctctggtt     180
aataatctca ggagcacaaa cattccagat ccggcgcgcc agggctggaa gctacctttg     240
tctagaaggc tcagaggcac acaggagttt ctgggctcac cctgcccct tccaaccct       300 cagttcccat cctccagcag ctgtttgtgt gctgcctctg aagtccacac tgaacaaact     360
tcagcctact catgtcccta aaatgggcaa acattgcaag cagcaaacag caaacacaca     420
gccctccctg cctgctgacc ttggagctgg ggcagaggtc agagacctct ctgggcccat     480
gccacctcca acatccactc gaccccttgg aatttcggtg gagaggagca gaggttgtcc     540
tggcgtggtt taggtagtgt gagaggggta cccgggatc ttgctaccag tggaacagcc      600
actaaggatt ctgcagtgag agcagagggc cagctaagtg gtactctccc agagactgtc     660
tgactcacgc cacccctcc accttggaca caggacgctg tggttctga gccaggtaca       720 atgactcctt tcggtaagtg cagtggaagc tgtacactgc ccaggcaaag cgtccgggca    780
gcgtaggcgg gcgactcaga tcccagccag tggacttagc cctgtttgc tcctccgata     840 actggggtga ccttggttaa tattcaccag cagcctcccc cgttgcccct ctggatccac    900
tgcttaaata cggacgagga cagggccctg tctcctcagc ttcaggcacc accactgacc    960
tgggacagt                                                            969

<210> SEQ ID NO 14
<211> LENGTH: 1050
<212> TYPE: DNA
<213> ORGANISM: Artificial Sequence
<220> FEATURE:
<223> OTHER INFORMATION: LSPX2 Promoter

<400> SEQUENCE: 14
aggctcagag gcacacagga gtttctgggc tcaccctgcc cccttccaac ccctcagttc      60
```

| | |
|---|---|
| ccatcctcca gcagctgttt gtgtgctgcc tctgaagtcc acactgaaca aacttcagcc | 120 |
| tactcatgtc cctaaaatgg gcaaacattg caagcagcaa acagcaaaca cacagccctc | 180 |
| cctgcctgct gaccttggag ctggggcaga ggtcagagac ctctctgggc ccatgccacc | 240 |
| tccaacatcc actcgacccc ttggaatttc ggtggagagg agcagaggtt gtcctggcgt | 300 |
| ggtttaggta gtgtgagagg gtctagaagg ctcagaggca cacaggagtt tctgggctca | 360 |
| ccctgccccc ttccaacccc tcagttccca tcctccagca gctgtttgtg tgctgcctct | 420 |
| gaagtccaca ctgaacaaac ttcagcctac tcatgtccct aaaatgggca acattgcaa | 480 |
| gcagcaaaca gcaaacacac agccctccct gcctgctgac cttggagctg ggcagaggt | 540 |
| cagagacctc tctgggccca tgccacctcc aacatccact cgacccctttg gaatttcggt | 600 |
| ggagaggagc agaggttgtc ctggcgtggt taggtagtg tgagaggggt acccggggat | 660 |
| cttgctacca gtggaacagc cactaaggat tctgcagtga gagcagaggg ccagctaagt | 720 |
| ggtactctcc cagagactgt ctgactcacg ccaccccctc caccttggac acaggacgct | 780 |
| gtggtttctg agccaggtac aatgactcct ttcggtaagt gcagtggaag ctgtacactg | 840 |
| cccaggcaaa gcgtccgggc agcgtaggcg ggcgactcag atcccagcca gtggacttag | 900 |
| cccctgtttg ctcctccgat aactgggtg accttggtta atattcacca gcagcctccc | 960 |
| ccgttgcccc tctggatcca ctgcttaaat acggacgagg cagggccct gtctcctcag | 1020 |
| cttcaggcac caccactgac ctgggacagt | 1050 |

<210> SEQ ID NO 15
<211> LENGTH: 1089
<212> TYPE: DNA
<213> ORGANISM: Artificial Sequence
<220> FEATURE:
<223> OTHER INFORMATION: LTP1 Promoter

<400> SEQUENCE: 15

| | |
|---|---|
| aggttaattt ttaaaaagca gtcaaaagtc caagtggccc ttggcagcat ttactctctc | 60 |
| tgtttgctct ggttaataat ctcaggagca caaacattcc agatccaggt taattttta | 120 |
| aaagcagtca aaagtccaag tggcccttgg cagcatttac tctctctgtt tgctctggtt | 180 |
| aataatctca ggagcacaaa cattccagat ccggcgcgcc agggctggaa gctacctttg | 240 |
| acatcatttc ctctgcgaat gcatgtataa tttctacaga acctattaga aaggatcacc | 300 |
| cagcctctgc ttttgtacaa cttttcccttta aaaaactgcc aattccactg ctgtttggcc | 360 |
| caatagtgag aactttttcc tgctgcctct tggtgctttt gcctatggcc ctattctgc | 420 |
| ctgctgaaga cactcttgcc agcatggact taaacccctc cagctctgac aatcctcttt | 480 |
| ctcttttgtt ttacatgaag ggtctggcag ccaaagcaat cactcaaagt tcaaaccttta | 540 |
| tcatttttg ctttgttcct cttggccttg gttttgtaca tcagctttga aaataccatc | 600 |
| ccagggttaa tgctggggtt aatttataac taagagtgct ctagttttgc aatacaggac | 660 |
| atgctataaa aatggaaaga tgttgctttc tgagaggatc ttgctaccag tggaacagcc | 720 |
| actaaggatt ctgcagtgag agcagagggc cagctaagtg gtactctccc agagactgtc | 780 |
| tgactcacgc caccccctcc accttggaca caggacgct tggtttctga gccaggtaca | 840 |
| gtgactcctt tcggtaagtg cagtggaagc tgtacactgc ccaggcaaag cgtccgggca | 900 |
| gcgtaggcgg gcgactcaga tcccagccag tggacttagc cctgtttgc tcctccgata | 960 |
| actggggtga ccttggttaa tattcaccag cagcctcccc cgttgcccct ctggatccac | 1020 |
| tgcttaaata cggacgagga cagggccctg tctcctcagc ttcaggcacc accactgacc | 1080 |

```
tgggacagt                                                                  1089

<210> SEQ ID NO 16
<211> LENGTH: 1579
<212> TYPE: DNA
<213> ORGANISM: Artificial Sequence
<220> FEATURE:
<223> OTHER INFORMATION: LMTP6 Promoter

<400> SEQUENCE: 16
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg gccactacgg gtttaggctg cccatgtaag gaggcaaggc    360
ctggggacac ccgagatgcc tggttataat taacccagac atgtggctgc ccccccccc    420
cccaacacct gctgcctcta aaataaccc tgtccctggt ggatcccact acgggtttag    480
gctgcccatg taaggaggca aggcctgggg acacccgaga tgcctggtta taattaaccc    540
agacatgtgg ctgccccccc ccccccaac acctgctgcc tctaaaaata acctgtccc    600
tggtggatcc cactacgggt ttaggctgcc catgtaagga ggcaaggcct ggggacaccc    660
gagatgcctg gttataatta acccagacat gtggctgccc ccccccccc caacacctgc    720
tgcctctaaa aataaccctg tccctggtgg atccctgca tgcgaagatc ttcgaacaag    780
gctgtggggg actgagggca ggctgtaaca ggcttggggg ccagggctta tacgtgcctg    840
ggactcccaa agtattactg ttccatgttc ccggcgaagg gccagctgtc ccccgccagc    900
tagactcagc acttagttta ggaaccagtg agcaagtcag cccttggggc agcccataca    960
aggccatggg gctgggcaag ctgcacgcct gggtccgggg tgggcacggt gcccgggcaa   1020
cgagctgaaa gctcatctgc tctcaggggc ccctccctgg gacagcccc tcctggctag   1080
tcacaccctg taggctcctc tatataaccc aggggcacag gggctgccct cattctacca   1140
ccacctccac agcacagaca gacactcagg agccagccag cgtcgagatc ttgctaccag   1200
tggaacagcc actaaggatt ctgcagtgag agcagagggc cagctaagtg gtactctccc   1260
agagactgtc tgactcacgc cacccctcc accttggaca caggacgctg tggtttctga   1320
gccaggtaca gtgactcctt tcggtaagtg cagtggaagc tgtacactgc ccaggcaaag   1380
cgtccgggca gcgtaggcgg gcgactcaga tcccagccag tggacttagc ccctgtttgc   1440
tcctccgata actggggtga ccttggttaa tattcaccag cagcctcccc cgttgccct    1500
ctggatccac tgcttaaata cggacgagga cagggccctg tctcctcagc ttcaggcacc   1560
accactgacc tgggacagt                                                 1579
```

TREATMENT OF MUCOPOLYSACCHARIDOSIS IVA

CROSS-REFERENCE TO RELATED APPLICATIONS

This application is a U.S. National Stage Application of International Patent Application No. PCT/US2019/043631, filed Jul. 26, 2019, which claims the benefit of U.S. Provisional Patent Application Nos. 62/711,238, filed Jul. 27, 2018, 62/756,880, filed Nov. 7, 2018, and 62/799,834, filed Feb. 1, 2019, which are incorporated by reference herein in their entireties.

REFERENCE TO SEQUENCE LISTING SUBMITTED ELECTRONICALLY

This application incorporates by reference a Sequence Listing submitted with this application in ASCII format via EFS-Web entitled "Sequence Listing_12656-116-999.txt" created on Jan. 21, 2021 and having a size of 27,074 bytes.

1. FIELD

The field relates to the treatment of mucopolysaccharidosis type IVA (MPS IVA). Provided herein are methods and compositions for treatment of MPS IVA involving recombinant adeno-associated viruses (rAAVs).

2. BACKGROUND

Mucopolysaccharidosis type IVA (MPS IVA; Morquio A Syndrome) is an autosomal recessive lysosomal storage disorder caused by the deficiency of N-acetylgalactosamine-6-sulfate sulfatase (GALNS) (Khan, et al., Mol Genet Metab., 2017; 120(1-2):78-95). Deficiency of the enzyme results in a progressive accumulation of the glycosaminoglycans (GAGs), chondroitin 6-sulfate (C6S), and keratan sulfate (KS) leading to a systemic and unique skeletal dysplasia with incomplete ossification and successive imbalance of growth resulting in a short neck and trunk, cervical spinal cord compression, tracheal obstruction, pectus carinatum, laxity of joints, kyphoscoliosis, coxa valga, and genu valgum. Other clinical manifestations of the disease can include hearing loss, heart valve involvement, and corneal opacity. Over 200 different mutations have been identified in patients and the prevalence in the United States is approximately 1 in 250,000.

Patients with a severe type die of airway compromise, cervical spinal cord complications or heart valve disease in their 20s or 30s if untreated (Khan, et al., Mol Genet Metab., 2017; 120(1-2):78-95); Tomatsu, S., et al. Mol. Genet. Metab. 2016; 117, 150-156; Montaño, A. M., et al. J. Inherit. Metab. Dis. 2007; 30, 165-174; Tomatsu, S., et al. Res. Rep. Endocr. Disord. 2012; 2012, 65-77; Pizarro, C., et al. Ann. Thorac. Surg. 2016; 102, e329-331). Enzyme replacement therapy (ERT), hematopoietic stem cell transplantation (HSCT), and various surgical intervention are currently available as supportive therapy for patients with MPS IVA in clinical practice. In February of 2014, the FDA approved the use of an ERT (elosulfase-alpha) (Hendriksz, et al., J Inherit Metab Dis., 2014; 37(6): 979-990). ERT, the current standard of care, results in partial improvement in soft tissue pathology and activity of daily living (ADL) of patients with MPS IVA, however, these therapies provide very limited impact in bone and cartilage due to the avascular character of these lesions. Current limitations of ERT include: i) weekly injections for 5-6 hours are required, ii) drug is rapidly cleared from the circulation, iii) the treatment cost is very expensive ($500,000 per year per patient), and v) the drug shows limited penetration to bone (Algahim and Almassi, Ther Clin Risk Manag., 2013; 9:45-53; Tomatsu et al., Curr Pharm Biotechnol., 2011; 12:931-945). For MPS IVA, weekly administration of recombinant human N-acetylgalactosamine-6-sulfate sulfatase (rhGALNS: Vimizim™, elosulfase alfa) currently provides no impact on bone and cartilage lesions of patients with MPS IVA. While HSCT may provide a better impact than ERT on bone, this cell-based therapy may not be applicable to all patients because of limited matched donors, the age-limit for effective treatment, a lack of well-trained facilities, the mortality risk of the procedure such as graft-versus-host disease (GVHD), infection, and other complications (Tomatsu et al., Drug Des Devel Ther., 2015; 9: 1937-1953). In this sense, a novel drug for MPS IVA, in particular a novel drug for treating skeletal dysplasia in patients with MPS IVA, is urgently required.

Gene therapy has the potential to be a one-time permanent therapy. Many preclinical studies of gene transfer using viral and non-viral vectors showed the therapeutic potential of this therapy in MPS diseases. Adeno-associated virus (AAV) vector is an attractive vehicle to deliver a therapeutic gene into target organs since vectors provide a long-term expression of transgene product and a low risk of immunogenicity. Because of these advantages, clinical trials of AAV-mediated gene therapy are either ongoing or scheduled for MPS I, II, IIIA, IIIB, and VI (ClinicalTrials.gov; Sawamoto et al., Expert Opin. Orphan Drugs, 2016; 4, 941-951). Delivery of the sufficient enzyme into the cartilage lesions and growth plate region has the potential to resolve the skeletal dysplasia in MPS IVA patients. Our previous study showed that GALNS gene transfer using AAV2 vector provided therapeutic enzyme level in tissues (Almeciga-Diaz, C. J., et al. Pediatr. Res. 2018; 84, 545-551); however, until now there has been no study demonstrating that AAV-mediated gene therapy corrects skeletal lesions of MPS IVA mouse model.

Dvorak-Ewell and colleagues showed that 10 mg/kg rhGALNS conjugated Alexa-488 fluorophore injected intravenously into wild-type mice five times every other day, resulted in the detection of the enzyme in the growth place and articular cartilage (Dvorak-Ewell, M., et al. PLoS One. 2010; 5, e12194). This finding indicates that a high level of circulating enzyme can provide enzyme penetration into cartilage lesions. AAV8 vectors efficient in transducing liver, and a 10-100-fold greater efficiency in liver gene transfer was shown with the recombinant AAV8 vector, compared to the early generation of the AAV2 vector (Gao, G. P., et al. Proc. Natl. Acad. Sci. USA. 2002; 99, 11854-11859). The use of liver-specific promoters exhibited a significantly reduced host immune response since liver-directed AAV gene therapy has been reported to induce immune tolerance to the transgene product, compared to ubiquitous promoters (Mingozzi, F., et al. J. Clin. Invest. 2003; 111, 1347-1356; Ziegler, R. J., et al. Mol. Ther. 2004; 9, 231-240; Dobrzynski, E., et al. Proc. Natl. Acad. Sci. USA. 2006; 103, 4592-4597; Cao, O., et al. Blood 2007; 110, 1132-1140; Mingozzi, F., et al. Blood 2007; 110, 2334-2341). This suppressed immune response can provide a long-term expression of the transgene product (Wang, L., et al. Mol. Ther. 2000; 1, 154-158; Sondhi, D., et al. Gene Ther. 2005; 12, 1618-1632). The previous study demonstrated that the recombinant AAV8 vector in combination with liver-specific promoter provided greater impact on skeletal lesions of mouse and feline model in MPS VI (Tessitore, A., et al. Mol. Ther. 2008; 16, 30-37; Cotugno, G., et al. Mol. Ther. 2011; 19, 461-469).

Patients with MPS IVA show the most severe skeletal abnormalities in all types of MPS (Melbouci, M., et al. Mol. Genet. Metab. 2018; 124, 1-10), and a bone-targeting strategy could supply sufficient enzyme to penetrate the cartilage region. We have previously demonstrated enhanced bone targeting by attaching a short acidic amino acid tag to the N- or C-terminus of several enzymes (Montano, A. M., et al Mol. Genet. Metab. 2008; 94, 178-189; Tomatsu, S., et al. Mol. Ther. 2010; 18, 1094-1102). Hydroxyapatite (HA) is the major inorganic component in bone and has a positively charged surface that contains calcium ion. Bone sialoprotein and osteopontin bind to HA and these phosphorylated acidic glycoproteins have repeated sequences of negatively charged acidic amino acids (Asp and Glu), which can be the potential target for bone-targeting strategy (Oldberg, A., et al. J. Biol. Chem. 1988; 263, 19430-19432; Kasugai, S., et al. J. Bone Miner. Res. 2000; 15, 936-943).

Due to its safety profile, versatility, and ability to be engineered for specific functions, rAAVs can be used in a wide range of gene therapy applications in many diseases (see, e.g., Naso et al., BioDrugs. 2017; 31(4): 317-334). Clinical trials using AAV gene therapy have been performed for a wide range of genetic diseases including neuromuscular, ocular, and immunological diseases (see, e.g., Kumar et al., Molecular Therapy-Methods & Clinical Development, 2016, 3:16034).

Citation of a reference herein shall not be construed as an admission that such is prior art to the present disclosure.

3. SUMMARY

Provided herein are gene therapy methods for the treatment of mucopolysaccharidosis type IVA (MPS IVA) involving the use of recombinant adeno-associated viruses (rAAVs) to deliver human N-acetylgalactosamine-6-sulfate sulfatase (hGALNS) to the bone of a human subject diagnosed with MPS IVA. Also provided herein are rAAVs that can be used in the gene therapy methods, methods of making such rAAVs, as well as polynucleotides, plasmids, and cells that can be used for making such rAAVs.

In one aspect, provided herein is a recombinant adeno-associated virus (rAAV) comprising: (a) an AAV capsid (for example, AAV8 capsid); and (b) a recombinant AAV genome comprising a human N-acetylgalactosamine-6-sulfate sulfatase (hGALNS) expression cassette flanked by AAV-inverted terminal repeats (ITRs) (for example, AAV8-ITRs), said hGALNS expression cassette comprising a nucleotide sequence encoding a transgene, such as the transgene encoding a fusion protein that is hGALNS fused to an acidic oligopeptide (for example, D8). In a specific embodiment, the hGALNS expression cassette further comprises a nucleotide sequence encoding a liver-specific promoter, wherein the nucleotide sequence encoding the liver-specific promoter is operably linked to the nucleotide sequence encoding the fusion protein. In a further specific embodiment, the liver-specific promoter is a thyroxine binding globulin (TBG) promoter.

In another aspect, provided herein is an rAAV comprising: (a) an AAV capsid (for example, AAV8 capsid); and (b) a recombinant AAV genome comprising an hGALNS expression cassette flanked by AAV-ITRs (for example, AAV8-ITRs), said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS. In a specific embodiment, the liver-specific promoter is a TBG promoter.

In another aspect, provided herein is a pharmaceutical composition comprising an rAAV provided herein and a pharmaceutically acceptable carrier.

In another aspect, provided herein is a polynucleotide comprising an hGALNS expression cassette flanked by AAV-ITRs (for example, AAV8-ITRs), said hGALNS expression cassette comprising a nucleotide sequence encoding a transgene, such as the transgene encoding a fusion protein that is hGALNS fused to an acidic oligopeptide (for example, D8). In a specific embodiment, the hGALNS expression cassette further comprises a nucleotide sequence encoding a liver-specific promoter, wherein the nucleotide sequence encoding the liver-specific promoter is operably linked to the nucleotide sequence encoding the fusion protein. In a further specific embodiment, the liver-specific promoter is a TBG promoter.

In another aspect, provided herein is a polynucleotide comprising an hGALNS expression cassette flanked by AAV-ITRs (for example, AAV8-ITRs), said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS. In a specific embodiment, the liver-specific promoter is a TBG promoter.

In another aspect, provided herein is an rAAV plasmid comprising a polynucleotide provided herein.

In another aspect, provided herein is an ex vivo cell comprising a polynucleotide provided herein or an rAAV plasmid provided herein.

In another aspect, provided herein is a method of making an rAAV comprising transfecting an ex vivo cell with an rAAV plasmid provided herein and one or more helper plasmids collectively comprising the nucleotide sequences of AAV genes Rep, Cap, VA, Eta and E4.

In another aspect, provided herein is a method for treating a human subject diagnosed with mucopolysaccharidosis type IVA (MPS IVA), which comprises administering to the human subject an rAAV provided herein or a pharmaceutical composition provided herein.

In another aspect, provided herein is a method for treating a human subject diagnosed with MPS IVA, which comprises delivering to the bone, cartilage, ligament, meniscus, growth plate, liver, spleen, lung, kidney, trachea, heart muscle, and/or heart valve of said human subject a therapeutically effective amount of a transgene, such as the transgene encoding a fusion protein that is hGALNS fused to an acidic oligopeptide (for example, D8), by administering to the human subject an rAAV provided herein. In a specific embodiment, the hGALNS is glycosylated with mannose-6-phosphate by having been produced in and secreted from a liver cell.

In another aspect, provided herein is a method for treating a human subject diagnosed with MPS IVA, which comprises delivering to the bone, cartilage, ligament, meniscus, growth plate, liver, spleen, lung, kidney, trachea, heart muscle, and/or heart valve of said human subject a therapeutically effective amount of hGALNS that is glycosylated with mannose-6-phosphate by having been produced in and secreted from a liver cell, by administering to the human subject an rAAV provided herein.

In another aspect, provided herein is a method for treating a human subject diagnosed with MPS IVA, which comprises delivering to the bone, cartilage, ligament, meniscus, growth plate, liver, spleen, lung, kidney, trachea, heart muscle, and/or heart valve of said human subject a therapeutically effective amount of a fusion protein that is hGALNS fused to an acidic oligopeptide (for example, D8), wherein the fusion protein is produced from an rAAV genome (for example, a recombinant AAV8 genome (i.e., a recombinant genome comprising the backbone of an AAV8 genome)).

In another aspect, provided herein is a method for treating a human subject diagnosed with MPS IVA, which comprises delivering to the bone, cartilage, ligament, meniscus, growth plate, liver, spleen, lung, kidney, trachea, heart muscle, and/or heart valve of said human subject a therapeutically effective amount of a transgene encoding a transgene, such as the transgene encoding a fusion protein that is hGALNS fused to an acidic oligopeptide (for example, D8), wherein the fusion protein is produced from an rAAV genome (for example, a recombinant AAV8 genome (i.e., a recombinant genome comprising the backbone of an AAV8 genome)) and is glycosylated with mannose-6-phosphate by having been produced in and secreted from a liver cell.

In another aspect, provided herein is a method for treating a human subject diagnosed with MPS IVA, which comprises delivering to the bone, cartilage, ligament, meniscus, growth plate, liver, spleen, lung, kidney, trachea, heart muscle, and/or heart valve of said human subject a therapeutically effective amount of hGALNS that is produced from an rAAV genome (for example, a recombinant AAV8 genome (i.e., a recombinant genome comprising the backbone of an AAV8 genome)) and is glycosylated with mannose-6-phosphate by having been produced in and secreted from a liver cell.

In certain aspects and embodiments of the method of treating a human subject diagnosed with MPS IVA that comprises delivering to the bone, cartilage, ligament, meniscus, growth plate, liver, spleen, lung, kidney, trachea, heart muscle, and/or heart valve of said human subject, the step of delivering to the bone, cartilage, ligament, meniscus, growth plate, liver, spleen, lung, kidney, trachea, heart muscle, and/or heart valve is a step of delivering to the bone and/or cartilage.

In certain aspects and embodiments of the method of treating a human subject diagnosed with MPS IVA that comprises delivering to the bone, cartilage, ligament, meniscus, growth plate, liver, spleen, lung, kidney, trachea, heart muscle, and/or heart valve of said human subject, the step of delivering to the bone, cartilage, ligament, meniscus, growth plate, liver, spleen, lung, kidney, trachea, heart muscle, and/or heart valve is a step of delivering to (a) the bone and/or cartilage, and (b) ligament, meniscus, growth plate, liver, spleen, lung, heart muscle, and/or heart valve.

3.1 Illustrative Embodiments (I)

1. A recombinant adeno-associated virus (rAAV) comprising:
   (a) an AAV capsid; and
   (b) a recombinant AAV genome comprising a human N-acetylgalactosamine-6-sulfate sulfatase (hGALNS) expression cassette flanked by AAV-inverted terminal repeats (ITRs), said hGALNS expression cassette comprising a nucleotide sequence encoding a fusion protein that is hGALNS fused to an acidic oligopeptide.

2. The rAAV of paragraph 1, wherein the acidic oligopeptide is D8.
3. The rAAV of paragraph 1 or 2, wherein the hGALNS expression cassette further comprises a nucleotide sequence encoding a liver-specific promoter, wherein the nucleotide sequence encoding the liver-specific promoter is operably linked to the nucleotide sequence encoding the fusion protein.
4. The rAAV of paragraph 3, wherein the liver-specific promoter is a TBG promoter.
5. The rAAV of any one of paragraphs 1-4, wherein the AAV is AAV8.
6. An rAAV comprising:
   (a) an AAV capsid; and
   (b) a recombinant AAV genome comprising an hGALNS expression cassette flanked by AAV-ITRs, said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS.
7. The rAAV of paragraph 6, wherein the liver-specific promoter is a TBG promoter.
8. The rAAV of paragraph 6 or 7, wherein the AAV is AAV8.
9. A pharmaceutical composition comprising the rAAV of any one of paragraphs 1-8 and a pharmaceutically acceptable carrier.
10. A polynucleotide comprising an hGALNS expression cassette flanked by AAV-ITRs, said hGALNS expression cassette comprising a nucleotide sequence encoding a fusion protein that is hGALNS fused to an acidic oligopeptide.
11. The polynucleotide of paragraph 10, wherein the acidic oligopeptide is D8.
12. The polynucleotide of paragraph 10 or 11, wherein the hGALNS expression cassette further comprises a nucleotide sequence encoding a liver-specific promoter, wherein the nucleotide sequence encoding the liver-specific promoter is operably linked to the nucleotide sequence encoding the fusion protein.
13. The polynucleotide of paragraph 12, wherein the liver-specific promoter is a TBG promoter.
14. A polynucleotide comprising an hGALNS expression cassette flanked by AAV-ITRs, said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS.
15. The polynucleotide of paragraph 14, wherein the liver-specific promoter is a TBG promoter.
16. The polynucleotide of any one of paragraphs 10-15, wherein the AAV is AAV8.
17. An rAAV plasmid comprising the polynucleotide of any one of paragraphs 10-16.
18. An ex vivo cell comprising the polynucleotide of any one of paragraphs 10-16 or the rAAV plasmid of paragraph 17.
19. A method of making an rAAV comprising transfecting an ex vivo cell with the rAAV plasmid of paragraph 17 and one or more helper plasmids collectively comprising the nucleotide sequences of AAV genes Rep, Cap, VA, E2a and E4.
20. A method for treating a human subject diagnosed with mucopolysaccharidosis type IVA (MPS IVA), comprising administering to the human subject the rAAV of any one of paragraphs 1-8 or the pharmaceutical composition of paragraph 9.

21. A method for treating a human subject diagnosed with MPS IVA, comprising delivering to the bone, cartilage, ligament, meniscus, growth plate, liver, spleen, lung, heart muscle, and/or heart valve of said human subject a therapeutically effective amount of a fusion protein that is hGALNS fused to an acidic oligopeptide, by administering to the human subject an rAAV of any one of paragraphs 1-5.

22. The method of paragraph 21, wherein said hGALNS is glycosylated with mannose-6-phosphate by having been produced in and secreted from a liver cell.

23. A method for treating a human subject diagnosed with MPS IVA, comprising delivering to the bone, cartilage, ligament, meniscus, growth plate, liver, spleen, lung, heart muscle, and/or heart valve of said human subject a therapeutically effective amount of hGALNS that is glycosylated with mannose-6-phosphate by having been produced in and secreted from a liver cell, by administering to the human subject an rAAV of any one of paragraphs 6-8.

24. A method for treating a human subject diagnosed with MPS IVA, comprising delivering to the bone, cartilage, ligament, meniscus, growth plate, liver, spleen, lung, heart muscle, and/or heart valve of said human subject a therapeutically effective amount of a fusion protein that is hGALNS fused to an acidic oligopeptide, wherein the fusion protein is produced from an rAAV genome.

25. A method for treating a human subject diagnosed with MPS IVA, comprising delivering to the bone, cartilage, ligament, meniscus, growth plate, liver, spleen, lung, heart muscle, and/or heart valve of said human subject a therapeutically effective amount of a fusion protein that is hGALNS fused to an acidic oligopeptide, wherein the fusion protein is produced from an rAAV genome and is glycosylated with mannose-6-phosphate by having been produced in and secreted from a liver cell.

26. A method for treating a human subject diagnosed with MPS IVA, comprising delivering to the bone, cartilage, ligament, meniscus, growth plate, liver, spleen, lung, heart muscle, and/or heart valve of said human subject a therapeutically effective amount of hGALNS that is produced from an rAAV genome and is glycosylated with mannose-6-phosphate by having been produced in and secreted from a liver cell.

27. The method of any one of paragraphs 24-26, wherein the AAV is AAV8.

28. The method of any one of paragraphs 21-27, wherein the step of delivering to the bone, cartilage, ligament, meniscus, growth plate, liver, spleen, lung, heart muscle, and/or heart valve is a step of delivering to the bone and/or cartilage.

29. The method of any one of paragraphs 21-27, wherein the step of delivering to the bone, cartilage, ligament, meniscus, growth plate, liver, spleen, lung, heart muscle, and/or heart valve is a step of delivering to (a) the bone and/or cartilage, and (b) ligament, meniscus, growth plate, liver, spleen, lung, heart muscle, and/or heart valve.

3.2 Illustrative Embodiments (II)

1. A recombinant adeno-associated virus (rAAV) comprising:
   (a) an AAV capsid; and
   (b) a recombinant AAV genome comprising a human N-acetylgalactosamine-6-sulfate sulfatase (hGALNS) expression cassette flanked by AAV-inverted terminal repeats (ITRs), said hGALNS expression cassette comprising a nucleotide sequence encoding a transgene, wherein the said transgene encodes a fusion protein that is hGALNS fused to an acidic oligopeptide.
2. The rAAV of paragraph 1, wherein the acidic oligopeptide is D8.
3. The rAAV of paragraph 1 or 2, wherein the hGALNS expression cassette further comprises a nucleotide sequence encoding a liver-specific promoter, wherein the nucleotide sequence encoding the liver-specific promoter is operably linked to the nucleotide sequence encoding the fusion protein.
4. The rAAV of paragraph 3, wherein the liver-specific promoter:
   (a) is a TBG promoter; or
   (b) comprises a nucleotide sequence that is at least 80% identical to SEQ ID NO:13; or
   (c) comprises a nucleotide sequence that is at least 85% identical to SEQ ID NO:13; or
   (d) comprises a nucleotide sequence that is at least 90% identical to SEQ ID NO:13; or
   (e) comprises a nucleotide sequence that is at least 95% identical to SEQ ID NO:13; or
   (f) comprises a nucleotide sequence that is at least 98% identical to SEQ ID NO:13; or
   (g) comprises a nucleotide sequence that is at least 100% identical to SEQ ID NO:13, or
   (h) comprises a nucleotide sequence that is at least 80% identical to SEQ ID NO:14; or
   (i) comprises a nucleotide sequence that is at least 85% identical to SEQ ID NO:14; or
   (j) comprises a nucleotide sequence that is at least 90% identical to SEQ ID NO:14; or
   (k) comprises a nucleotide sequence that is at least 95% identical to SEQ ID NO:14; or
   (l) comprises a nucleotide sequence that is at least 98% identical to SEQ ID NO:14; or
   (m) comprises a nucleotide sequence that is at least 100% identical to SEQ ID NO:14, or
   (n) comprises a nucleotide sequence that is at least 80% identical to SEQ ID NO:15; or
   (o) comprises a nucleotide sequence that is at least 85% identical to SEQ ID NO:15; or
   (p) comprises a nucleotide sequence that is at least 90% identical to SEQ ID NO:15; or
   (q) comprises a nucleotide sequence that is at least 95% identical to SEQ ID NO:15; or
   (r) comprises a nucleotide sequence that is at least 98% identical to SEQ ID NO:15; or
   (s) comprises a nucleotide sequence that is at least 100% identical to SEQ ID NO:15.
5. The rAAV of paragraph 1 or 2, wherein the hGALNS expression cassette further comprises a nucleotide sequence encoding a promoter, which nucleotide sequence encoding the promoter is operably linked to the nucleotide sequence encoding the fusion protein.
6. The rAAV of paragraphs 5, wherein the promoter is a CAG promoter.

7. The rAAV of paragraph 5, wherein the promoter is a liver- and muscle-specific promoter.
8. The rAAV of paragraph 7, wherein the liver- and muscle-specific promoter:
   (a) comprises a nucleotide sequence that is at least 80% identical to SEQ ID NO:16; or
   (b) comprises a nucleotide sequence that is at least 85% identical to SEQ ID NO:16; or
   (c) comprises a nucleotide sequence that is at least 90% identical to SEQ ID NO:16; or
   (d) comprises a nucleotide sequence that is at least 95% identical to SEQ ID NO:16; or
   (e) comprises a nucleotide sequence that is at least 98% identical to SEQ ID NO:16; or
   (f) comprises a nucleotide sequence that is at least 100% identical to SEQ ID NO:16.
9. The rAAV of any one of paragraphs 1-10, wherein the AAV is AAV8.
10. The rAAV of any one of paragraphs 1-10, wherein the AAV is AAV9.
11. The rAAV of any one of paragraphs 1-10, wherein the nucleotide sequence encoding hGALNS or the nucleotide sequence encoding the fusion protein is codon-optimized.
12. The rAAV of any one of paragraphs 1-13, wherein the nucleotide sequence encoding hGALNS or the nucleotide sequence encoding the fusion protein has CpG sites depleted.
13. An rAAV comprising:
    (a) an AAV capsid; and
    (b) a recombinant AAV genome comprising an hGALNS expression cassette flanked by AAV-ITRs, said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS.
14. The rAAV of paragraph 13, wherein the liver-specific promoter:
    (a) is a TBG promoter; or
    (b) comprises a nucleotide sequence that is at least 80% identical to SEQ ID NO:13; or
    (c) comprises a nucleotide sequence that is at least 85% identical to SEQ ID NO:13; or
    (d) comprises a nucleotide sequence that is at least 90% identical to SEQ ID NO:13; or
    (e) comprises a nucleotide sequence that is at least 95% identical to SEQ ID NO:13; or
    (f) comprises a nucleotide sequence that is at least 98% identical to SEQ ID NO:13; or
    (g) comprises a nucleotide sequence that is at least 100% identical to SEQ ID NO:13, or
    (h) comprises a nucleotide sequence that is at least 80% identical to SEQ ID NO:14; or
    (i) comprises a nucleotide sequence that is at least 85% identical to SEQ ID NO:14; or
    (j) comprises a nucleotide sequence that is at least 90% identical to SEQ ID NO:14; or
    (k) comprises a nucleotide sequence that is at least 95% identical to SEQ ID NO:14; or
    (l) comprises a nucleotide sequence that is at least 98% identical to SEQ ID NO:14; or
    (m) comprises a nucleotide sequence that is at least 100% identical to SEQ ID NO:14, or
    (n) comprises a nucleotide sequence that is at least 80% identical to SEQ ID NO:15; or
    (o) comprises a nucleotide sequence that is at least 85% identical to SEQ ID NO:15; or
    (p) comprises a nucleotide sequence that is at least 90% identical to SEQ ID NO:15; or
    (q) comprises a nucleotide sequence that is at least 95% identical to SEQ ID NO:15; or
    (r) comprises a nucleotide sequence that is at least 98% identical to SEQ ID NO:15; or
    (s) comprises a nucleotide sequence that is at least 100% identical to SEQ ID NO:15.
15. An rAAV comprising:
    (a) an AAV capsid; and
    (b) a recombinant AAV genome comprising an hGALNS expression cassette flanked by AAV-ITRs, said hGALNS expression cassette comprising a nucleotide sequence encoding a promoter and a nucleotide sequence encoding hGALNS, wherein the nucleotide sequence encoding the promoter is operably linked to the nucleotide sequence encoding hGALNS, and wherein the promoter is a CAG promoter.
16. An rAAV comprising:
    (a) an AAV capsid; and
    (b) a recombinant AAV genome comprising an hGALNS expression cassette flanked by AAV-ITRs, said hGALNS expression cassette comprising a nucleotide sequence encoding a liver- and muscle-specific promoter and a nucleotide sequence encoding hGALNS, wherein the nucleotide sequence encoding the promoter is operably linked to the nucleotide sequence encoding hGALNS, and wherein the liver- and muscle-specific promoter:
    (a) comprises a nucleotide sequence that is at least 80% identical to SEQ ID NO:16; or
    (b) comprises a nucleotide sequence that is at least 85% identical to SEQ ID NO:16; or
    (c) comprises a nucleotide sequence that is at least 90% identical to SEQ ID NO:16; or
    (d) comprises a nucleotide sequence that is at least 95% identical to SEQ ID NO:16; or
    (e) comprises a nucleotide sequence that is at least 98% identical to SEQ ID NO:16; or
    (f) comprises a nucleotide sequence that is at least 100% identical to SEQ ID NO:16.
17. The rAAV of any one of paragraphs 13-18, wherein the AAV is AAV8.
18. The rAAV of any one of paragraphs 13-18, wherein the AAV is AAV9.
19. The rAAV of any one of paragraphs 13-18, wherein the nucleotide sequence encoding hGALNS or the nucleotide sequence encoding the fusion protein is codon-optimized.
20. The rAAV of any one of paragraphs 13-19, wherein the nucleotide sequence encoding hGALNS or the nucleotide sequence encoding the fusion protein has CpG sites depleted.
21. A pharmaceutical composition comprising the rAAV of any one of paragraphs 1-20 and a pharmaceutically acceptable carrier.
22. A polynucleotide comprising an hGALNS expression cassette flanked by AAV-ITRs, said hGALNS expression cassette comprising a nucleotide sequence encoding a transgene, wherein the said transgene encodes a fusion protein that is hGALNS fused to an acidic oligopeptide.
23. The polynucleotide of paragraph 22, wherein the acidic oligopeptide is D8.

24. The polynucleotide of paragraph 22 or 23, wherein the hGALNS expression cassette further comprises a nucleotide sequence encoding a liver-specific promoter, wherein the nucleotide sequence encoding the liver-specific promoter is operably linked to the nucleotide sequence encoding the fusion protein.

25. The polynucleotide of paragraph 24, wherein the liver-specific promoter:
   (a) is a TBG promoter; or
   (b) comprises a nucleotide sequence that is at least 80% identical to SEQ ID NO:13; or
   (c) comprises a nucleotide sequence that is at least 85% identical to SEQ ID NO:13; or
   (d) comprises a nucleotide sequence that is at least 90% identical to SEQ ID NO:13; or
   (e) comprises a nucleotide sequence that is at least 95% identical to SEQ ID NO:13; or
   (f) comprises a nucleotide sequence that is at least 98% identical to SEQ ID NO:13; or
   (g) comprises a nucleotide sequence that is at least 100% identical to SEQ ID NO:13, or
   (h) comprises a nucleotide sequence that is at least 80% identical to SEQ ID NO:14; or
   (i) comprises a nucleotide sequence that is at least 85% identical to SEQ ID NO:14; or
   (j) comprises a nucleotide sequence that is at least 90% identical to SEQ ID NO:14; or
   (k) comprises a nucleotide sequence that is at least 95% identical to SEQ ID NO:14; or
   (l) comprises a nucleotide sequence that is at least 98% identical to SEQ ID NO:14; or
   (m) comprises a nucleotide sequence that is at least 100% identical to SEQ ID NO:14, or
   (n) comprises a nucleotide sequence that is at least 80% identical to SEQ ID NO:15; or
   (o) comprises a nucleotide sequence that is at least 85% identical to SEQ ID NO:15; or
   (p) comprises a nucleotide sequence that is at least 90% identical to SEQ ID NO:15; or
   (q) comprises a nucleotide sequence that is at least 95% identical to SEQ ID NO:15; or
   (r) comprises a nucleotide sequence that is at least 98% identical to SEQ ID NO:15; or
   (s) comprises a nucleotide sequence that is at least 100% identical to SEQ ID NO:15.

26. The polynucleotide of paragraph 22 or 23, wherein the hGALNS expression cassette further comprises a nucleotide sequence encoding a liver- and muscle-specific promoter, wherein the nucleotide sequence encoding the liver- and muscle-specific is operably linked to the nucleotide sequence encoding the fusion protein.

27. The polynucleotide of paragraph 26, wherein the liver- and muscle-specific promoter:
   (a) comprises a nucleotide sequence that is at least 80% identical to SEQ ID NO:16; or
   (b) comprises a nucleotide sequence that is at least 85% identical to SEQ ID NO:16; or
   (c) comprises a nucleotide sequence that is at least 90% identical to SEQ ID NO:16; or
   (d) comprises a nucleotide sequence that is at least 95% identical to SEQ ID NO:16; or
   (e) comprises a nucleotide sequence that is at least 98% identical to SEQ ID NO:16; or
   (f) comprises a nucleotide sequence that is at least 100% identical to SEQ ID NO:16.

28. The polynucleotide of paragraph 22 or 23, wherein the hGALNS expression cassette further comprises a nucleotide sequence encoding a promoter, wherein the nucleotide sequence encoding the promoter is operably linked to the nucleotide sequence encoding the fusion protein.

29. The polynucleotide of paragraph 28, wherein the promoter is a CAG promoter.

30. A polynucleotide comprising an hGALNS expression cassette flanked by AAV-ITRs, said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS, wherein the liver-specific promoter:
   (a) is a TBG promoter; or
   (b) comprises a nucleotide sequence that is at least 80% identical to SEQ ID NO:13; or
   (c) comprises a nucleotide sequence that is at least 85% identical to SEQ ID NO:13; or
   (d) comprises a nucleotide sequence that is at least 90% identical to SEQ ID NO:13; or
   (e) comprises a nucleotide sequence that is at least 95% identical to SEQ ID NO:13; or
   (f) comprises a nucleotide sequence that is at least 98% identical to SEQ ID NO:13; or
   (g) comprises a nucleotide sequence that is at least 100% identical to SEQ ID NO:13, or
   (h) comprises a nucleotide sequence that is at least 80% identical to SEQ ID NO:14; or
   (i) comprises a nucleotide sequence that is at least 85% identical to SEQ ID NO:14; or
   (j) comprises a nucleotide sequence that is at least 90% identical to SEQ ID NO:14; or
   (k) comprises a nucleotide sequence that is at least 95% identical to SEQ ID NO:14; or
   (l) comprises a nucleotide sequence that is at least 98% identical to SEQ ID NO:14; or
   (m) comprises a nucleotide sequence that is at least 100% identical to SEQ ID NO:14, or
   (n) comprises a nucleotide sequence that is at least 80% identical to SEQ ID NO:15; or
   (o) comprises a nucleotide sequence that is at least 85% identical to SEQ ID NO:15; or
   (p) comprises a nucleotide sequence that is at least 90% identical to SEQ ID NO:15; or
   (q) comprises a nucleotide sequence that is at least 95% identical to SEQ ID NO:15; or
   (r) comprises a nucleotide sequence that is at least 98% identical to SEQ ID NO:15; or
   (s) comprises a nucleotide sequence that is at least 100% identical to SEQ ID NO:15.

31. A polynucleotide comprising an hGALNS expression cassette flanked by AAV-ITRs, said hGALNS expression cassette comprising a nucleotide sequence encoding a promoter and a nucleotide sequence encoding hGALNS, wherein the nucleotide sequence encoding the promoter is operably linked to the nucleotide sequence encoding hGALNS, wherein the promoter is a CAG promoter.

32. A polynucleotide comprising an hGALNS expression cassette flanked by AAV-ITRs, said hGALNS expression cassette comprising a nucleotide sequence encoding a liver- and muscle-specific promoter and a nucleotide sequence encoding hGALNS, wherein the nucleotide sequence encoding the liver- and muscle-specific promoter is operably linked to the nucleotide sequence encoding hGALNS, wherein the liver- and muscle-specific promoter:
(a) comprises a nucleotide sequence that is at least 80% identical to SEQ ID NO:16; or
(b) comprises a nucleotide sequence that is at least 85% identical to SEQ ID NO:16; or
(c) comprises a nucleotide sequence that is at least 90% identical to SEQ ID NO:16; or
(d) comprises a nucleotide sequence that is at least 95% identical to SEQ ID NO:16; or
(e) comprises a nucleotide sequence that is at least 98% identical to SEQ ID NO:16; or
(f) comprises a nucleotide sequence that is at least 100% identical to SEQ ID NO:16.

33. The polynucleotide of any one of paragraphs 22-32, wherein the AAV is AAV8.
34. The polynucleotide of any one of paragraphs 22-32, wherein the AAV is AAV9.
35. An rAAV plasmid comprising the polynucleotide of any one of paragraphs 22-34.
36. An ex vivo cell comprising the polynucleotide of any one of paragraphs 22-34 or the rAAV plasmid of paragraph 35.
37. A method of making an rAAV comprising transfecting an ex vivo cell with the rAAV plasmid of paragraph 35 and one or more helper plasmids collectively comprising the nucleotide sequences of AAV genes Rep, Cap, VA, E2a and E4.
38. A method for treating a human subject diagnosed with mucopolysaccharidosis type IVA (MPS IVA), comprising administering to the human subject the rAAV of any one of paragraphs 1-20 or the pharmaceutical composition of paragraph 21.
39. A method for treating a human subject diagnosed with MPS IVA, comprising delivering to the bone, cartilage, ligament, meniscus, growth plate, liver, spleen, lung, kidney, trachea, heart muscle, and/or heart valve of said human subject a therapeutically effective amount of a fusion protein that is hGALNS fused to an acidic oligopeptide, by administering to the human subject an rAAV of any one of paragraphs 1-5 and 7-12.
40. The method of paragraph 39, wherein said hGALNS is glycosylated with mannose-6-phosphate by having been produced in and secreted from a liver cell.
41. A method for treating a human subject diagnosed with MPS IVA, comprising delivering to the bone, cartilage, ligament, meniscus, growth plate, liver, spleen, lung, kidney, trachea, heart muscle, and/or heart valve of said human subject a therapeutically effective amount of hGALNS that is glycosylated with mannose-6-phosphate by having been produced in and secreted from a liver cell, by administering to the human subject an rAAV of any one of paragraphs 13-14 and 16-20.
42. A method for treating a human subject diagnosed with MPS IVA, comprising delivering to the bone, cartilage, ligament, meniscus, growth plate, liver, spleen, lung, kidney, trachea, heart muscle, and/or heart valve of said human subject a therapeutically effective amount of a fusion protein that is hGALNS fused to an acidic oligopeptide, wherein the fusion protein is produced from an rAAV genome.
43. A method for treating a human subject diagnosed with MPS IVA, comprising delivering to the bone, cartilage, ligament, meniscus, growth plate, liver, spleen, lung, kidney, trachea, heart muscle, and/or heart valve of said human subject a therapeutically effective amount of a fusion protein that is hGALNS fused to an acidic oligopeptide, wherein the fusion protein is produced from an rAAV genome and is glycosylated with mannose-6-phosphate by having been produced in and secreted from a liver cell.
44. A method for treating a human subject diagnosed with MPS IVA, comprising delivering to the bone, cartilage, ligament, meniscus, growth plate, liver, spleen, lung, kidney, trachea, heart muscle, and/or heart valve of said human subject a therapeutically effective amount of hGALNS that is produced from an rAAV genome and is glycosylated with mannose-6-phosphate by having been produced in and secreted from a liver cell.
45. The method of any one of paragraphs 42-44, wherein the AAV is AAV8.
46. The method of any one of paragraphs 42-44, wherein the AAV is AAV9.
47. The method of any one of paragraphs 39-46, wherein the step of delivering to the bone, cartilage, ligament, meniscus, growth plate, liver, spleen, lung, kidney, trachea, heart muscle, and/or heart valve is a step of delivering to the bone and/or cartilage.
48. The method of any one of paragraphs 39-46, wherein the step of delivering to the bone, cartilage, ligament, meniscus, growth plate, liver, spleen, lung, kidney, trachea, heart muscle, and/or heart valve is a step of delivering to (a) the bone and/or cartilage, and (b) ligament, meniscus, growth plate, liver, spleen, lung, kidney, trachea, heart muscle, and/or heart valve.
49. A recombinant adeno-associated virus (rAAV) comprising:
(a) an AAV capsid; and
(b) a recombinant AAV genome comprising a human N-acetylgalactosamine-6-sulfate sulfatase (hGALNS) expression cassette flanked by AAV-inverted terminal repeats (ITRs), said hGALNS expression cassette comprising a nucleotide sequence encoding a transgene, wherein the said transgene encodes hGALNS.
50. The rAAV of paragraph 49, wherein the AAV is AAV8.
51. The rAAV of paragraph 49, wherein the AAV is AAV9.
52. The rAAV of paragraph 49, wherein the nucleotide sequence encoding hGALNS is codon-optimized.
53. The rAAV of paragraph 49, wherein the nucleotide sequence encoding hGALNS has CpG sites depleted.

4. ABBREVIATIONS

MPS IVA mucopolysaccharidosis type IVA
GALNS N-acetylgalactosamine-6-sulfate sulfatase
hGALNS human N-acetylgalactosamine-6-sulfate sulfatase
GAG glycosaminoglycan
C6S chondroitin 6-sulfate
KS keratan sulfate
ERT enzyme replacement therapy
HSCT hematopoietic stem cell transplantation
AAV adeno-associated virus
TBG thyroxine binding globulin
ITR inverted terminal repeats
D8 aspartic acid octapeptide
ECM extracellular matrix
ELISA enzyme-linked immunosorbent assay
HS heparan sulfate
IS internal standard LC-MS/MS liquid chromatography/tandem mass spectrometry
OD optical density
PBS phosphate buffered saline
RBG pA rabbit beta-globin poly A
KO knockout

5. BRIEF DESCRIPTION OF THE FIGURES

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

Figure 1:
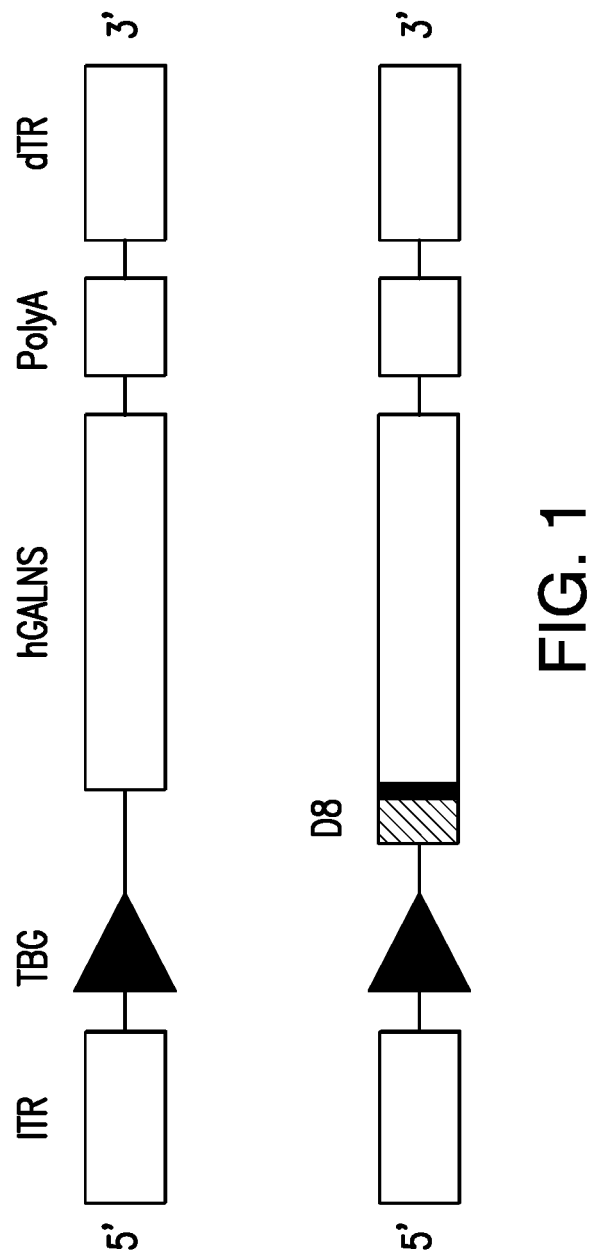

FIG. 1. Schematics of rAAV genomes.

FIGS. 2A-2D. (A) Intracellular enzyme activity was determined in HuH-7 cells after transfection with either the TBG-hGALNS plasmid, TBG-hGALNS-CoOpt plasmid, TBG-D8-hGALNS plasmid, or TBG-D8-hGALNS-CoOpt plasmid (n=2). (B) Depiction of individual runs of the intracellular enzyme activity determined in HuH-7 cells. (C) Enzyme activity in the media was determined after HuH-7 cells were transfected with the TBG-hGALNS plasmid, TBG-hGALNS-CoOpt plasmid, TBG-D8-hGALNS plasmid, or TBG-D8-hGALNS-CoOpt plasmid (n=2). (D) Depiction of individual runs of the enzyme activity in media determined in HuH-7 cells.

Figure 3:
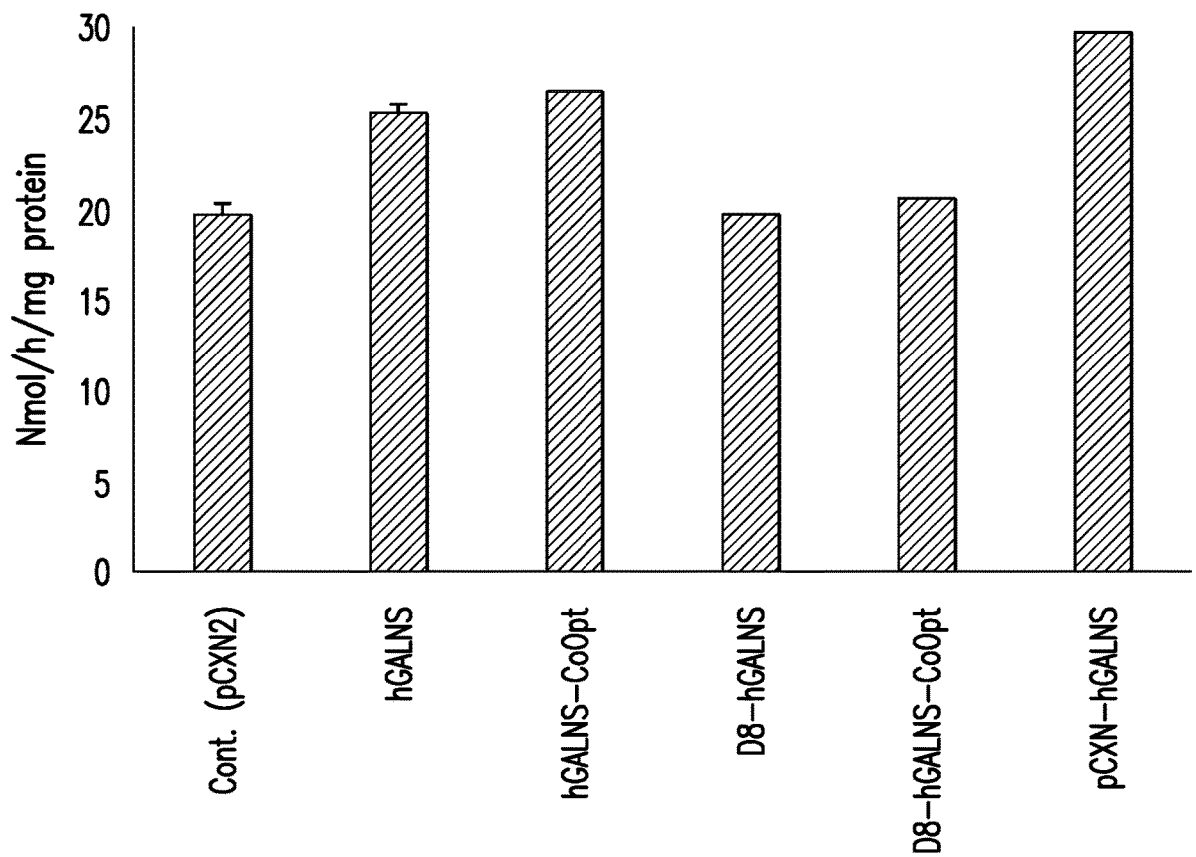

FIG. 3. Intracellular enzyme activity was determined in HepG2 cells after transfection with either the TBG-hGALNS plasmid, TBG-hGALNS-CoOpt plasmid, TBG-D8-hGALNS plasmid, or TBG-D8-hGALNS-CoOpt plasmid.

Figure 4:
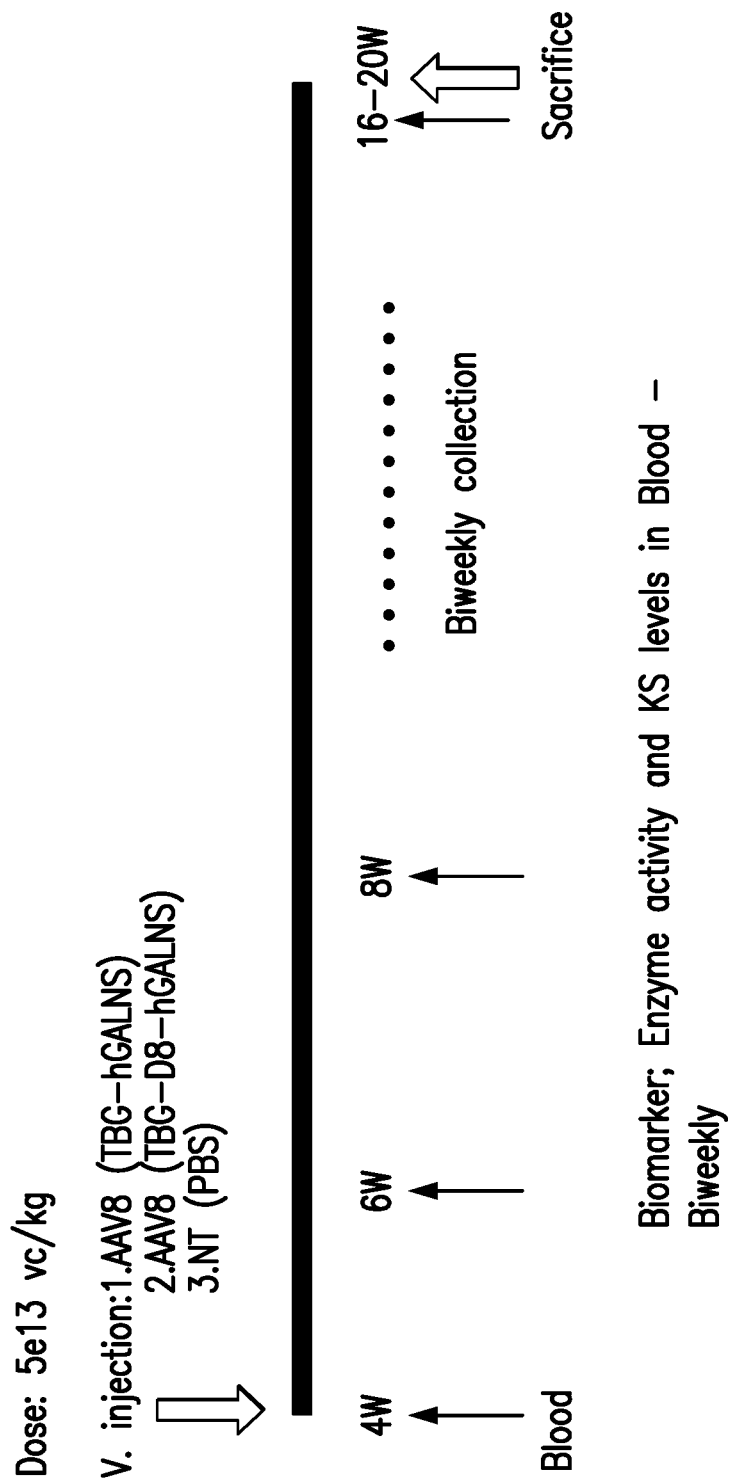

FIG. 4. Schedule of the in vivo study in which AAV8-TBG-hGALNS or AAV8-TBG-D8-hGALNS were administered to 4-week-old MPS IVA KO mice (galns −/−) and immune tolerant mice (Galns$^{tm(hC79S\ mC76S)slu}$ Mtol). The schedule of enzyme assay and KS assay in blood is shown. When describing dosage, vector copies per kilogram (vc/kg) and gene copies per kilogram (GC/kg) are used interchangeably.

Figure 5A:
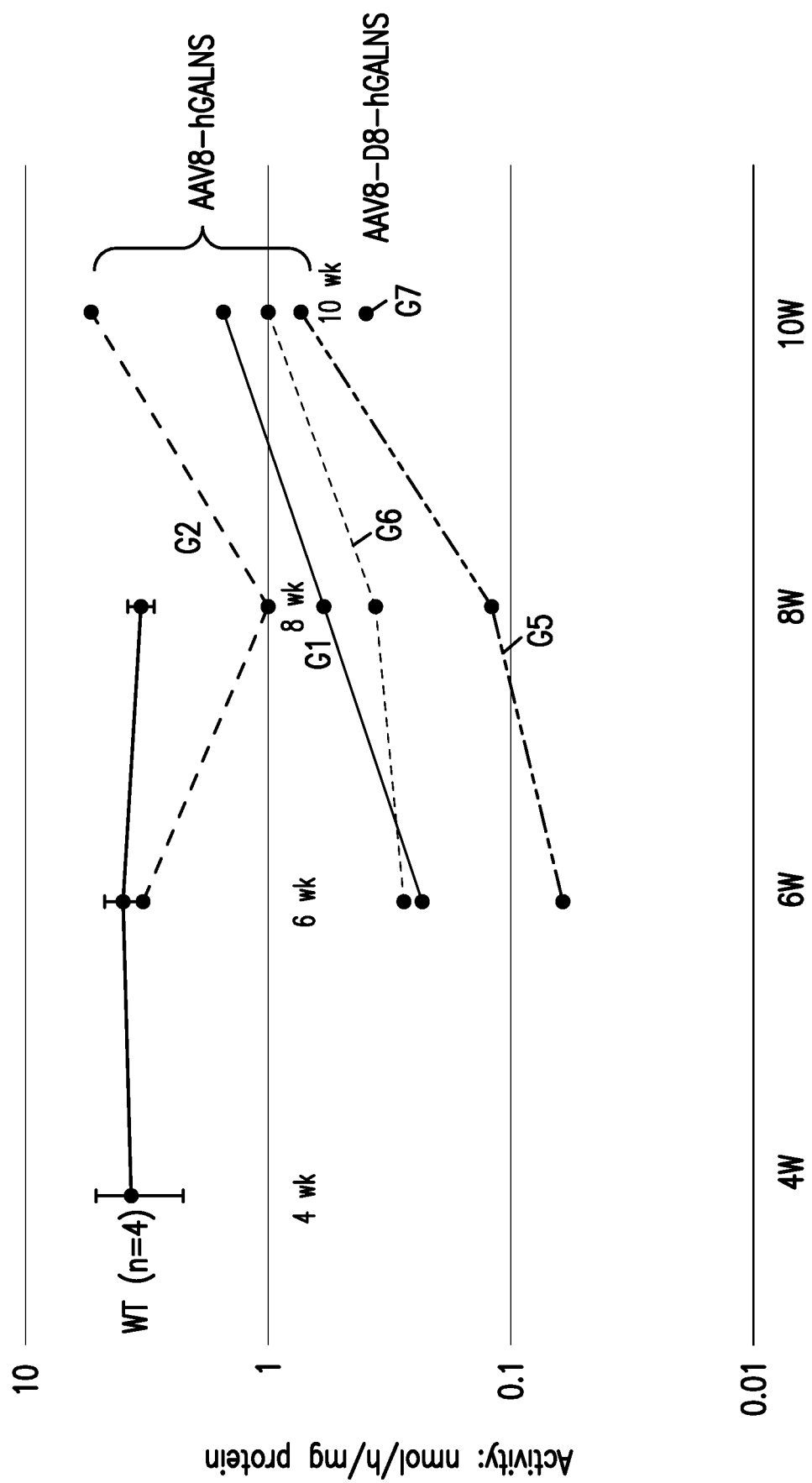
Figure 5B:
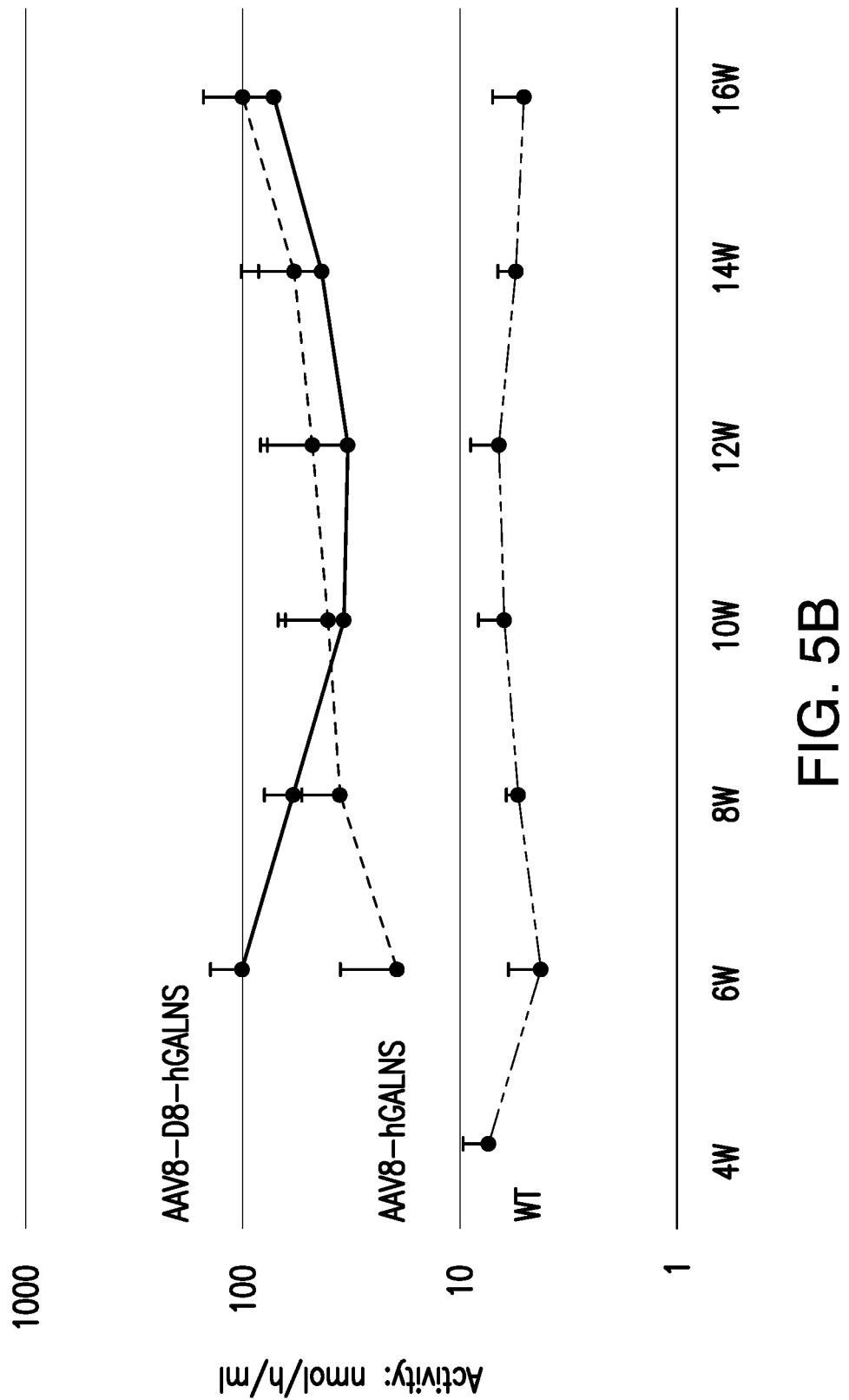

FIGS. 5A-5B. hGALNS enzyme activity over time measured in (A) white blood cells (WBCs) and (B) plasma of MPS IVA KO mice (galns −/−) after administration with AAV8-TBG-hGALNS r or AAV-TBG-D8-hGALNS.

Figure 6:
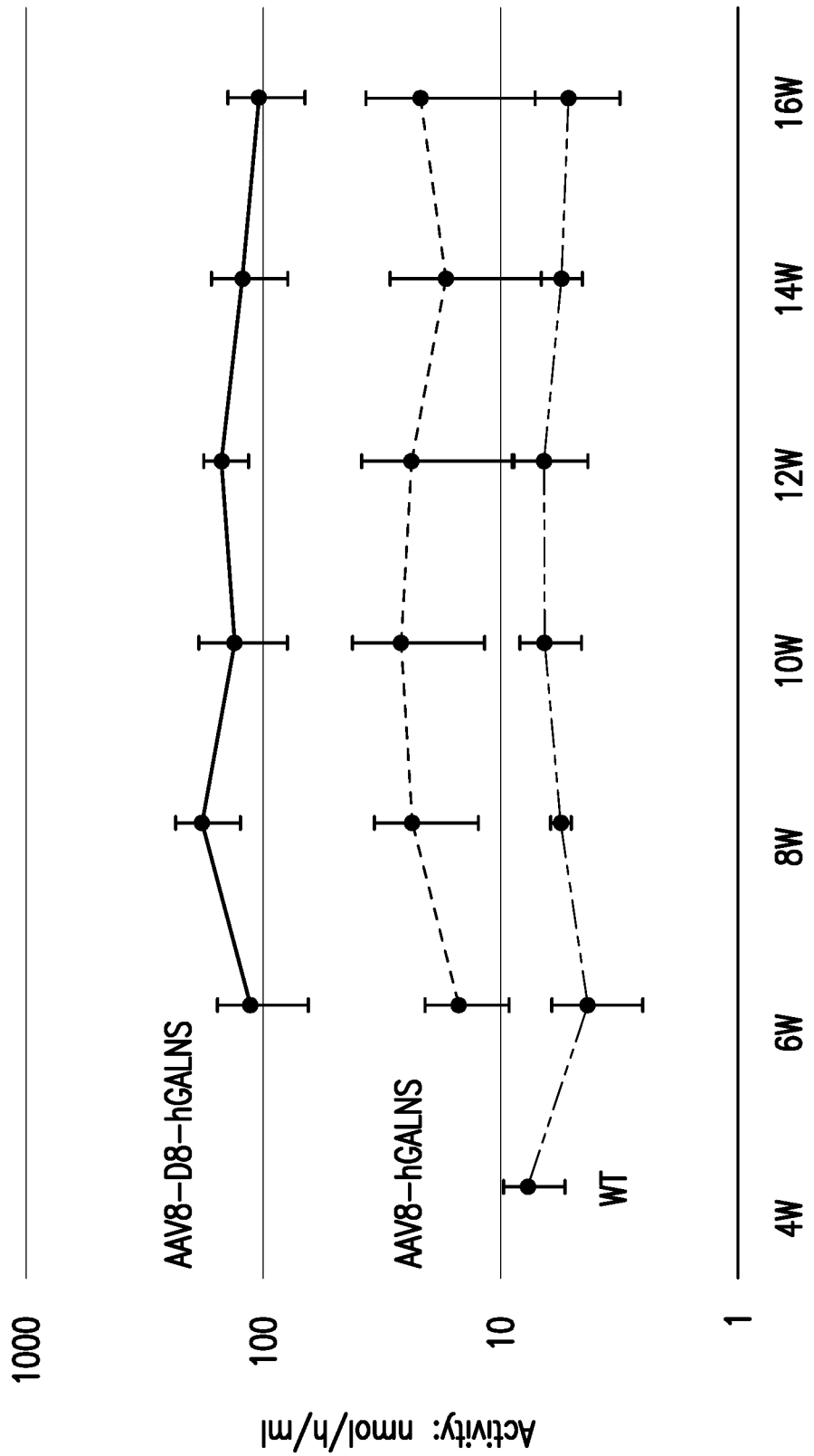

FIG. 6. hGALNS enzyme activity over time measured in plasma of Mtol mice after administration with AAV8-TBG-hGALNS (n=4) or AAV8-TBG-D8-hGALNS (n=4).

FIGS. 7A-7D. hGALNS enzyme activity measured in (A) the liver of MPS IVA KO mice (galns −/−), (B) the liver of Mtol mice, (C) the heart of MPS IVA KO mice (galns −/−) and the heart of Mtol mice, and (D) the bone of MPS IVA KO mice (galns −/−) and the bone of Mtol mice.

Figure 8:
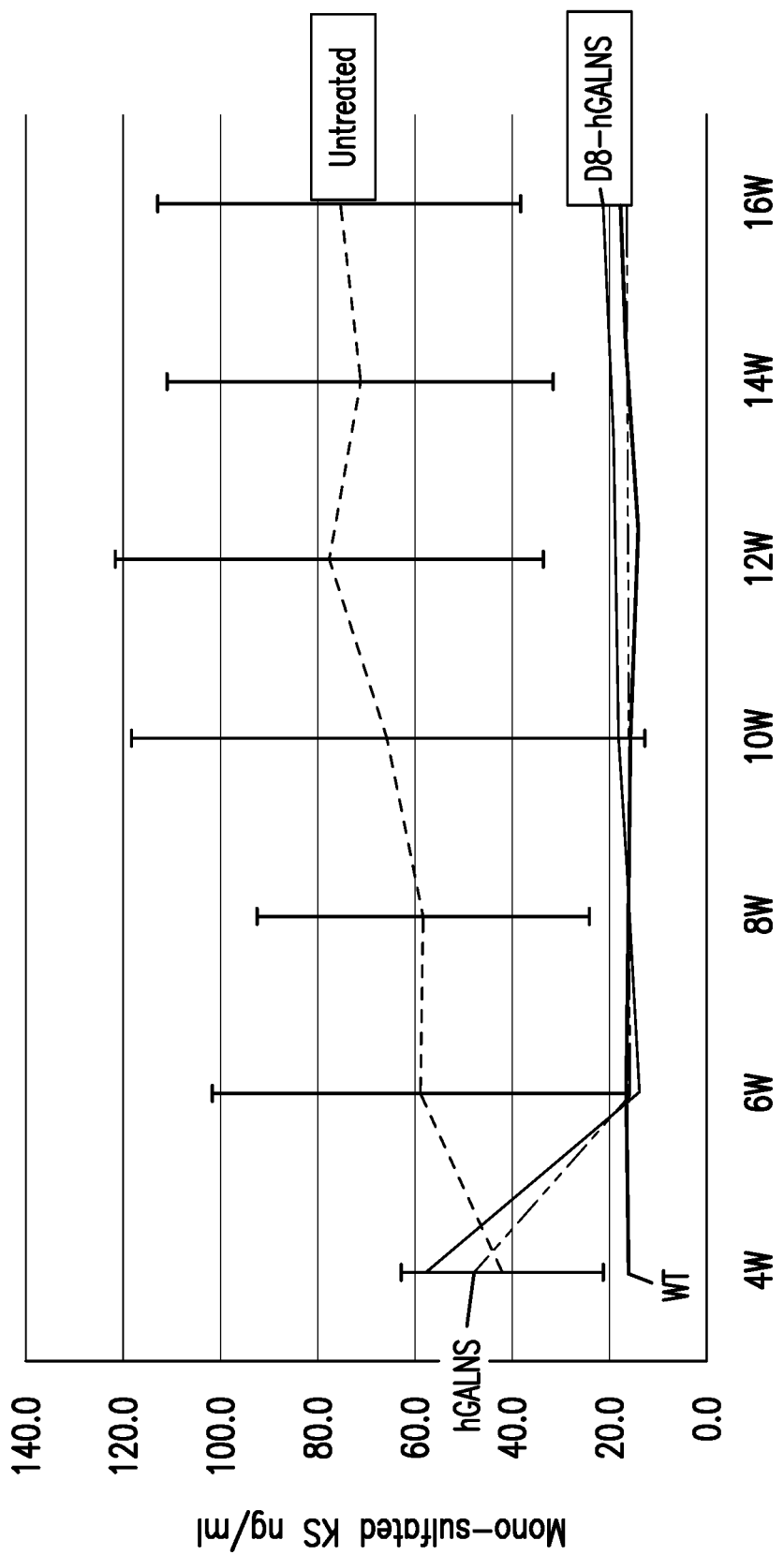

FIG. 8. Mono-sulfated KS levels in the plasma of MPS IVA KO mice (galns −/−) treated with AAV8-TBG-hGALNS or AAV8-TBG-D8-hGALNS.

Figure 9A:
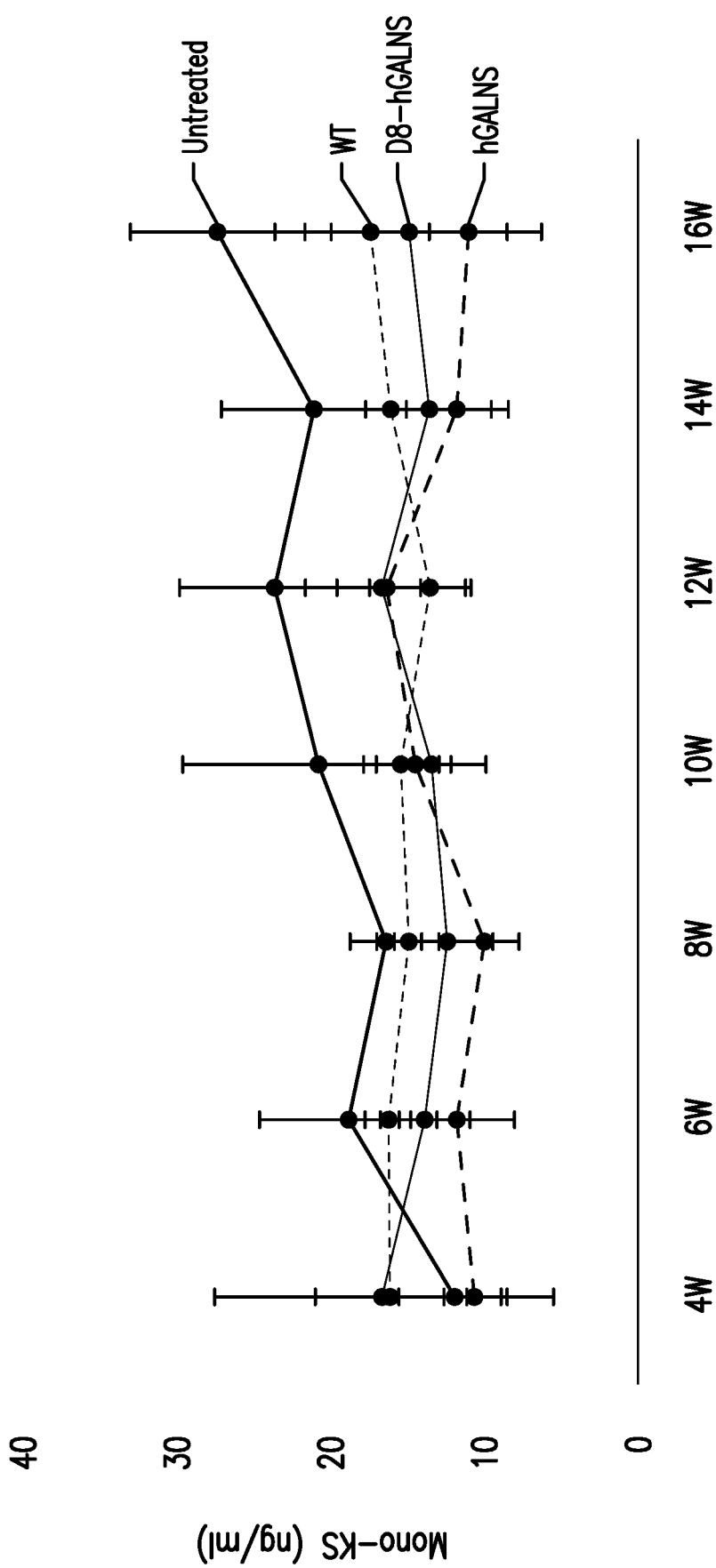
Figure 9B:
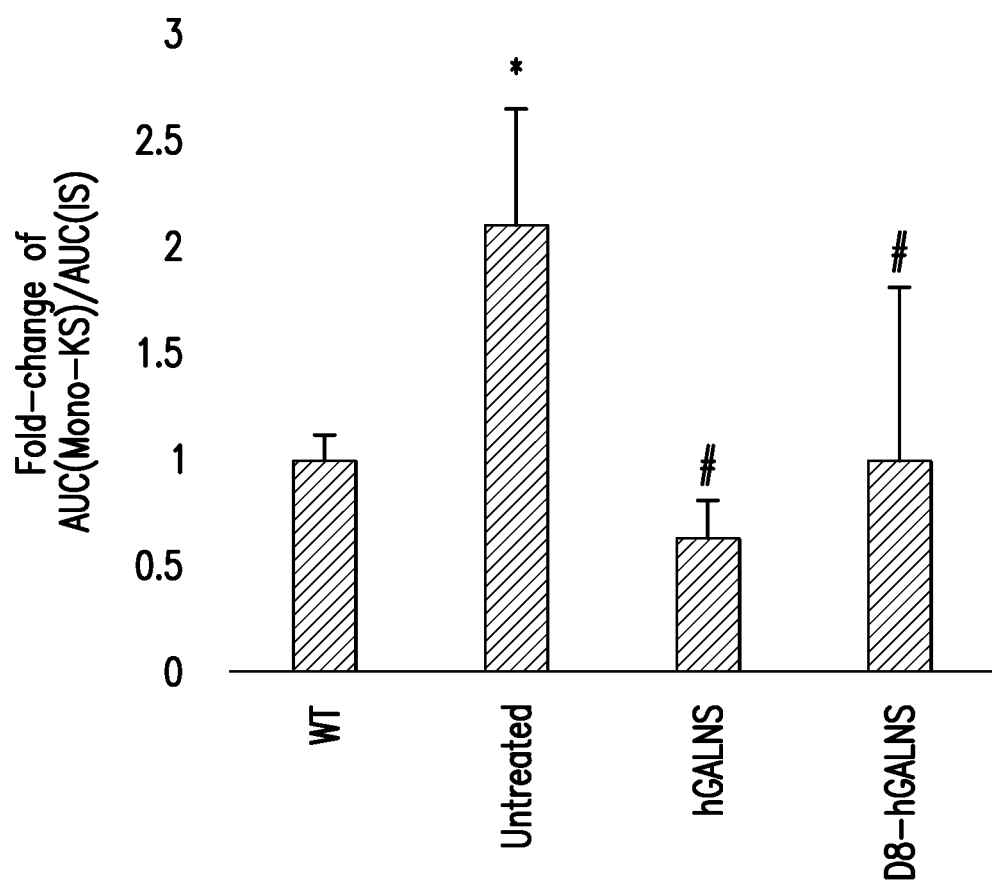

FIGS. 9A-9B. (A) Mono-sulfated KS levels in the plasma of Mtol mice treated with AAV8-TBG-hGALNS or AAV8-TBG-D8-hGALNS over time as compared to untreated Mtol and WT mice. (B) Mono-sulfated KS levels in the plasma of Mtol mice treated with AAV8-TBG-hGALNS or AAV8-TBG-D8-hGALNS were significantly less as compared to untreated Mtol mouse levels at 16 weeks of age (n=4-5; mean±SD; *p<0.05 vs. WT; #p<0.05 vs. Untreated; one-way ANOVA).

Figure 10:
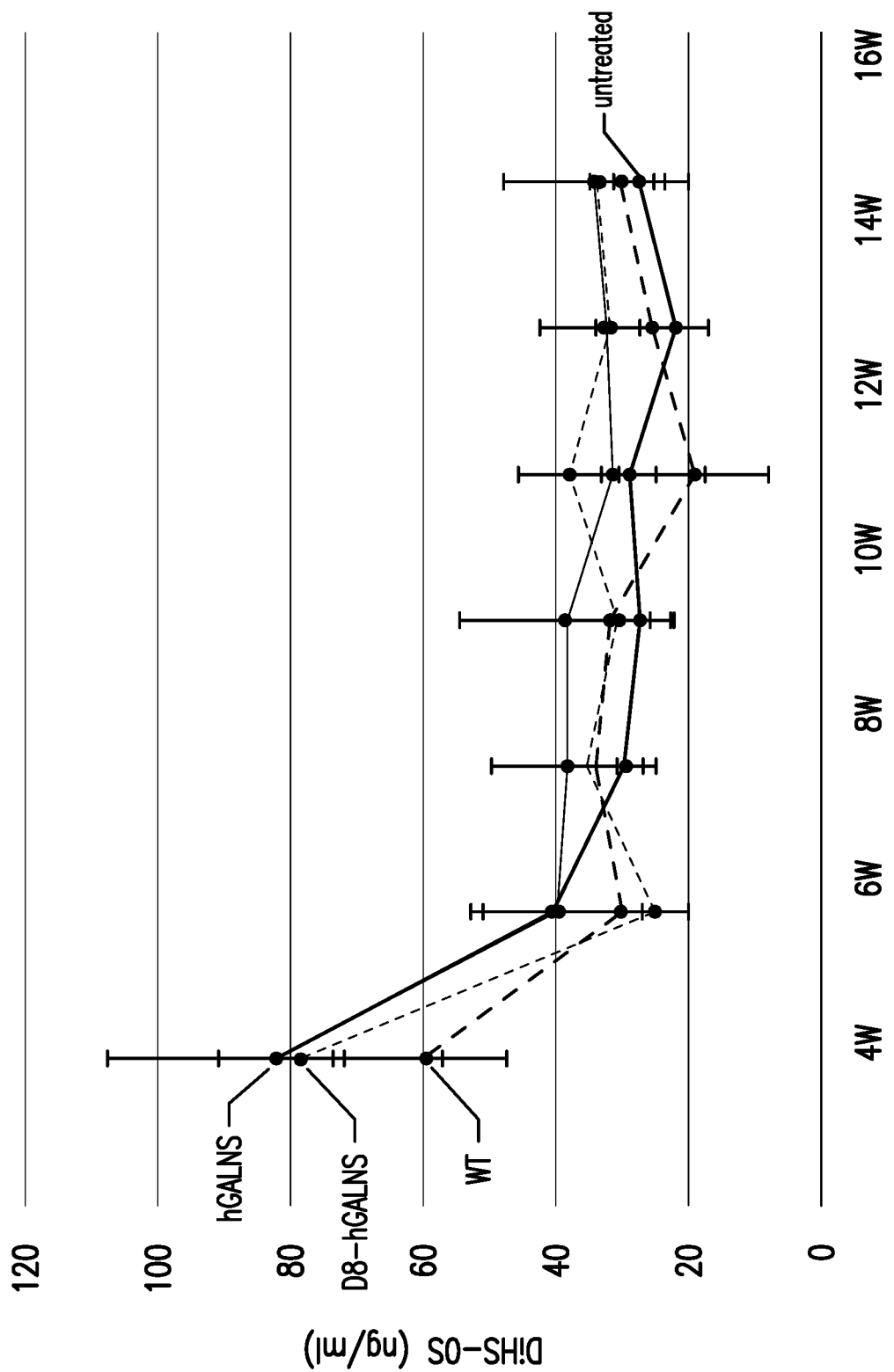

FIG. 10. Blood diHS-0S levels measured over time in MPS IVA KO mice (galns −/−) treated with AAV8-TBG-hGALNS, treated with AAV8-TBG-D8-hGALNS, untreated, or WT mice.

Figure 11A:
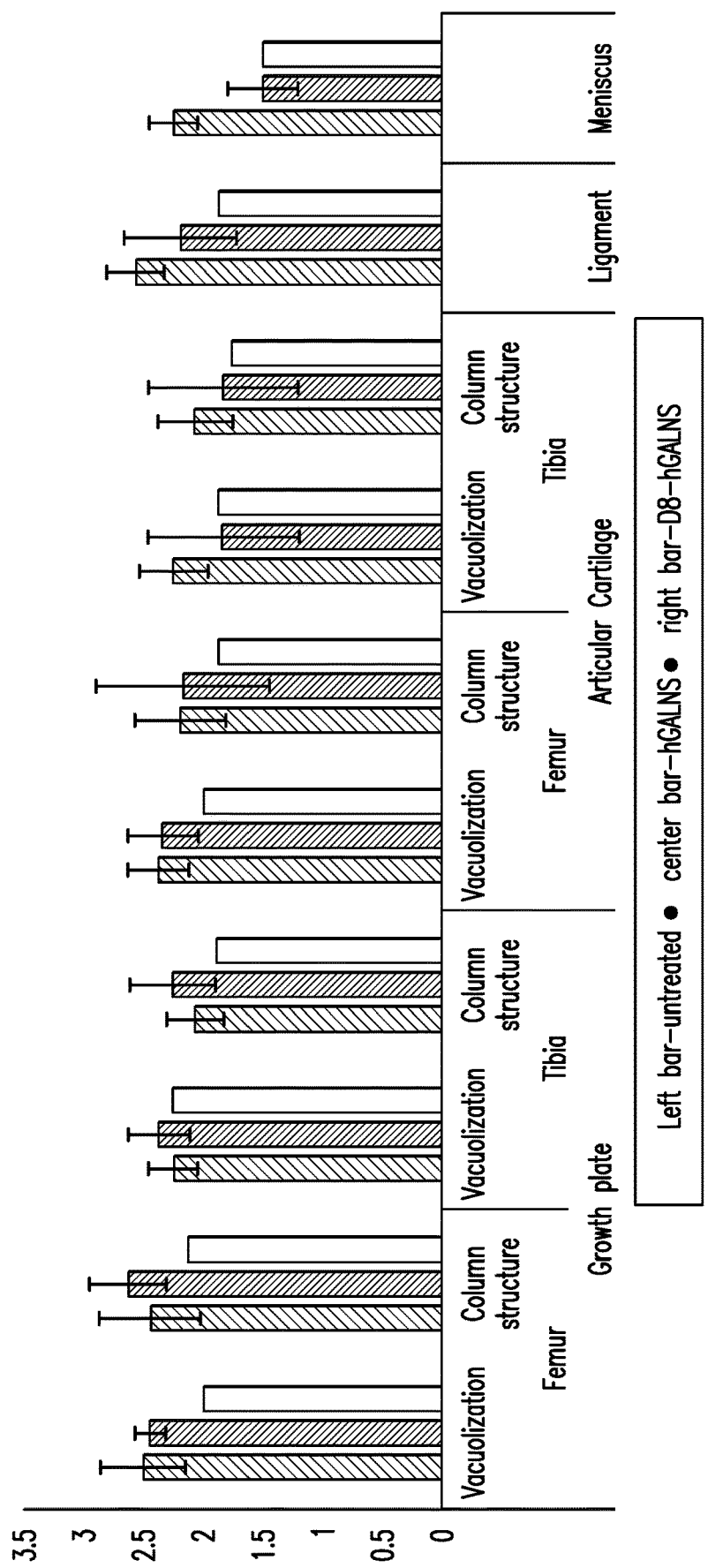
Figure 11B:
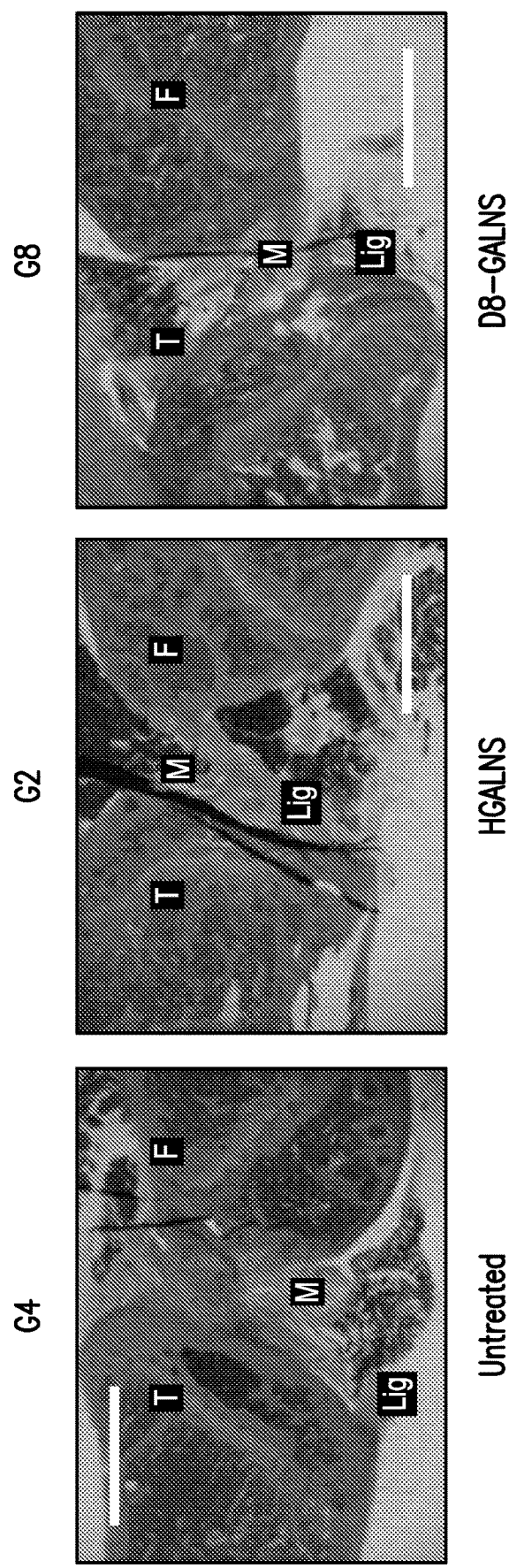
Figure 11C:
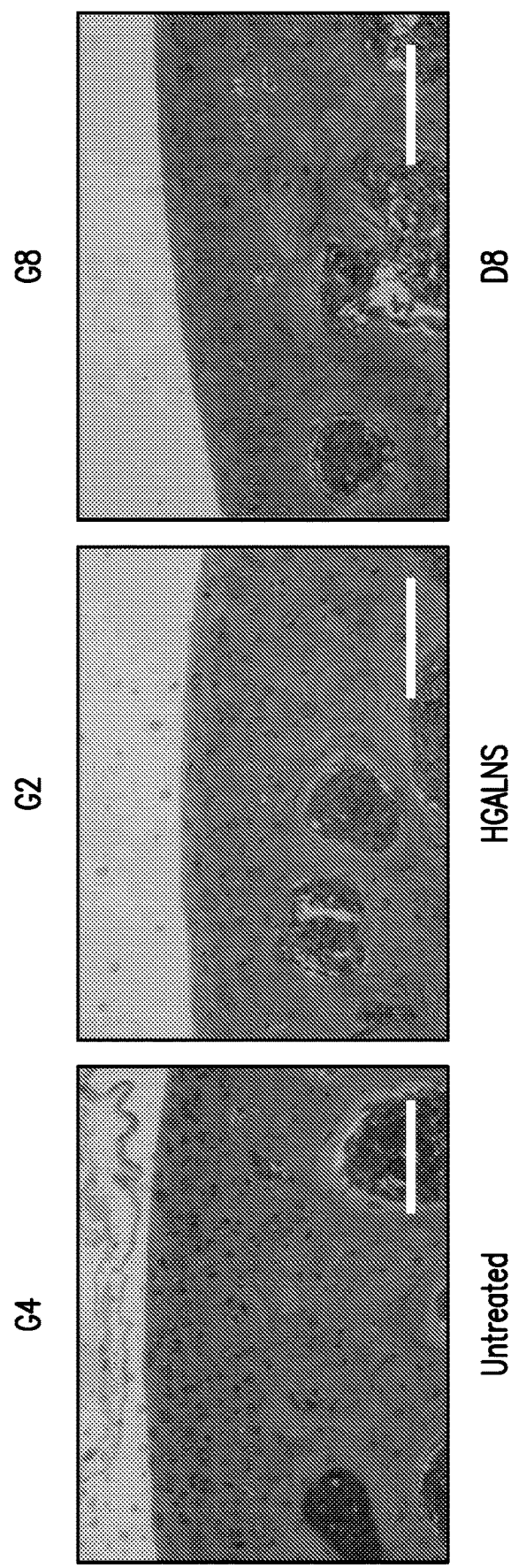
Figure 11D:
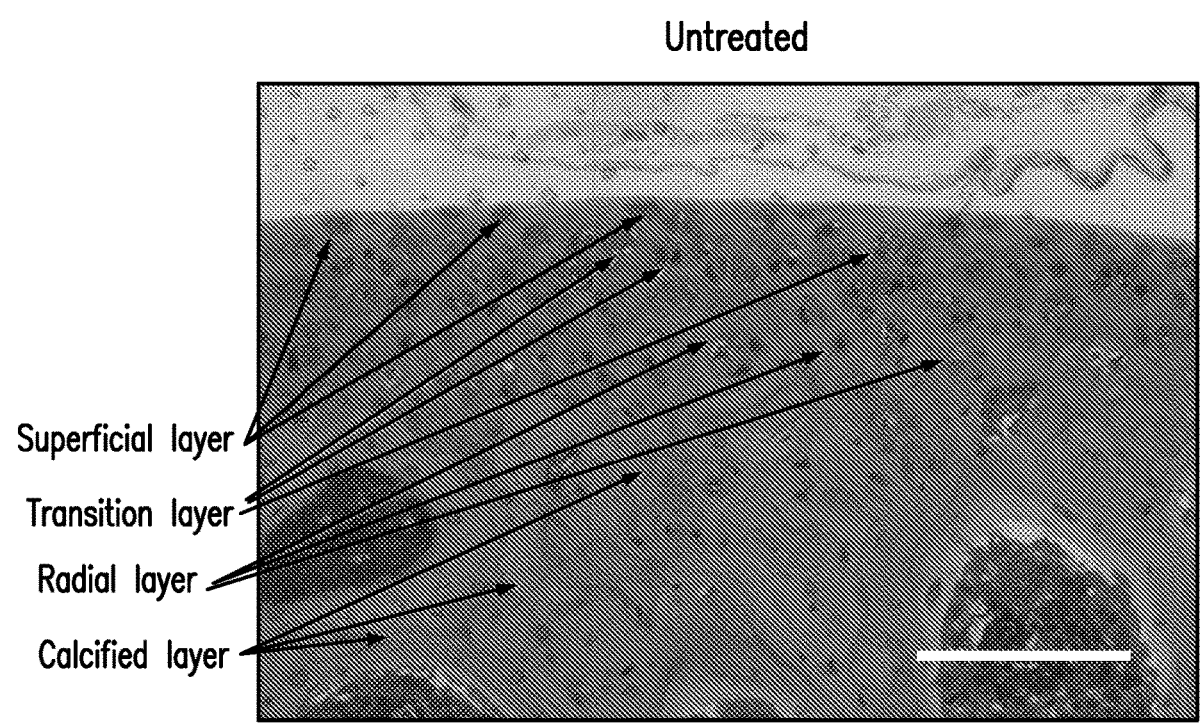
Figure 11E:
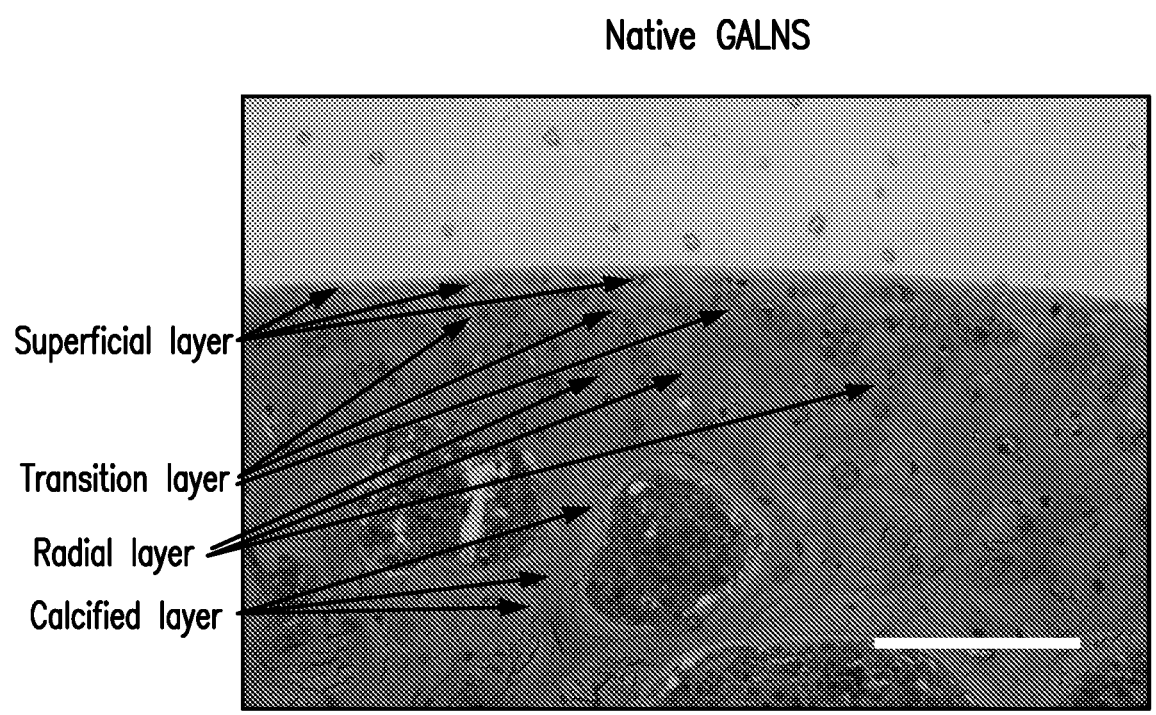
Figure 11F:
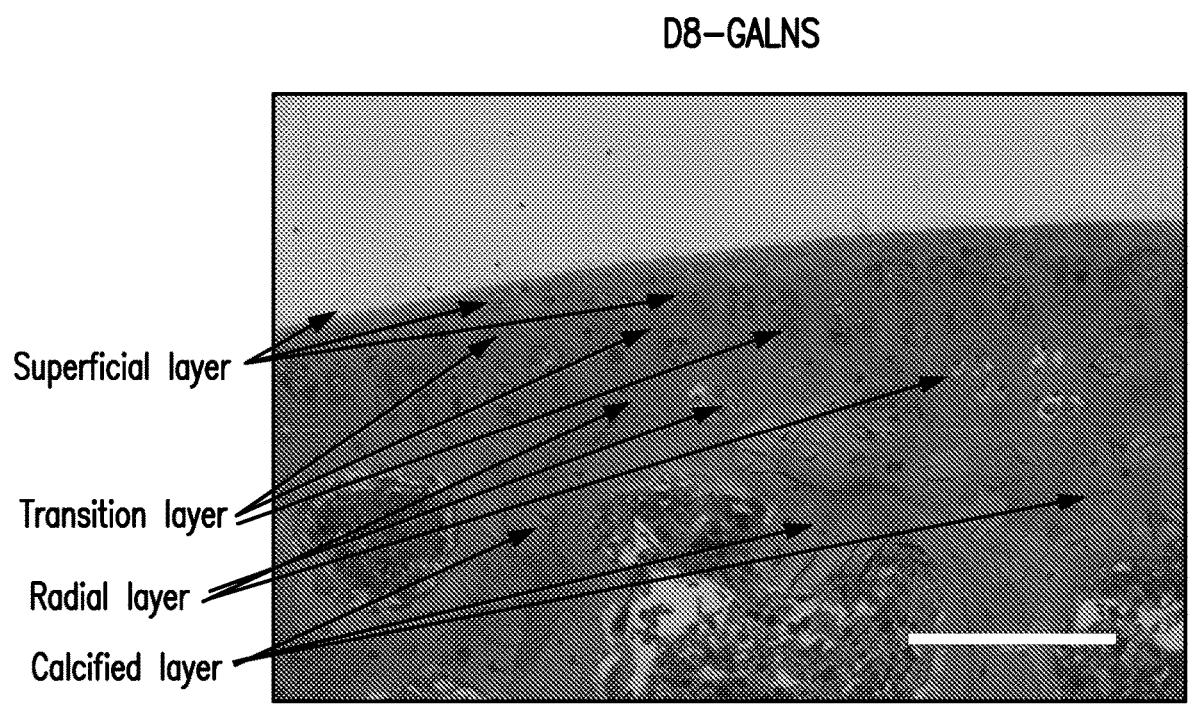
Figure 11G:
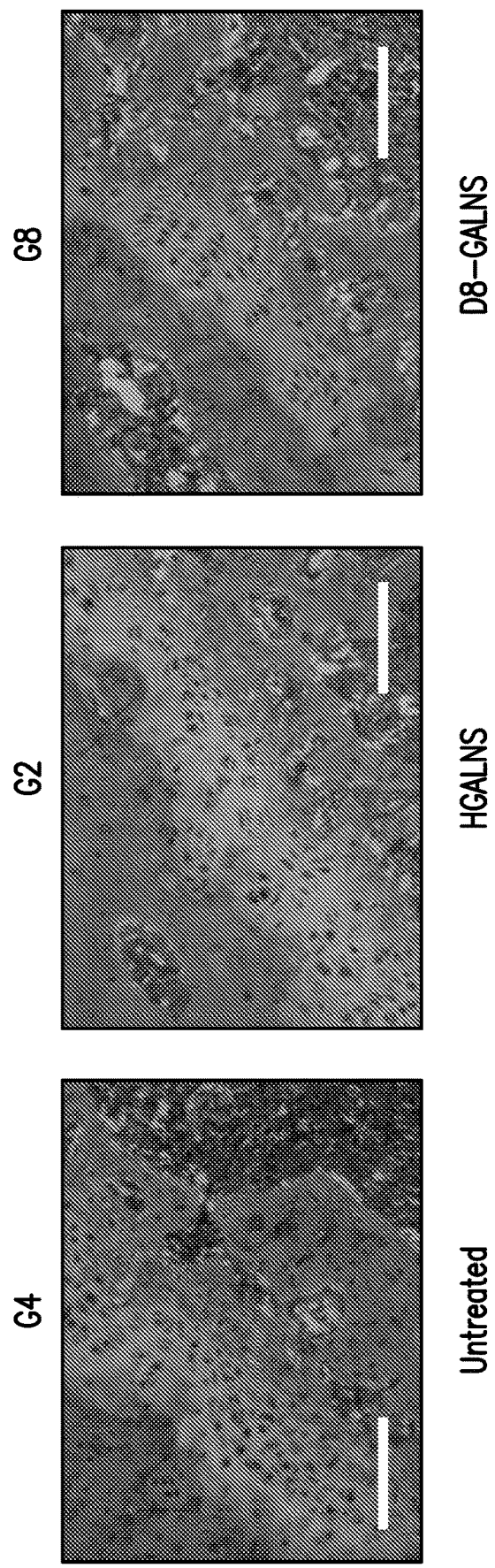
Figure 11H:
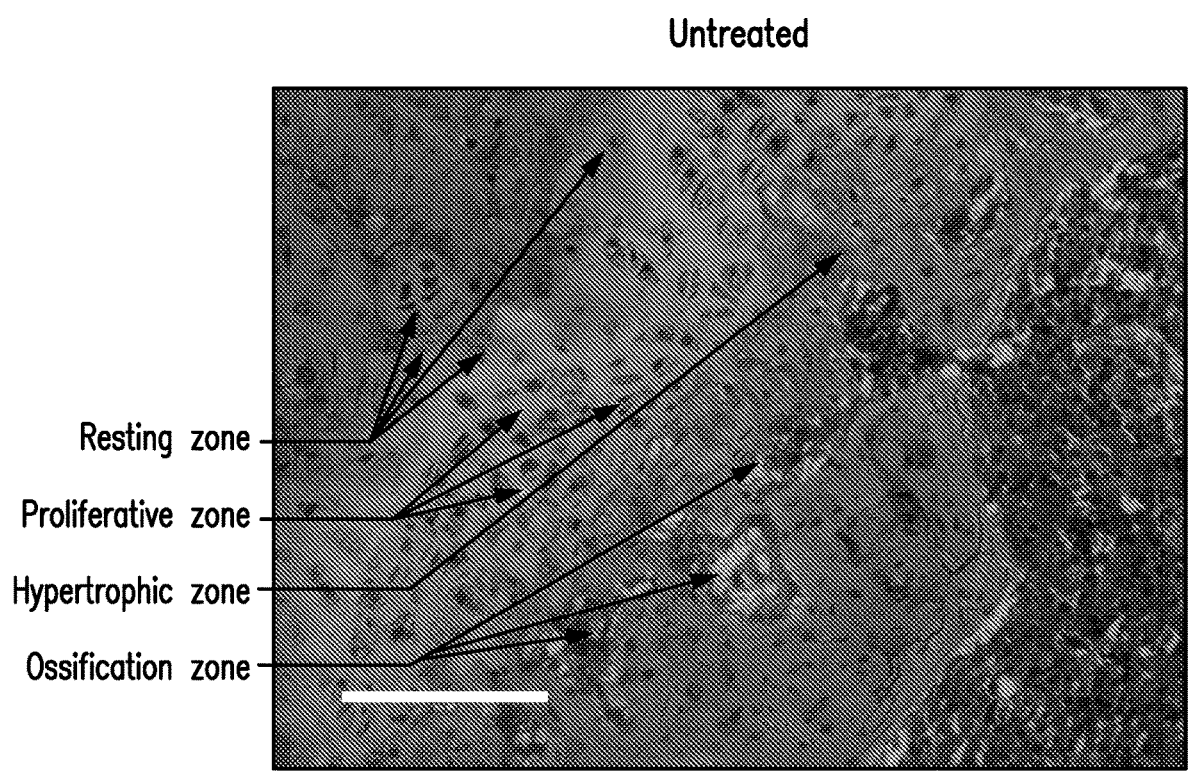
Figure 11I:
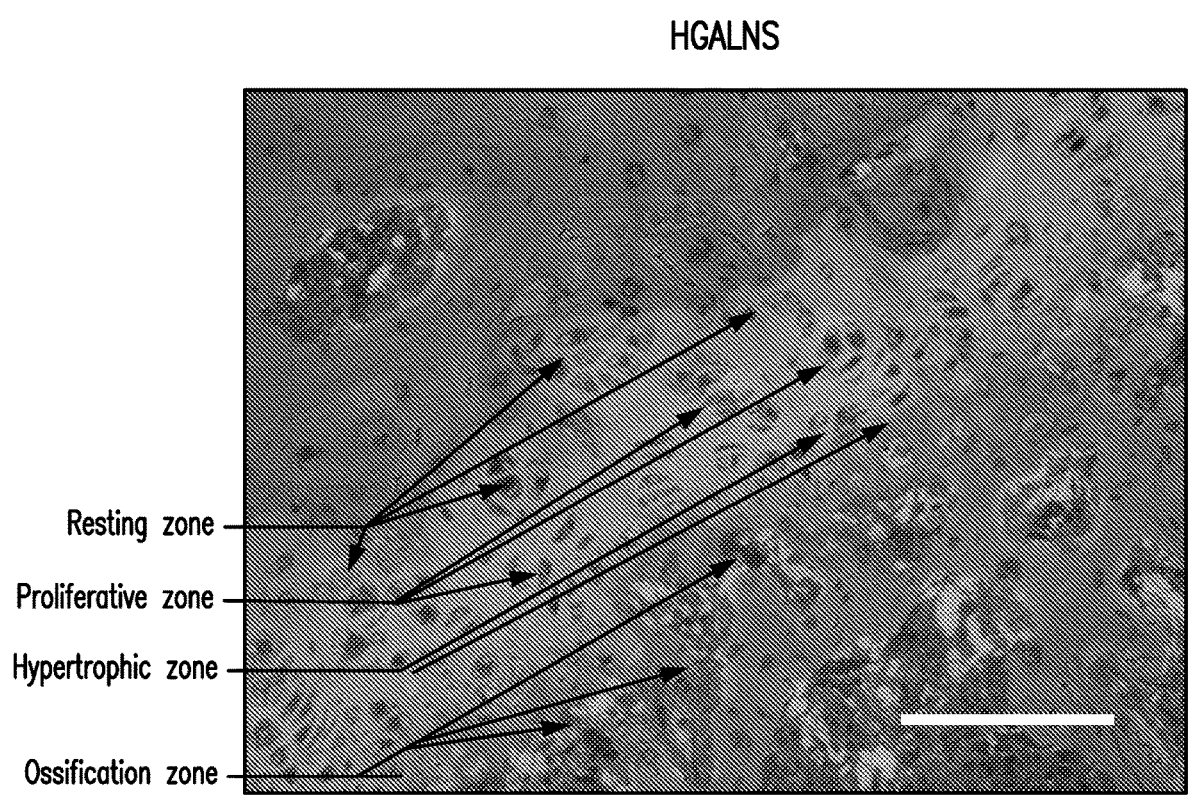
Figure 11J:
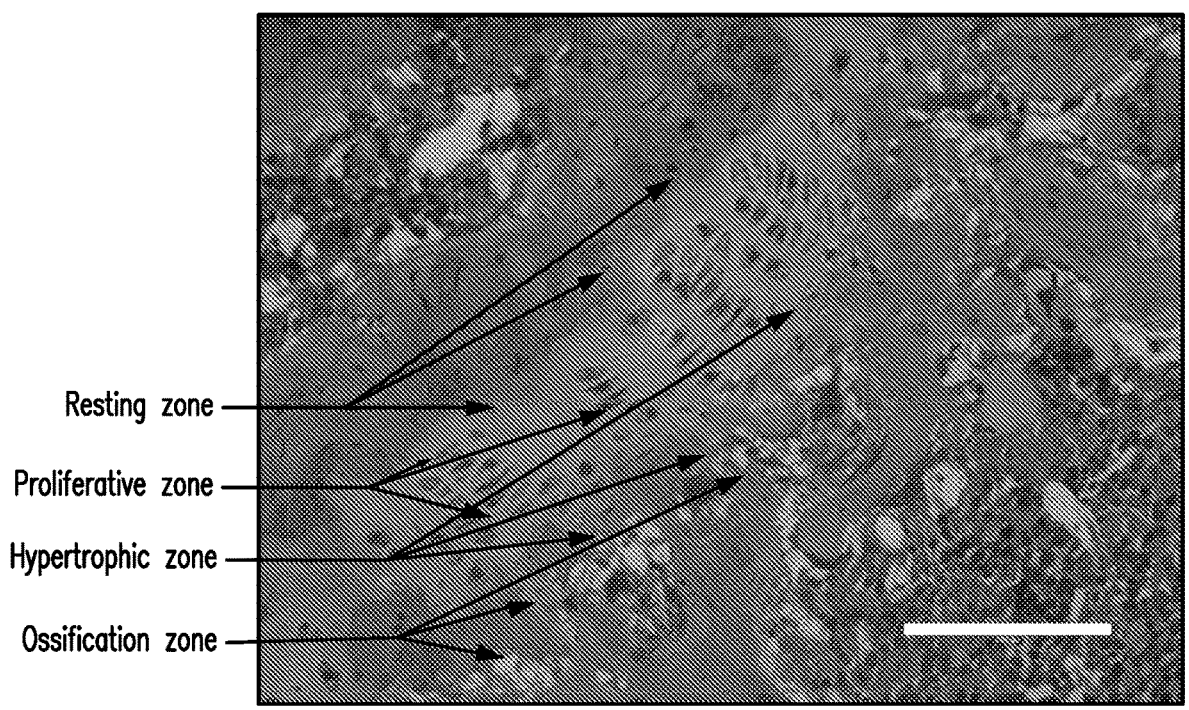
Figure 11K:
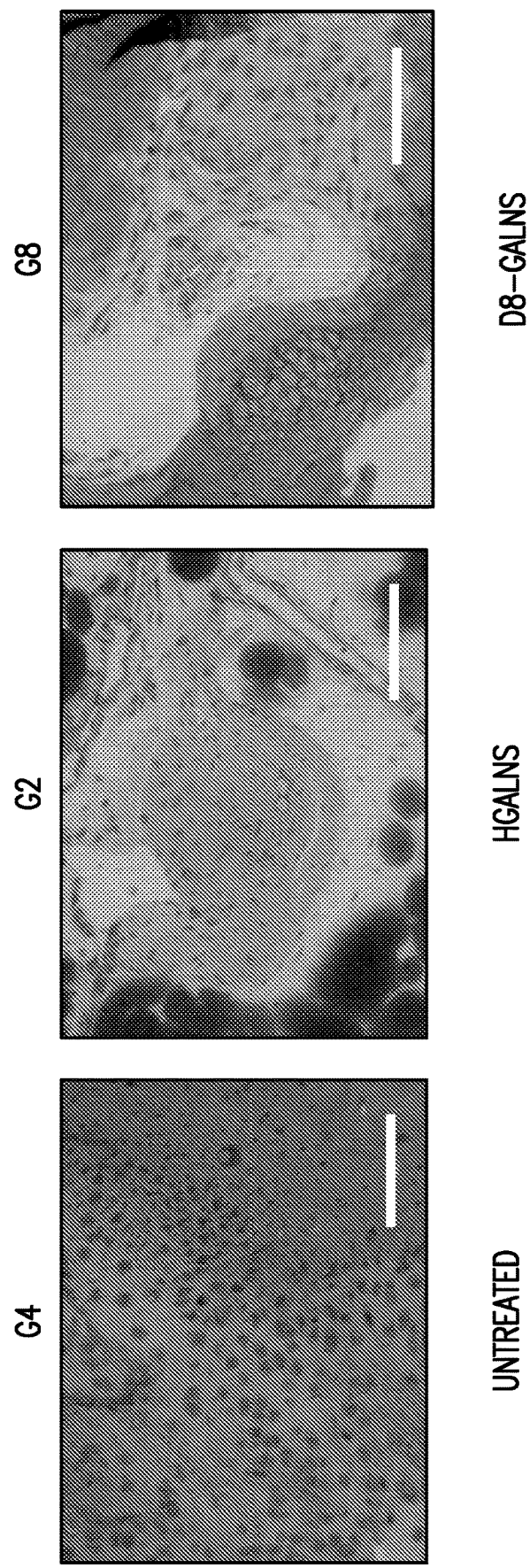
Figure 11L:
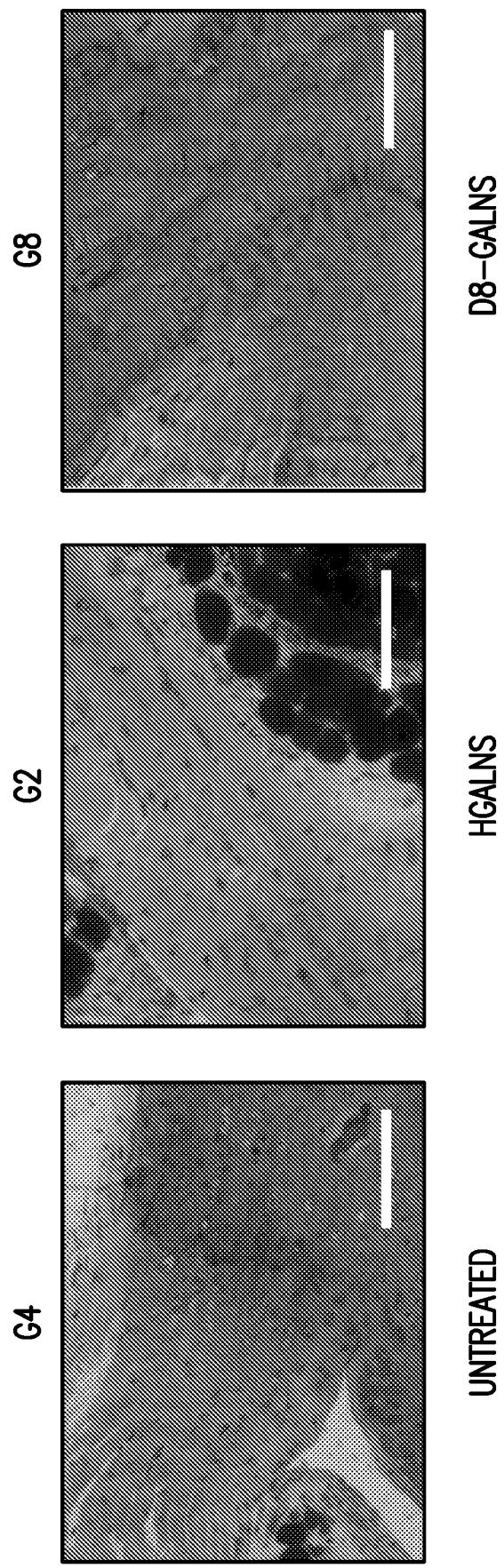
Figure 11N:
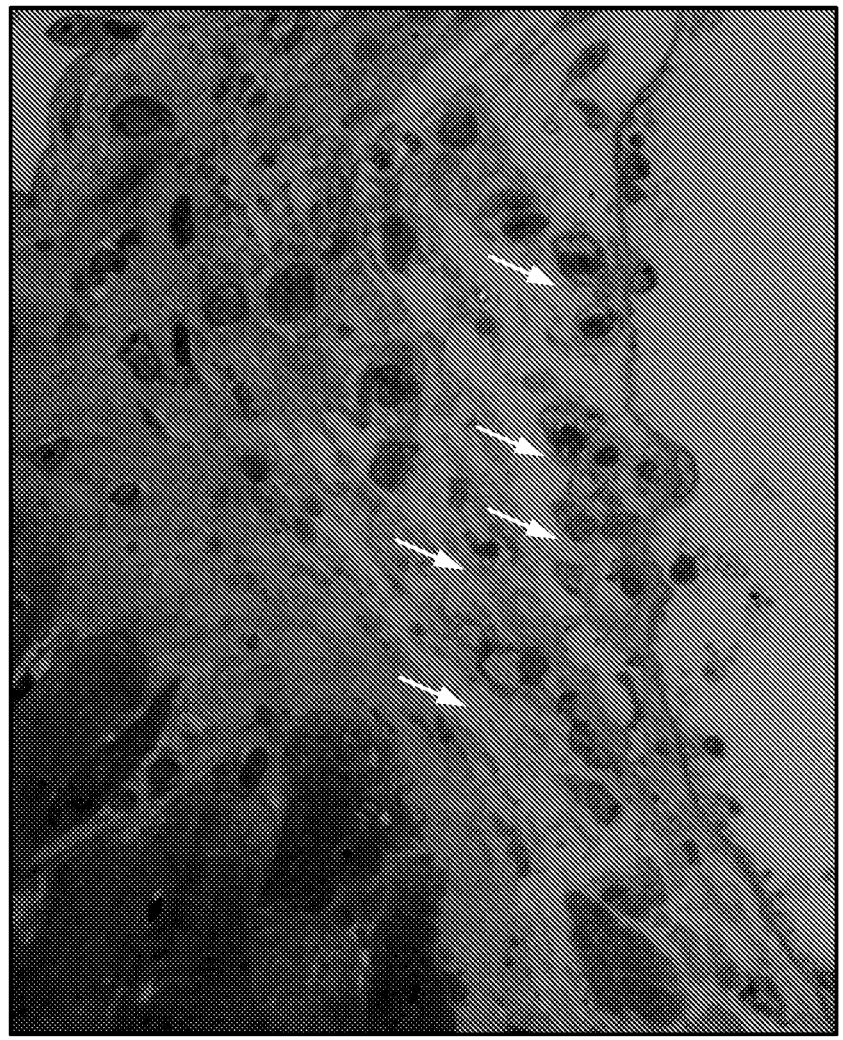
Figure 11P:
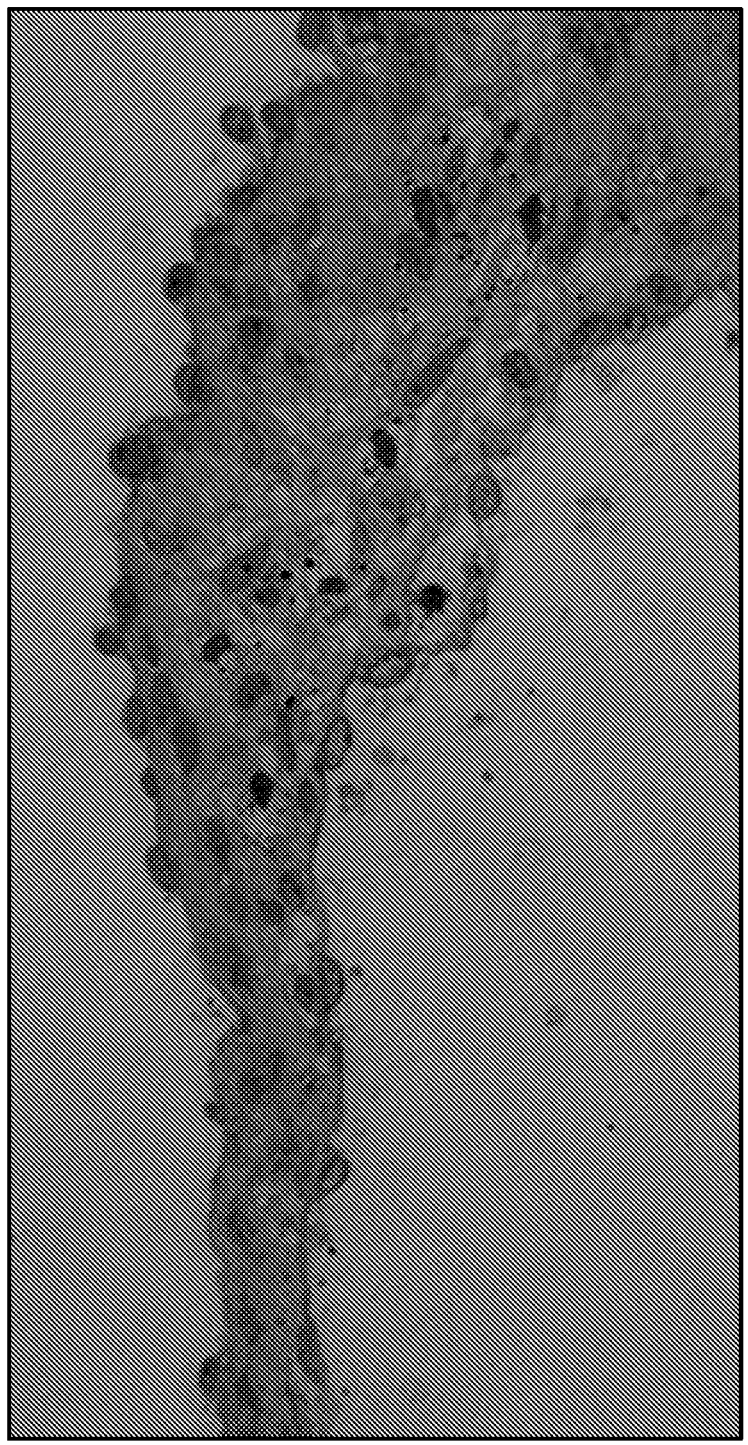

FIGS. 11A-11P. (A) Graphical depiction of bone pathology scores. Bone pathology was evaluated by histopathological analysis 12 weeks after administration of vectors AAV8-hGALNS or AAV8-D8-hGALNS in MPS IVA KO mice (galns −/−). Histopathology of (B) knee joints (Lig-Ligament; M-meniscus; F-Femur; T-Tibia), (C-F) femur articular cartilage (40× magnification), (G-J) femur growth plate (40× magnification), (K) meniscus (40× magnification), (L) ligament (tibia side, 40× magnification), (M, N) base of the heart valve (40× magnification), and (O, P) heart valve (40× magnification).

Figure 12A:
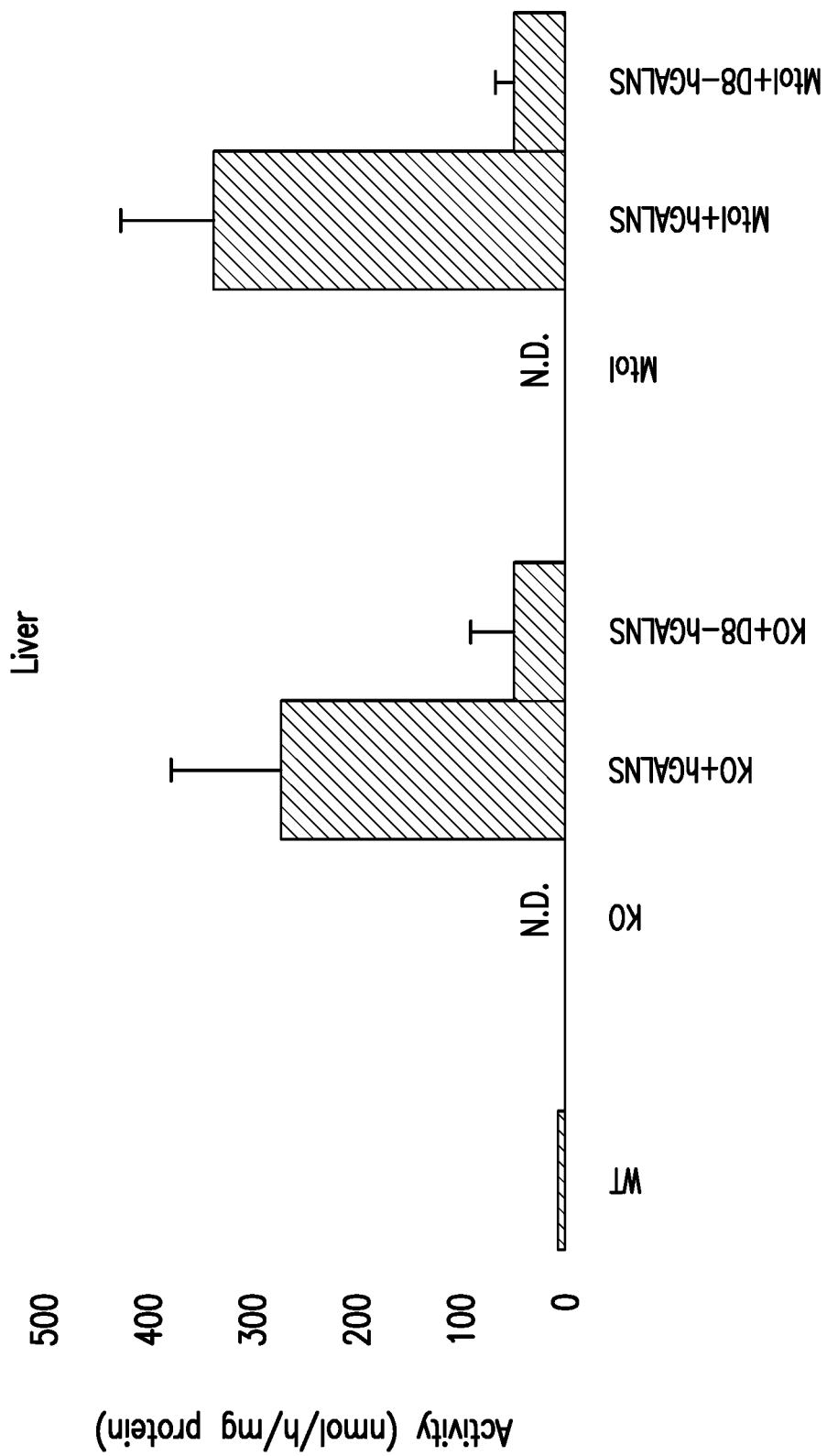
Figure 12B:
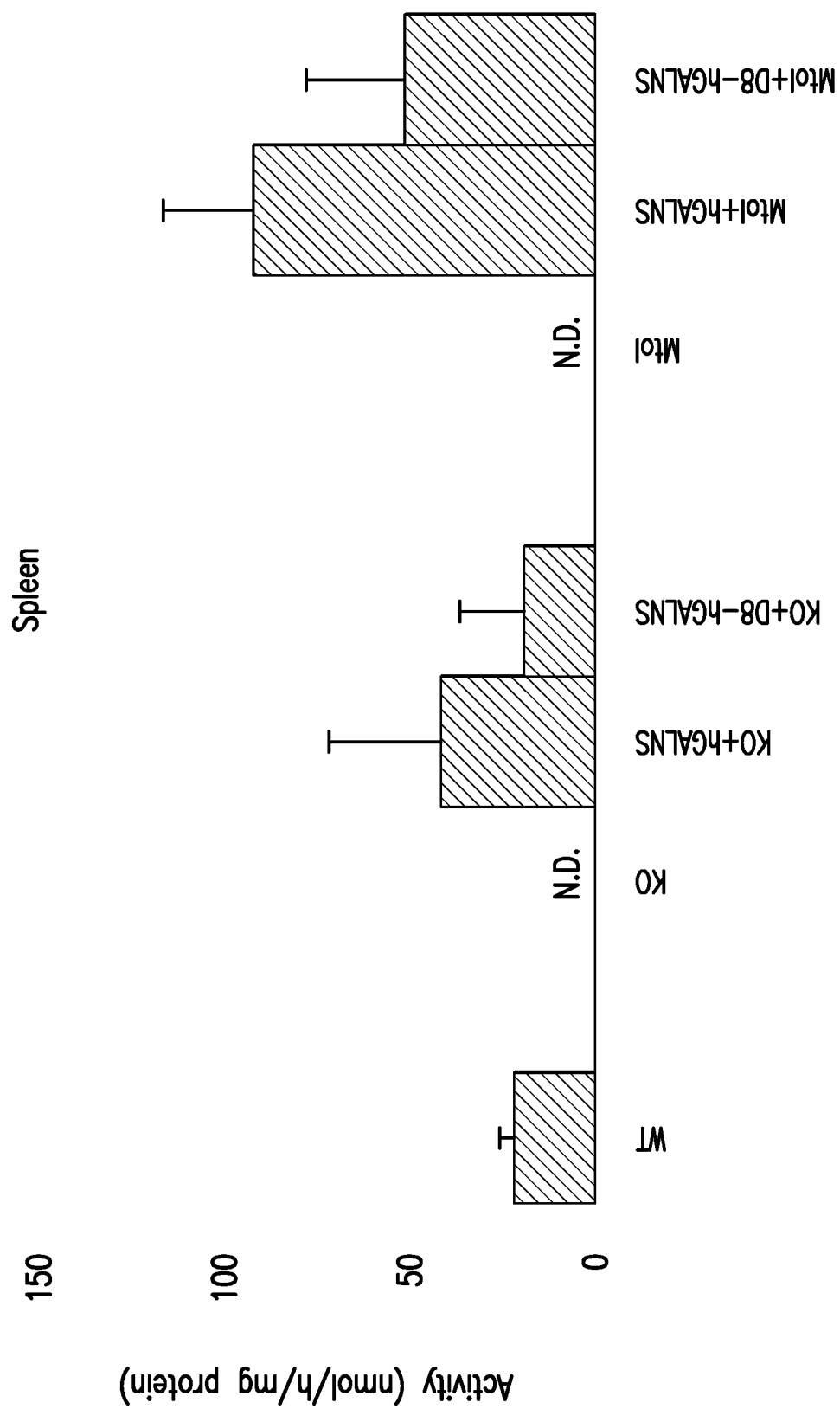
Figure 12C:
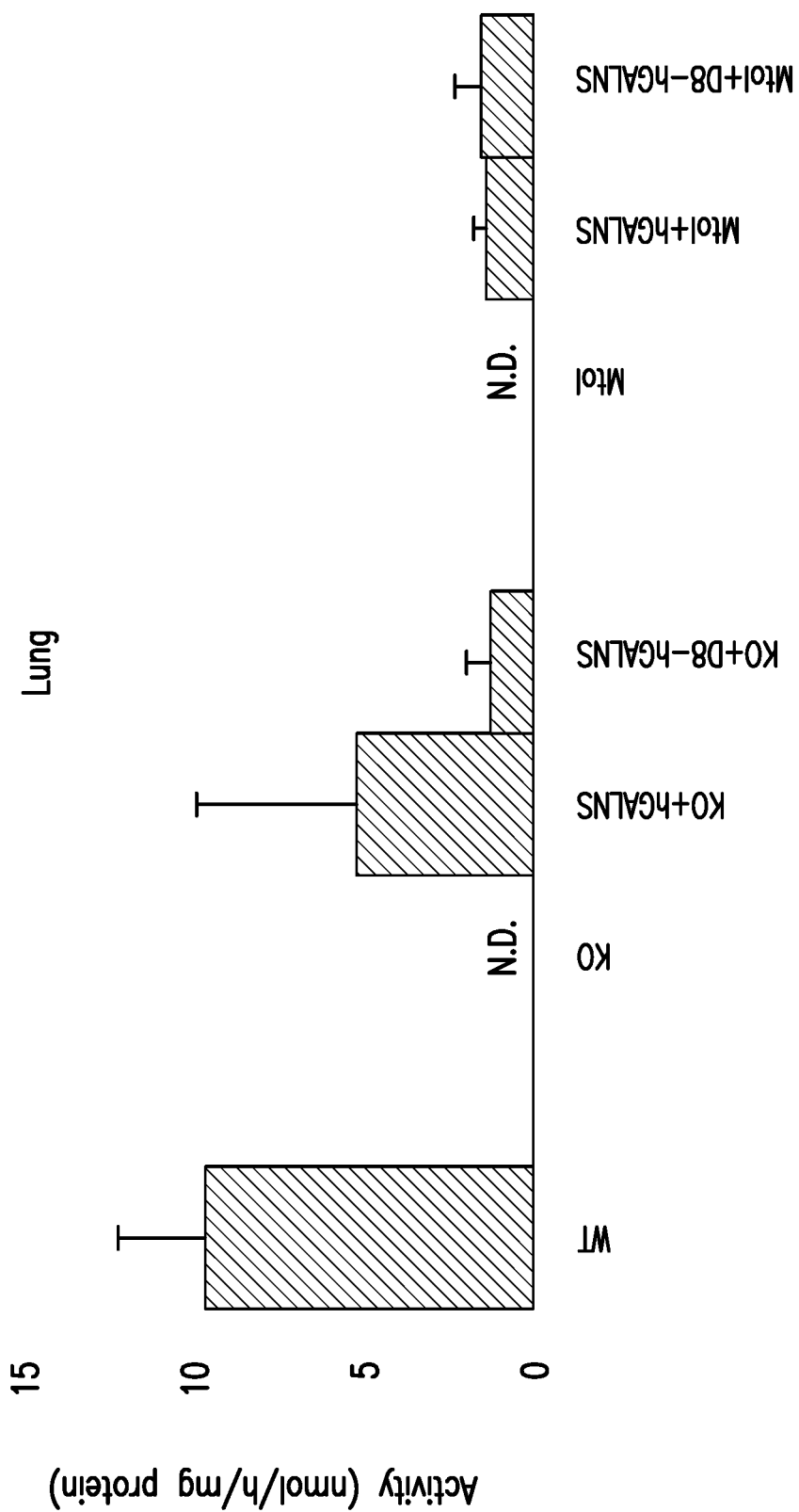

FIGS. 12A-12C. (A) hGALNS enzyme activity levels measured in the liver of MPS IVA KO mice (galns −/−) and Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD). (B) hGALNS enzyme activity levels measured in the spleen of MPS IVA KO mice (galns −/−) and the spleen of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD). (C) hGALNS enzyme activity levels measured in the lung of MPS IVA KO mice (galns −/−) and the lung of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD).

Figure 13A:
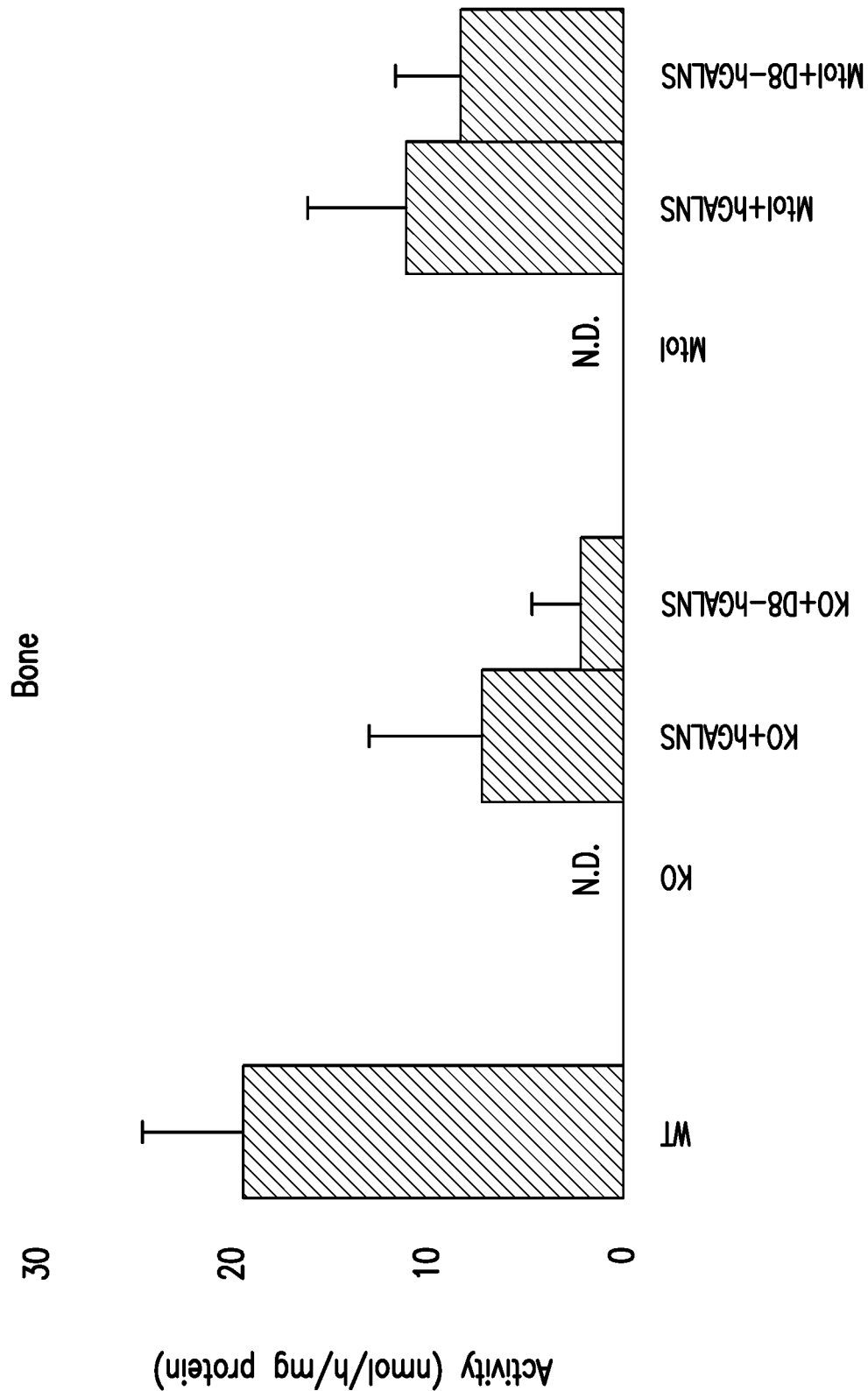
Figure 13B:
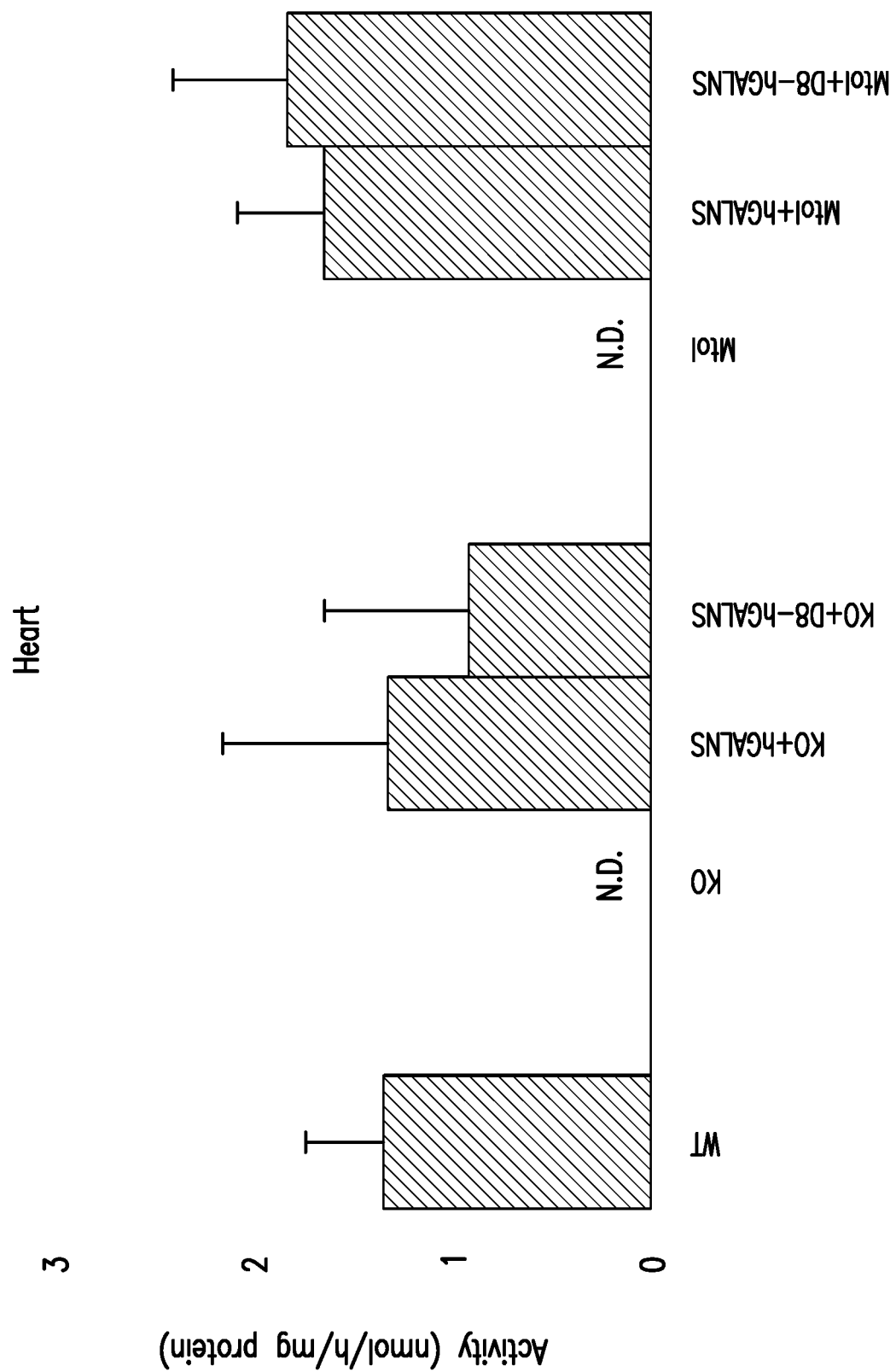

FIGS. 13A-13B. (A) hGALNS enzyme activity levels measured in the bone of MPS IVA KO mice (galns −/−) and the bone of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD). (B) hGALNS enzyme activity levels measured in the heart of MPS IVA KO mice (galns −/−) and the heart of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD).

Figure 14:
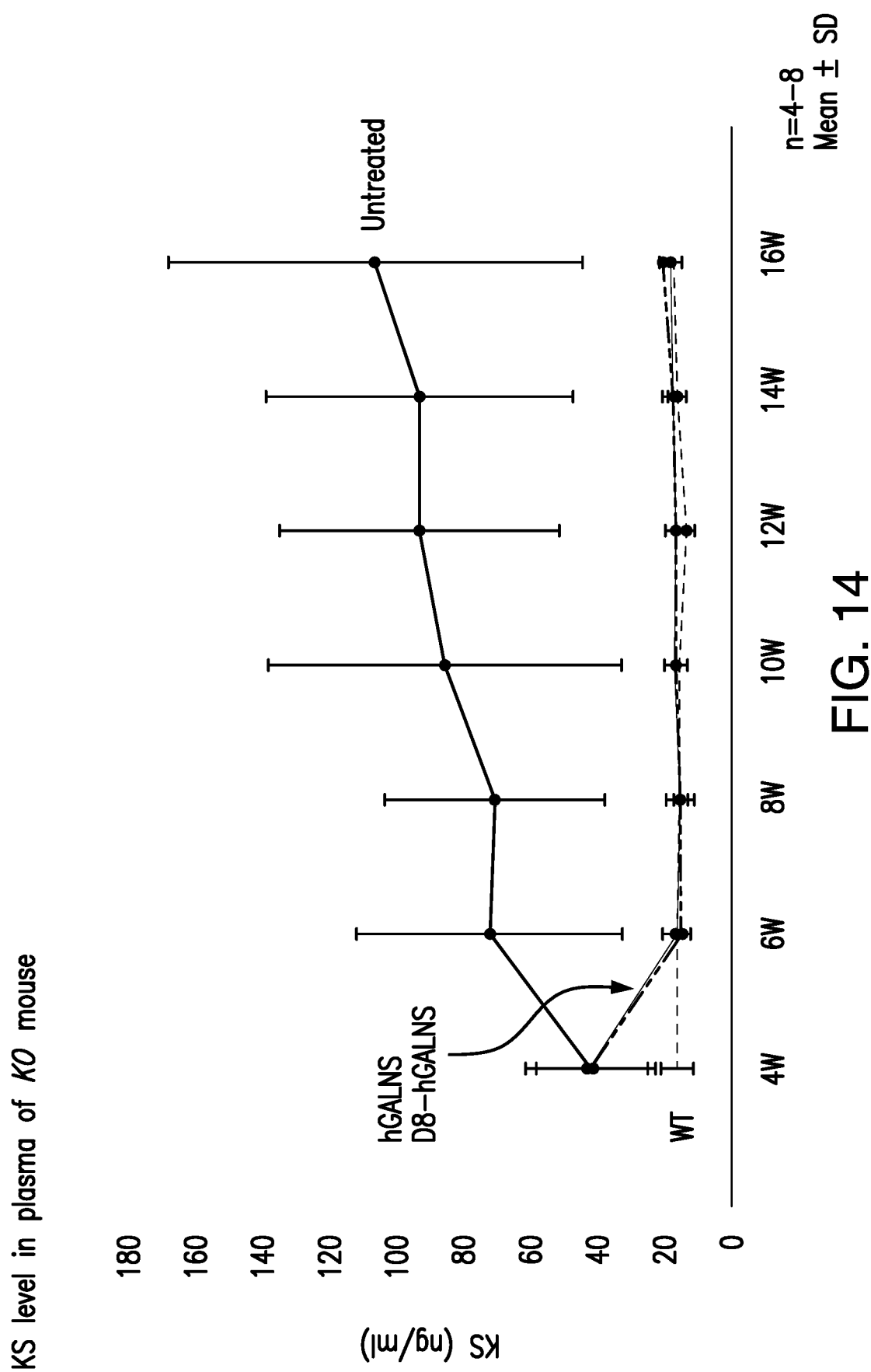

FIG. 14. Mono-sulfated KS levels in the plasma of MPS IVA KO mice (galns −/−) treated with AAV8-TBG-D8-hGALNS as compared to untreated MPS IVA KO mice and untreated wild type mice (n=4-8; mean±SD).

Figure 15A:
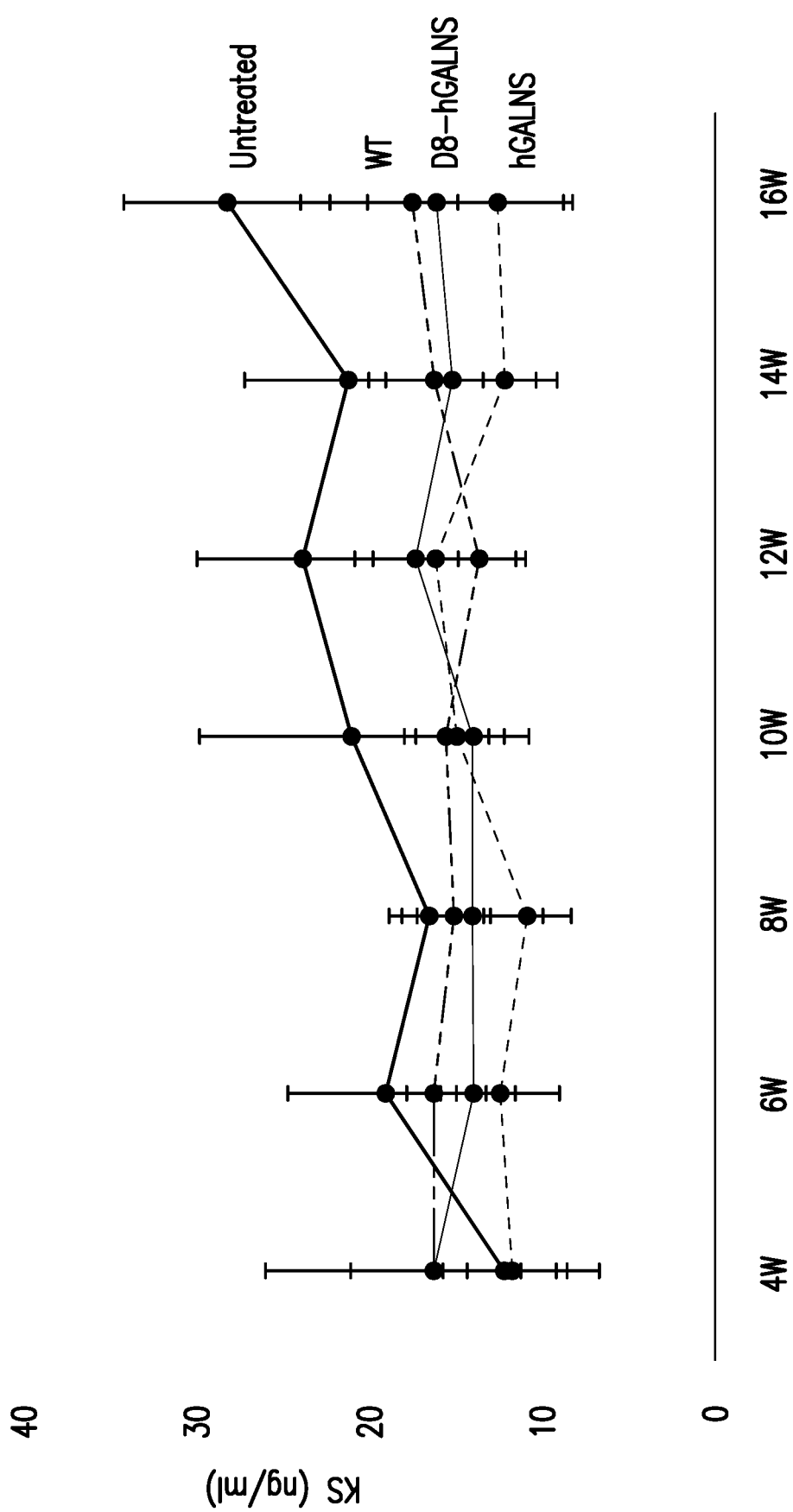
Figure 15B:
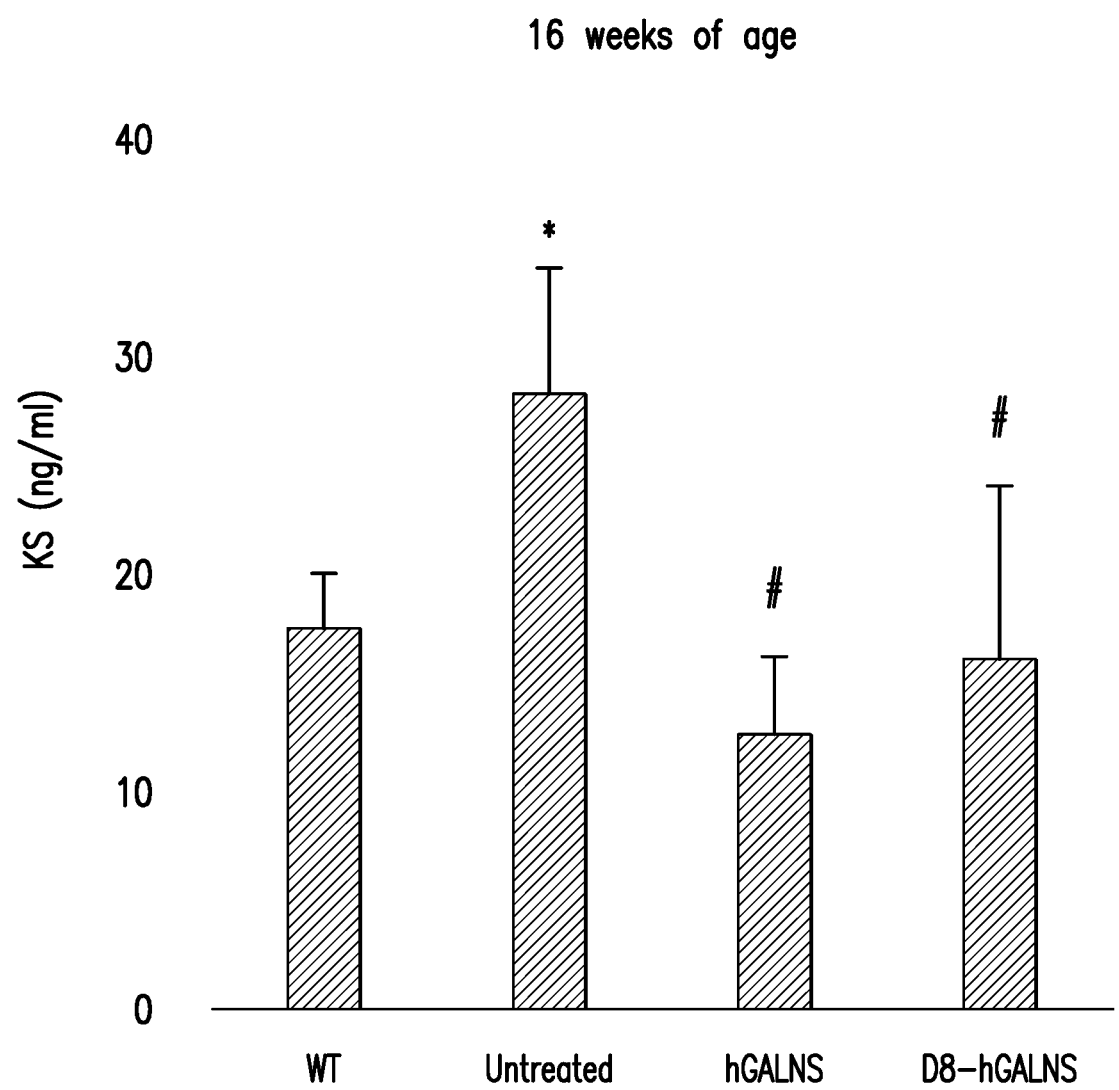

FIGS. 15A-15B. (A) Mono-sulfated KS levels in the plasma of Mtol mice treated with AAV8-TBG-hGALNS or AAV8-TBG-D8-hGALNS over time as compared to untreated Mtol and WT mice. (B) Mono-sulfated KS levels in the plasma of Mtol mice treated with AAV8-TBG-hGALNS or AAV8-TBG-D8-hGALNS were significantly less as compared to untreated Mtol mouse levels at 16 weeks of age (n=4-5; mean±SD; *p<0.05 vs. WT; #p<0.05 vs. Untreated; one-way ANOVA).

Figure 16A:
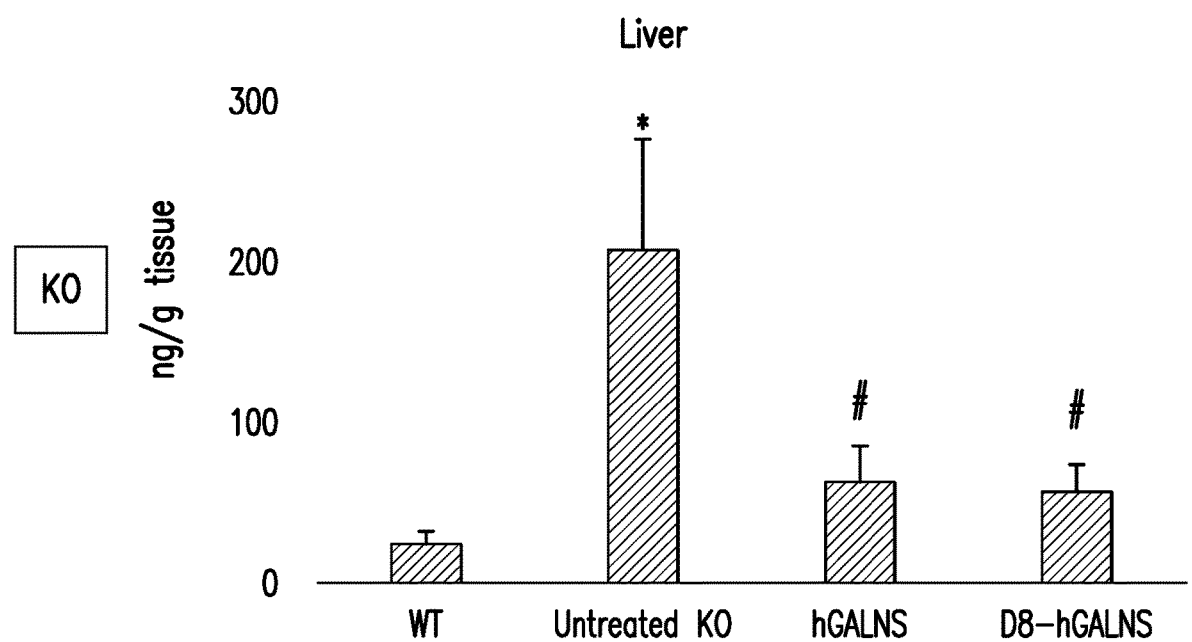
Figure 16B:
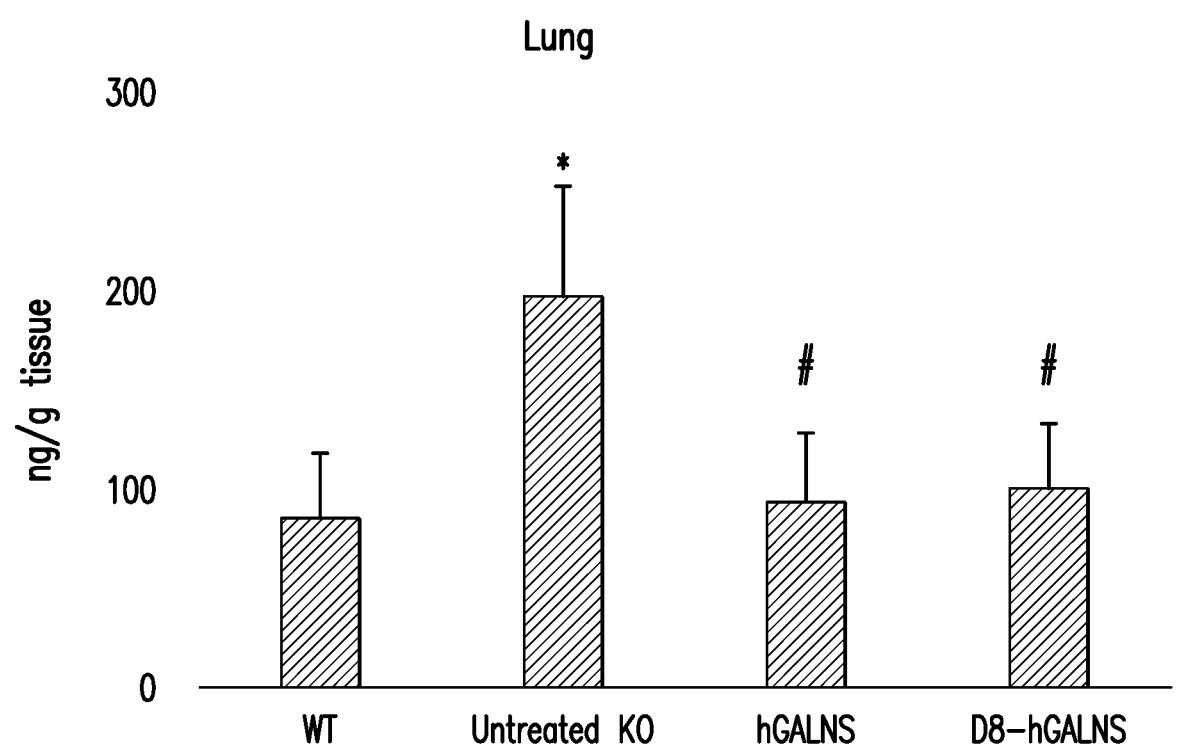
Figure 16C:
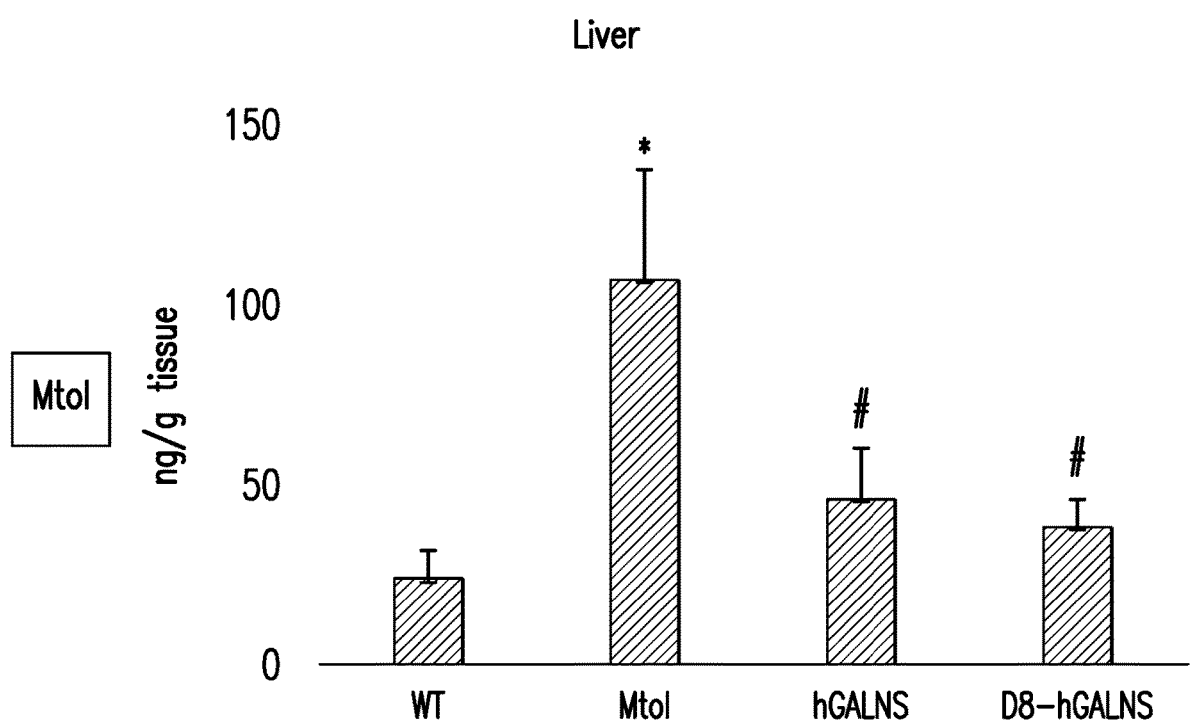

FIGS. 16A-16C. (A) Mono-sulfated KS levels in the liver of MPS IVA KO mice (galns −/−) treated with AAV8-TBG-hGALNS or AAV8-TBG-D8-hGALNS as compared to untreated MPS IVA KO mice and untreated wild type mice. (B) Mono-sulfated KS levels in the lung of MPS IVA KO mice (galns −/−) treated with AAV8-TBG-hGALNS or AAV8-TBG-D8-hGALNS as compared to untreated MPS IVA KO mice and untreated wild type mice. (C) Mono-sulfated KS levels in the liver of Mtol mice treated with AAV8-TBG-hGALNS or AAV8-TBG-D8-hGALNS as compared to untreated Mtol mice and untreated wild type mice. For (A)-(C), n=3-8; mean±SD; *p<0.05 vs. WT; #p<0.05 vs. Untreated; one-way ANOVA.

FIGS. 17A-17E. Histopathology of femur growth plate (40× magnification) in (A) wild type mice (all chondrocytes were non-vacuolated and column structure was well organized), (B) untreated MPS IVA KO mice (galns −/−) (all chondrocytes were vacuolated and column structure was largely disorganized and distorted), (C) untreated Mtol mice (all chondrocytes were vacuolated and column structure was largely disorganized and distorted), (D) AAV8-TBG-hGALNS treated Mtol mice (chondrocytes were moderately vacuolated but column structure was better), and (E) AAV8-TBG-D8-hGALNS treated Mtol mice (chondrocytes were moderately vacuolated but column structure was partially recovered).

FIGS. 18A-18D. (A) Chondrocyte cell size measured in the femur growth plate of untreated wild type mice, untreated MPS IVA KO mice (galns −/−), AAV8-TBG-hGALNS treated MPS IVA KO mice (galns −/−), or AAV8-TBG-D8-hGALNS treated MPS IVA KO mice (galns −/−). (B) Chondrocyte cell size measured in the femur growth plate of untreated wild type mice, untreated Mtol mice, AAV8-TBG-hGALNS treated Mtol mice, or AAV8-TBG-D8-hGALNS treated Mtol mice. (C) Chondrocyte cell size measured in the tibia growth plate of untreated wild type mice, untreated MPS IVA KO mice (galns −/−), AAV8-TBG-hGALNS treated MPS IVA KO mice (galns −/−), or AAV8-TBG-D8-hGALNS treated MPS IVA KO mice (galns −/−). (D) Chondrocyte cell size measured in the tibia growth plate of untreated wild type mice, untreated Mtol mice, AAV8-TBG-hGALNS treated Mtol mice, or AAV8-TBG-D8-hGALNS treated Mtol mice. For (A)-(D), n=4-6; mean±SD; *p<0.05 vs. WT; #p<0.05 vs. untreated; one-way ANOVA.

FIG. 19. Histopathology of heart valve (40× magnification) in MPS IVA KO mice (galns −/−) and Mtol mice treated with AAV8-TBG-hGALNS or AAV8-TBG-D8-hGALNS, as compared to untreated mice.

FIG. 20. Histopathology of heart muscle (40× magnification) in Mtol mice treated with AAV8-TBG-hGALNS or AAV8-TBG-D8-hGALNS, as compared to untreated Mtol mice.

FIGS. 21A-21D. (A) Pathology score of the heart valve tissue of untreated wild type mice, untreated MPS IVA KO(galns −/−) mice, MPS IVA KO(galns −/−) mice treated with AAV8-TBG-hGALNS, or MPS IVA KO(galns −/−) mice treated with AAV8-TBG-D8-hGALNS. (B) Pathology score of the heart valve tissue of untreated wild type mice, untreated Mtol mice, Mtol mice treated with AAV8-TBG-hGALNS, or Mtol mice treated with AAV8-TBG-D8-hGALNS. (C) Pathology score of the heart muscle tissue of untreated wild type mice, untreated MPS IVA KO(galns −/−) mice, MPS IVA KO(galns −/−) mice treated with AAV8-TBG-hGALNS, or MPS IVA KO(galns −/−) mice treated with AAV8-TBG-D8-hGALNS. (D) Pathology score of the heart muscle tissue for untreated wild type mice, untreated Mtol mice, Mtol mice treated with AAV8-TBG-hGALNS, or Mtol mice treated with AAV8-TBG-D8-hGALNS. (For FIGS. 21A-21D, n=4-6; mean±SD; *p<0.05 vs. WT; #p<0.05 vs. Untreated; one-way ANOVA).

Figure 22:
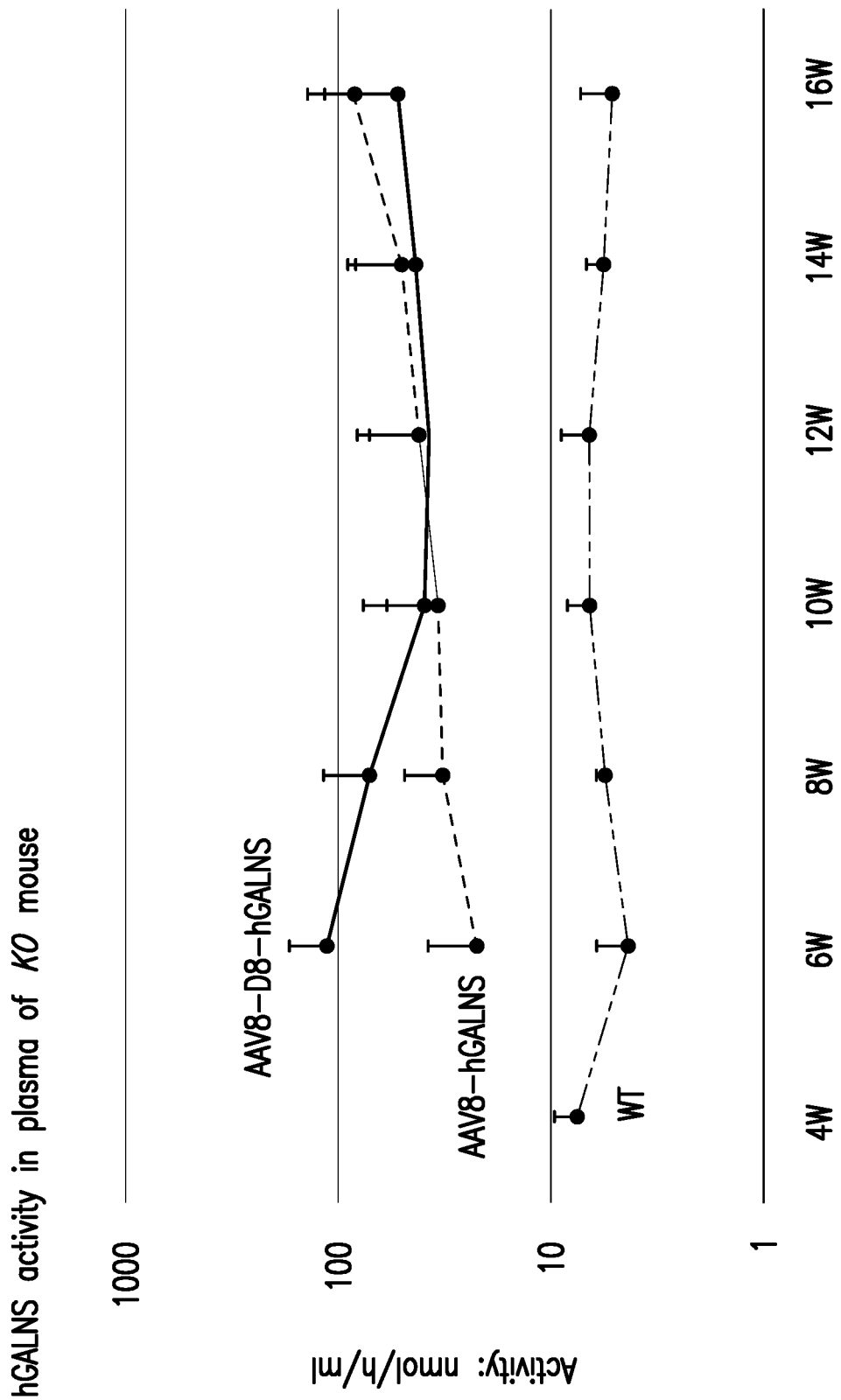

FIG. 22. hGALNS enzyme activity over time measured in plasma of MPS IVA KO mice (galns −/−) after administration with AAV8-TBG-hGALNS or AAV-TBG-D8-hGALNS (n=4-7; mean+SD).

Figure 23:
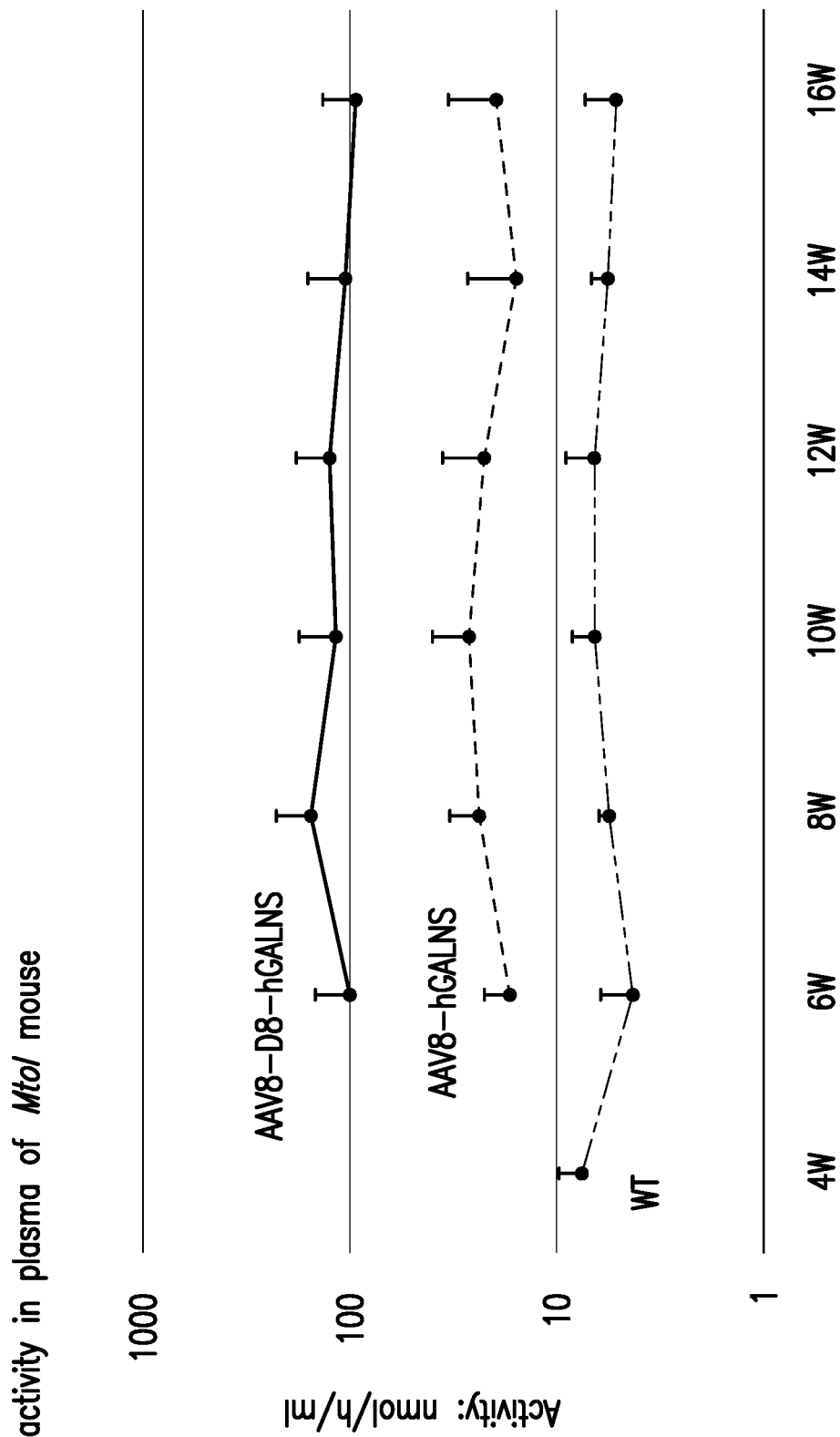

FIG. 23. hGALNS enzyme activity over time measured in plasma of Mtol mice after administration with AAV8-TBG-hGALNS or AAV8-TBG-D8-hGALNS (n=4-5; mean+SD).

FIGS. 24A-24K. Blood and tissue human N-acetylgalactosamine-6-sulfate sulfatase (hGALNS) enzyme activity in MPS IVA mice treated with AAV8 vectors. (A) Schematic structure of AAV8-TBG-hGALNS and AAV8-TBG-D8-hGALNS viral vector genome. A blood sample was collected from MPS IVA mice every other week until 16 weeks of age, and plasma hGALNS enzyme activity was measured in (B) knock-out (KO), and (C) tolerant (MTOL) mice. n=4-7. The tissue sample was collected from MPS IVA mice 12 weeks post-injection of AAV vectors with or without bone-targeting signal. hGALNS enzyme activity in tissues including (D) liver, (E) spleen, (F) lung, (G) kidney, (H) heart and (I) bone (leg) was measured in KO and MTOL mice (n=3-8; statistics were analyzed by one-way ANOVA with the Bonferroni's post-hoc test and data are presented as mean±SD. *p<0.05). The levels of hGALNS activity in the liver, spleen, lung, kidney, heart, and bond in MPS IVA KO mice 12 weeks after IV delivery of AAV vectors are shown in (J). The levels of hGALNS activity in the liver, spleen, lung, kidney, heart, and bond in MTOL mice 12 weeks after IV delivery of AAV vectors are shown in (K).

FIGS. 25A-25D. Blood and tissue glycosaminoglycan (GAG) level in MPS IVA mice treated with AAV8 vectors. A blood sample was collected from MPS IVA mice every other week until 16 weeks of age, and plasma mono-sulfated KS level was measured in (A) knock-out (KO), and (B) tolerant (MTOL) mice. n=4-8. The tissue sample was collected from MPS IVA mice 12 weeks post-injection of AAV vectors with or without bone-targeting signal. The amount of KS in tissues including (C) liver and (D) lung was measured in KO and MTOL mice. n=4-8. Statistics were analyzed by one-way ANOVA with the Bonferroni's post-hoc test. Data are presented as mean±SD. *p<0.05.

Figure 26A:
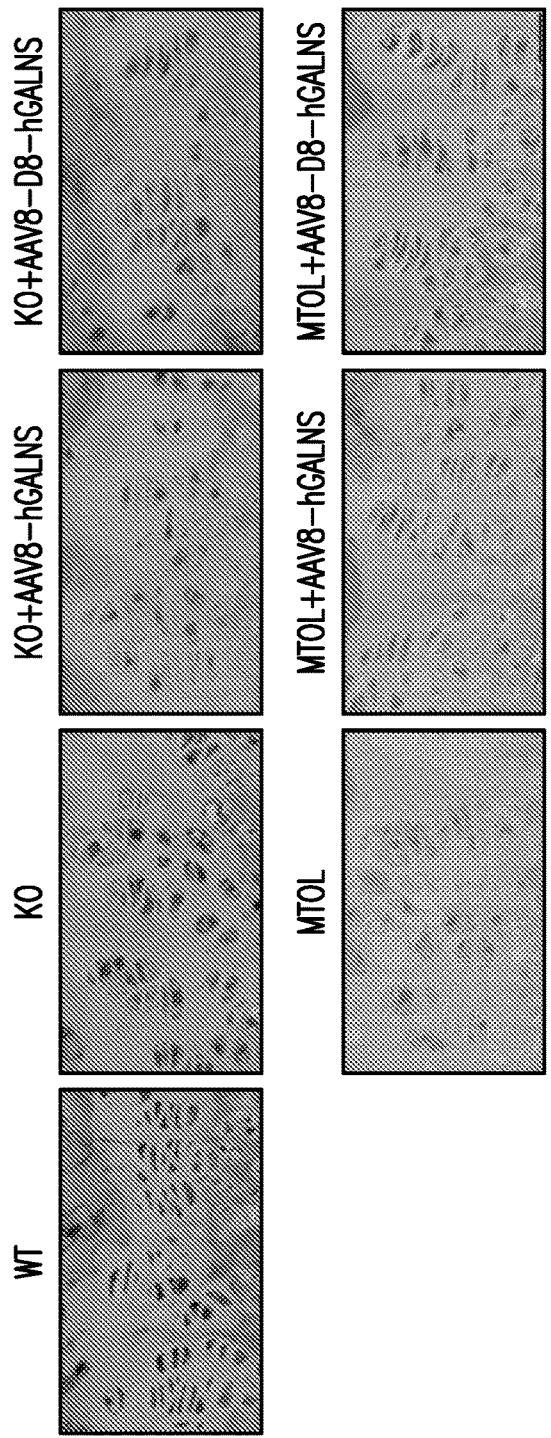
Figure 26B:
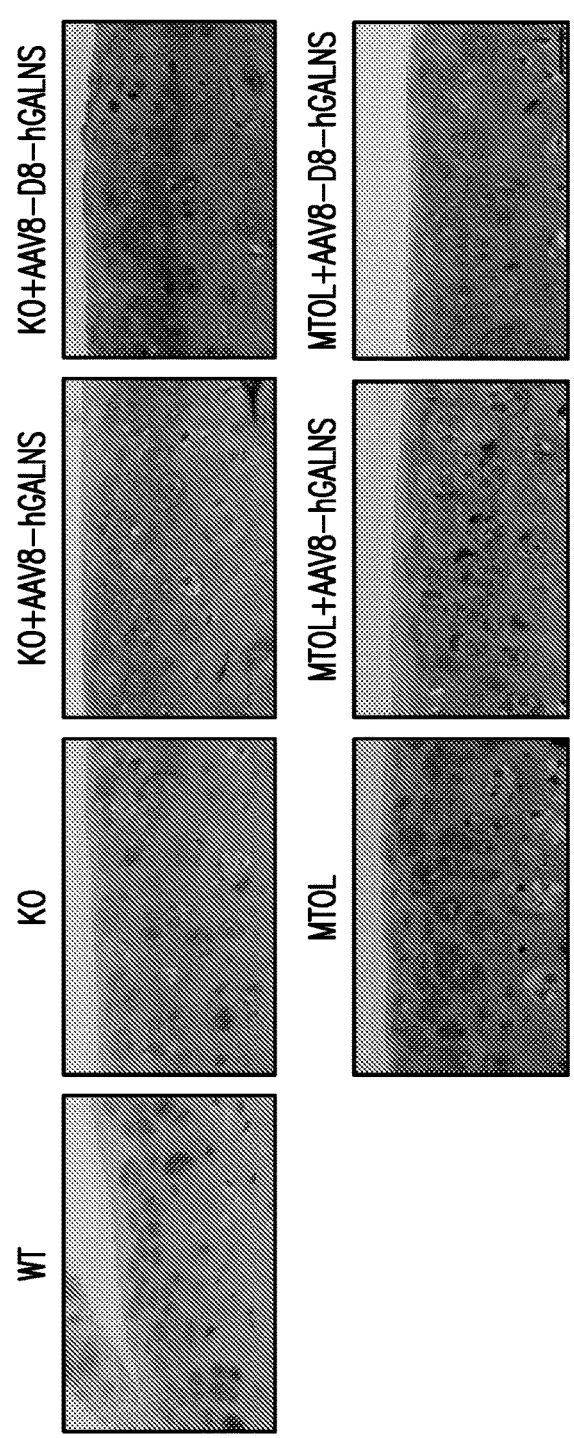
Figure 26C:
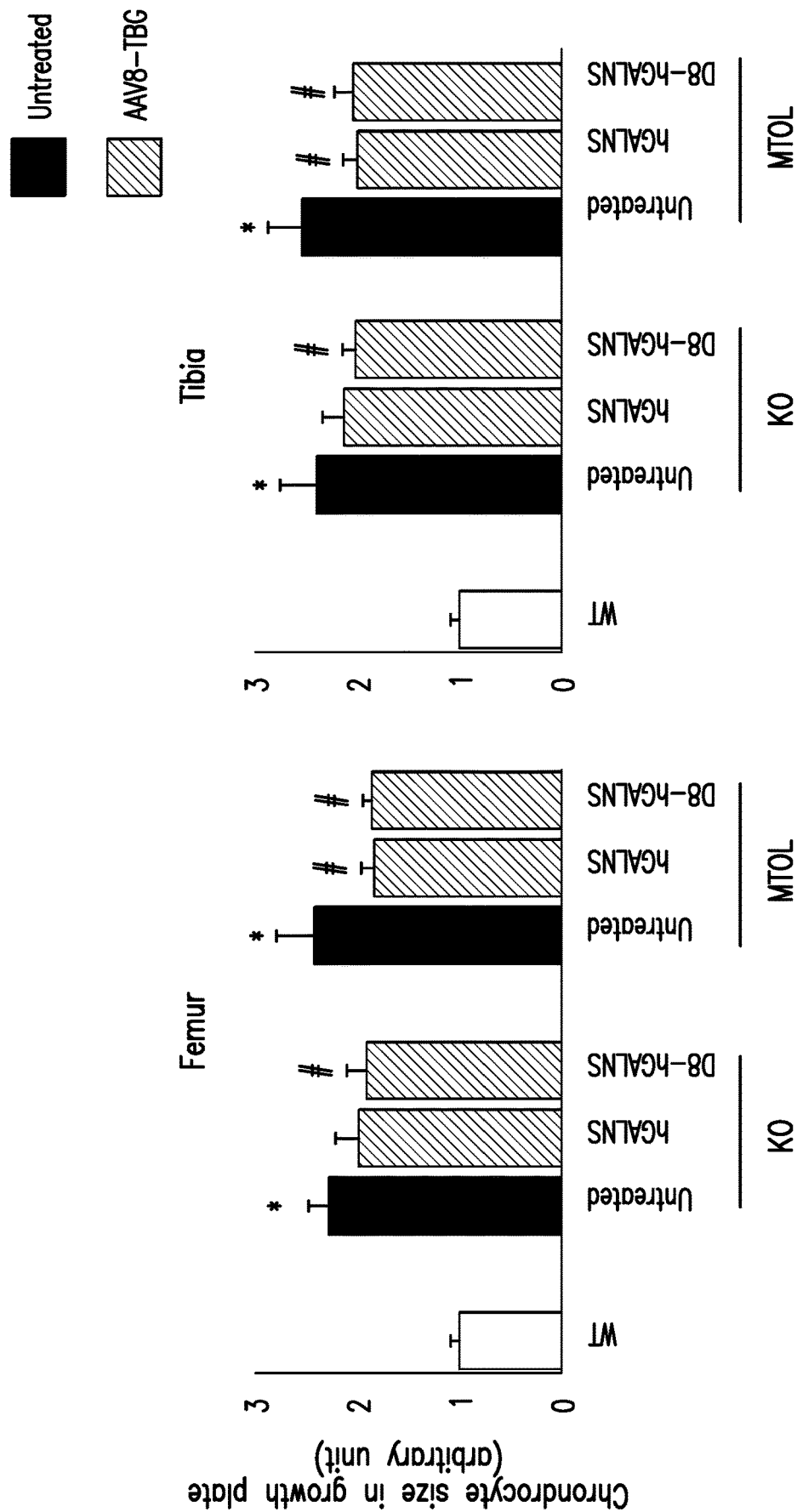

FIGS. 26A-26C. Correction of bone pathology in MPS IVA mice treated with AAV8 vectors. Correction of chondrocytes vacuolization was assessed by toluidine blue staining analysis using light microscopy of (A) growth plate and (B) articular disc in the knee joint of MPS IVA mice treated with AAV8 vectors. Bone pathology in knock-out (KO), and tolerant (MTOL) mice were compared with wild-type, untreated MPS IVA and treated MPS IVA with AAV8 vectors with or without bone-targeting signal. Scale bars=25 μm. (C) Chondrocyte cell size in growth plate lesions of femur or tibia was quantified by Image J software. Data expressed fold-change from wild-type group. n=4-7. Statistics were analyzed by one-way ANOVA with the Bonferroni's post-hoc test. Data are presented as mean±SD. *p<0.05.

Figure 27A:
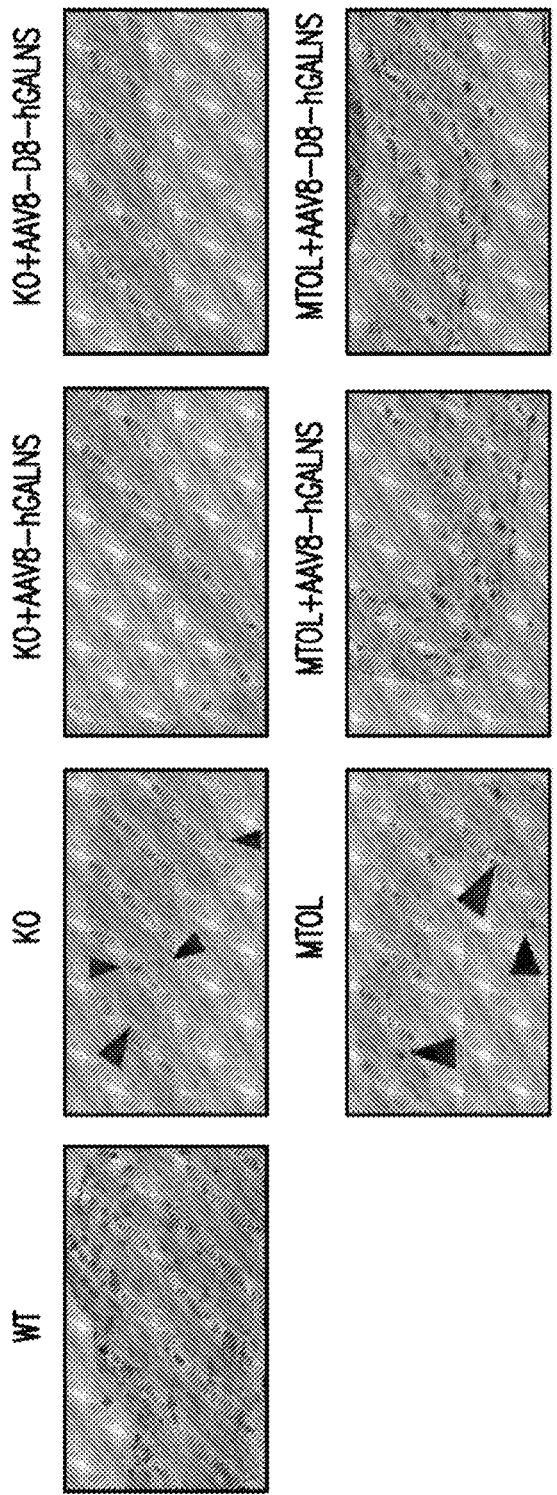
Figure 27B:
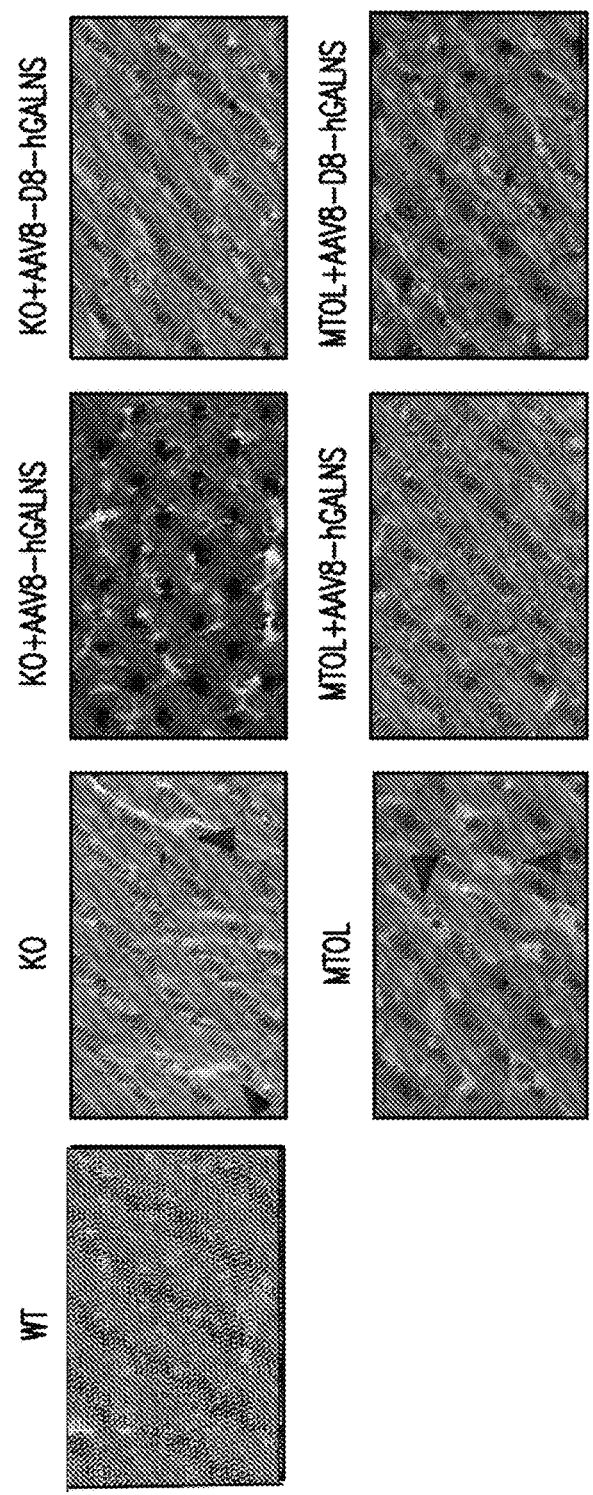

FIGS. 27A-27C. Correction of heart pathology in MPS IVA mice treated with AAV8 vectors. Correction of vacuolization was assessed by toluidine blue staining analysis using light microscopy of (A) heart valve and (B) heart muscle of MPS IVA mice treated with AAV8 vectors. Heart pathology in knock-out (KO) and tolerant (MTOL) mice were compared with wild-type, untreated MPS IVA, and treated MPS IVA with AAV8 vectors with or without bone-targeting signal. The arrows indicate the location of disease-related vacuoles. Scale bars=25 μm.

Figure 28:
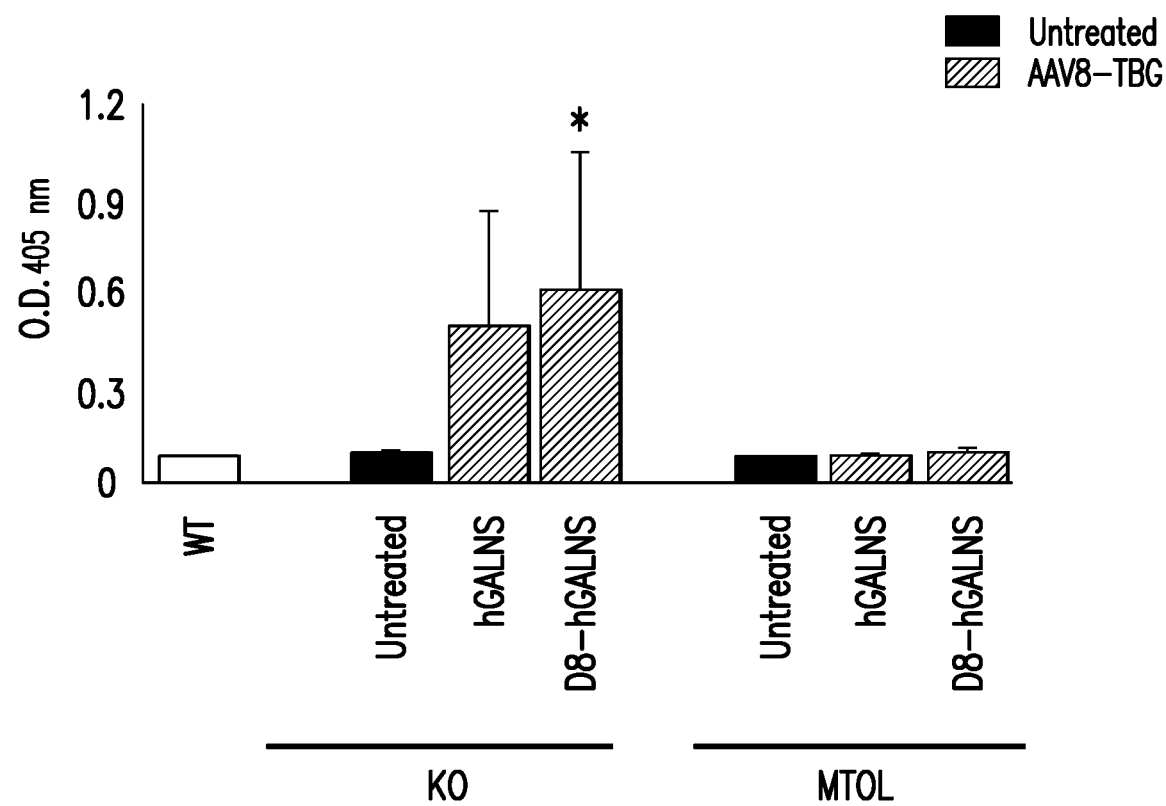

FIG. 28. Circulating of anti-hGALNS antibody titers in MPS IVA mice treated with AAV8 vectors. Plasma was collected from MPS IVA mice 12 weeks post-injection of AAV8 vectors with or without bone targeting signal. Circulating snit-hGALNS antibody titers were detected by indirect ELISA assay. OD 405 values were measured in a microplate spectrophotometer. n=4-8. Statistics were analyzed by one-way ANOVA with the Bonferroni's post-hoc test. Data are presented as mean±SD. *p<0.05.

Figure 29A:
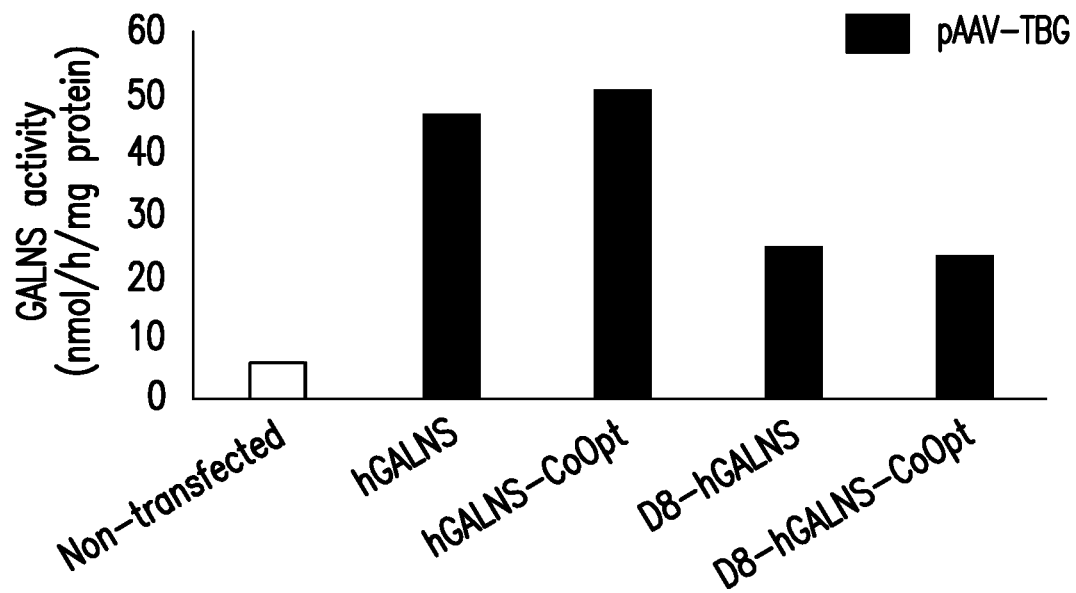
Figure 29B:
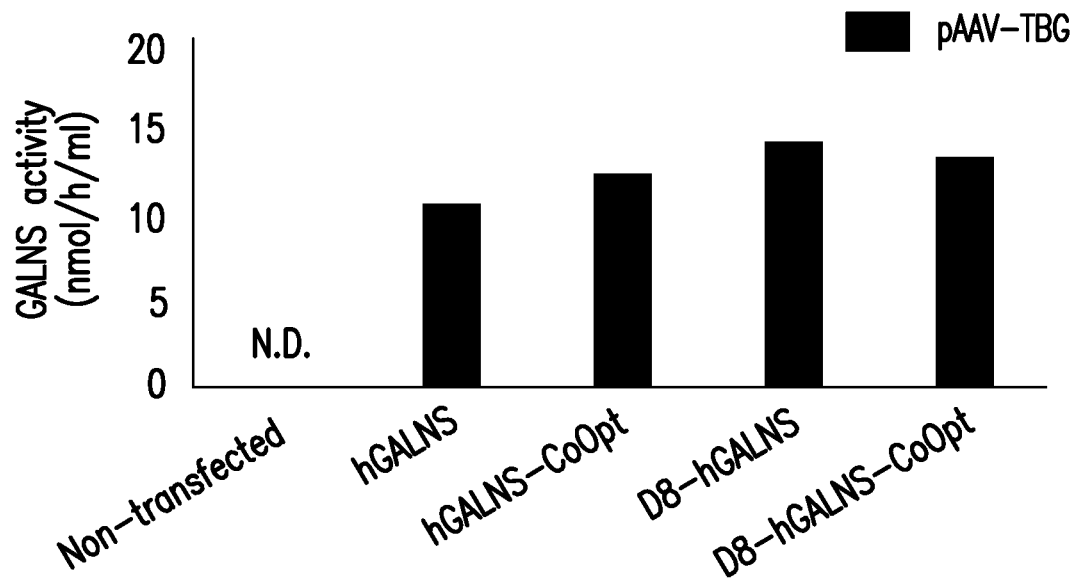

FIGS. 29A-29B. Evaluation of optimized hGALNS with or without bone targeting signal. Huh-7 cells were transfected with AAV8 vector plasmid expressing hGALNS or codon-optimized hGALNS with or without bone targeting signal, respectively. After 48 hr transfection, cell pellet and medium were collected, and hGALNS activity was measured. (A) Intracellular enzyme activity was determined in HuH-7 cells after transfection with either the TBG-hGALNS plasmid, TBG-hGALNS-CoOpt plasmid, TBG-D8-hGALNS plasmid, or TBG-D8-hGALNS-CoOpt plasmid. (B) Enzyme activity in the media was determined after HuH-7 cells were transfected with the TBG-hGALNS plasmid, TBG-hGALNS-CoOpt plasmid, TBG-D8-hGALNS plasmid, or TBG-D8-hGALNS-CoOpt plasmid. Data are presented as mean. n=2.

Figure 30:
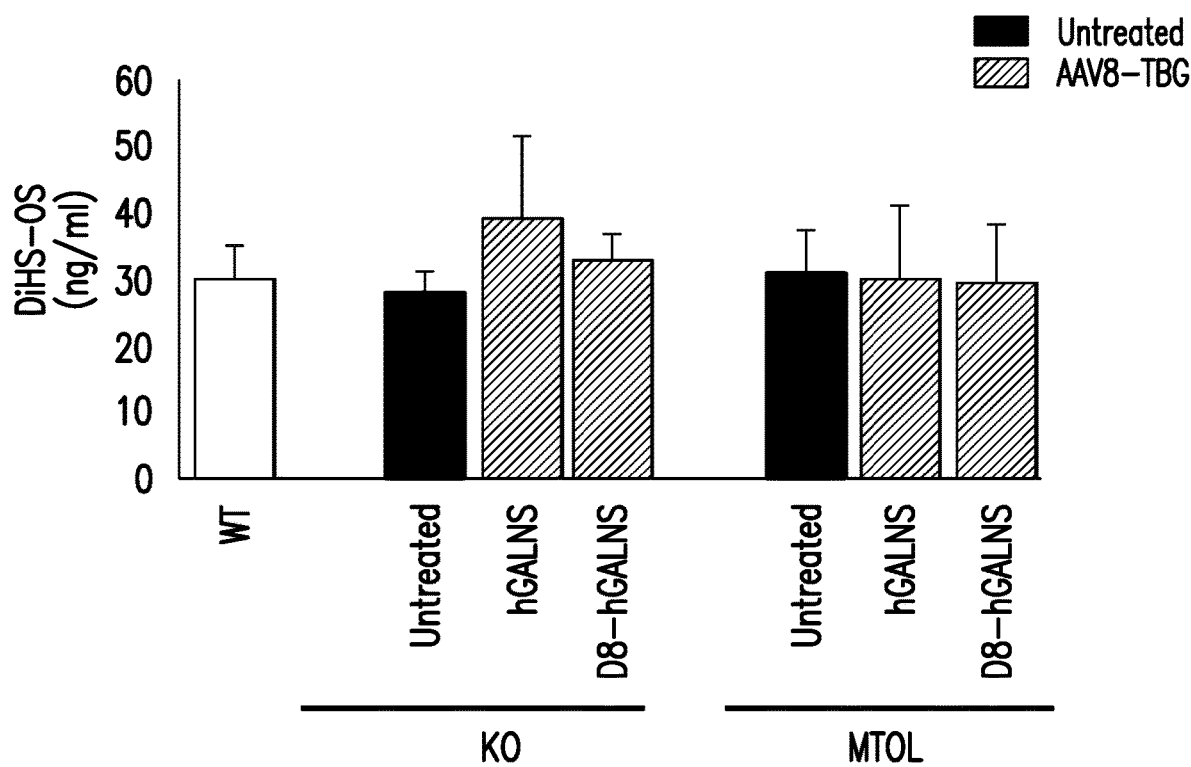

FIG. 30. Blood heparan sulfate (HS) level in MPS IVA mice treated with AAV8 vectors. A blood sample was collected from MPS IVA mice and plasma diHS-0S level was measured in knock-out (KO), and tolerant (MTOL) mice at 16 weeks of age. Data are presented as mean±SD. AAV: adeno-associated virus, TBG: thyroxin-binding globulin, hGALNS: N-acetylgalactosamine-6-sulfate sulfatase.

Figure 31:
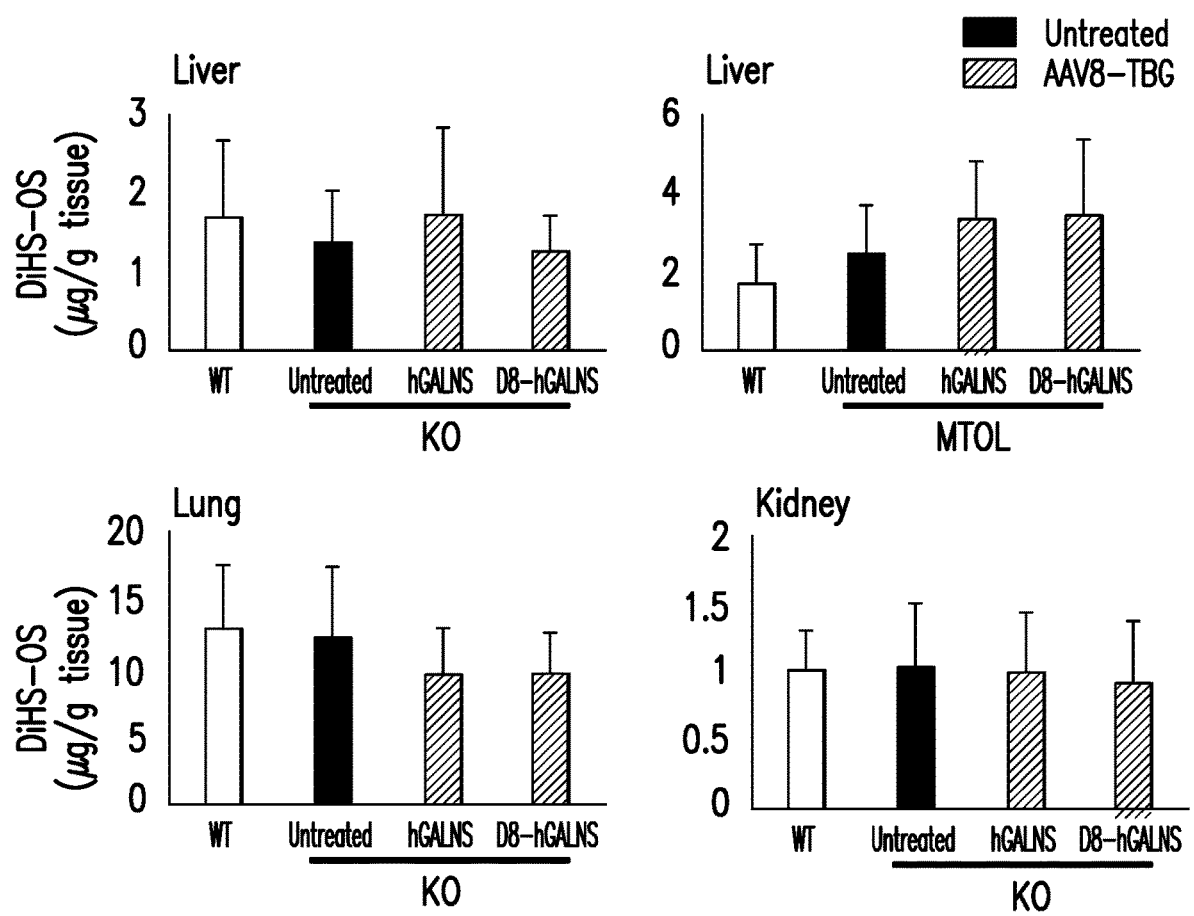

FIG. 31. Tissue heparin sulfate (HS) level in MPS IVA mice treated with AAV8 vectors. The tissue sample was collected from MPS IVA mice 12 weeks post-injection of AAV vectors with or without bone-targeting signal. The amount of diHS-0S in tissues including liver, spleen, lung and kidney was measured in KO and MTOL mice. Data are presented as mean±SD.

FIGS. 32A-32B. Correction of bone pathology in MPS IVA mice treated with AAV8 vectors. Correction of chondrocytes vacuolization was assessed by toluidine blue staining analysis using light microscopy of (A) ligament and (B) meniscus in the knee joint of MPS IVA mice treated with AAV8 vectors. Bone pathology in knock-out (KO), and tolerant mice (MTOL) were compared with wild-type, untreated MPS IVA and treated MPS IVA with AAV8 vectors with or without bone-targeting signal. The arrows indicate the location of disease-related vacuoles (scale bars=25 μm).

Figure 33:
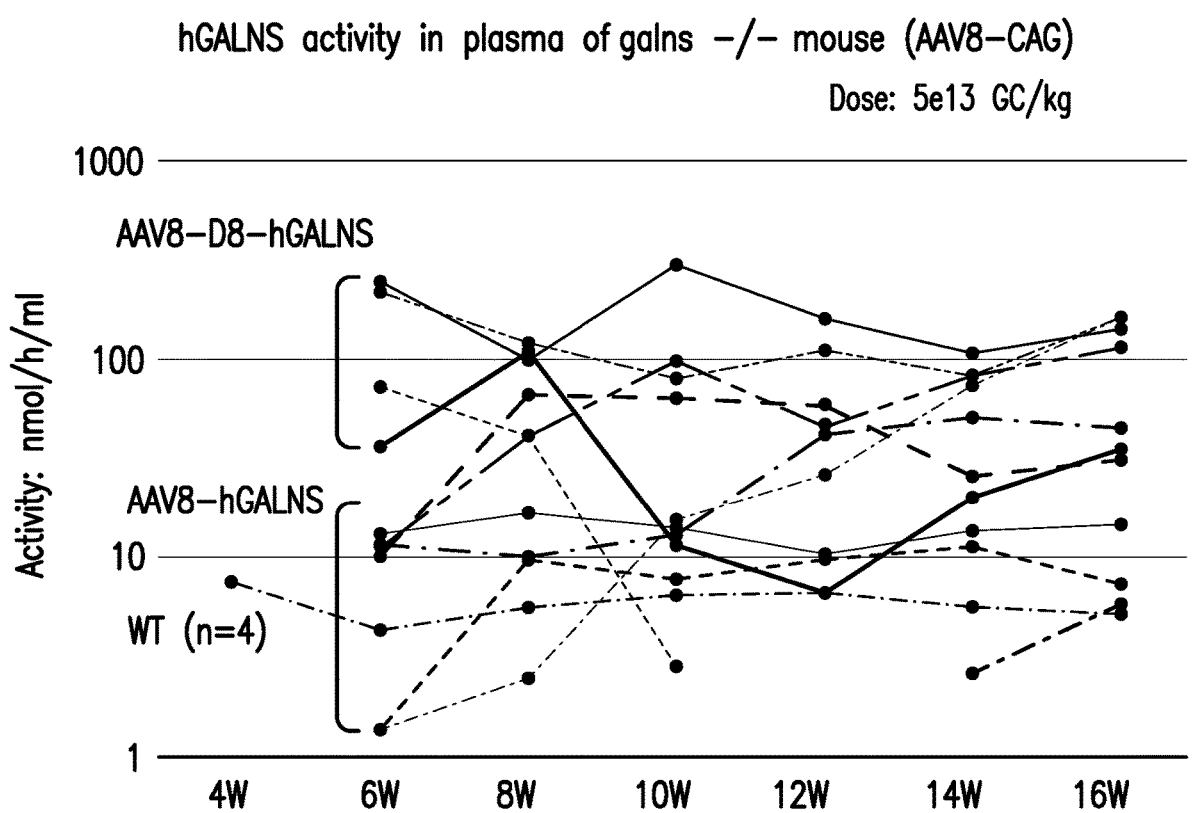

FIG. 33. hGALNS enzyme activities in the plasma of MPSIVA KO mice administered with $5 \times 10^{13}$ GC/kg body weight of AAV8-CAG-hGALNS, or AAV8-CAG-D8-hGALNS, as compared with untreated wild type mice.

Figure 34:
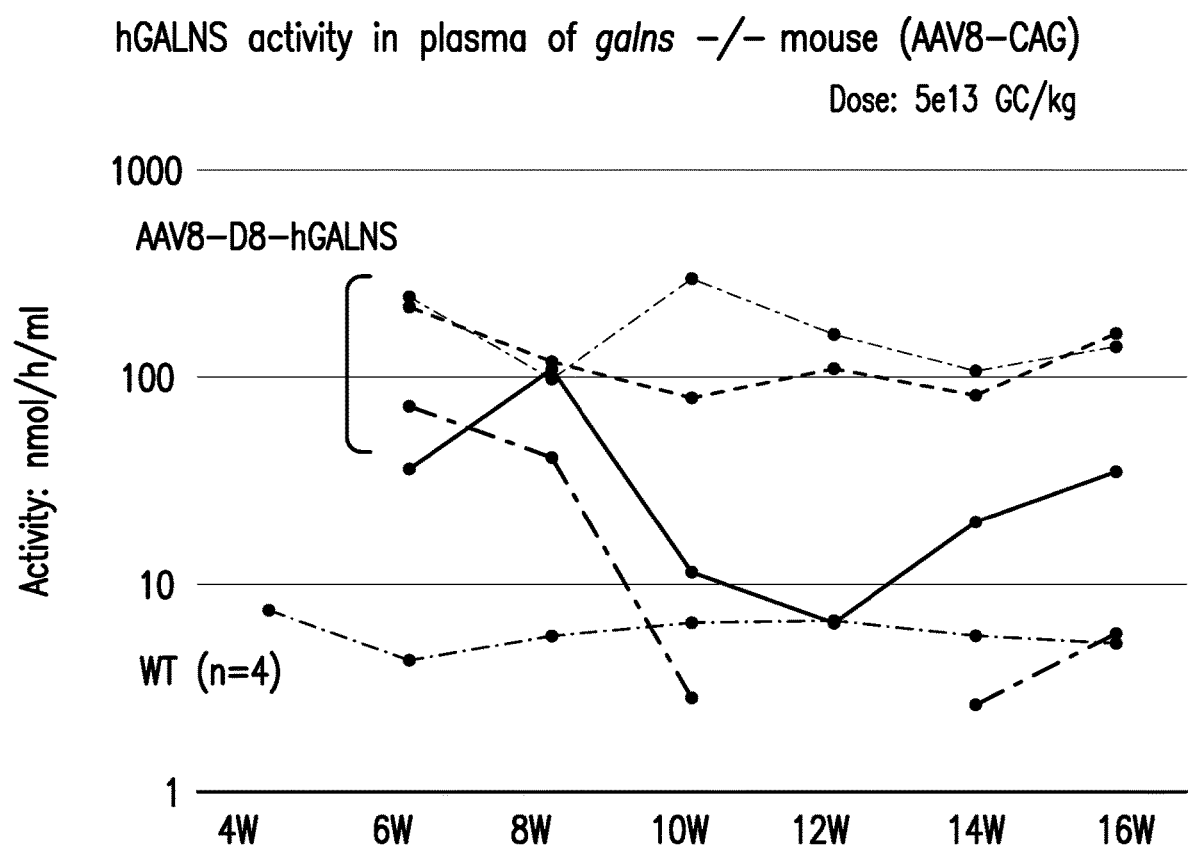

FIG. 34. hGALNS enzyme activities in the plasma of MPSIVA KO mice administered with $5 \times 10^{13}$ GC/kg body weight of AAV8-CAG-D8-hGALNS, as compared with untreated wild type mice.

Figure 35:
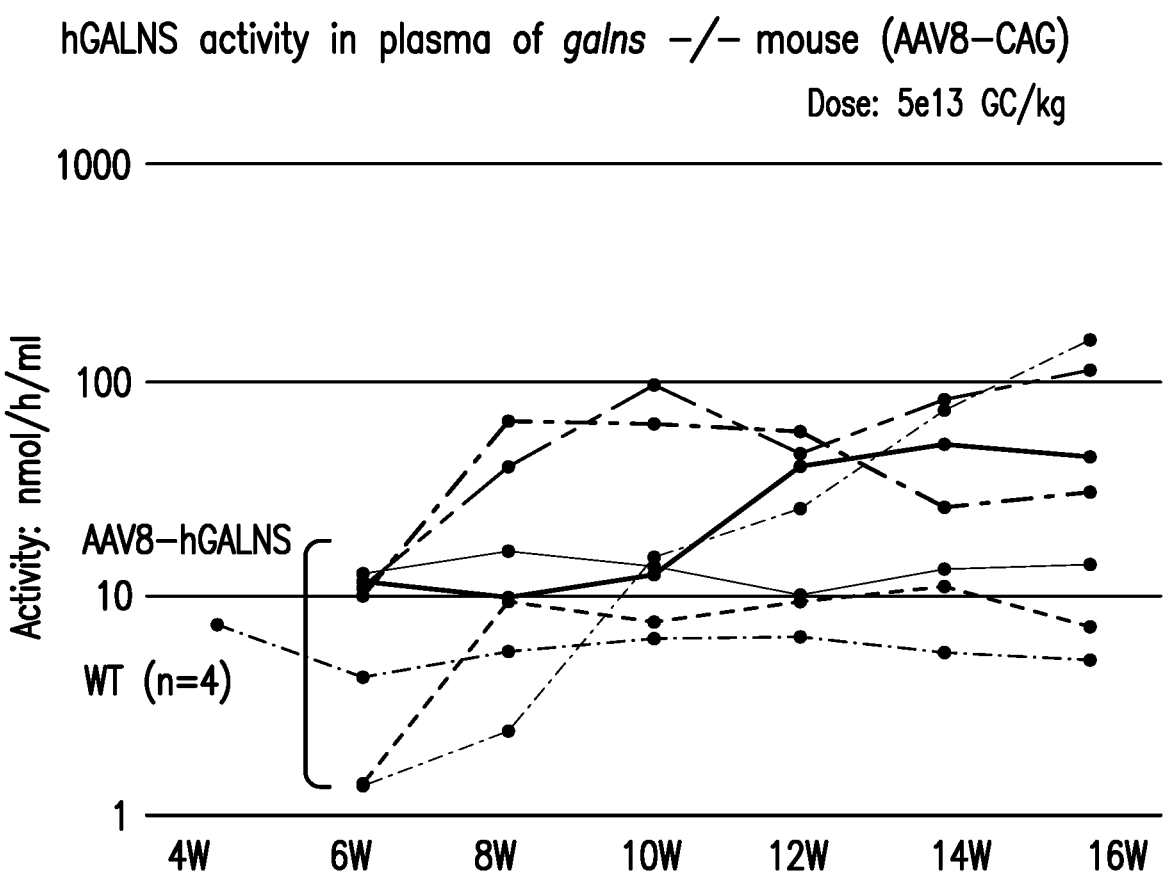

FIG. 35. hGALNS enzyme activities in the plasma of MPSIVA KO mice administered with $5 \times 10^{13}$ GC/kg body weight of AAV8-CAG-hGALNS, as compared with untreated wild type mice.

Figure 36:
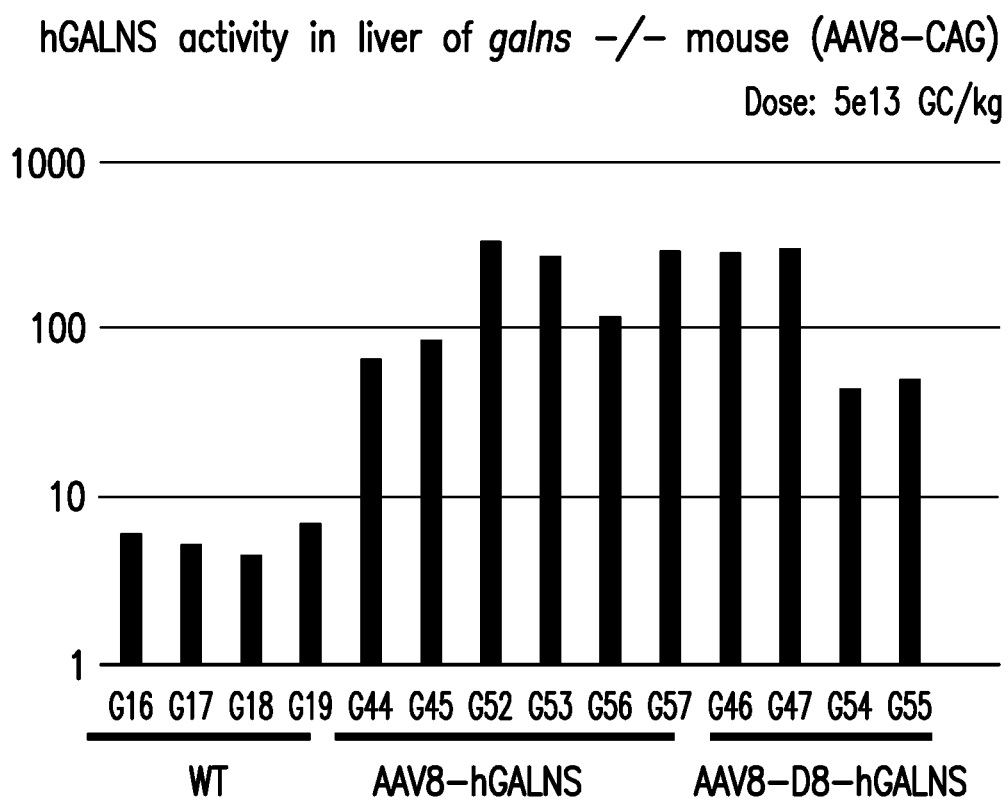

FIG. 36. hGALNS enzyme activities in the liver of MPSIVA KO mice administered with $5 \times 10^{13}$ GC/kg body weight of AAV8-CAG-hGALNS, or AAV8-CAG-D8-hGALNS, as compared with untreated wild type mice.

Figure 37:
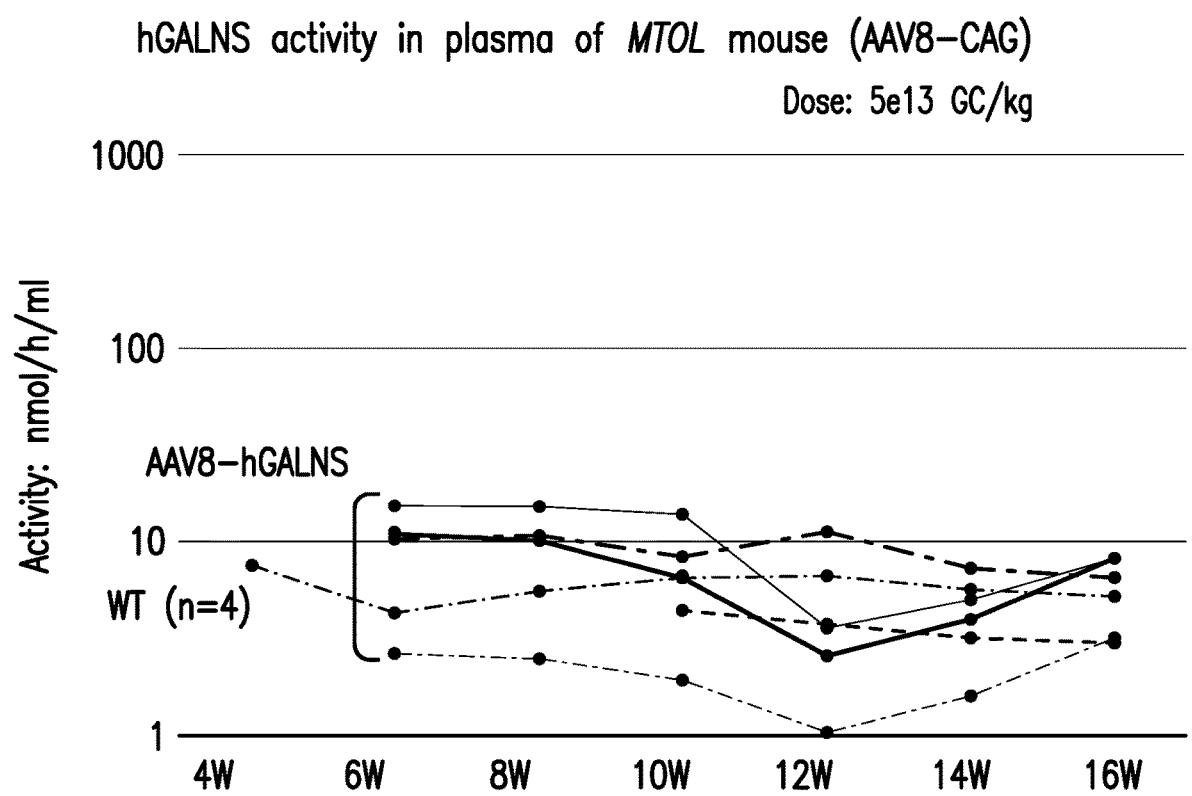

FIG. 37. hGALNS enzyme activities in the plasma MTOL mice administered with $5 \times 10^{13}$ GC/kg body weight of AAV8-CAG-hGALNS, as compared with untreated wild type mice.

Figure 38:
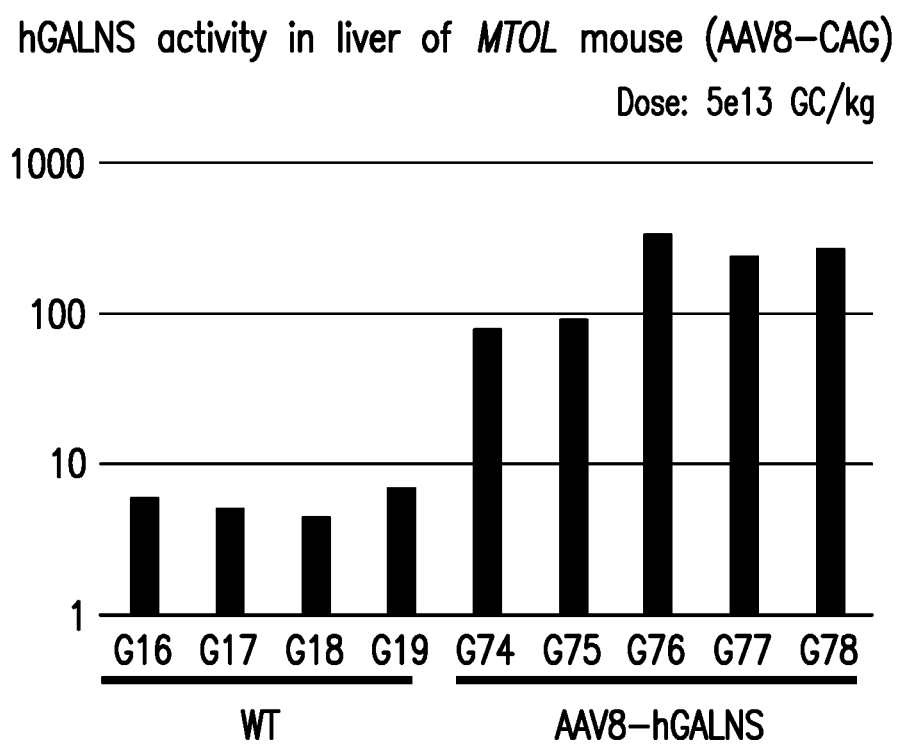

FIG. 38. hGALNS enzyme activities in the liver MTOL mice administered with $5 \times 10^{13}$ GC/kg body weight of AAV8-CAG-hGALNS, as compared with untreated wild type mice.

Figure 39:
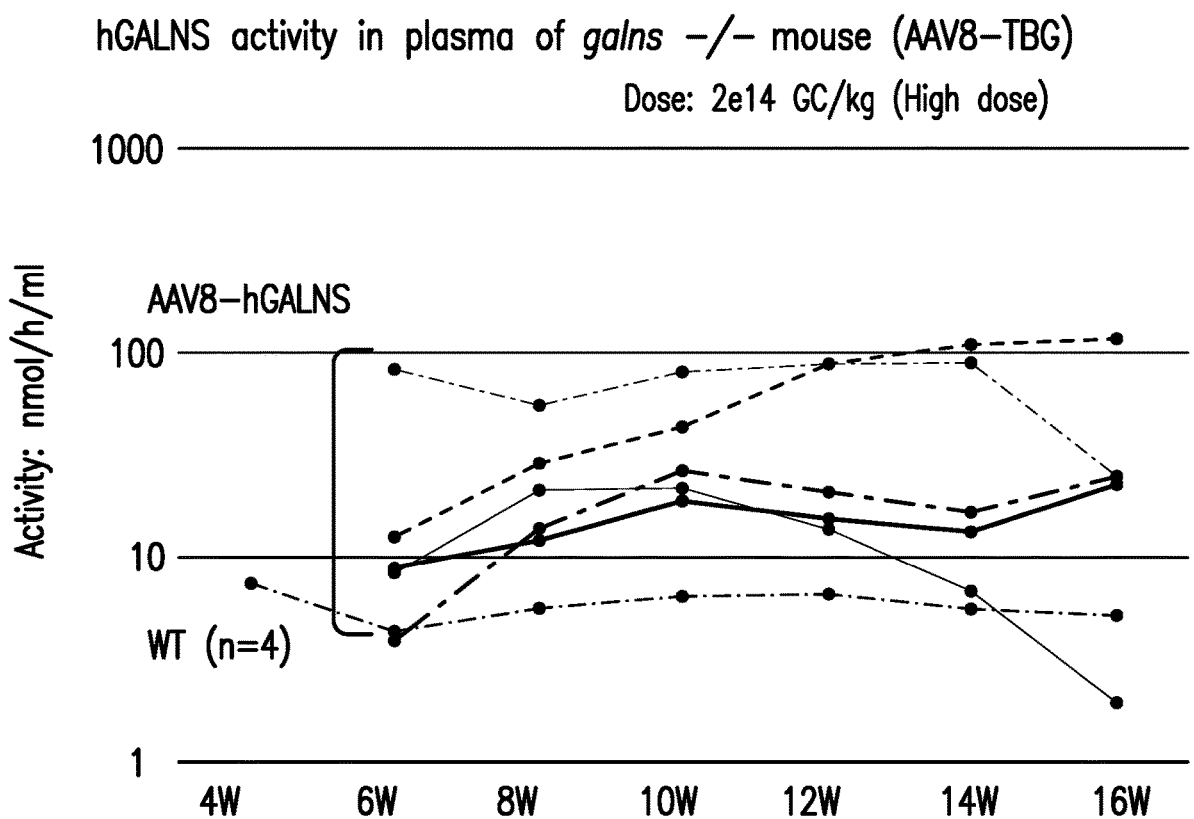

FIG. 39. hGALNS enzyme activities in the plasma of MPSIVA KO mice administered with $2 \times 10^{14}$ GC/kg body weight of AAV8-TBG-hGALNS, as compared with untreated wild type mice.

Figure 40:
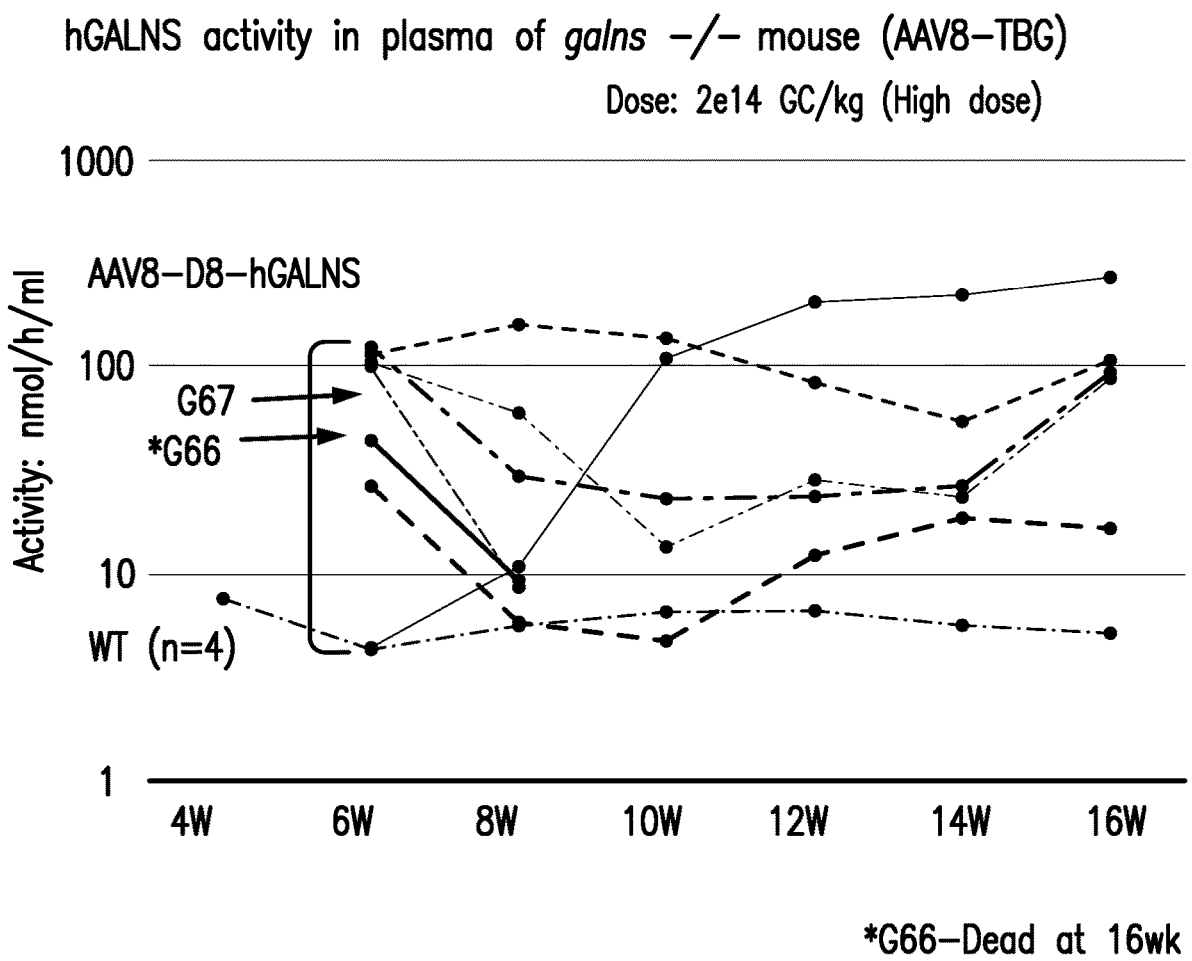

FIG. 40. hGALNS enzyme activities in the plasma of MPSIVA KO mice administered with $2 \times 10^{14}$ GC/kg body weight of AAV8-TBG-D8-hGALNS, as compared with untreated wild type mice.

Figure 41:
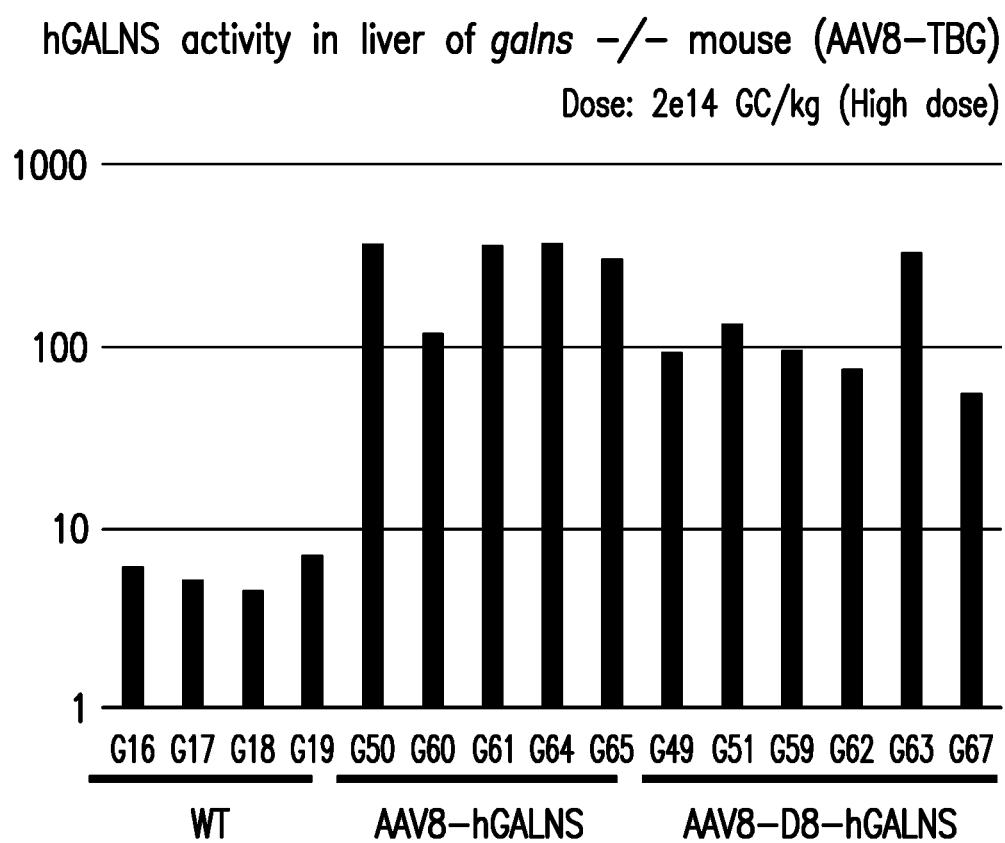

FIG. 41. hGALNS enzyme activities in the liver of MPSIVA KO mice administered with $2 \times 10^{14}$ GC/kg body weight of AAV8-TBG-hGALNS, or AAV8-TBG-D8-hGALNS, as compared with untreated wild type mice.

6. DETAILED DESCRIPTION

The present invention is at least partially based on a surprising finding that administration of recombinant adeno-associated viruses (rAAVs) comprising certain hGALNS expression cassettes in animal models of mucopolysaccharidosis type IVA (MPS IVA) maintained high levels of hGALNS enzymatic activity throughout the monitoring period and resulted in improvement in tissues including the bone, cartilage, ligament, meniscus, growth plate, liver, spleen, lung, kidney, trachea, heart muscle, and heart valve, exhibiting an improvement over what has been achieved by enzyme replacement therapy (ERT).

Described herein are rAAVs for use in the treatment of MPS IVA in a human subject in need of treatment. These rAAVs comprise a recombinant AAV genome encoding for hGALNS. The rAAV can be administered to an MPS IVA patient resulting in the synthesis of hGALNS and the delivery of hGALNS to the affected tissues, such as bone, cartilage, ligament, meniscus, growth plate, liver, spleen, lung, kidney, trachea, heart muscle, and/or heart valve, thereby improving pathology, and preventing the progression of the disease.

Provided is a recombinant adeno-associated virus (rAAV) comprising an AAV capsid and a recombinant AAV genome comprising an hGALNS expression cassette flanked by AAV-inverted terminal repeats (ITRs). In certain embodiments, the rAAV capsid is at least 80%, at least 85%, at least 90%, at least 95%, or 100% identical to the serotype AAV8 capsid. In certain embodiments, the amino acid sequence of the rAAV capsid is at least 80%, at least 85%, at least 90%, at least 95%, or 100% identical to SEQ ID: NO. 1. In certain embodiments, the amino acid sequence of the rAAV capsid is 80-85%, 85-90%, 90-95%, 95-99% or 99-99.9% identical to SEQ ID: NO. 1. For more detail regarding rAAV capsids, see Section 6.1.1. In some embodiments, the hGALNS expression cassette comprises a nucleotide sequence encoding a fusion protein that is hGALNS fused to an acidic oligopeptide. In certain embodiments, the acidic oligopeptide is D8. In certain embodiments, the hGALNS expression cassette further comprises a nucleotide sequence encoding a liver-specific promoter (for example, a thyroxine binding globulin (TBG) promoter). In certain embodiments, the hGALNS expression cassette additionally comprises a nucleotide sequence encoding a poly A site. In other embodiments, the hGALNS expression cassette comprises a nucleotide sequence encoding a liver-specific promoter (for example, a TBG promoter) and a nucleotide sequence encoding hGALNS, wherein the nucleotide sequence encoding the liver-specific promoter is operably linked to the nucleotide sequence encoding hGALNS. In certain embodiments, the hGALNS expression cassette additionally comprises a nucleotide sequence encoding a poly A site.

Also provided herein are polynucleotides comprising an hGALNS expression cassette as described herein. Further provided are plasmids and cells (e.g., ex vivo host cells) comprising a polynucleotide provided herein for making the rAAVs for use with the methods and compositions provided herein.

Further provided herein are methods for making an rAAV described herein.

Also provided herein are methods for treating a human subject diagnosed with mucopolysaccharidosis type IVA (MPS IVA). In one aspect, the method comprises administering an rAAV described herein to the human subject. In another aspect, the method comprises delivering glycosylated hGALNS (for example, hGALNS that is glycosylated with mannose-6-phosphate by having been produced in and secreted from a liver cell) to the affected tissue(s). In another aspect, the method comprises delivering a fusion protein that is hGALNS fused to an acidic oligopeptide to the affected tissue(s). The fusion protein can be glycosylated with mannose-6-phosphate by having been produced in and secreted from a liver cell.

Further provided herein are pharmaceutical compositions and kits comprising an rAAV described herein.

The rAAVs provided herein are described in Section 6.1, which includes a description of rAAV capsids in Section 6.1.1 and a description of the hGALNS expression cassette in Section 6.1.2. Methods of making an rAAV provided herein as well as polynucleotides, plasmids and cells that can be used in such methods are described in Section 6.2. Methods for treating a human subject diagnosed with MPS IVA, including target patient populations, routes of administration and dosage regimens are described in Section 6.3. Combination therapies are described in Section 6.4. Disease markers and methods to assess clinical outcomes are described in Section 6.5. Non-limiting illustrative examples are provided in Section 7.

Without being bound by theory, the manufacture, composition, and method of use of the rAAVs can be modified such that it still results in delivery of the hGALNS enzyme to the bone, cartilage, ligament, meniscus, and/or heart valve of a human subject as a treatment for MPS IVA.

6.1 Recombinant Adeno-Associated Viruses (rAAVs)

Provided herein are rAAVs useful for the treatment of MPS IVA in a human subject in need thereof, which rAAVs comprise an AAV capsid and a recombinant AAV genome comprising an hGALNS expression cassette.

In one aspect, provided herein is an rAAV comprising: (a) an AAV capsid; and (b) a recombinant AAV genome comprising an hGALNS expression cassette flanked by AAV-ITRs, said hGALNS expression cassette comprising a nucleotide sequence encoding a transgene, such as the transgene encoding a fusion protein that is hGALNS fused to an acidic oligopeptide. The hGALNS expression cassette may further comprise a nucleotide sequence encoding a liver-specific promoter, wherein the nucleotide sequence encoding the liver-specific promoter is operably linked to the nucleotide sequence encoding the fusion protein.

In another aspect, provided herein is an rAAV comprising: (a) an AAV capsid; and (b) a recombinant AAV genome comprising an hGALNS expression cassette flanked by AAV-ITRs, said hGALNS expression cassette comprising a nucleotide sequence encoding a liver-specific promoter and a nucleotide sequence encoding hGALNS, wherein the nucleotide sequence encoding the liver-specific promoter is operably linked to the nucleotide sequence encoding hGALNS.

Preferably, the hGALNS expression cassette comprises a nucleotide sequence encoding a liver-specific promoter, such that the hGALNS protein is expressed in the liver, which hGALNS protein, once secreted from liver cells, is translocated to other tissues, including, but are not limited to, the severely affected organs, such as the bone, cartilage and associated tissue, and heart valve.

The different components of rAAVs provided herein are described in detail below.

6.1.1 Capsid

The capsid is the protein shell of a virus that packages and protects the viral genome while interacting with the host environment. According to the invention, an rAAV provided herein comprises an AAV capsid. In a specific embodiment, an AAV capsid is the capsid of a naturally found AAV (for example, the capsid of AAV1, AAV2, AAV3, AAV4, AAV5, AAV6, AAV7, AAV8, AAV9, AAVrh10, or AAV11). In another specific embodiment, an AAV capsid is derived from the capsid of a naturally found AAV (for example, the capsid of AAV1, AAV2, AAV3, AAV4, AAV5, AAV6, AAV7, AAV8, AAV9, AAVrh10, or AAV11), for example, by having an amino acid sequence that is at least 80%, at least 85%, at least 90%, at least 95%, at least 96%, at least 97%, at least 98%, at least 99%, at least 99.9%, or 100% identical to the amino acid sequence of the capsid of the naturally found AAV.

In certain embodiments, AAV variant capsids that can be used according to the invention described herein include Anc80 or Anc80L65, as described in Zinn et al., 2015, Cell Rep. 12(6): 1056-1068, which is incorporated by reference in its entirety. In certain embodiments, AAV variant capsids that can be used according to the invention described herein comprise one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In certain embodiments, AAV variant capsids that can be used according to the invention described herein include AAV.7m8, as described in U.S. Pat. Nos. 9,193,956; 9,458,517; and 9,587, 282 and US patent application publication no. 2016/ 0376323, each of which is incorporated herein by reference in its entirety. In certain embodiments, AAV variant capsids that can be used according to the invention described herein include any AAV disclosed in U.S. Pat. No. 9,585,971, such as AAV-PHP.B. In certain embodiments, AAV variant capsids that can be used according to the invention include, but are not limited to, those disclosed in any of the following patents and patent applications, each of which is incorporated herein by reference in its entirety: U.S. Pat. Nos. 7,282,199; 7,906,111; 8,524,446; 8,906,675; 8,999,678; 8,628,966; 8,927,514; 8,734,809; 9,284,357; 9,409,953; 9,169,299; 9,193,956; 9,458,517; 9,587,282; 9,737,618; 9,840,719; US patent application publication nos. 2015/ 0374803; 2015/0126588; 2017/0067908; 2013/0224836; 2016/0215024; 2017/0051257; and International Patent Application Nos. PCT/US2002/033630; PCT/US2004/ 028817; PCT/2002/033629; PCT/US2006/013375; PCT/ US2015/034799; PCT/EP2015/053335; PCT/US2016/ 042472; PCT/US2017/027392.

In certain embodiments, a single-stranded AAV (ssAAV) may be used supra. In certain embodiments, a self-complementary vector, e.g., scAAV, may be used (see, e.g., Wu, 2007, Human Gene Therapy, 18(2):171-82, McCarty et al, 2001, Gene Therapy, Vol 8, Number 16, Pages 1248-1254;

and U.S. Pat. Nos. 6,596,535; 7,125,717; and 7,456,683, each of which is incorporated herein by reference in its entirety).

In preferred embodiments, the AAV capsid contained in the rAAV is the capsid of AAV8 or derived from the capsid of AAV8. AAV8 has greater liver transduction efficiency than other serotypes and low reactivity to antibodies against human AAVs. Importantly, specific regions of the AAV8 capsid contribute to the high liver transduction by mediating nuclear entry and capsid uncoating (Tenney et al., Virology, 2014, 454-455: 227-236; Nam et al., J Virol., 2007 81(22): 12260-12271). As a result, AAV8 has a tropism for hepatocytes (Sands, M., Methods Mol Biol., 2011; 807:141-157). In certain embodiments, the amino acid sequence of the AAV capsid contained in the rAAV is identical to the amino acid sequence of the AAV8 capsid (SEQ ID NO: 1). In certain embodiments, the amino acid sequence of the AAV capsid contained in the rAAV is at least 80%, at least 85%, at least 90%, at least 95%, at least 96%, at least 97%, at least 98%, at least 99%, or at least 99.9% identical to the amino acid sequence of the AAV8 capsid (SEQ ID NO: 1), while retaining the ability of the AAV8 capsid to package a viral genome and preferably also the ability of the AAV8 capsid to transduce liver cells at a high efficiency. In certain embodiments, the amino acid sequence of the AAV capsid contained in the rAAV is identical to the amino acid sequence of the AAV8 capsid (SEQ ID NO: 1) except for 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid residues, while retaining the ability of the AAV8 capsid to package a viral genome and preferably also the ability of the AAV8 capsid to transduce liver cells at a high efficiency. In a preferred embodiment of the treatment method described herein, AAV8 is used for targeted liver expression of the hGALNS protein.

6.1.2 hGALNS Expression Cassette

AAV has a linear single-stranded DNA (ssDNA) genome that contains two inverted terminal repeats (ITRs) at the termini. AAV enters into cells by endocytosis (Meier and Greber, J Gene Med., 2004; 6 Suppl 1:S152-63). Upon capsid breakdown, the ssDNA genome is released and converted to double-stranded DNA (dsNDA), from which genes encoded by the viral genome can be expressed (Ding et al., 2005, Gene Ther., 12: 873-880).

According to the invention, an rAAV provided herein comprises a recombinant AAV genome. The recombinant AAV genome can comprise the backbone of an AAV genome or its variant (for example, the backbone of an AAV1, AAV1, AAV2, AAV3, AAV4, AAVS, AAV6, AAV7, AAV8, AAV9, AAVrh10, or AAV11 genome or its variant). Preferably, the recombinant AAV genome can comprise the backbone of an AAV8 genome or its variant.

According to the invention, the recombinant AAV genome comprises an hGALNS expression cassette flanked by AAV-ITRs. In some embodiments, the hGALNS expression cassette comprises a nucleotide sequence encoding a fusion protein that is hGALNS fused to an acidic oligopeptide. The hGALNS expression cassette may further comprise a nucleotide sequence encoding a liver-specific promoter, wherein the nucleotide sequence encoding the liver-specific promoter is operably linked to the nucleotide sequence encoding the fusion protein. In other embodiments, the hGALNS expression cassette comprises a nucleotide sequence encoding a liver-specific promoter and a nucleotide sequence encoding hGALNS, wherein the nucleotide sequence encoding the liver-specific promoter is operably linked to the nucleotide sequence encoding hGALNS.

(a) hGALNS

In certain embodiments, the nucleotide sequence encoding hGALNS or the hGALNS portion of the fusion protein comprises the sequence of SEQ ID NO: 2 or 3. In certain embodiments, the nucleotide sequence encoding hGALNS or the hGALNS portion of the fusion protein is at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to the sequence set forth in SEQ ID NO: 2 or 3.

In certain embodiments, the nucleotide sequence encoding the fusion protein comprises the sequence of SEQ ID NO: 4 or 5. In certain embodiments, the nucleotide sequence encoding the fusion protein is at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to the sequence set forth in SEQ ID NO: 4 or 5.

In certain embodiments, the nucleotide sequence encoding hGALNS or the hGALNS portion of the fusion protein comprises the cDNA sequence of hGALNS. In certain embodiments, the nucleotide sequence encoding hGALNS or the hGALNS portion of the fusion protein is at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to the cDNA sequence of hGALNS.

In certain embodiments, the nucleotide sequence encoding the fusion protein comprises the cDNA sequence of the fusion protein. In certain embodiments, the nucleotide sequence encoding the fusion protein is at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to the cDNA sequence of the fusion protein.

In certain embodiments, the nucleotide sequence encoding hGALNS or the nucleotide sequence encoding the fusion protein is codon-optimized, for example, via any codon-optimization technique known to one of skill in the art (see, e.g., review by Quax et al., 2015, Mol Cell 59:149-161).

In certain embodiments, CpG sites are depleted in the nucleotide sequence encoding hGALNS or the nucleotide sequence encoding the fusion protein.

(b) Acidic Oligopeptide

Acidic oligopeptides have high binding affinities for hydroxyapatite, a major component of bones and cartilages. The term "acid oligopeptide" as used herein refers to an oligopeptide with a repeating amino acid sequence of glutamic acid (E) and/or aspartic acid (D) residues. The number of amino acid residues in an acidic oligopeptide may be, for example, 4, 5, 6, 7, 8, 9, 10, 11, 12, 13, 14, or 15. In specific embodiments, the number of amino acid residues in an acidic oligopeptide is 4-8. In specific embodiments, the number of amino acid residues in an acidic oligopeptide is 6-8. In a specific embodiment, the number of amino acid residues in an acidic oligopeptide is 6. In another specific embodiment, the number of amino acid residues in an acidic oligopeptide is 8.

In a preferred embodiment, the acidic oligopeptide is D8 (i.e., an oligopeptide with an amino acid sequence of eight aspartic acid residues. In another embodiment, the acidic oligopeptide is E6 (i.e., an oligopeptide with an amino acid sequence of six glutamic acid residues. The E6 sequence is described in Tomatsu et al., 2010, Molecular Therapy, 18(6):11094-1102, which is incorporated by reference herein in its entirety.

In a preferred embodiment, the acidic oligopeptide is fused to the N-terminus of hGALNS. In another embodiment, the acidic oligopeptide is fused to the C-terminus of hGALNS.

In a specific embodiment, the acidic oligopeptide is fused directly to hGALNS, with no intervening amino acid sequence. In another specific embodiment, the acidic oligopeptide is fused to hGALNS via a linker amino acid sequence (e.g., an amino acid sequence that is 1-10, 2-8, or 4-6 amino acid residues in length).

In certain embodiments, the hGALNS enzyme can be delivered to the lysosomes in the bone and cartilage area to improve bone and cartilage pathology.

(c) Promoters and Modifiers of Gene Expression:

In certain embodiments, the hGALNS expression cassette described herein comprises components that modulate gene delivery or gene expression (e.g., "expression control elements"). In certain embodiments, the hGALNS expression cassette described herein comprises components that modulate gene expression. In certain embodiments, the hGALNS expression cassette described herein comprises components that influence binding or targeting to cells. In certain embodiments, the hGALNS expression cassette described herein comprises components that influence the localization of the hGALNS within the cell after uptake. In certain embodiments, the hGALNS expression cassette described herein comprises components that can be used as detectable or selectable markers, e.g., to detect or select for cells that have taken up the hGALNS expression cassette. In certain embodiments, the hGALNS expression cassette described herein comprises nucleotide sequence(s) encoding one or more promoters, at least one of which is operably linked to the nucleotide sequence encoding hGALNS or the fusion protein that is hGALNS fused to an acidic oligopeptide. In certain embodiments, the promoter can be a constitutive promoter. In alternate embodiments, the promoter can be an inducible promoter.

In certain embodiments, the promoter is a CAG promoter.

In certain embodiments, the promoter is a liver-specific promoter.

The liver-specific promoter can be, but is not limited to, a thyroxine binding globulin (TBG) promoter (see, e.g., Yan et al., 2012, Gene, 506(2):289-94, incorporated by reference herein in its entirety).

In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:13. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:14. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:15. In certain embodiments, the liver-specific promoter is SEQ ID NO:13. In certain embodiments, the liver-specific promoter is SEQ ID NO:14. In certain embodiments, the liver-specific promoter is SEQ ID NO:15.

In certain embodiments, the promoter is a liver- and muscle-specific promoter.

In certain embodiments, the liver- and muscle-promoter comprises a nucleotide sequence having at least 80%, 85%, 90%, 91%, 92%, 93%, 94%, 95%, 96%, 97%, 98%, 99% or 100% sequence identity to SEQ ID NO:16. In certain embodiments, the liver- and muscle-promoter is SEQ ID NO:16.

In certain embodiments, the promoter comprises one or more elements that enhance the expression of hGALNS or the fusion protein. In certain embodiments, the promoter comprises a TATA box.

In certain embodiments, the one or more promoter elements can be inverted or moved relative to one another. In certain embodiments, the elements of the promoter can be positioned to function cooperatively. In certain embodiments, the elements of the promoter can be positioned to function independently. In certain embodiments, the hGALNS expression cassette described herein comprises one or more promoters selected from the group consisting of the liver-specific TBG promoter, the human CMV immediate early gene promoter, the SV40 early promoter, the Rous sarcoma virus (RS) long terminal repeat, and rat insulin promoter. In certain embodiments, the hGALNS expression cassette provided herein comprise one or more tissue specific promoters. In a specific embodiment, the tissue-specific promoter is a liver-specific promoter. In a specific embodiment, the TBG promoter has the nucleotide sequence of SEQ ID NO. 6.

In certain embodiments, the hGALNS expression cassette comprises one or more additional expression control elements, which can include a nucleotide sequence encoding an enhancer (e.g., an alpha mic/bik enhancer), a repressor, a nucleotide sequence encoding an intron or a chimeric intron (e.g., first intron of the chicken beta-actin gene), and/or a nucleotide sequence encoding a poly A site (e.g., a rabbit globin poly A site). In a specific embodiment, the nucleotide sequence encoding the rabbit globin poly A site has the sequence of SEQ ID NO: 9. In a specific embodiment, the nucleotide sequence encoding the intron has the sequence of SEQ ID NO: 10. In a specific embodiment, the nucleotide sequence encoding the alpha mic/bik enhancer has the sequence of SEQ ID NO: 11.

In a specific embodiment, the hGALNS expression cassette comprises an alpha mic/bik enhancer, a nucleotide sequence encoding an intron, a nucleotide sequence encoding a TBG promoter, a nucleotide sequence encoding hGALNS or a fusion protein that is hGALNS fused to an acidic oliopeptide (preferably, D8), and a nucleotide sequence encoding a rabbit globin poly A site. In a specific embodiment, the nucleotide sequence encoding the rabbit globin poly A site has the sequence of SEQ ID NO: 9. In a specific embodiment, the nucleotide sequence encoding the intron has the sequence of SEQ ID NO: 10. In a specific embodiment, the nucleotide sequence encoding the alpha mic/bik enhancer has the sequence of SEQ ID NO: 11.

(d) Inverted Terminal Repeats

According to the invention, the hGALNS expression cassette described herein is flanked by two AAV-inverted terminal repeats (ITRs). ITR sequences may be used for packaging a recombinant gene expression cassette into the virion (see, e.g., Yan et al., 2005, J. Virol., 79(1):364-379; U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety). In a specific embodiment, the flanking ITRs are AAV8 ITRs. In a specific embodiment, the ITR sequence can have a sequence of SEQ ID NO.: 7. In a specific embodiment, the ITR sequence can have a sequence of SEQ ID NO.: 8. In a specific embodiment, the 5' ITR can have a sequence of SEQ ID NO.: 7. In a specific embodiment, the 3' ITR can have a sequence of SEQ ID NO.: 8.

(e) Untranslated Regions

In certain embodiments, the hGALNS expression cassette described herein comprises one or more untranslated regions (UTRs), e.g., 3' and/or 5' UTRs. In certain embodiments, the UTRs are optimized for the desired level of protein expression. In certain embodiments, the UTRs are optimized for the mRNA half life of the hGALNS. In certain embodiments, the UTRs are optimized for the stability of the mRNA of the hGALNS. In certain embodiments, the UTRs are optimized for the secondary structure of the mRNA of the hGALNS.

6.1.3 Pharmaceutical Compositions and Kits

In certain embodiments, provided herein are pharmaceutical compositions comprising an rAAV provided herein and a pharmaceutically acceptable carrier. The pharmaceutical composition may be prepared as individual, single unit dosage forms. The pharmaceutical compositions provided herein can be formulated for, for example, parenteral, subcutaneous, intramuscular, intravenous, intraperitoneal, intranasal, intrathecal, or transdermal administration. In a specific embodiment, the pharmaceutical composition is formulated for intravenous administration. A suitable pharmaceutically acceptable carrier (e.g., for intravenous administration and transduction in liver cells) would be readily selected by one of skill in the art.

Provided herein are kits comprising a pharmaceutical composition described herein, contained in one or more containers. The containers that the pharmaceutical composition can be packaged in can include, but are not limited to, bottles, packets, ampoules, tubes, inhalers, bags, vials, and containers. In certain embodiments, the kit comprises instructions for administering the pharmaceutical administration. In certain embodiments, the kit comprises devices that can be used to administer the pharmaceutical composition, including, but not limited to, syringes, needle-less injectors, drip bags, patches and inhalers.

Also provided are devices and blood circulation systems that can be utilized when treating MPS IVA using an rAAV described herein by gene therapy. Such devices and systems would be readily selected by one of skill in the art.

6.2 Manufacture of rAAVS

Also provided herein are polynucleotides comprising an hGALNS expression cassette as described herein, plasmids and cells that can be used to generate an rAAV provided herein, and methods of making an rAAV provided herein.

6.2.1 Polynucleotides, Plasmids and Cells

Provided herein are polynucleotides comprising an hGALNS expression cassette.

In one aspect, provide herein is a polynucleotide comprising an hGALNS expression cassette flanked by AAV-ITRs, said hGALNS expression cassette comprising a nucleotide sequence encoding a transgene, such as the transgene encoding a fusion protein that is hGALNS fused to an acidic oligopeptide (for example, D8). The hGALNS expression cassette may further comprise a nucleotide sequence encoding a liver-specific promoter (for example, a TBG promoter), wherein the nucleotide sequence encoding the liver-specific promoter is operably linked to the nucleotide sequence encoding the fusion protein. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:13. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:14. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:15. In certain embodiments, the liver-specific promoter is SEQ ID NO:13. In certain embodiments, the liver-specific promoter is SEQ ID NO:14. In certain embodiments, the liver-specific promoter is SEQ ID NO:15.

In another aspect, provided herein is a polynucleotide comprising an hGALNS expression cassette flanked by AAV-ITRs, said hGALNS expression cassette comprising a nucleotide sequence encoding a liver-specific promoter (for example, a TBG promoter) and a nucleotide sequence encoding hGALNS, wherein the nucleotide sequence encoding the liver-specific promoter is operably linked to the nucleotide sequence encoding hGALNS.

In one aspect, provide herein is a polynucleotide comprising an hGALNS expression cassette flanked by AAV-ITRs, said hGALNS expression cassette comprising a nucleotide sequence encoding a transgene, such as the transgene encoding a fusion protein that is hGALNS fused to an acidic oligopeptide (for example, D8). The hGALNS expression cassette may further comprise a nucleotide sequence encoding a promoter, wherein the nucleotide sequence encoding the promoter is operably linked to the nucleotide sequence encoding the fusion protein. In certain embodiments, the promoter is a CAG promoter.

In one aspect, provide herein is a polynucleotide comprising an hGALNS expression cassette flanked by AAV-ITRs, said hGALNS expression cassette comprising a nucleotide sequence encoding a transgene, such as the transgene encoding a fusion protein that is hGALNS fused to an acidic oligopeptide (for example, D8). The hGALNS expression cassette may further comprise a nucleotide sequence encoding a liver- and muscle specific-promoter, wherein the nucleotide sequence encoding the liver- and muscle specific-promoter is operably linked to the nucleotide sequence encoding the fusion protein. In certain embodiments, the liver- and muscle specific-promoter comprises a nucleotide sequence having at least 80%, 85%, 90%, 91%, 92%, 93%, 94%, 95%, 96%, 97%, 98%, 99% or 100% sequence identity to SEQ ID NO:16. In certain embodiments, the promoter is SEQ ID NO:16.

In another aspect, provided herein is a polynucleotide comprising an hGALNS expression cassette flanked by AAV-ITRs, said hGALNS expression cassette comprising a nucleotide sequence encoding a promoter and a nucleotide sequence encoding hGALNS, wherein the nucleotide sequence encoding the promoter is operably linked to the nucleotide sequence encoding hGALNS. In certain embodiments, the promoter is a CAG promoter. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:13. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:14. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:15. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:16. In certain embodiments, the promoter is SEQ ID NO:13. In certain embodiments, the promoter is SEQ ID NO:14. In certain embodiments, the promoter is SEQ ID NO:15. In certain embodiments, the promoter is SEQ ID NO:16.

The hGALNS expression cassette can be as described in Section 6.1.2.

In a specific embodiment, the polynucleotide is in the form of a ssDNA. In another specific embodiment, the polynucleotide is in the form of a dsDNA.

Also provided herein are plasmids comprising a polynucleotide provided herein (hereinafter "rAAV plasmids"). In a specific embodiment, the rAAV plasmid is a ssDNA plasmid. In another specific embodiment, the rAAV plasmid is a dsDNA plasmid. In some embodiments, the rAAV plasmid is in a circular form. In other embodiments, the rAAV plasmid is in a linear form.

In a certain embodiment, the constructs described herein comprise the following components (LSPX1): (1) AAV inverted terminal repeats (ITRs) that flanks the expression cassette; (2) control elements, which include a) two tandem Mik/BikE enhancers, b) ApoE enhancer, c) human AAT promoter, d) a poly A signal, and e) optionally an intron; (3) a nucleotide sequence encoding hGALNS or hGALNSco. In a specific embodiment, the constructs described herein comprise the following components: (1) AAV2 inverted terminal repeats that flank the expression cassette; (2) control elements, which include a) two tandem Mik/BikE enhancers, b) ApoE enhancer, c) human AAT promoter, d) a rabbit β-globin poly A signal and e) optionally a chimeric intron derived from human β-globin and Ig heavy chain; and (3) a nucleotide sequence encoding hGALNS or hGALNSco.

In a certain embodiment, the constructs described herein comprise the following components (LSPX2): (1) AAV inverted terminal repeats (ITRs) that flanks the expression cassette; (2) control elements, which include a) two tandem ApoE enhancers, b) human AAT promoter, c) a poly A signal; and d) optionally an intron; and (3) nucleotide sequence encoding hGALNS or hGALNSco. In a specific embodiment, the constructs described herein comprise the following components: (1) AAV2 inverted terminal repeats that flank the expression cassette; (2) control elements, which include a) two tandem ApoE enhancers, b) human AAT promoter, c) a poly A signal; and d) optionally a chimeric intron derived from human β-globin and Ig heavy chain; and (3) a nucleotide sequence encoding hGALNS or hGALNSco.

In a certain embodiment, the constructs described herein comprise the following components (LTP1): (1) AAV inverted terminal repeats (ITRs) that flanks the expression cassette; (2) control elements, which include a) two tandem Mik/BikE enhancers, b) TBG promoter, c) human AAT (AATG) promoter, d) a poly A signal; and e) optionally an intron; and (3) a nucleotide sequence encoding hGALNS or hGALNSco. In a specific embodiment, the constructs described herein comprise the following components: (1) AAV2 inverted terminal repeats that flank the expression cassette; (2) control elements, which include a) two tandem Mik/BikE enhancers, b) TBG promoter, c) human AAT (AATG) promoter, d) a poly A signal; and e) optionally a chimeric intron derived from human β-globin and Ig heavy chain; and (3) a nucleotide sequence encoding hGALNS or hGALNSco.

In a certain embodiment, the constructs described herein comprise the following components (LTP2): (1) AAV inverted terminal repeats (ITRs) that flanks the expression cassette; (2) control elements, which include a) ApoE enhancer, b) two tandem Mik/BikE enhancers, c) TBG promoter, d) human AAT (AATG) promoter, e) a poly A signal; and f) optionally an intron; and (3) a nucleotide sequence encoding hGALNS or hGALNSco. In a specific embodiment, the constructs described herein comprise the following components: (1) AAV2 inverted terminal repeats that flank the expression cassette; (2) control elements, which include a) ApoE enhancer, b) two tandem McKE enhancers, c) TBG promoter, d) human AAT (ΔATG) promoter, e) a poly A signal; and f) optionally a chimeric intron derived from human β-globin and Ig heavy chain; and (3) a nucleotide sequence encoding hGALNS or hGALNSco.

In a certain embodiment, the constructs described herein comprise the following components (LMTP6): (1) AAV inverted terminal repeats (ITRs) that flanks the expression cassette; (2) control elements, which include a) ApoE enhancer, b) three tandem McKE enhancers, c) CK promoter, d) human AAT (ΔATG) promoter, e) a poly A signal; and f) optionally an intron; and (3) a nucleotide sequence encoding hGALNS or hGALNSco. In a specific embodiment, the constructs described herein comprise the following components: (1) AAV2 inverted terminal repeats that flank the expression cassette; (2) control elements, which include a) ApoE enhancer, b) three tandem McKE enhancers, c) CK promoter, d) human AAT (ΔATG) promoter, e) a poly A signal; and f) optionally a chimeric intron derived from human β-globin and Ig heavy chain; and (3) a nucleotide sequence encoding hGALNS or hGALNSco.

Further provided herein are cells (preferably ex vivo cells) expressing (e.g., recombinantly) an rAAV provided herein. In certain embodiments, the cell (preferably ex vivo cell) comprises a polynucleotide provided herein or an rAAV plasmid provided herein. In certain embodiments, the cell (preferably ex vivo cell) further comprises helper polynucleotide(s) or helper plasmids providing the AAV Rep, Cap, and Ad5 functions. The cell (preferably ex vivo cells) can by a mammalian host cell, for example, HEK293, HEK293-T, A549, WEHI, 10T1/2, BHK, MDCK, COS1, COST, BSC 1, BSC 40, BMT 10, VERO, W138, HeLa, 293, Saos, C2C12, L, HT1080, HepG2, primary fibroblast, hepatocyte, and myoblast cells. The mammalian host cell can be derived from, for example, human, monkey, mouse, rat, rabbit, or hamster. In a specific embodiment, the mammalian host cell is a human embryonic kidney 293 (HEK293) cell or HEK293-T cell.

6.2.2 Methods of Making rAAVs

Provided are methods of making an rAAV provided herein. In certain embodiments, the method comprises transfecting a cell (preferably an ex vivo cell) with an rAAV plasmid provided in Section 6.2.1 and one or more helper plasmids collectively providing the AAV Rep, Cap, and Ad5 functions. In certain embodiments, the one or more helper plasmids collectively comprising the nucleotide sequences of AAV genes Rep, Cap, VA, E2a and E4.

The manufacture of an rAAV provided herein for gene therapy applications can use methods known in the art, for example, as described in Clement et al., 2016, Molecular Therapy-Methods & Clinical Development, 27:16002, which is incorporated by reference herein in its entirety. In certain embodiments, transfection of the plasmid DNA is performed using calcium phosphate plasmid precipitation on human embryonic kidney 293 cells (HEK293) or HEK293-T with the rAAV plasmid and the helper plasmid(s) that provide the AAV Rep and Cap functions as well as the Ad5 genes (VA RNAs, E2a, and E4) as is described in the art. In certain embodiments, the Rep, Cap, and Ad5 genes can be on the same helper plasmid. In certain embodiments, a two-helper method (or triple transfection) is utilized where AAV Rep, Cap, and Ad5 functions are provided from separate plasmids. In certain embodiments, the HEK293 cells can be adapted to grow in suspension in an animal component and antibiotic-free media.

In certain embodiments, rAAV can be manufactured using packaging and producer cell lines. The rAAV provided herein may be manufactured using mammalian host cells, for example, A549, WEHI, 10T1/2, BHK, MDCK, COS1, COST, BSC 1, BSC 40, BMT 10, VERO, W138, HeLa, HEK293, HEK293-T, Saos, C2C12, L, HT1080, HepG2, primary fibroblast, hepatocyte, and myoblast cells. The rAAV provided herein may be manufactured using host cells from human, monkey, mouse, rat, rabbit, or hamster. In certain embodiments, stable cell lines can be engineered by introducing the means of producing viruses in the host cells, for example, the replication and capsid genes (e.g., the rep and cap genes of AAV) and the rAAV plasmid provided herein. In a specific embodiment, the rAAV can be manufactured using HEK293 cells. In certain embodiments, rAAV can be produced in Sf9 insect cells by coinfecting three recombinant baculovirus plasmids with genes encoding the rep gene, the cap gene, and the rAAV genome.

The cells can be cultured, transfected, and harvested according to appropriate protocols which would be readily selected by one of skill in the art. In certain embodiments, the cells can be cultured in standard Dulbecco's modified Eagle medium (DMEM), including, but not limited to, fetal calf serum, glucose, penicillin, streptomycin, and 1-glutamine (McClure et al., J Vis Exp. 2011, (57): 3348; Shin et al., Methods Mol Biol. 2012, 798: 267-284). Cells can be transfected in components which would be readily selected by one of skill in the art. In certain embodiments, transfection can take place in media solutions including, but not limited to, DMEM and Iscove's modified Dulbecco's medium (IMDM). In certain embodiments, the transfection time can take 46 hr, 47 hr, 48 hr, 49 hr, 50 hr, 51 hr, 52 hr, 53 hr, 54 hr, 55 hr, 56 hr, 57 hr, 58 hr, 59 hr, 60 hr, 61 hr, 62 hr, 63 hr, 64 hr, 65 hr, 66 hr, 67 hr, 68 hr, 69 hr, 70 hr, 50-55 hr, 55-60 hr, 60-65 hr, or 65-70 hr. After transfection, the cells can be harvested by scraping cells to remove them from the culture wells and washing the wells to collect all of the transfected cells.

For a method of producing rAAV comprising AAV8 capsids, see Section IV of the Detailed Description of U.S. Pat. No. 7,282,199 B2, which is incorporated herein by reference in its entirety. Genome copy titers of said vectors may be determined, for example, by TAQMAN® analysis. Virions may be recovered, for example, by $CsCl_2$ sedimentation. In a specific embodiment, the rAAV described herein is an isolated or purified rAAV.

Multiple AAV serotypes have been identified. In certain embodiments, rAAVs or polynucleotides provided herein comprise one or more components derived from one or more serotypes of AAV. In certain embodiments, rAAVs or polynucleotides provided herein comprise one or more components derived from one or more of AAV1, AAV2, AAV3, AAV4, AAV5, AAV6, AAV7, AAV8, AAV9, AAVrh10, or AAV11. In a certain embodiment, rAAVs or polynucleotides provided herein can comprise one or more components from one or more of AAV8, AAV9, AAV10, or AAV11 serotypes. In a preferred embodiment, rAAVs or polynucleotides provided herein can comprise one or more components from the AAV8 serotype. Nucleic acid sequences of AAV components and methods of making recombinant AAV and AAV capsids are described, for example, in U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety. In specific embodiments, provided herein are rAAV8s which encode hGALNS.

Described in certain embodiments are rAAV8s comprising (i) a recombinant genome comprising an expression cassette containing the hGALNS or the fusion protein that is hGALNS fused to an acidic oligopeptide under the control of regulatory elements and flanked by ITRs; and (ii) a viral capsid that has the amino acid sequence of the AAV8 capsid protein or is at least 95%, 96%, 97%, 98%, 99% or 99.9% identical to the amino acid sequence of the AAV8 capsid protein (SEQ ID NO: 1) while retaining the ability of the AAV8 capsid to package a viral genome and preferably also the ability of the AAV8 capsid to transduce liver cells at a high efficiency. In certain embodiments, the AAV8 capsid has the sequence of SEQ ID NO: 1 with 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions and retaining the ability of the AAV8 capsid to package a viral genome and preferably also the ability of the AAV8 capsid to transduce liver cells at a high efficiency.

6.2.3 Assessment of Efficacy

In vitro assays, e.g., cell culture assays, can be used to measure hGALNS expression from an rAAV described herein, thus indicating, e.g., potency of the rAAV. Cells utilized for the assay can include, but are not limited to, A549, WEHI, 10T1/2, BHK, MDCK, COS1, COS7, BSC 1, BSC 40, BMT 10, VERO, W138, HeLa, HEK293, HEK293-T, HuH7, Saos, C2C12, L, HT1080, HepG2, primary fibroblast, hepatocyte, and myoblast cells. In a specific embodiment, the cells utilized in the cell culture assay comprise HuH7 cells. In certain embodiments, cells transfected with the rAAV can be analyzed for hGALNS enzyme activity.

Animal models may also be used to assess the expression of hGALNS from an rAAV described herein and its efficacy. Mouse models for MPS IVA have been described (see, e.g., Tomatsu et al., 2003, Hum Mol Genet 12(24):3349-3358). The mouse model for MPS IVA has a targeted disruption of Exon 2 of mouse GALNS. These mice have no detectable GALNS enzyme activity and increased levels of GAGs are detected in the urine. At 2 months old, increased storage of GAGs is seen in the reticuloendothelial cells, Kupffer cells, and the sinusoidal cells which line the spleen. At 12 months old, vacuolar change is observed in the visceral epithelial cells of glomeruli and cells at the base of heart valves but it is not present in parenchymal cells such as hepatocytes and renal tubular epithelial cells. Lysosomal storage of GAGs is seen in hippocampal and neocortical neurons, meningeal cells. Keratan sulfate (KS) and chondroitin-6-sulfate (C6S) is increased in the corneal epithelial cells of this mouse model compared to wild type, however no skeletal indications become evident in the mouse model. Additionally, a mouse model for MPS IVA which is tolerant to human GALNS has also been described (see, e.g., Tomatsu et al., 2005, Hum Mol Genet 14(22):3321-3335). See Examples in Section 7 for exemplary assays to assess the hGALNS expression from an rAAV described herein and its efficacy.

According to some embodiments, the methods include gene therapy vectors, e.g. the combination of regulatory elements and transgenes that provide increased expression of a functional hGALNS protein. Such expression may be measured 1) by several protein (hGALNS) determination assays known to the skilled person, not limited to sandwich ELISA, Western Blot, histological staining, and liquid chromatography tandem mass spectrometry (LC-MS/MS); 2) by several protein activity assays, such as enzymatic assays or functional assays; and/or 3) by several substrate detection assays, not limited to keratan sulfate (KS), glycosaminoglycans (CAG), and/or chondroitin-6-sulfate (C6S) detection, and be determined as efficacious and suitable for human treatment (Hintze, J. P. et al, Biomarker Insights 2011:6 69-78). Assessment of the quantitative and functional properties of hGALNS using such in vitro and in vivo cellular, blood and tissue studies have been shown to correlate to the efficacy of certain therapies (Hintze, J. P. et al, 2011, supra), and were utilized to evaluate response to gene therapy treatment of MPS IVA with the vectors described herein.

The invention thus provides methods and gene therapy vectors that increase intracellular hGALNS enzyme activity in tissue cells, e.g. including hepatic, muscle, white blood cells, kidney, lung, spleen cardiac, bone, or cartilage cells of the subject to levels compared to wild-type levels, or that increase intracellular hGALNS enzyme activity to about 2-fold wild-type hGALNS activity levels, or about 5-fold wild-type hGALNS activity levels, about 10-fold wild-type hGALNS activity levels, about 25-fold wild-type hGALNS activity levels, about 40-fold wild-type hGALNS activity levels, about 50-fold wild-type hGALNS activity levels, about 60-fold wild-type hGALNS activity levels, about 70-fold wild-type hGALNS activity levels, about 75-fold wild-type hGALNS activity levels, about 80-fold wild-type hGALNS activity levels, about 85-fold wild-type hGALNS activity levels, about 90-fold wild-type hGALNS activity levels, about 95-fold wild-type hGALNS activity levels, or about 100-fold wild-type hGALNS activity levels, as measured by a hGALNS enzymatic activity assay, e.g. using an assay format as described in Examples 2, 3 and 8 herein, or a substantially similar assay. In some embodiments, the gene therapy provides a method of increasing hGALNS activity levels in the subject two weeks after administration of the gene therapy as compared to the levels prior administration or the average levels in the untreated subjects. In some embodiments, the gene therapy provides a method of increasing hGALNS activity levels in the subject two weeks after administration of the gene therapy. In some embodiments, the gene therapy provides a method of increasing hGALNS activity levels in blood or tissues, for example liver, muscle, kidney, lung, spleen, heart, bone, or cartilage of the subject two weeks after administration of the gene therapy. In some embodiments, the increase in hGALNS activity levels in the subject is measured ten weeks after administration of the gene therapy.

The invention also provides methods and gene therapy vectors that reduce blood (e.g. plasma or serum) levels or tissue levels of KS in the subject to levels compared to the levels of KS in untreated wild-type subjects, or that reduce KS levels to about 1.1-fold wild-type KS levels, or about 1.2-fold wild-type KS levels, about 1.3-fold wild-type KS levels, about 1.4-fold wild-type KS levels, about 1.5-fold wild-type KS levels, about 1.6-fold wild-type KS levels, about 1.7-fold wild-type KS levels, about 1.8-fold wild-type KS levels, about 1.9-fold wild-type KS levels, about 2-fold wild-type KS levels, about 2.5-fold wild-type KS levels, about 3-fold wild-type KS levels, about 3.5-fold wild-type KS levels, or about 4-fold wild-type KS levels, as measured by a KS assay, e.g. using an assay format as described in Examples 2, 3 and 8 herein, or a substantially similar assay. In some embodiments, the gene therapy provides a method of reducing KS levels in the subject two weeks after administration of the gene therapy. In some embodiments, the gene therapy provides a method of reducing tissue levels of KS in the subject two weeks after administration of the gene therapy. In some embodiments, the KS assay comprises measurement of mono-sulfated KS in blood or tissue, and the gene therapy provides a method of reducing mono-sulfated KS levels in the subject two weeks after administration of the gene therapy.

6.3 Methods for Treatment

Provided herein are methods for treating a human subject diagnosed with MPS IVA.

In one aspect, the method comprises administering to the human subject an rAAV described herein or a pharmaceutical composition described herein.

In another aspect, the method comprises delivering to the bone, cartilage, ligament, meniscus, growth plate, liver, spleen, lung, kidney, trachea, heart muscle, and/or heart valve (e.g., delivering to the bone and/or cartilage) of said human subject a therapeutically effective amount of a transgene, such as the transgene encoding a fusion protein that is hGALNS fused to an acidic oligopeptide, by administering to the human subject an rAAV provided herein. In a specific embodiment, said hGALNS is glycosylated with mannose-6-phosphate by having been produced in and secreted from a liver cell.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of hGALNS that is glycosylated with mannose-6-phosphate by having been produced in and secreted from a liver cell, by administering to the human subject an rAAV provided herein.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of a fusion protein that is hGALNS fused to an acidic oligopeptide (such as an acidic oligopeptide described in Section 6.1.2 (b), for example, D8), wherein the fusion protein is produced from an rAAV genome. The rAAV genome may comprise an hGALNS expression cassette as described in Section 6.1.2.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of a fusion protein that is hGALNS fused to an acidic oligopeptide (such as an acidic oligopeptide described in Section 6.1.2 (b), for example, D8), wherein the fusion protein is produced from an rAAV genome and is glycosylated with mannose-6-phosphate by having been produced in and secreted from a liver cell. The rAAV genome may comprise an hGALNS expression cassette as described in Section 6.1.2. In a preferred embodiment, the rAAV genome comprises a nucleotide sequence encoding a liver-specific promoter, wherein the nucleotide sequence encoding the liver-specific promoter is operably linked to a nucleotide sequence encoding the fusion protein. In a preferred embodiment, the liver-specific promoter is a TBG promoter. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:13. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:14. In certain embodiments, the liver-specific promoter comprises a nucleotide sequence having at least 80%, 85%, 90%, 91%, 92%, 93%, 94%, 95%, 96%, 97%, 98%, 99% or 100% sequence identity to SEQ ID NO:15. In certain embodiments, the liver-specific promoter is SEQ ID NO:13. In certain embodiments, the liver-specific promoter is SEQ ID NO:14. In certain embodiments, the liver-specific promoter is SEQ ID NO:15.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of a fusion protein that is hGALNS fused to an acidic oligopeptide (such as an acidic oligopeptide described in Section 6.1.2 (b), for example, D8), wherein the fusion protein is produced from an rAAV genome and is glycosylated with mannose-6-phosphate by having been produced in and secreted from a liver cell. The rAAV genome may comprise an hGALNS expression cassette as described in Section 6.1.2. In a preferred embodiment, the rAAV genome comprises a nucleotide sequence encoding a liver- and muscle-specific promoter, wherein the nucleotide sequence encoding the liver- and muscle-specific promoter is operably linked to a nucleotide sequence encoding the fusion protein. In certain embodiments, the liver- and muscle-promoter comprises a nucleotide sequence having at least 80%, 85%, 90%, 91%, 92%, 93%, 94%, 95%, 96%, 97%, 98%, 99% or 100% sequence identity to SEQ ID NO:16. In certain embodiments, the promoter is SEQ ID NO:16.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of a fusion protein that is hGALNS fused to an acidic oligopeptide (such as an acidic oligopeptide described in Section 6.1.2 (b), for example, D8), wherein the fusion protein is produced from an rAAV genome and is glycosylated with mannose-6-phosphate by having been produced in and secreted from a liver cell. The rAAV genome may comprise an hGALNS expression cassette as described in Section 6.1.2. In a preferred embodiment, the rAAV genome comprises a nucleotide sequence encoding a promoter, wherein the nucleotide sequence encoding the promoter is operably linked to a nucleotide sequence encoding the fusion protein. In certain embodiments, the promoter is a CAG promoter.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of hGALNS that is produced from an rAAV genome and is glycosylated with mannose-6-phosphate by having been produced in and secreted from a liver cell. The rAAV genome may comprise an hGALNS expression cassette as described in Section 6.1.2. In a preferred embodiment, the rAAV genome comprises a nucleotide sequence encoding a liver-specific promoter, wherein the nucleotide sequence encoding the liver-specific promoter is operably linked to a nucleotide sequence encoding hGALNS. In a preferred embodiment, the liver-specific promoter is a TBG promoter.

In another aspect, the method comprises delivering to the bone, cartilage, ligament, growth plate, meniscus, liver, spleen, lung, kidney, trachea, heart muscle, and/or heart valve (e.g., delivering to the bone and/or cartilage) of said human subject a therapeutically effective amount of hGALNS that is produced from an rAAV genome and is glycosylated with mannose-6-phosphate by having been produced in and secreted from a liver cell. The rAAV genome may comprise an hGALNS expression cassette as described in Section 6.1.2. In a preferred embodiment, the rAAV genome comprises a nucleotide sequence encoding a promoter, wherein the nucleotide sequence encoding the promoter is operably linked to a nucleotide sequence encoding hGALNS. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:13. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:14. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:15. In certain embodiments, the promoter comprises a nucleotide sequence having at least 80%, 85%, 90%, 91%, 92%, 93%, 94%, 95%, 96%, 97%, 98%, 99% or 100% sequence identity to SEQ ID NO:16. In certain embodiments, the promoter is SEQ ID NO:13. In certain embodiments, the promoter is SEQ ID NO:14. In certain embodiments, the promoter is SEQ ID NO:15. In certain embodiments, the promoter is SEQ ID NO:16.

In various embodiments of the methods of treating described herein, the rAAV or rAAV genome comprises one or more components derived from one or more serotypes of AAV. In certain embodiments, the rAAV or rAAV genome comprises one or more components derived from one or more of AAV1, AAV2, AAV3, AAV4, AAV5, AAV6, AAV7, AAV8, AAV9, AAVrh10, or AAV11. In a certain embodiment, the rAAV or rAAV genome comprises one or more components from one or more of AAV8, AAV9, AAV10, or AAV11 serotypes. In a preferred embodiment, the rAAV or rAAV genome comprises one or more components from the AAV8 serotype. Nucleic acid sequences of AAV components and methods of making recombinant AAV and AAV capsids are described, for example, in U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety.

In various embodiments of the methods of treating described herein, the step of delivering to the bone, cartilage, ligament, meniscus, growth plate, liver, spleen, lung, kidney, trachea, heart muscle, and/or heart valve is a step of delivering to (a) the bone and/or cartilage, and (b) ligament, meniscus, growth plate, liver, spleen, lung, kidney, trachea, heart muscle, and/or heart valve.

6.3.1 Target Patient Populations

According to the invention, the human subject or patient is an individual who has been diagnosed with MPS IVA (Morquio A syndrome). In specific embodiments, the patient has one or more of the following symptoms of MPS IVA: abnormal heart valve morphology, carious teeth, cervical myelopathy, cervical subluxation, chondroitin sulfate excretion in urine, coarse facial features, constricted iliac wings, coxa valga, disproportionate short-trunk, short stature, epiphyseal deformities of tubular bones, flaring of rib cage, genu valgum, grayish enamel, hearing impairment, hepatomegaly, hyperlordosis, hypoplasia of the odontoid process, inguinal hernia, joint laxity, juvenile onset, keratin sulfate excretion in urine, kyphosis, large elbow, mandibular prognathia, metaphyseal widening, opacification of the corneal stroma, osteoporosis, ovoid vertebral bodies, platyspondyly, pointed proximal second through fifth metacarpals, prominent sternum, recurrent upper respiratory tract infection, restrictive ventilator defect, scoliosis, ulnar deviation of the wrist, wide mouth, and widely spaced teeth.

In certain embodiments, the patient has been identified as responsive to treatment with hGALNS.

In a specific embodiment, the patient has a severe and rapidly progressive, early-onset form of MPS IVA. In another specific embodiment, the patient has a slowly progressive, later-onset form of MPS IVA.

In a specific embodiment, the patient is an adult (at least age 16). In another specific embodiment, the patient is an adolescent (age 12-15). In another specific embodiment, the patient is a child (under age 12).

In a specific embodiment, the patient is under age 6.

6.3.2 Administration and Dosage

The route of administration of an rAAV described herein and the amount of rAAV to be administered to the human patient can be determined based on the severity of the disease, condition of the human patient and the knowledge of the treating physician.

(a) Therapeutic Dosage

In preferred embodiments, the amount of rAAV administered to a human subject is sufficient to supply a therapeutically effective amount of hGALNS to the affected tissue (bone, cartilage, ligament, meniscus, and/or heart valve).

In certain embodiments, dosages are measured by the number of genome copies administered to the human subject via rAAVs provided herein. In a specific embodiment, $1 \times 10^{10}$ to $1 \times 10^{16}$ genome copies are administered. In another specific embodiment, $1 \times 10^{10}$ to $1 \times 10^{11}$ genome copies are administered. In another specific embodiment, $1 \times 10^{11}$ to $1 \times 10^{12}$ genome copies are administered. In another specific embodiment, $1 \times 10^{12}$ to $1 \times 10^{13}$ genome copies are administered. In another specific embodiment, $1 \times 10^{13}$ to $1 \times 10^{14}$ genome copies are administered. In another specific embodiment, $1 \times 10^{14}$ to $1 \times 10^{15}$ genome copies are administered. In another specific embodiment, $1 \times 10^{15}$ to $1 \times 10^{16}$ genome copies are administered.

Without being bound by theory, at least 10% of the rAAV administered infects the liver of the human subject to which is was administered. In certain embodiments, 10-15%, 15-20%, 20-25%, 25-35%, 30-40%, 35-45%, 40-50%, 45-55%, 50-60%, 55-65%, 60-70%, 65-75%, 70-80%, 75-85%, 80-90%, 85-95%, or 90-100% of the rAAV administered infects the liver of the human subject.

Without being bound by theory, at least 10% of the hGALNS enzyme expressed from the rAAV viral genome is expressed in liver cells. In certain embodiments, 10-15%, 15-20%, 20-25%, 25-35%, 30-40%, 35-45%, 40-50%, 45-55%, 50-60%, 55-65%, 60-70%, 65-75%, 70-80%, 75-85%, 80-90%, 85-95%, or 90-100% of the hGALNS enzyme expressed from the rAAV viral genome is expressed in liver cells.

Without being bound by theory, at least 10% of the hGALNS enzyme expressed from the rAAV viral genome reaches the affected tissue (e.g., bone) of the human subject. In certain embodiments, 10-15%, 15-20%, 20-25%, 25-35%, 30-40%, 35-45%, 40-50%, 45-55%, 50-60%, 55-65%, 60-70%, 65-75%, 70-80%, 75-85%, 80-90%, 85-95%, or 90-100% of the hGALNS enzyme expressed from the rAAV viral genome reaches the affected tissue (e.g., bone) of the human subject.

Without being bound by theory, at least 10% of the hGALNS enzyme expressed from the rAAV viral genome is glycosylated by having been expressed in and secreted from the liver cells. In certain embodiments, 10-15%, 15-20%, 20-25%, 25-35%, 30-40%, 35-45%, 40-50%, 45-55%, 50-60%, 55-65%, 60-70%, 65-75%, 70-80%, 75-85%, 80-90%, 85-95%, or 90-100% of the hGALNS enzyme expressed from the rAAV viral genome is glycosylated by having been expressed in and secreted from the liver cells.

Without being bound by theory, at least 10% of the liver-cell glycosylated hGALNS enzyme can reach the affected tissue (e.g., bone) of the human subject. In certain embodiments, 10-15%, 15-20%, 20-25%, 25-35%, 30-40%, 35-45%, 40-50%, 45-55%, 50-60%, 55-65%, 60-70%, 65-75%, 70-80%, 75-85%, 80-90%, 85-95%, or 90-100% of the liver-cell glycosylated hGALNS enzyme can reach the affected tissue (e.g., bone) of the human subject.

(b) Routes of Administration

In a specific embodiment, the rAAV can be present in a pharmaceutical composition in order to be administered to the human subject (see Section 6.1.3).

The rAAV can be administered, for example, by parenteral, subcutaneous, intramuscular, intravenous, intraperitoneal, intranasal, intrathecal, or transdermal administration. In a specific embodiment, the rAAV is administered by intravenous administration.

6.4 Combination Therapies 6.4.1 Co-Therapy with Immune Suppression

While the delivery of rAAV should minimize immune reactions, the clearest potential source of toxicity related to gene therapy is generating immunity against the expressed hGALNS protein in human subjects who are genetically deficient for hGALNS and, therefore, potentially not tolerant of the enzyme or the rAAV. Thus, in a certain embodiment, it is advisable to co-treat the patient with immune suppression therapy—especially when treating patients with severe disease who have close to zero levels of hGALNS. Immune suppression therapies involving a regimen of tacrolimus or rapamycin (sirolimus) in combination with mycophenolic acid, or other immune suppression regimens used in tissue transplantation procedures can be employed. Such immune suppression treatment may be administered during the course of gene therapy, and in certain embodiments, pre-treatment with immune suppression therapy may be preferred. Immune suppression therapy can be continued subsequent to the gene therapy treatment, based on the judgment of the treating physician, and may thereafter be withdrawn when immune tolerance is induced; e.g., after 180 days.

In certain embodiments, the methods of treatment provided herein further comprise administering to the human patient an immune suppression regimen comprising prednisolone, mycophenolic acid, and tacrolimus. In certain embodiments, the methods of treatment provided herein further comprise administering to the human patient an immune suppression regimen comprising prednisolone, mycophenolic acid, and rapamycin (sirolimus). In certain embodiments, the methods of treatment provided herein further comprise administering to the human patient an immune suppression regimen that does not comprise tacrolimus. In certain embodiments, the methods of treatment provided herein further comprise administering to the human patient an immune suppression regimen comprising one or more corticosteroids such as methylprednisolone and/or prednisolone, as well as tacrolimus and/or sirolimus. In certain embodiments, the immune suppression therapy comprises administering a combination of (a) tacrolimus and mycophenolic acid, or (b) rapamycin and mycophenolic acid to said subject before or concurrently with the hGALNS treatment and continuing thereafter. In certain embodiments, the immune suppression therapy is withdrawn after 180 days. In certain embodiments, the immune suppression therapy is withdrawn after 30, 60, 90, 120, 150, or 180 days.

6.4.2 Co-Therapy with Other Treatments

Combination therapy involving administration of the rAAV as described herein to the human subject accompanied by administration of other available treatments are encompassed by the methods of the described embodiment. The additional treatments may be administered before, concurrently or subsequent to the gene therapy treatment. Available treatments for MPS IVA that could be combined with the gene therapy of the invention include but are not limited to enzyme replacement therapy (ERT) and/or HSCT therapy. In a specific embodiment, ERT can be performed using the D8-hGALNS enzyme produced in human cell lines by recombinant DNA technology. Human cell lines that can be used for such enzyme production include but are not limited to HT-22, SK-N-MC, HCN-1A, HCN-2, NT2, SH-SY5y, hNSC11, ReNcell VM, human embryonic kidney 293 cells (HEK293), HEK293-T, fibrosarcoma HT-1080, HKB-11, CAP, HuH-7, and retinal cell lines, PER.C6, or RPE (see, e.g., Dumont et al., 2016, Critical Rev in Biotech 36(6): 1110-1122 "Human cell lines for biopharmaceutical manufacturing: history, status, and future perspectives" which is incorporated by reference in its entirety.

6.5 Disease Markers and Treatment Assessment

In certain embodiments, efficacy of a treatment method as described herein may be monitored by measuring reductions in biomarkers of disease (such as GAG, KS, and C6S storage) and/or increase in hGALNS enzyme activity in bone, cartilage, ligament, meniscus, heart valve, urine, and/or serum. Signs of inflammation and other safety events may also be monitored.

In certain embodiments, efficacy of a treatment method as described herein is monitored by measuring the level of a disease biomarker in the patient. In certain embodiments, the level of the disease biomarker is measured in the serum of the patient. In certain embodiments, the level of the disease biomarker is measured in the urine of the patient. In certain embodiments, the disease biomarker is GAG. In certain embodiments, the disease biomarker is KS. In certain embodiments, the disease biomarker is C6S. In certain embodiments, the disease biomarker is hGALNS enzyme activity.

In certain embodiments, efficacy of a treatment method as described herein can be monitored by measuring physical characteristics associated with lysosomal storage deficiency in the patient. In certain embodiments, the physical characteristics can be storage lesions. In certain embodiments, the physical characteristic can be short neck and trunk. In certain embodiments, the physical characteristic can be pectus carinatum. In certain embodiments, the physical characteristic can be laxity of joints. In certain embodiments, the physical characteristic can be kyphoscoliosis. In certain embodiments, the physical characteristic can be tracheal obstruction. In certain embodiments, the physical characteristic can be spinal cord compression. In certain embodiments, the physical characteristic can be hearing impairment. In certain embodiments, the physical characteristic can be corneal opacity. In certain embodiments, the physical characteristics can be bone and joint deformities. In certain embodiments, the physical characteristic can be cardiac valve disease. In certain embodiments, the physical characteristics can be restrictive/obstructive airway. Such physical characteristics may be measured by any method known to one of skill in the art.

7. EXAMPLES

Certain embodiments provided herein are illustrated by the following non-limiting examples.

7.1 Example 1. Design of Plasmids Encoding rAAV Genomes and In Vitro Transfection Assays To generate recombinant AAV genomes containing an hGALNS expression cassette, which were to be packaged in AAV8 capsids, plasmids encoding the recombinant AAV genomes were designed. Four plasmids were designed and generated: TBG-hGALNS (the hGALNS expression cassette contains a nucleotide sequence encoding hGALNS, whose expression is under the regulation of the liver-specific TBG promoter), TBG-hGALNS CoOpt (the hGALNS expression cassette contains a codon optimized nucleotide sequence encoding hGALNS, whose expression is under the regulation of the liver-specific TBG promoter), TBG-D8-hGALNS (the hGALNS expression cassette contains a nucleotide sequence encoding a fusion protein that is hGALNS fused to D8, whose regulation is under the regulation of the liver-specific TBG promoter), or TBG-D8-hGALNS CoOpt (the hGALNS expression cassette contains a codon optimized nucleotide sequence encoding a fusion protein that is hGALNS fused to D8, whose regulation is under the regulation of the liver-specific TBG promoter). The resulting rAAVs fall into two categories: (a) rAAVs comprising a recombinant AAV genome that contains an hGALNS expression cassette flanked by AAV-inverted terminal repeats (ITRs), wherein the hGALNS expression cassette comprises an hGALNS cDNA sequence operably linked to the liver-specific TBG promoter sequence and a nucleotide sequence encoding a poly A site; and (b) rAAVs comprising a recombinant AAV genome that contains an hGALNS expression cassette flanked by AAV-inverted terminal repeats (ITRs), wherein the hGALNS expression cassette comprises a D8-hGALNS cDNA sequence operably linked to the liver-specific TBG promoter sequence and a nucleotide sequence encoding a poly A site (FIG. 1). D8 is a bone-targeting aspartic acid octapeptide.

Figure 2A:
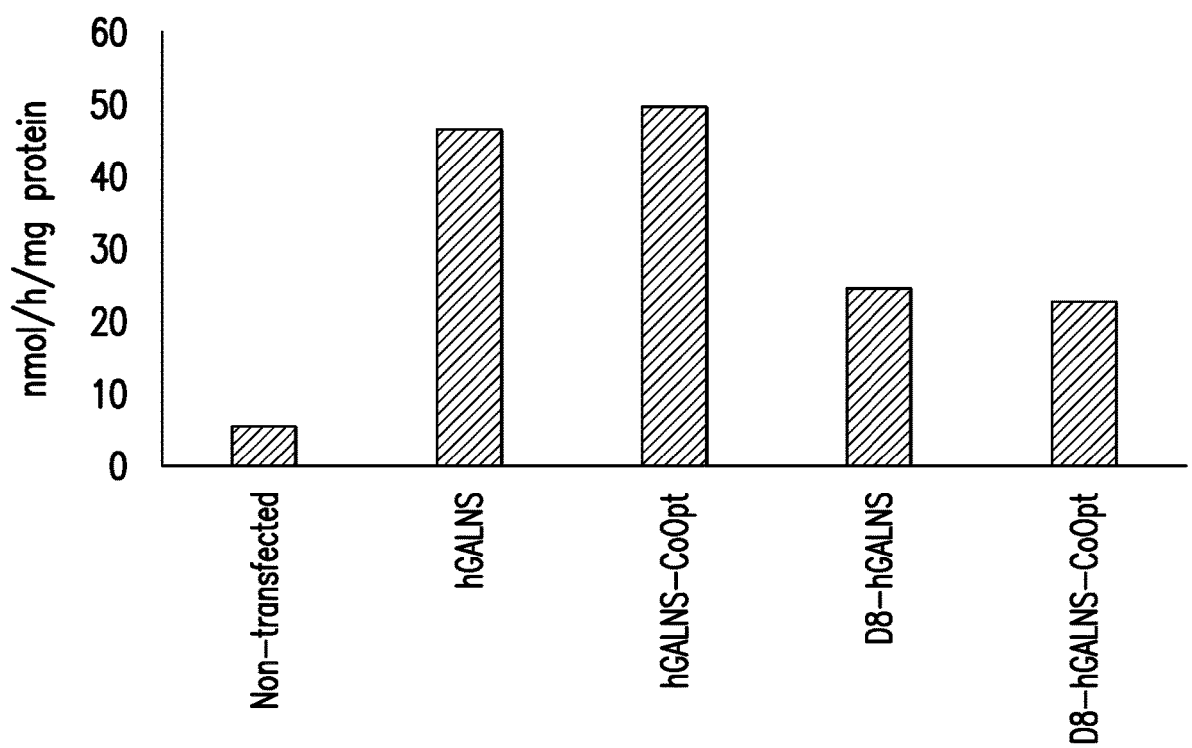
Figure 2B:
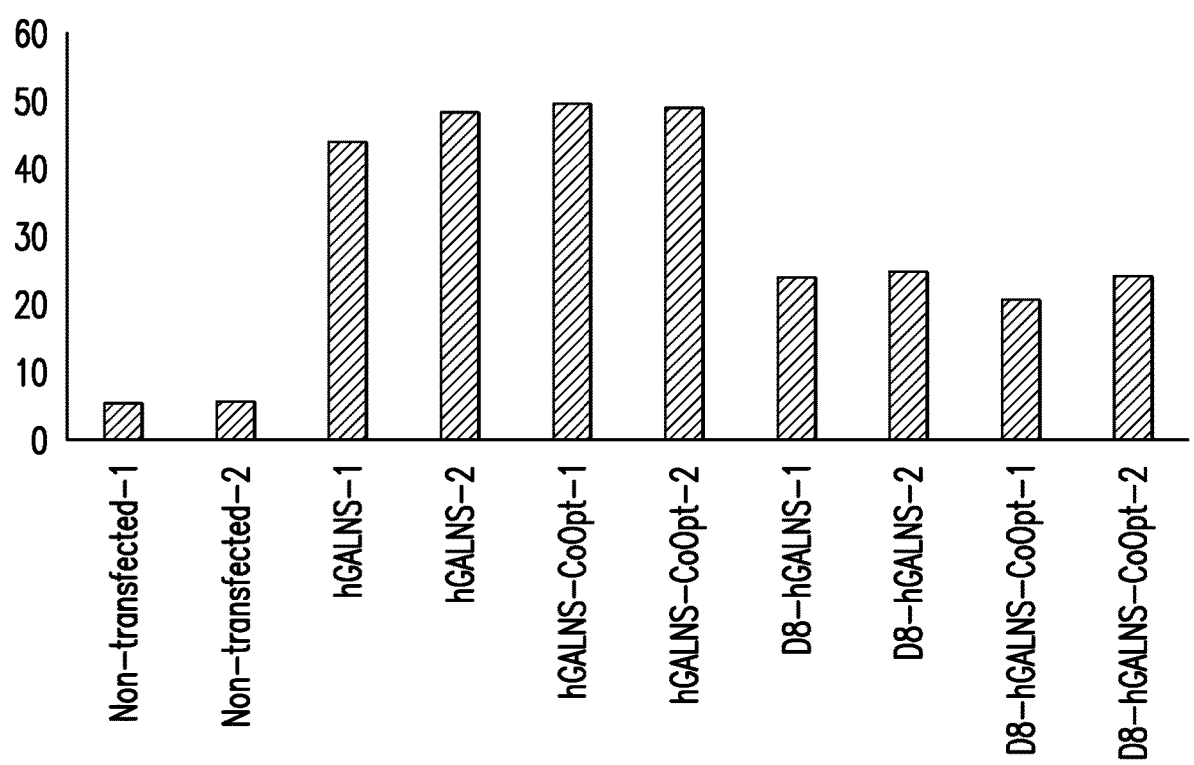
Figure 2C:
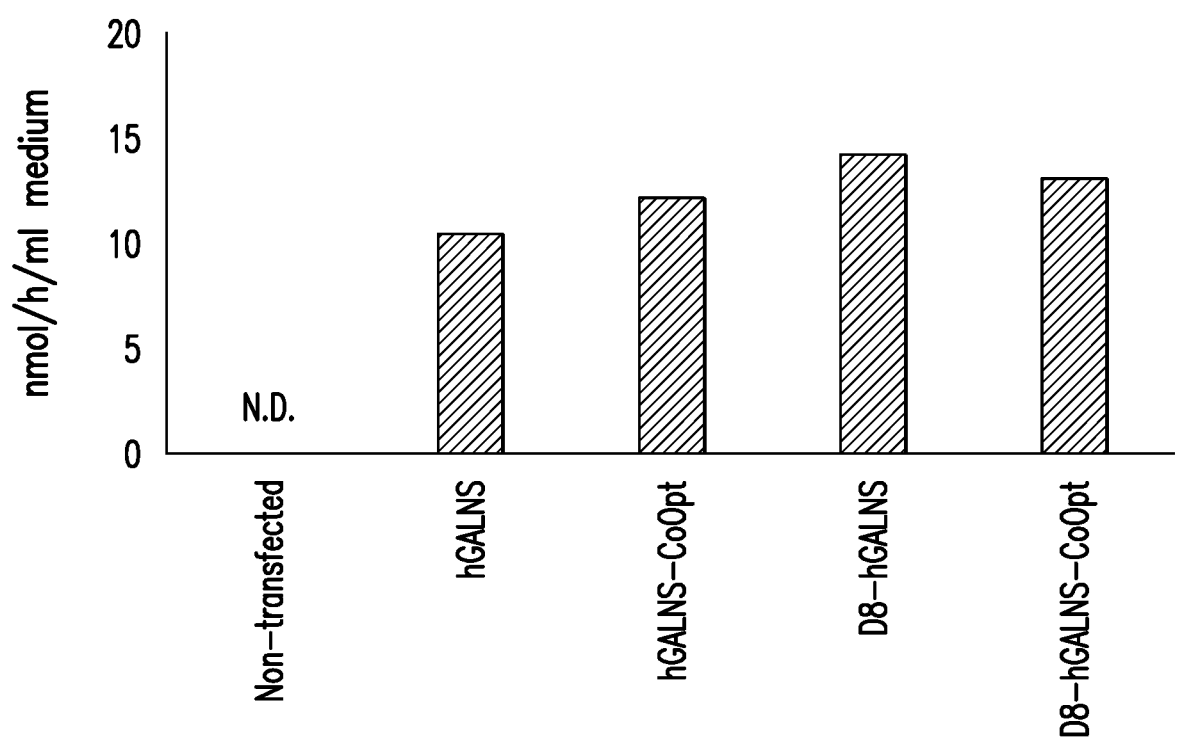
Figure 2D:
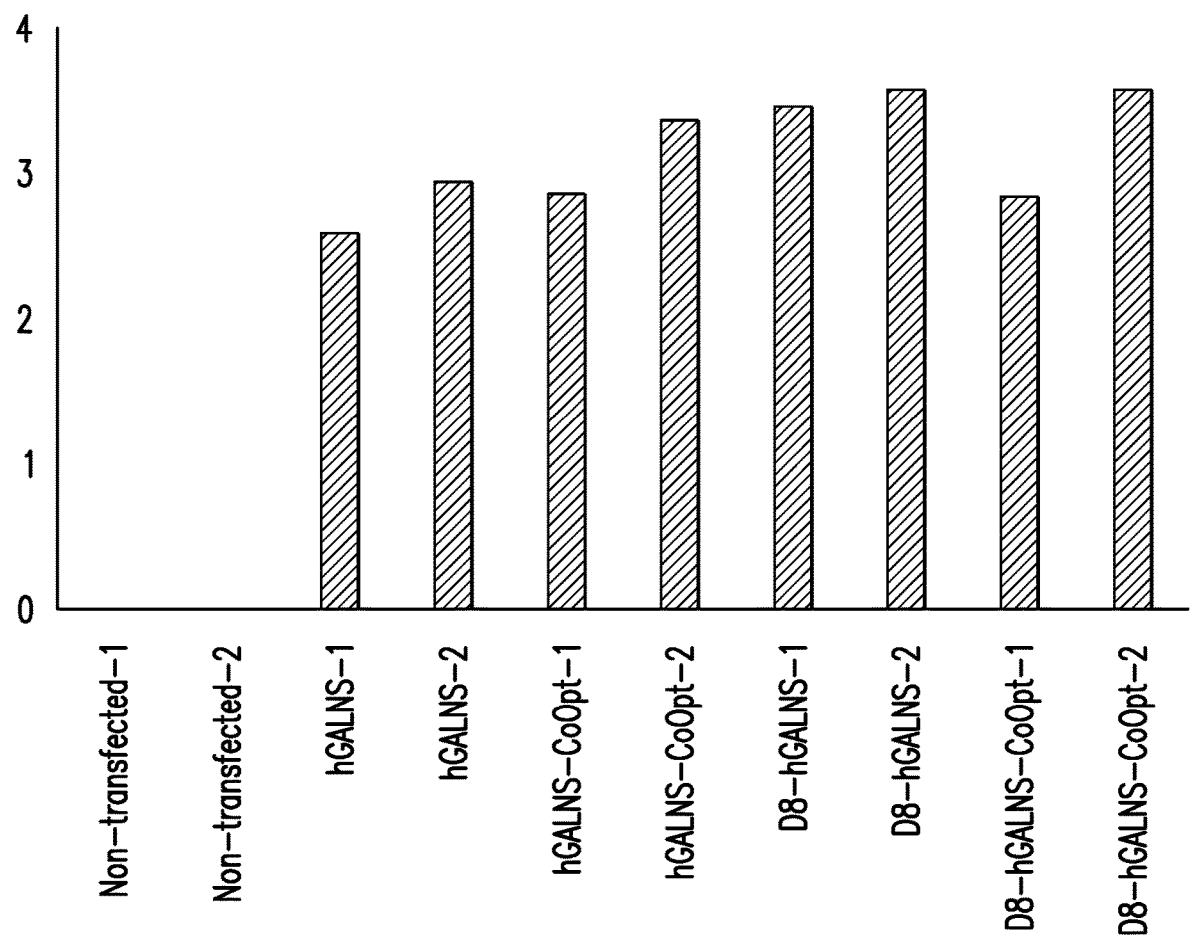

Next, human hepatocellular carcinoma (HuH7) cells were transfected with one of the four plasmids using Lipofectamine-3000 protocol to test expression of hGALNS in vitro. After a 48 hour incubation, the transfected HuH7 cells and the supernatant were collected and analyzed for GALNS enzyme activity in cell pellets and media. Huh7 cells transfected with a GFP plasmid were used as a control. Intracellular hGALNS enzyme activity was increased equally by transfection with the TBG-hGALNS or TBG-hGALNS CoOpt plasmid (FIGS. 2A and 2B). Intracellular enzyme activity was also increased after transfection with the TBG-D8-hGALNS or TBG-D8-hGALNS CoOpt plasmid, although to a lesser extent than transfection with the TBG-hGALNS or TBG-hGALNS CoOpt plasmid (FIGS. 2A and 2B). Enzyme activity detected in the cell media was increased by the transfection of any of the plasmids (FIGS. 2C and 2D).

Similarly, human liver carcinoma cells (HepG2) were transfected with one of the four plasmids using Lipofectamine-3000 protocol to test expression of hGALNS in vitro (FIG. 3). After a 72 hour incubation, the transfected HepG2 cells were collected and analyzed for hGALNS enzyme activity in cell pellets. Intracellular hGALNS enzyme activity was increased by transfection with the TBG-hGALNS or TBG-hGALNS CoOpt plasmid as compared to transfection with the control plasmid. Transfection with the TBG-D8-hGALNS or TBG-D8-hGALNS CoOpt plasmid did not lead to increased hGALNS activity as compared to the control plasmid.

7.2 Example 2. In Vivo Administration of rAAV to MPS IVA Knock Out (Galns −/−) Mice rAAV8 were generated that comprise viral genomes capable of expressing native human GALNS (hGALNS) under the liver-specific promoter TBG (AAV8-TBG-hGALNS, also labeled as AAV8-hGALNS in some figures) or hGALNS with an aspartic acid octapeptide (D8) under the liver-specific promoter (AAV8-TBG-D8-hGALNS, also labeled as AAV8-D8-hGALNS in some figures). The TBG-hGALNS CoOpt and TBG-D8-hGALNS CoOpt plasmids were used to generate the viral genomes respectively. The two types of viruses were each administered intravenously to 4-week-old MPS IVA knock-out (KO) mice and Mtol immunotolerant mice at a dose of $5 \times 10^{13}$ GC/kg body weight. KO mice have a targeted disruption of Exon 2 of mGALNS and have no detectable GALNS enzyme activity. Mtol mice are tolerized to human GALNS protein. Untreated KO mice and wild-type (WT) mice served as controls. These mice were monitored for 14 weeks post-injection. Blood was collected biweekly and assayed for hGALNS activity and keratan sulfate (KS). The schedule of rAAV administration, blood collection, GALNS enzyme assay, and KS assay is shown in FIG. 4. At necropsy, bone pathology was evaluated by histopathological analysis.

Figure 7A:
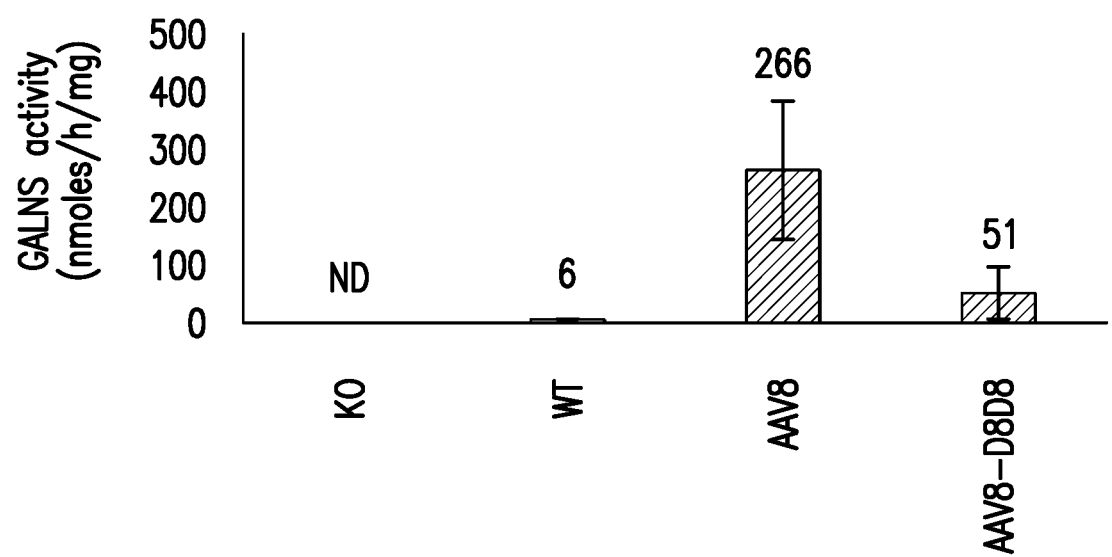
Figure 7B:
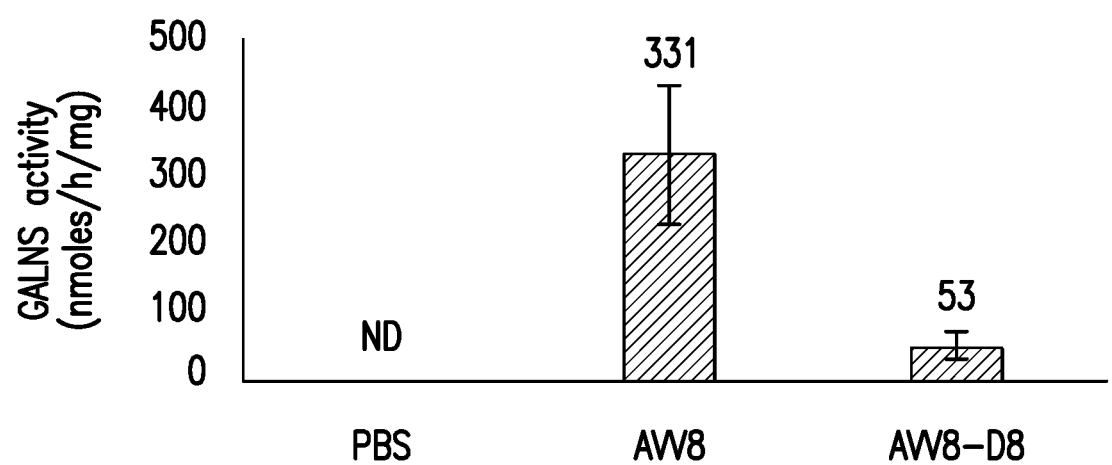
Figure 7C:
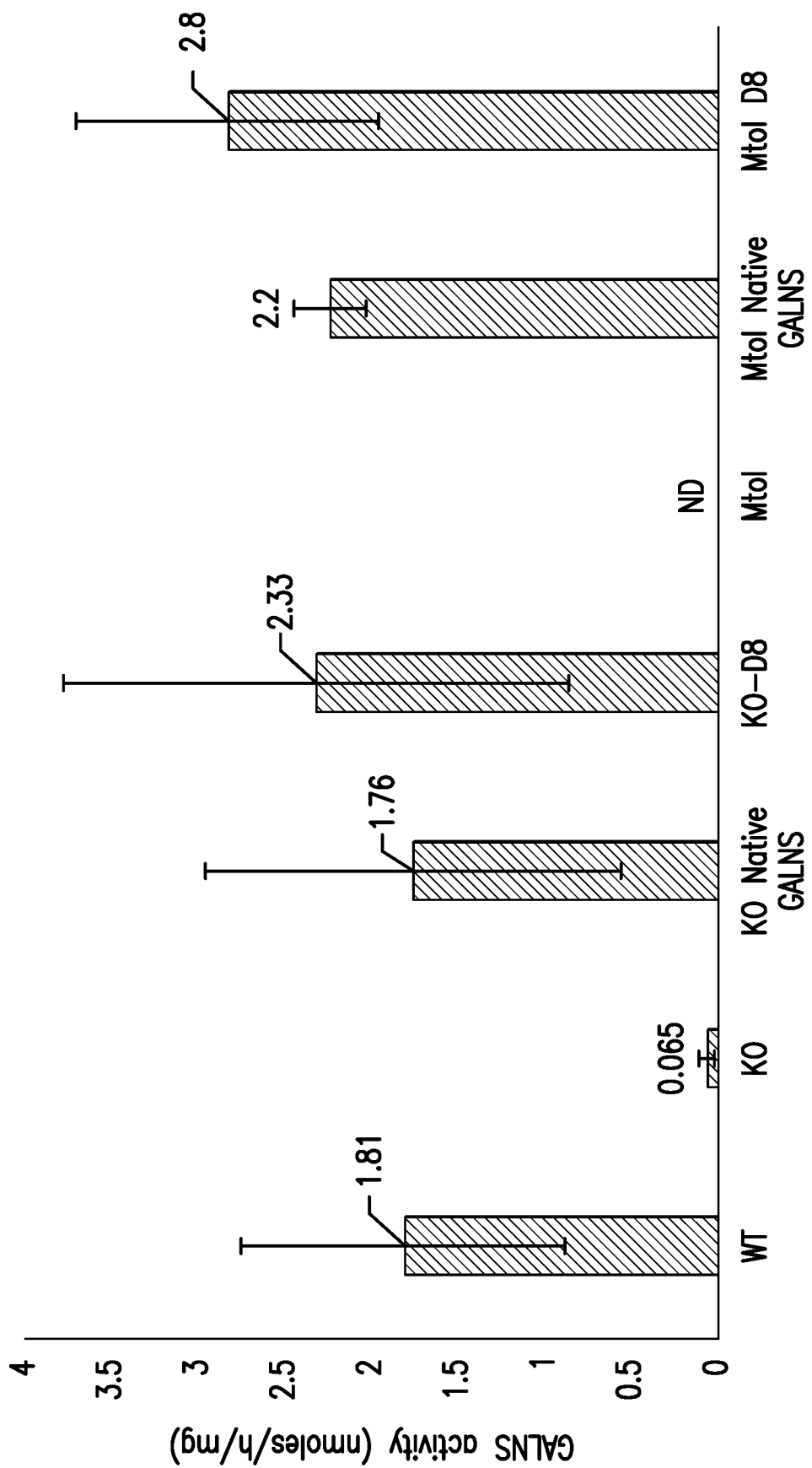

As seen in FIG. 5A, hGALNS enzyme activity increased in the white blood cells (WBCs) of rAAV-treated mice, reaching close to WT mice-levels 10 weeks after treatment. Two weeks after administration of rAAV, hGALNS enzyme activity in the plasma of all rAAV-treated mice was elevated on average 20-fold compared to levels in WT mice (ranging from 5-100 fold compared to levels in WT mice) (FIG. 5B). This increase was maintained throughout the 14 weeks monitoring period (FIG. 5B). Similar data is shown in FIG. 22. Plasma enzyme activity levels in Mtol mice treated with AAV8-TBG-D8-hGALNS were significantly higher than the levels in the mice treated with AAV8-TBG-hGALNS (FIG. 6), but enzyme activity levels of both treated groups were elevated above WT levels. Similar data is shown in FIG. 23.

hGALNS activity measured in the liver of KO (galns −/−) mice treated with AAV8-TBG-hGALNS or AAV8-TBG-D8-hGALNS was compared to the liver hGALNS activity of WT mice (FIG. 7A). The mice treated with AAV8-TBG-hGALNS had 40 times greater levels of hGALNS activity in the liver compared to WT levels, while mice treated with AAV8-TBG-D8-hGALNS had 8 times higher liver hGALNS activity than WT levels. hGALNS activities in liver of Mtol mice treated with AAV8-TBG-hGALNS or AAV8-TBG-D8-hGALNS were elevated over untreated Mtol mice (PBS-treated) (FIG. 7B). Mice treated with AAV8-TBG-hGALNS had 50 times greater levels of hGALNS activity in the liver compared with untreated mice, while mice treated with AAV8-TBG-D8-hGALNS had 8 times higher liver hGALNS activity than untreated Mtol mice. See FIG. 12A for more data regarding hGALNS activity levels measured in the liver of MPS IVA KO mice (galns −/−) and Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD).

hGALNS activity was also measured in the heart of (a) WT mice, (b) untreated MPS IVA KO (galns −/−) mice, (c) MPS IVA KO (galns −/−) mice treated with AAV8-TBG-hGALNS, (d) MPS IVA KO (galns −/−) mice treated with AAV8-TBG-D8-hGALNS, (e) untreated Mtol mice, (f) Mtol mice treated with AAV8-TBG-hGALNS, and (g) Mtol mice treated with AAV8-TBG-D8-hGALNS (FIG. 7C). For both MPS IVA KO (galns −/−) mice and Mtol mice, mice treated with AAV8-TBG-hGALNS and mice treated with AAV8-TBG-D8-hGALNS both had greater levels of hGALNS activity in the heart compared with untreated mice. See FIG. 13B for more data regarding hGALNS activity levels measured in the heart of MPS IVA KO mice (galns −/−) and Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD).

Figure 7D:
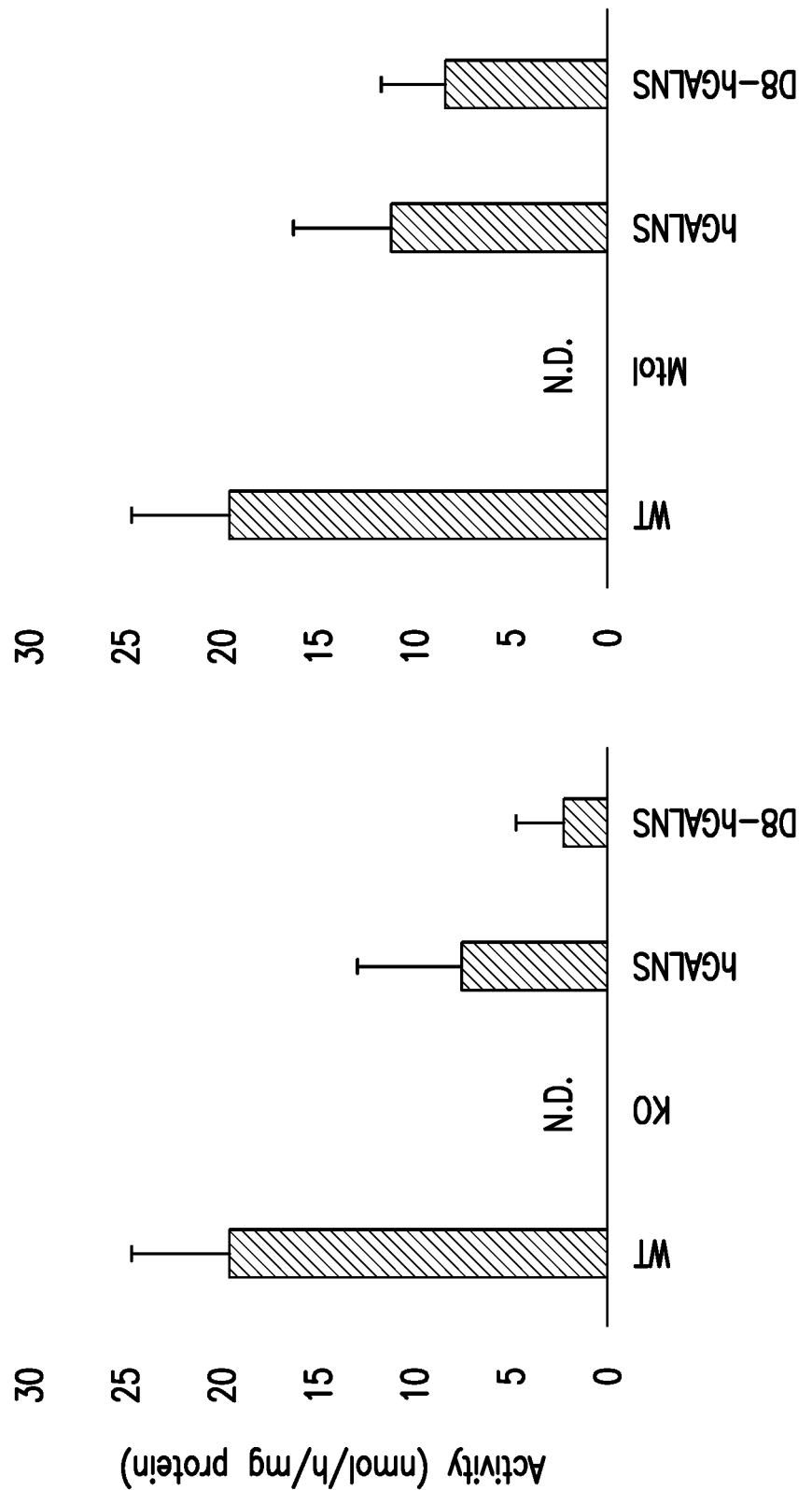

Similarly, hGALNS activity was measured in the bone of (a) WT mice, (b) untreated MPS IVA KO (galns −/−) mice, (c) MPS IVA KO (galns −/−) mice treated with AAV8-TBG-hGALNS, (d) MPS IVA KO (galns −/−) mice treated with AAV8-TBG-D8-hGALNS, (e) untreated Mtol mice, (f) Mtol mice treated with AAV8-TBG-hGALNS, and (g) Mtol mice treated with AAV8-TBG-D8-hGALNS (FIG. 7D). For both MPS IVA KO (galns −/−) mice and Mtol mice, mice treated with AAV8-TBG-hGALNS and mice treated with AAV8-TBG-D8-hGALNS both had greater levels of hGALNS activity in the bone compared with untreated mice. See FIG. 13A for more data regarding hGALNS activity levels measured in the bone of MPS IVA KO mice (galns −/−) and Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD).

In both MPS IVA KO (galns −/−) mice and Mtol mice, hGALNS activity levels in liver, heart and bone of treated mice were elevated after the delivery of AAV8-TBG-hGALNS or AAV8-TBG-D8-hGALNS vectors. In addition, there was a direct correlation between hGALNS enzyme activities in blood and bone.

hGALNS enzyme activity levels were also measured in the spleen of MPS IVA KO mice (galns −/−) and the spleen of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD) (FIG. 12B). For both MPS IVA KO (galns −/−) mice and Mtol mice, mice treated with AAV8-TBG-hGALNS and mice treated with AAV8-TBG-D8-hGALNS both had greater levels of hGALNS activity in the spleen compared with untreated mice.

In addition, hGALNS enzyme activity levels were also measured in the lung of MPS IVA KO mice (galns −/−) and the lung of Mtol mice, respectively, after administration with AAV8-TBG-hGALNS or AAV8-TBG-D8-hGALNS, as compared to untreated MPS IVA KO mice (galns −/−), untreated Mtol mice and wild type mice (n=3-8; mean±SD) (FIG. 12C). For both MPS IVA KO (galns −/−) mice and Mtol mice, mice treated with AAV8-TBG-hGALNS and mice treated with AAV8-TBG-D8-hGALNS both had greater levels of hGALNS activity in the lung compared with untreated mice.

Blood keratan sulfate (KS) levels were measured. In the KO (galns −/−) mice, rAAV treatment in both groups resulted in a reduction of mono-sulfated keratan sulfate (KS) levels in the plasma to WT levels two weeks after administration (FIG. 8 and FIG. 14). These reduced levels in the plasma of both rAAV-treated groups were maintained until necropsy at 12 weeks post-injection. In contrast, the KS levels in the plasma of the untreated KO mice did not decrease and remained elevated over the monitored time period. Administration of either of the rAAV in Mtol mice resulted in a reduction of mono-sulfated keratan sulfate (KS) levels in the plasma as compared to WT levels two weeks after treatment and the KS levels in the plasma were significantly reduced as compared to untreated Mtol mice (FIGS. 9A-9B and FIGS. 15A-15B). Blood diHS-0S levels, however, did not differ between the untreated, AAV8-TBG-hGALNS-treated, AAV8-TBG-D8-hGALNS-treated, and WT mice groups (FIG. 10).

Mono-sulfated KS levels were measured in the liver of MPS IVA KO mice (galns −/−), the liver of Mtol mice, and the lung of MPS IVA KO mice (galns −/−), respectively, treated with AAV8-TBG-hGALNS or AAV8-TBG-D8-hGALNS, as compared to untreated MPS IVA KO mice and untreated wild type mice (FIGS. 16A-16C). Administration of either of the rAAV resulted in a significant reduction of mono-sulfated KS in the liver and a significant reduction of mono-sulfated KS in the lung as compared to untreated mice. KS levels in liver and lung of MPS IVA KO mice (galns −/−) and Mtol mice were almost normalized after AAV vector administration.

Histo-pathological evaluation of the liver from the treated KO mice showed complete clearance of GAG storage in sinus lining cells and Kupffer cells.

Administration of AAV8-TBG-hGALNS and AAV8-TBG-D8-hGALNS maintained high levels of enzymatic activity in the plasma KO and Mtol mouse models throughout the monitoring period. This continuous presence of circulating enzyme reduced KS in plasma to WT levels which is a significant improvement over what has been achieved by ERT (Tomatsu et al., Human Molecular Genetics, 2008, 17(6): 815-824). While KS levels in the plasma were normalized two weeks post rAAV administration in both mouse models and for both AAV8-TBG-hGALNS and AAV8-TBG-D8-hGALNS, in previous studies where the KO mice were treated with ERT, the KS levels in the plasma were not normalized even after 12 weeks of weekly infusions (Tomatsu et al., Human Molecular Genetics, 2008, 17(6): 815-824). Additionally, the high enzyme levels combined with longer circulation time increased the penetration into bone and cartilage therapy thereby improving storage in these regions.

Mice were euthanized 12 weeks after rAAV treatment and tissues were collected and assessed for the storage of glycosaminoglycans (GAGs). Tissues were stained with toluidine blue. Bone pathology was evaluated by histopathological analysis and the pathology scores are presented in a graphical depiction for MPS IVA KO (galns −/−) mice (FIG. 11A). FIG. 11B shows staining images of the knee joints (MPS IVA KO (galns −/−) mice).

FIG. 11C shows 40× magnified staining images of femur articular cartilage for MPS IVA KO (galns −/−) mice. In the untreated mice (left panel), the superficial cells were disorganized and the chondrocytes were ballooned and vacuolated. Further, the column structure was distorted and disorganized. In contrast, the tissue of the MPS IVA KO (galns −/−) mice treated with either AAV8-TBG-hGALNS or AAV8-TBG-D8-hGALNS showed organized superficial cells, less vacuolated chondrocytes, and the maintenance of the column structure (right two panels). These aspects are shown in greater detail in FIGS. 11D-11F.

FIG. 11G shows 40× magnified staining images of femur growth plate of untreated or rAAV-treated MPS IVA KO (galns −/−) mice. In the untreated mice (left panel), the chondrocytes were vacuolated and the column structure was largely disorganized and distorted. The chondrocytes in mice treated with AAV8-TBG-hGALNS (middle panel) were also vacuolated but the column structure was only moderately distorted. In contrast, for the tissue of the MPS IVA KO (galns −/−) mice treated with AAV8-TBG-D8-hGALNS (right panel), the chondrocytes were moderately vacuolated and the column structure was more organized. These aspects are shown in greater detail in FIGS. 11H-11J. FIGS. 17A-17E also show 40× magnified staining images of femur growth plate in (A) wild type mice (all chondrocytes were non-vacuolated and column structure was well organized), (B) untreated MPS IVA KO mice (galns −/−) (all chondrocytes were vacuolated and column structure was largely disorganized and distorted), (C) untreated Mtol mice (all chondrocytes were vacuolated and column structure was largely disorganized and distorted), (D) AAV8-TBG-hGALNS treated Mtol mice (chondrocytes were moderately vacuolated but column structure was better), and (E) AAV8-TBG-D8-hGALNS treated Mtol mice (chondrocytes were moderately vacuolated but column structure was partially recovered).

Figure 18B:
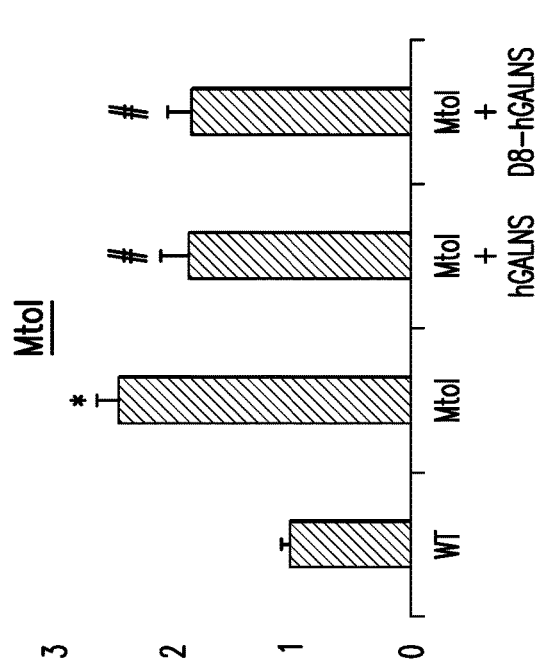
Figure 18D:
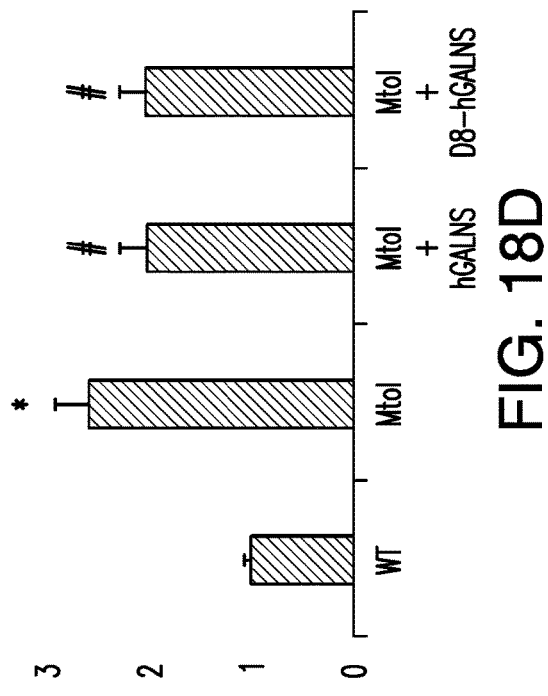
Figure 18A:
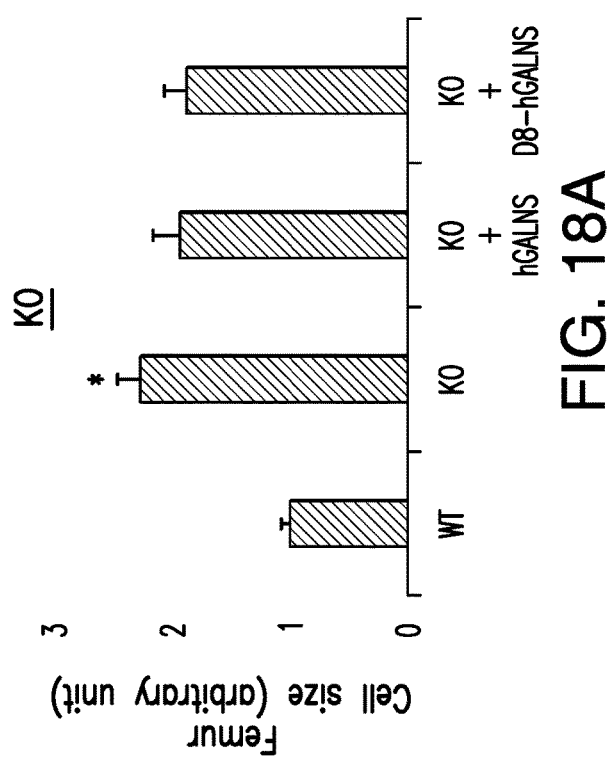
Figure 18C:
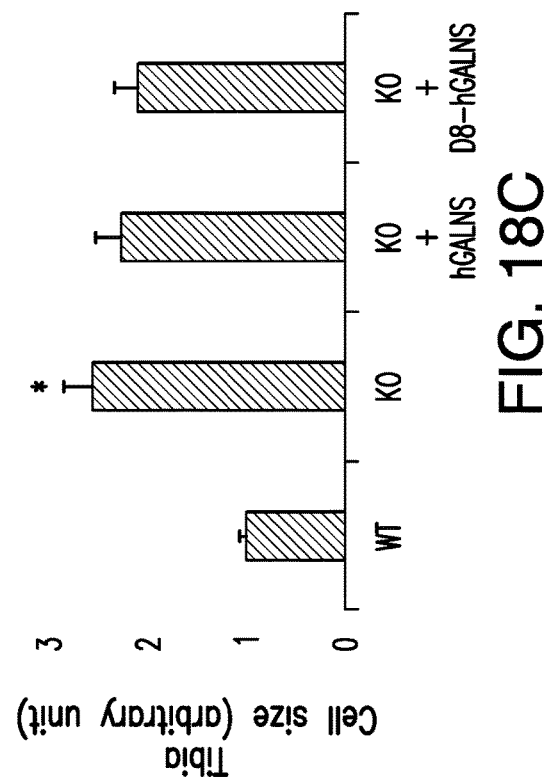

FIG. 18A shows the chondrocyte cell size measured in the femur and tibia growth plate of untreated wild type mice, untreated MPS IVA KO mice (galns −/−), AAV8-TBG-hGALNS treated MPS IVA KO mice (galns −/−), or AAV8-TBG-D8-hGALNS treated MPS IVA KO mice (galns −/−). FIG. 18B shows the chondrocyte cell size measured in the femur growth plate of untreated wild type mice, untreated Mtol mice, AAV8-TBG-hGALNS treated Mtol mice, or AAV8-TBG-D8-hGALNS treated Mtol mice. FIG. 18C shows the chondrocyte cell size measured in the tibia growth plate of untreated wild type mice, untreated MPS IVA KO mice (galns −/−), AAV8-TBG-hGALNS treated MPS IVA KO mice (galns −/−), or AAV8-TBG-D8-hGALNS treated MPS IVA KO mice (galns −/−). FIG. 18D shows the chondrocyte cell size measured in the tibia growth plate of untreated wild type mice, untreated Mtol mice, AAV8-TBG-hGALNS treated Mtol mice, or AAV8-TBG-D8-hGALNS treated Mtol mice.

Chondrocyte size and column structure in growth plate in MPS IVA KO mice and Mtol mice were both substantially improved after AAV gene transfer.

FIG. 11K shows 40× magnified staining images of the meniscus of untreated or rAAV-treated MPS IVA KO (galns −/−) mice. In the untreated mice (left panel), most of the cells were ballooned and vacuolated. Some cells in the meniscus of mice treated with AAV8-TBG-hGALNS (middle panel) were vacuolated. Most of the cells in the tissue of mice treated with AAV8-TBG-D8-hGALNS (right panel) were not vacuolated.

FIG. 11L shows 40× magnified staining images of the ligament on the tibia side of untreated or rAAV-treated MPS IVA KO (galns −/−) mice. In the untreated mice (left panel), most of the cells were vacuolated. Some cells in the ligament of mice treated with AAV8-TBG-hGALNS or AAV8-TBG-D8-hGALNS (right two panels) remained vacuolated.

FIG. 11M shows 40× magnified staining images of the base of the heart valve of untreated or rAAV-treated MPS IVA KO (galns −/−) mice. Many of the cells at the base of the mitral valve in the untreated mice (left panel) were vacuolated, while no vacuolated cells were seen at the base of the mitral valve tissue of mice treated with AAV8-TBG-hGALNS (middle panel) or AAV8-TBG-D8-hGALNS (right panel). These aspects of the untreated mice tissue are shown in greater detail in FIG. 11N. Similar results were seen in the tissue of the heart valve (FIG. 11O). Similar results for the Mtol mice are shown in FIG. 19 (bottom panel). Many heart valve cells in the untreated mice (left panel) were vacuolated, while no vacuolated cells were seen in heart valve tissue of mice treated with AAV8-TBG-hGALNS (middle panel) or AAV8-TBG-D8-hGALNS (right panel). These aspects of the untreated mice tissue are shown in greater detail in FIG. 11P.

FIG. 20 shows the histopathology of heart muscle (40× magnification) in Mtol mice treated with AAV8-TBG-hGALNS or AAV8-TBG-D8-hGALNS, as compare to untreated Mtol mice.

Heart valve and heart muscle had no obvious vacuolated cells in both of MPS IVA KO (galns −/−) mice and Mtol mice after AAV gene transfer.

Figure 21A:
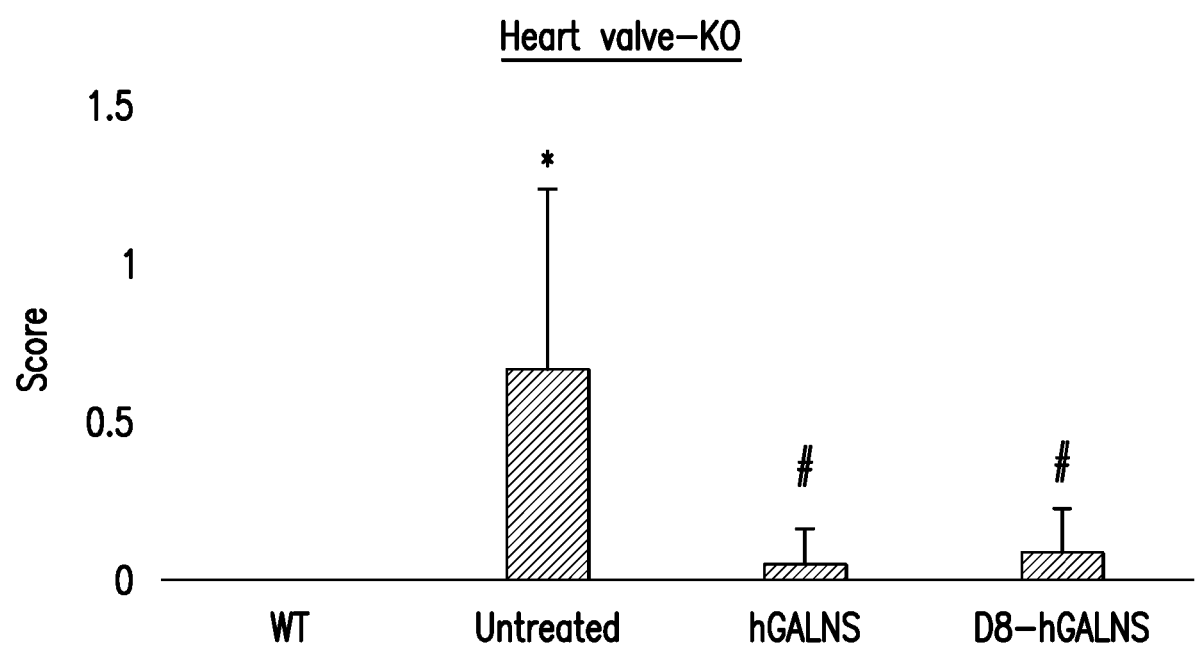
Figure 21B:
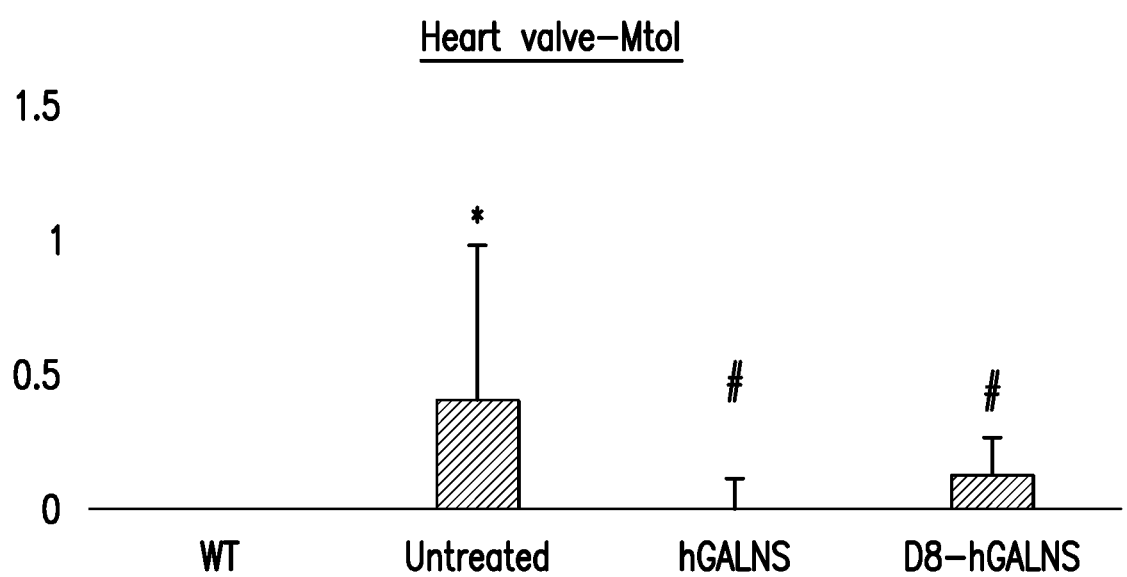
Figure 21C:
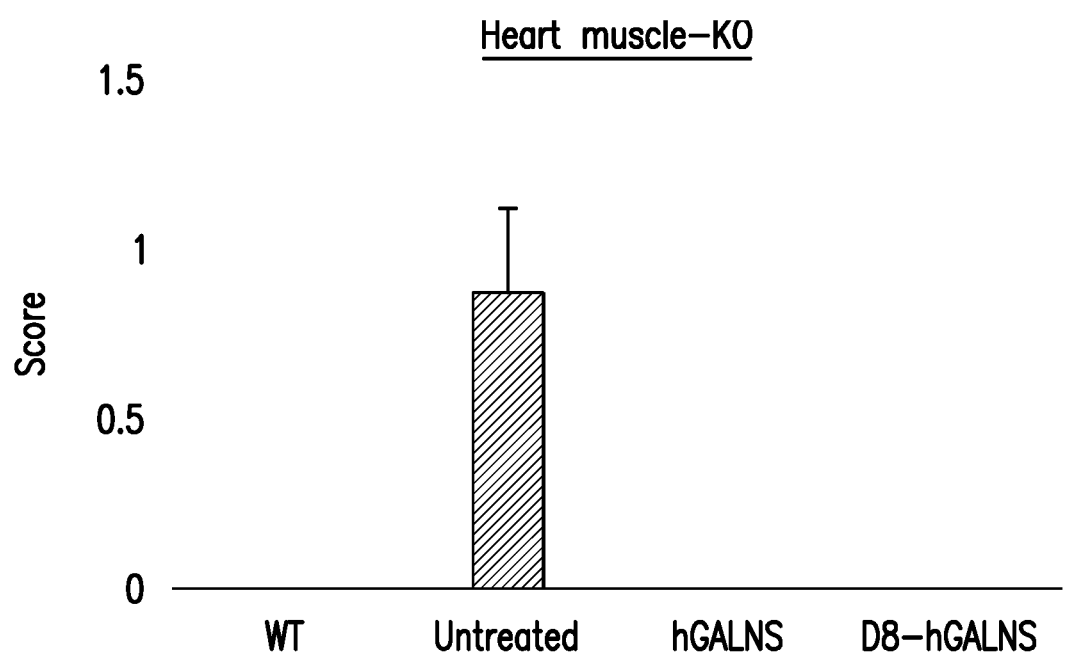
Figure 21D:
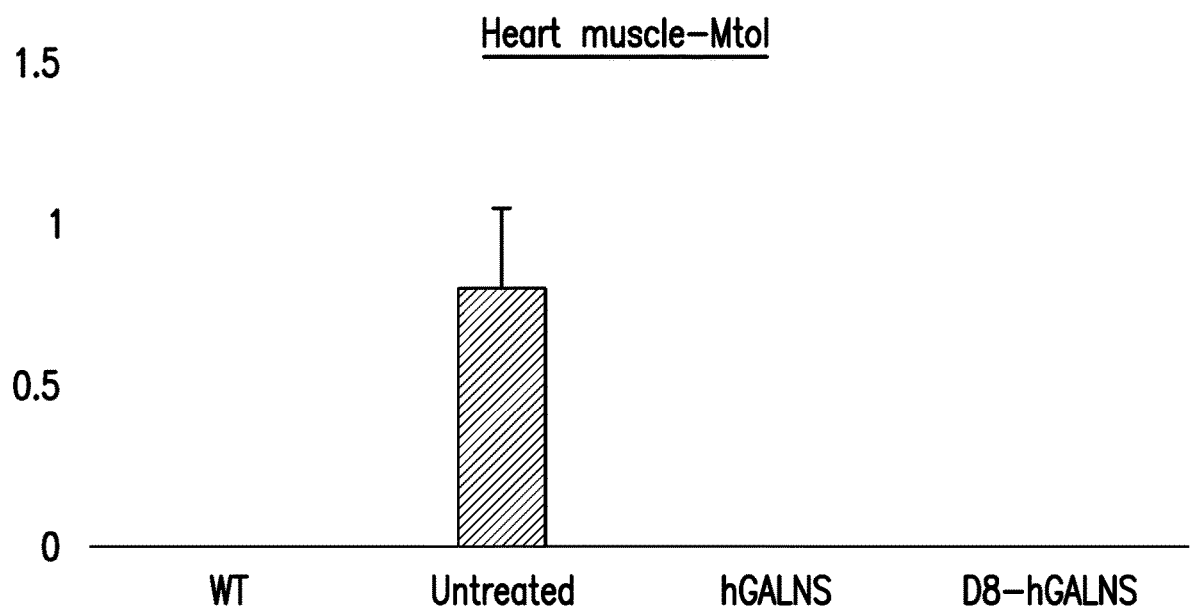

FIG. 21A shows the pathology score of the heart valve tissue of untreated wild type mice, untreated MPS IVA KO(galns −/−) mice, MPS IVA KO(galns −/−) mice treated with AAV8-TBG-hGALNS, or MPS IVA KO(galns −/−) mice treated with AAV8-TBG-D8-hGALNS. FIG. 21B shows the pathology score of the heart valve tissue of untreated wild type mice, untreated Mtol mice, Mtol mice treated with AAV8-TBG-hGALNS, or Mtol mice treated with AAV8-TBG-D8-hGALNS. FIG. 21C shows the pathology score of the heart muscle tissue of untreated wild type mice, untreated MPS IVA KO(galns −/−) mice, MPS IVA KO(galns −/−) mice treated with AAV8-TBG-hGALNS, or MPS IVA KO(galns −/−) mice treated with AAV8-TBG-D8-hGALNS. FIG. 21D shows the pathology score of the heart muscle tissue for untreated wild type mice, untreated Mtol mice, Mtol mice treated with AAV8-TBG-hGALNS, or Mtol mice treated with AAV8-TBG-D8-hGALNS.

Bone pathology was evaluated by histopathological analysis for Mtol mice as well. Unpaired t-test was used to examine the differences of pathology scores between the untreated and each of the treated groups (Score: 0 (Normal)-3 (Severe)), see Table 1.

TABLE 1

Pathology score in bone of Mtol mice (n = 2-5, mean ± SD)

| | | | Untreated | AAV8-TBG-hGALNS-treated | AAV8-TBG-D8-hGALNS-treated |
|---|---|---|---|---|---|
| Growth plate | Femur | Vacuolization | 2.90 ± 0.10 | 1.38 ± 0.34 * | 1.41 ± 0.21 * |
| | | Column structure | 2.93 ± 0.11 | 1.44 ± 0.33 * | 1.47 ± 0.16 * |
| | Tibia | Vacuolization | 2.85 ± 0.21 | 1.56 ± 0.26 * | 1.50 ± 0.29 * |
| | | Column structure | 2.75 ± 0.31 | 1.63 ± 0.20 * | 1.41 ± 0.33 * |
| Articular cartilage | Femur | Vacuolization | 2.48 ± 0.34 | 1.38 ± 0.18 * | 1.16 ± 0.33 * |
| | Tibia | Column structure | 2.35 ± 0.44 | 1.38 ± 0.18 * | 1.22 ± 0.19 * |
| | | Vacuolization | 2.53 ± 0.16 | 1.19 ± 0.14 * | 1.27 ± 0.21 * |
| | | Column structure | 2.44 | 1.38 | 1.21 ± 0.26 |
| | Ligament | | 2.80 ± 0.26 | 1.72 ± 0.56 * | 1.66 ± 0.26 * |
| | Meniscus | | 2.73 ± 0.34 | 1.41 ± 0.33 * | 1.34 ± 0.26 * |

* $p < 0.05$ vs untreated

Both viruses reduced GAG storage in articular cartilage, ligaments, and meniscus surrounding the articular cartilage and growth plate region in tibia and femur. The reduction of GAG storage observed in the bone and cartilage was comparatively greater for the AAV-TBG-D8-hGALNS treated mice.

Bone, growth plate, articular cartilage, meniscus, ligament, and heart tissues were substantially improved in rAAV treated mice. In addition, treated mice had almost complete remission with respect to defects in the heart valve and base of the heart valve, and no obvious vacuolated cells were seen at both the heart valve base and heart valve. The results show significant improvement over ERT since ERT-treated mice showed no clearance of vacuolated cells in growth plate, had disorganized column structure in growth plate, and had substantial vacuolated cells in heart valve (Tomatsu et al., Human Molecular Genetics, 2008, 17(6): 815-824).

The fact that therapeutic effect was observed in tissues other than liver (where the hGALNS and D8-hGALNS proteins were produced) suggests that there was mannose-6-phosphate receptor mediated cross correction.

7.3 Example 3. Liver Targeted AAV8 Gene Therapy Ameliorates Skeletal and Cardiovascular Pathology in Mucopolysaccharidosis IVA Murine Model This example relates to the experiments described and performed in other examples described herein, including, Examples 1-2 and presents additional data from Examples 1-2. In this example, AAV8 vectors expressing hGALNS with or without a bone-targeting signal, under the control of liver-specific thyroxin-binding globulin (TBG) promoter are evaluated and the therapeutic efficacy of these recombinant AAV8 vectors in bone and heart lesions of both mouse models of MPS IVA disease are studied. Both bone and heart are major organs affected in this disorder.

7.3.1 Results
(a) GALNS Enzyme Activity in Blood and Tissues: AAV-hGALNS Delivery Results in a Marked Increase of GALNS Activity in Plasma and Various Tissues in Mouse Models of MPS IVA.

Two mouse models (MPS IVA KO and MTOL) with MPS IVA recapitulate the human disease in terms of the deficiency of hGALNS activity, increased levels of KS in blood and tissues, and storage materials (vacuoles) in various tissues including chondrocytes, meniscus, ligaments, and heart muscle and valves. These biomarkers have been widely used to evaluate the severity of phenotype and the therapeutic efficacy of several approaches in these mouse models (Tomatsu, S., et al., Hum. Mol. Genet., 2008, 17, 815-824; Tomatsu, S., et al., Hum. Mol. Genet., 2003, 12, 3349-3358; Tomatsu, S., et al., Hum. Mol. Genet., 2005, 14, 3321-3335; Tomatsu, S., et al., Mol. Ther., 2010, 18, 1094-1102). For this study, we delivered AAV8-TBG-hGALNSco and AAV8-TBG-D8-hGALNSco (FIG. 24A) intravenously into 4-week-old MPS IVA KO and MTOL mice at a uniform dose of $5\times10^{13}$ GC/kg body weight. The mice were monitored for 12 weeks post-injection and blood samples were collected every other week to analyze the enzyme activity and KS levels. Additionally, at necropsy, tissue samples were taken from different organs for enzymatic activity and KS levels as well as knee joints and heart valves for histopathology analysis.

Plasma enzyme activity in MPS IVA KO and MTOL mice are shown in FIGS. 24B-24C. No plasma hGALNS activity was detected in untreated MPS IVA mice. Two weeks post-injection, plasma hGALNS activity in MPS IVA KO mice treated with AAV8-TBG-hGALNS or AAV8-TBG-D8-hGALNS was significantly increased, compared to that in wild-type mice. The enzyme activity from AAV8-TBG-D8-hGALNS was higher than that from AAV8-TBG-hGALNS 2 weeks post-injection; however, plasma hGALNS activity was not different between these two AAV vectors 12 weeks post-injection. In MTOL mice treated with both AAV vectors, plasma hGALNS activity was significantly increased compared to that in wild-type mice 2 weeks post-injection. The levels of enzyme activity from mice treated with AAV8-TBG-D8-hGALNS were higher than that from mice treated with AAV8-TBG-hGALNS throughout the entire study duration, suggesting that hGALNS with a bone-targeting signal had prolonged blood circulation, compared to native hGALNS possible due to the reduced uptake into tissues. These results demonstrated that supraphysiological levels of circulating hGALNS activity were achieved after a single injection of AAV8-TBG-hGALNS or AAV8-TBG-D8-hGALNS in both MPS IVA mouse models, and the high levels of enzyme activities were maintained during the study.

Figure 24J:
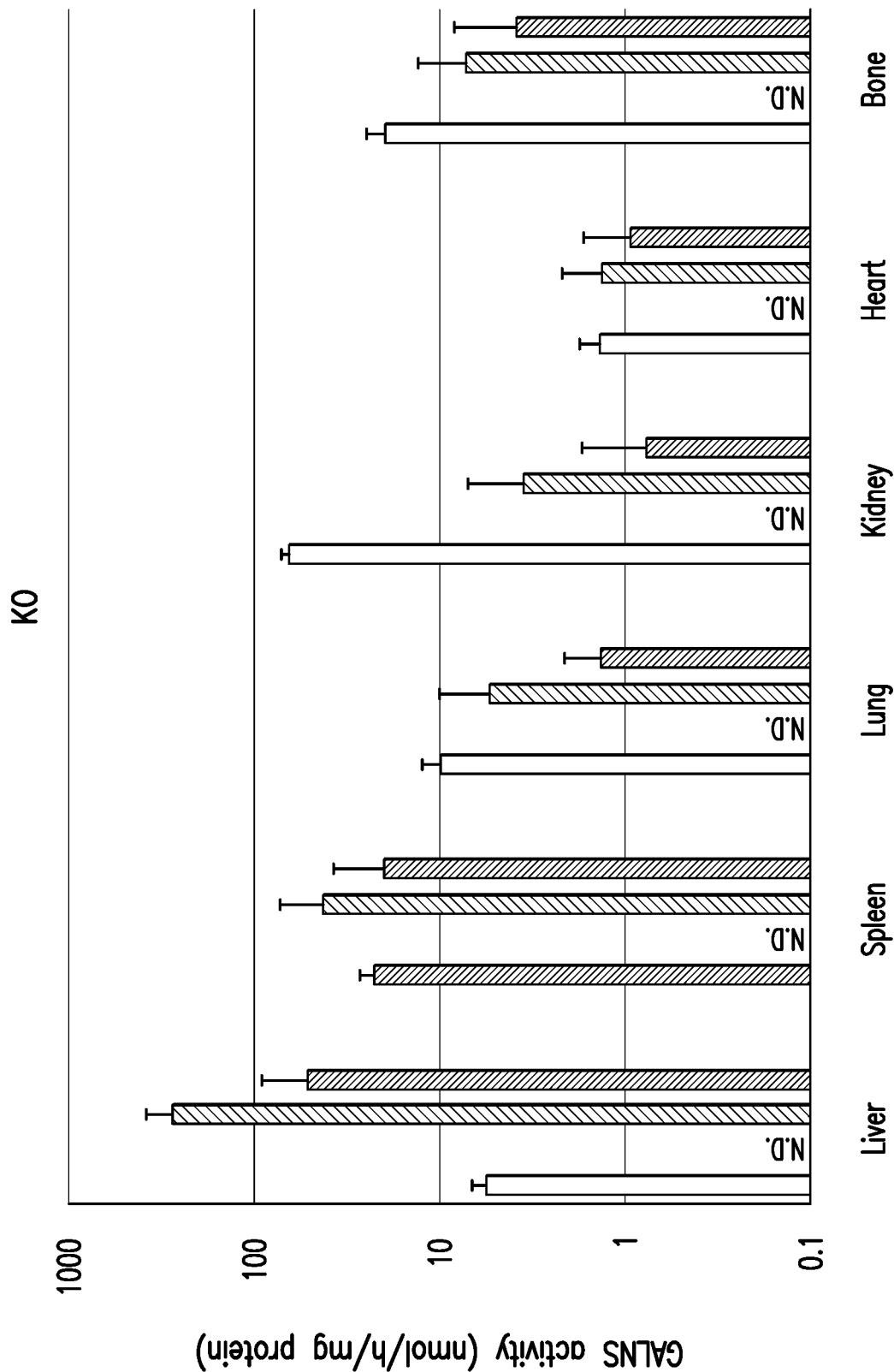
Figure 24K:
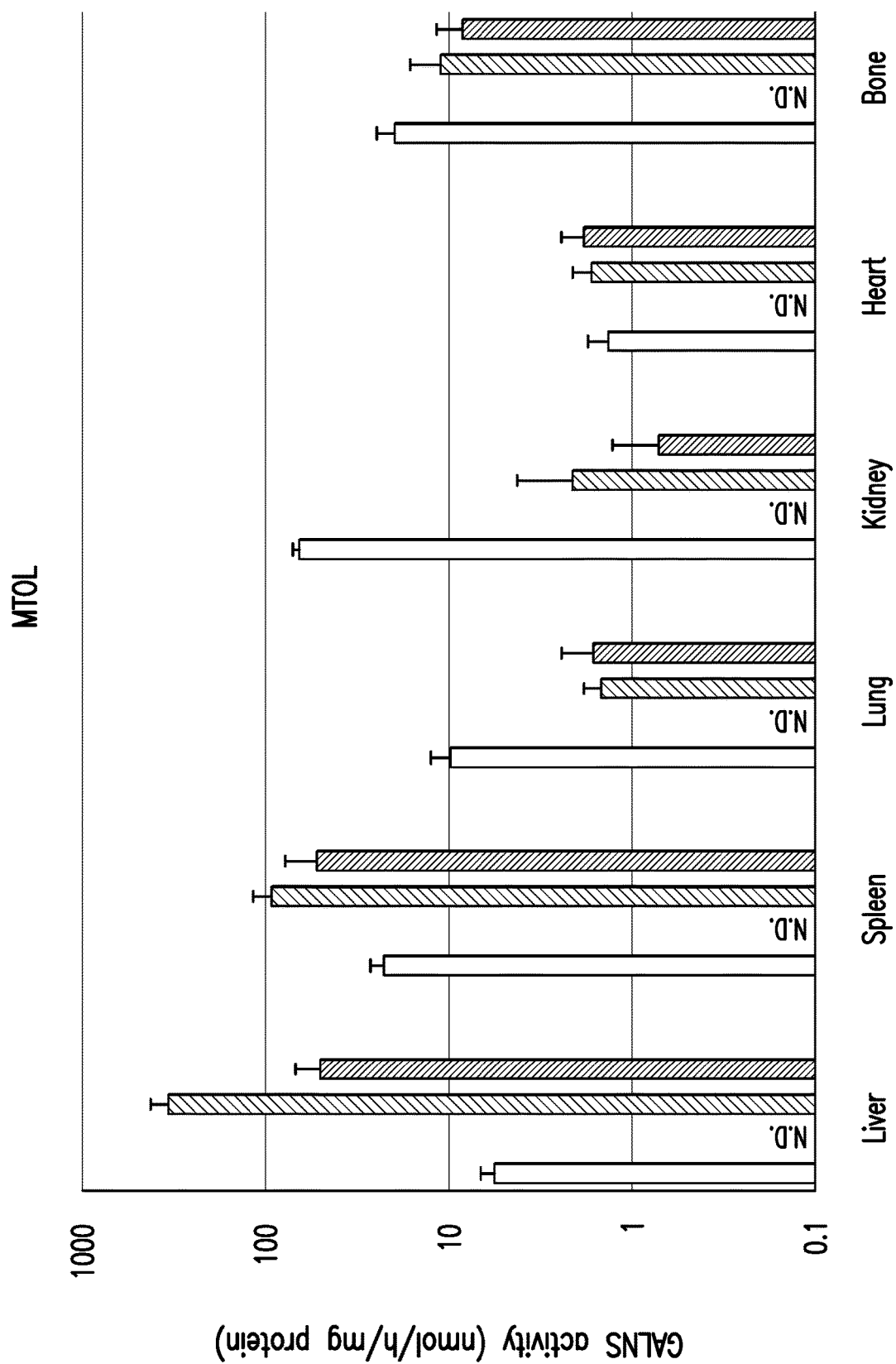

The levels of hGALNS activity in the liver 12 weeks after IV delivery of AAV vectors are shown in FIG. 24J and FIG. 24K. The hGALNS activity levels in all treated MPS IVA mice were significantly higher than that in untreated MPS IVA mice. The mean enzyme activity levels in MPS IVA KO mice, treated with AAV8-TBG-hGALNS and AAV8-TBG-D8-hGALNS, were 49-, and 9-fold, respectively, higher than the levels observed in wild-type mice. In MTOL mice treated with AAV8-TBG-hGALNS and AAV8-TBG-D8-hGALNS, hGALNS activity was 60-, and 9-fold higher than levels found in wild-type mice. GALNS activities in livers of KO and MTOL mice treated with AAV8-TBG-D8-hGALNS was significantly lower than those in mice treated with AAV8-TBG-hGALNS.

The levels of tissue hGALNS activity in tissues of MPS IVA mice were examined to evaluate the potential cross-correction of hGALNS deficiency. The hGALNS activity was observed in all examined tissues including spleen, lung, kidney, bone (leg), and heart in both KO and MTOL mice after both AAV8-TBG-hGALNS or AAV8-TBG-D8-hGALNS treatments (FIGS. 24J-24K). The enzyme activities were similar or higher than wild-type level in spleen, and heart, and slightly lower levels of activities were observed in the lung and kidney. Notably, 37% and 20% of wild-type enzyme activities were observed in the bone of KO mice treated with AAV8-TBG-hGALNS and AAV8-TBG-D8-hGALNS, respectively. Also, 57% and 43% of wild-type enzyme activities were observed in MTOL mice treated with these two AAV vectors. These results suggest that stable supraphysiological levels of hGALNS enzyme contributed to the penetration of the enzyme into various tissues including the bone of MPS IVA mice after AAV gene transfer. The hGALNS activity levels in bone were no statistically different between AAV8-TBG-hGALNS and AAV8-TBG-D8-hGALNS.

Figure 25B:
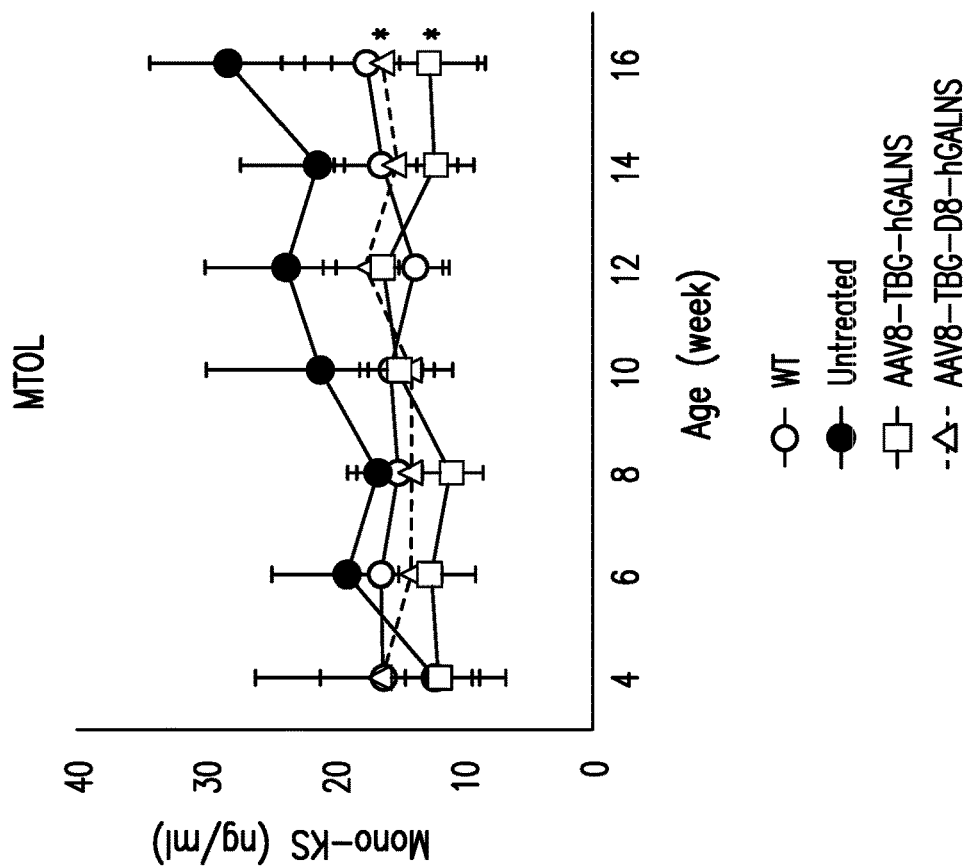
Figure 25A:
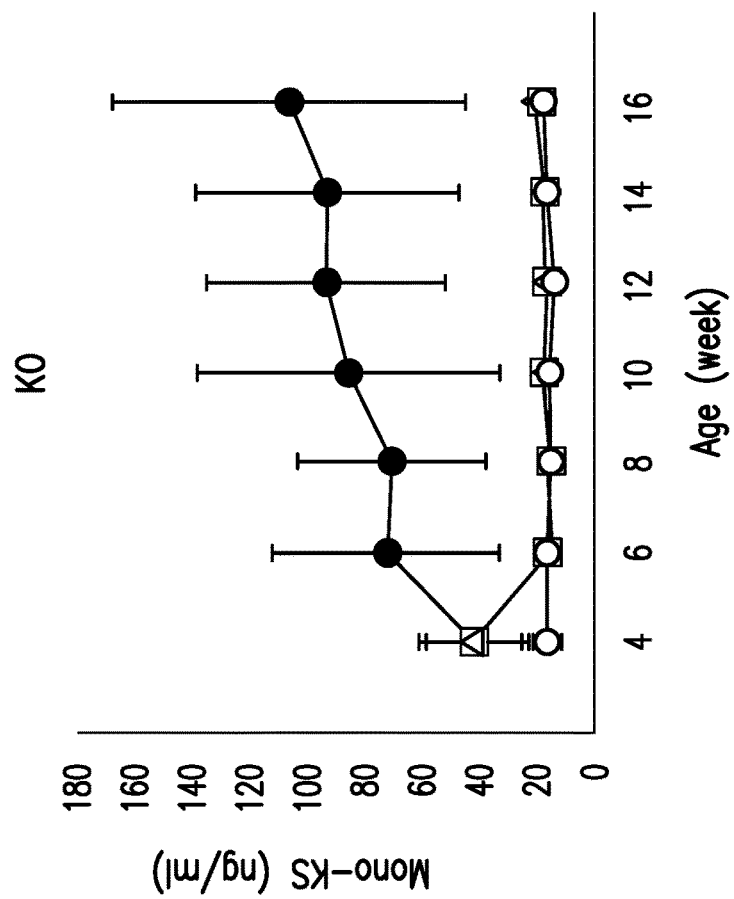

(b) Levels of Mono-Sulfated KS in the Blood and Tissue Decreased as a Result of AAV-GALNS Delivery We measured mono-sulfated KS, which is the major component of KS, in plasma and tissues of MPS IVA mice. The levels of plasma mono-sulfated KS in KO and MTOL mice are shown in FIGS. 25A-25B. Before administration of AAV vectors, plasma KS levels in untreated KO mice were significantly higher than that in wild-type mice (mean: 41.8 vs. 16.3 ng/ml). Two weeks post-injection, mono-sulfated KS levels in plasma were completely normalized for both AAV vectors, and this level was maintained for at least another 10 weeks (at necropsy). Mono-sulfated KS levels were similar in wild-type mice and untreated MTOL mice at four weeks of age. The mono-sulfated KS levels in wild-type mice were maintained at a constant level throughout the study; however, the levels of mono-sulfated KS in untreated MTOL mice gradually increased with age. MTOL mice treated with either of the AAV vector maintained the normal levels throughout the entire study period. At 16 weeks of age, mono-sulfated KS levels in MTOL mice treated with AAV vectors were significantly decreased when compared with those in the untreated MTOL mice.

Figure 25C:
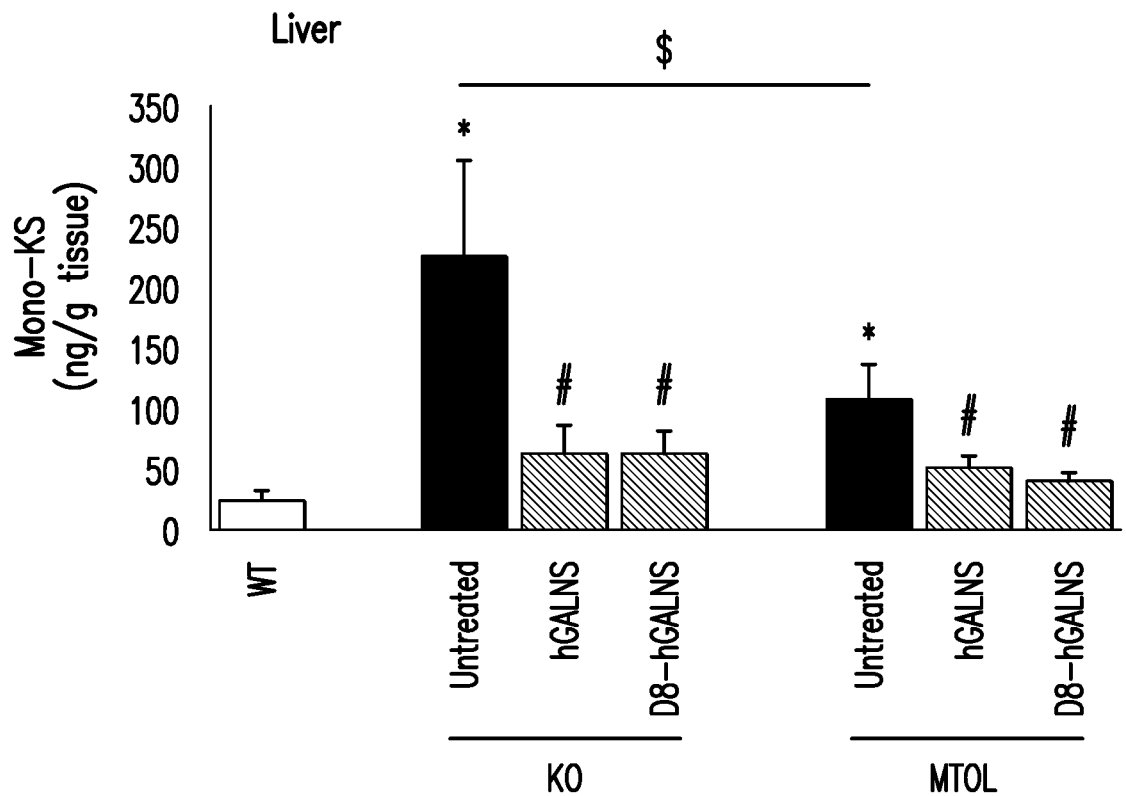
Figure 25D:
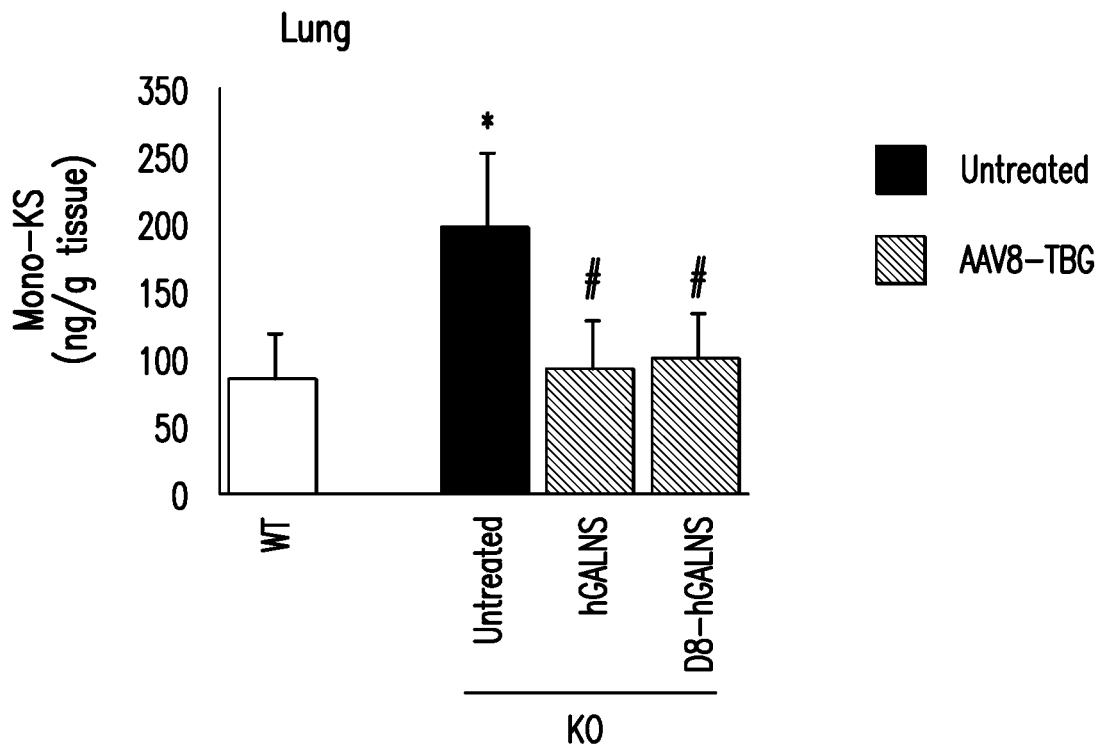

Mono-KS levels in tissues of MPS IVA mice are measured. At necropsy, excessive storage of GAG was present in tissues of both KO and MTOL mice. The amount of mono-sulfated KS in liver and lung of KO and MTOL mice were significantly decreased 12 weeks post-injection of either AAV vector (FIGS. 25C-25D). To assess the effect of these AAV vectors expressing hGALNS on other GAG levels, the levels of heparan sulfate (HS) were analyzed in blood and tissues of MPS IVS mice. Both KO and MTOL had normal levels of diHS-0S in plasma, and the levels were not affected after injection by AAV vectors (FIG. 30). Tissue diHS-0S levels in the liver and lung were also not changed between all groups 12 weeks post-injection of AAV vectors (FIG. 31).

(c) Delivery of AAV GALNS Vectors Improved Bone and Cartilage Pathology in MPS IVA Mice Tissues including bone (femur and tibia) and heart (muscle and valve) were assessed from MPS IVA mice 12 weeks post-injection of AAV8-TBG-hGALNS or AAV8-TBG-D8-hGALNS.

Untreated MPS IVA KO and MTOL mice at 16 weeks of age exhibited GAG storage vacuoles in the growth plate of the femur and tibia (hyaline cartilage) (FIG. 27A), articular disc (FIG. 27B), ligament surrounding knee joint (FIG. 32A), and meniscus (FIG. 32B). The growth plate also exhibited a disorganized column structure with ballooned and vacuolated chondrocytes (FIG. 27A-27B). In KO mice treated with AAV8-TBG-hGALNS or AAV8-TBG-D8-hGALNS, the growth plate, articular cartilage, ligaments, and meniscus in the knee joint had a partial reduction of storage material, and the column structure of chondrocytes was improved but remained disorganized and distorted. In MTOL mice treated with these AAV vectors, the growth plate, articular cartilage, ligaments, and meniscus in the knee joint had greater observable reduction of storage, and column structure of the growth plate and articular cartilage showed greater recovery than in untreated MTOL mice.

To objectively assess the improvement of vacuolization in cartilage cells of the growth plate, chondrocyte cell size was quantified in the growth plate lesions of KO and MTOL mice (4C). We observed a moderate reduction of chondrocyte size in these growth plate lesions, which reached statistical significance in the MTOL mice. Untreated MPS IVA mice exhibited GAG storage vacuoles in heart valves and muscle. AAV8-TBG-hGALNS or AAV8-TBG-D8-hGALNS provided nearly complete clearance in these heart lesions of treated KO and MTOL mice (FIG. 27A-27B).

(d) Circulating of Anti-hGALNS Antibodies

Overall, improvement of bone pathology in KO mice was less remarkable when compared to that in MTOL mice 12 weeks post-injection of AAV8 vectors. To investigate the possibility of a humoral response to hGALNS, antibody titers to hGALNS were measured by enzyme-linked immunosorbent assay (ELISA). Indirect ELISA method detected anti-hGALNS antibodies in plasma by using full-length rhGALNS coated on the plate. Plasma from KO mice treated with AAV vectors showed significantly higher levels of circulating anti-hGALNS antibodies, compared to that from other groups (0.50±0.38 or 0.62±0.43 optical density (OD) unit for KO treated with AAV8-TBG-hGALNS or AAV8-TBG-D8-hGALNS) (FIG. 28).

Circulating anti-hGALNS antibodies were not detected in wild-type, untreated KO, and MTOL mice.

7.3.2 Materials and Methods (a) Developing AAV hGALNS Expression Cassette

To develop an AAV8 vector with hGALNS, we determined the optimized codon sequence of hGALNS. The optimized 1569 bp sequence, translated into 526 amino acids, under the control of liver-specific TBG promoter was packaged in AAV8 capsid. In the vector plasmid with the bone-targeting signal, an Aspartic Acid Octapeptide (D8) sequence was inserted after N-terminal signal peptide of hGALNS, producing bone-targeting hGALNS with high affinity for major bone matrix, hydroxyapatites (FIG. 24A). Production of GALNS by these AAV vector plasmids was confirmed after performing transfection experiment with Huh-7 cell. Intra- and extra-cellular hGALNS activity levels from the codon-optimized open reading frame were similar to that produced by native hGALNS coding sequence (FIGS. 29A-29B).

(b) Expression Cassette Design and AAV Vector Production

The expression cassettes carrying the native and D8 containing GALNS transgenes were designed for packaging into AAV8 vector (FIG. 28). The bone-targeting signal, an Aspartic Acid Octapeptide (D8) sequence was inserted after N-terminal signal peptide of hGALNS. The design included a liver-specific thyroxin-binding globulin (TBG) promoter along with a rabbit betaglobulin polyadenylation tail (polyA). We used a codon optimized hGALNS sequence for both vectors for the mouse studies. We confirmed the GALNS enzymatic activity of these expression cassette plasmids in a transfection experiment using Huh-7 cells. We determined the activity levels in both cell lysate and supernatant 48 hours post transfection (FIGS. 29A-29B). The GALNS activity levels from the codon-optimized construct were similar to that produced by native hGALNS coding sequence.

AAV8-TBG-hGALNS and AAV8-TBG-D8-hGALNS vectors were generated following a scaled down version of the proprietary GMP vector production protocols at REGENXBIO (Rockville, Md.). Briefly, HEK293 cells (RGX293) were triple-transfected with the helper plasmid, AAV8 Capsid Plasmid and the transgene plasmid containing the hGALNS/D8-hGALNS plasmid. The packaged vectors were purified from the cell culture supernatant using affinity chromatography and tittered using Digital Droplet PCR (BioRad) method.

(c) Murine Models and In Vivo Study Design

We tested the therapeutic potential of AAV8-TBG-hGALNS and AAV8-TBG-D8-hGALNS by using two MPS IVA murine models (Tomatsu et al., Hum Mol Genet 2003; 12(24):3349-3358; Tomatsu et al., Hum. Mol. Genet. 2005; 14, 3321-3335). The first type is a Galns knock-out mouse model (KO: Galns−/−) with disrupt of the gene ((Tomatsu et al., Hum Mol Genet 2003; 12(24):3349-3358). The second one is a murine model (MTOL: $Galns^{tm(hC79S,mC76S)slu}$) tolerant to human GALNS containing both a transgene expressing hGALNS in intron 1 and an active site mutation (C76S) adjacent to exon 2, thereby introducing both the inactive hGALNS coding sequence with C79S active site mutation and the C76S mutation into the murine Galns gene by targeted mutagenesis (Tomatsu et al., Hum. Mol. Genet. 2005; 14, 3321-3335). Both models had no detectable enzyme activity in blood and tissues and showed the accumulation of storage materials primarily within reticuloendothelial Kupffer cells, heart valves cardiac muscle, and chondrocytes including growth plate and articular cartilage.

We had previously described the development of two MPS IVA murine models, MPS IVA knockout mouse (Galns−/−) (Tomatsu et al., Hum Mol Genet 2003; 12(24): 3349-3358) and MPS IVA mouse tolerant to human GALNS protein ($Galns^{tm(hC79S\_mC76S)slm}$) (Tomatsu et al., Hum. Mol. Genet. 2005; 14, 3321-3335) in C57BL/6 background. The GALNS knock-out mouse model (KO: Galns−/−) was developed by targeted disruption of the GALNS gene (Tomatsu et al., Hum Mol Genet 2003; 12(24):3349-3358). The mouse model tolerant to human GALNS (MTOL: $Galns^{tm(hC79S,mC76S)slu}$) contain a transgene expressing hGALNS in intron 1 and an active site mutation (C76S) adjacent to exon 2, thereby introducing both the inactive hGALNS coding sequence with C79S active site mutation (Tomatsu et al., Hum. Mol. Genet. 2005; 14, 3321-3335). Both mouse models had no detectable enzyme activity in blood and tissues and showed the accumulation of storage materials primarily within reticuloendothelial Kupffer cell, heart valves and muscle, and chondrocytes including growth plate and articular cartilage.

Genotyping for the experimental cohorts were done by PCR on day 14. Homozygous MPS IVA mice at 4 weeks of age were treated with either AAV8 vector, intravenously at a uniform dose of $5×10^{13}$ GC/kg. Another cohort of MPS IVA mice as well as unaffected C57BL/6 littermates were administered with phosphate-buffered saline (PBS). The total dose volume administration was approximately 100 µl per mouse. All animal cares and experiments were approved by the Institutional Animal Care and Use Committee of Nemours/Alfred I. duPont Hospital for Children.

(d) Blood and Tissue Collection

Approximately 100 µl of blood was collected in tubes with EDTA (BD, Franklin Lakes, N.J., USA) every other week from all animals in the study. The blood was centrifuged at 8,000 rpm for 10 min and plasma separated was kept at −20° C. until performing GALNS enzyme assay and GAG assay. At 16 weeks of age, mice were euthanized in a $CO_2$ chamber and perfused with 20 ml of 0.9% saline. Liver, kidney, lung, spleen, heart, and knee joint were collected and stored at −80° C. until processing for GALNS enzyme assay and GAG assay. Additionally, various tissue samples were collected and stored in 10% neutral buffered formalin for histopathology analysis.

(e) GALNS Activity Assay

Blood and tissue GALNS activity was determined as described previously (Toietta, G., et al. Hum. Gene Ther. 2001; 12, 2007-2016). Frozen tissue was homogenized with homogenization buffer consisting of 25 mmol/l Tris-HCl, pH 7.2, and 1 mmol/l phenylmethylsulfonyl fluoride by using a homogenizer. Tissue lysate or plasma, and 22 mM 4-methylumbelliferyl-β-galactopyranoside-6-sulfate (Research Products International, Mount Prospect, Ill., USA) in 0.1 M NaCl, 0.1 M sodium acetate, pH 4.3 were incubated at 37° C. for 16 h. Then, 10 mg/ml β-galactosidase from *Aspergillus oryzae* (Sigma-Aldrich, St. Louis, Mo., USA) in 0.1 M NaCl, 0.1 M sodium acetate, pH 4.3 was added to reaction sample, and additional incubation was at 37° C. for 2 hours. The sample was transferred to stop solution (1 M glycine, NaOH, pH 10.5), and the plate was read at excitation 366 nm and emission 450 nm on a Perkin Elmer Victor X4 plate reader (PerkinElmer, Waltham, Mass., USA). Activity was expressed as nanomoles of 4-methylumbelliferone released per hour per microliter of plasma or milligram of protein. Protein concentration was determined by BCA protein assay kit (Thermo Fisher Scientific, Waltham, Mass., USA).

(f) Extraction of GAG from Tissue

GAG extraction from various mouse tissues was modified from that developed by Mochizuki et al. (Mochizuki, H., et al. J. Biol. Chem. 2008; 283, 31237-31245). Briefly, excised tissues were frozen in liquid nitrogen and homogenized with acetone using a homogenizer. The obtained powder was dried under centrifuge vacuum. The defatted tissue powder was suspended in 0.5 M NaOH and incubated at 50° C. for 2 h to remove GAG chains from its core protein. After neutralization with 1 M HCl, NaCl was added to a final concentration of 3 M. Insoluble materials were removed by centrifugation, and the pH of the supernatant was adjusted below 1.0 with 1 M HCl. Precipitated nucleotides were removed by centrifugation, and the supernatant was neutralized with 1 M NaOH. The crude GAG was precipitated by the addition of two volumes of ethanol containing 1.3% potassium acetate. After centrifugation, the precipitate was dissolved in distilled water.

(g) GAG Assay

Blood and tissue GAG level were measured by LC-MS/MS as described previously (Oguma, T., et al. Biomed. Chromatogr. 2007; 21, 356-362; Oguma, T., et al. Anal. Biochem. 2007; 368, 79-86; Shimada, T., et al. JIMD. Rep. 2014; 16, 15-24; Shimada, T., et al. JIMD. Rep. 2015; 21, 1-13; Kubaski, F., et al. J. Inherit. Metab. Dis. 2017; 40, 151-158). Briefly, 50 mM Tris-HCl (pH 7.0) and sample were into a 96 well omega 10K filter plate (Pall Corporation, Port Washington, N.Y., USA) on a 96 well receiver plate. Samples centrifuged for 15 min at 2,500 g. The filter plate was transferred to a new receiver plate, and a cocktail mixture of 50 mM Tris-HCl (pH 7.0), 5 µg/mL chondrosine as internal standard (IS), 1 mU heparitinase, and 1 mU keratanase II was added to the filter plate. Samples were incubated at 37° C. water bath overnight. Then, the samples were centrifuged for 15 min at 2,500 g. The apparatus consisted of a 1290 Infinity LC system with a 6460 triple quad mass spectrometer (Agilent Technologies, Palo Alto, Calif., USA). Disaccharides were separated on a Hypercarb column (2.0 mm i.d. 50 mm length; 5 µm particles; Thermo Fisher Scientific, Waltham, Mass., USA), thermostated at 60° C. The mobile phase was a gradient elution of 5 mM ammonium acetate, pH 11.0 (solution A) to 100% acetonitrile (solution B). The flow rate was 0.7 ml/min, and the gradient was as follows: 0 min 100% solution A, 1 min 70% solution A, 2 min 70% solution A, 2.20 min 0% solution A, 2.60 min 0% solution A, 2.61 min 100% solution A, 5 min 100% solution A. The mass spectrometer was operated with electrospray ionization in the negative ion mode (Agilent Jet Stream technology). Specific precursor and product ions, m/z, were used to quantify each disaccharide respectively (IS, 354.3→193.1; mono-sulfated KS, 462→97; HS-0S 378.3→175.1). The injection volume was 10 µl with a running time of 5 min per sample.

(h) Toluidine Blue Staining and Pathological Assessment

Toluidine blue staining was performed as described previously (Tomatsu, S., et al. Mol. Genet. 2005, 14, 3321-3335). Briefly, knee joint and mitral heart valve were collected from MPS IVA and WT mice at 16-week-age to evaluate levels of storage granules by light microscopy. Tissues were fixed in 2% paraformaldehyde, 4% glutaraldehyde in PBS, and post-fixed in osmium tetroxide and embedded in Spurr's resin. Then, toluidine blue-stained 0.5-µm-thick sections were examined. To evaluate chondrocyte cell size (vacuolization) in the growth plate of femur or tibia, approximately 300 chondrocytes in the proliferative area were measured in each mouse by Image J software, and results were expressed as fold-change from wild-type group.

(i) Detection of Antibodies Against GALNS by Enzyme-Linked Immunosorbent Assay (ELISA)

An indirect ELISA method was used to detect antibodies against GALNS in plasma of treated and untreated mice as described previously (Tomatsu, S., et al. Hum. Mol. Genet. 2003; 12, 961-973). Briefly, 96 well microtiter plate was coated overnight with 2 µg/ml purified rhGALNS (R&D Systems, Minneapolis, Minn., USA) in 15 mM $Na_2CO_3$, 35 mM $NaHCO_3$, 0.02% $NaN_3$, pH 9.6. The wells were washed three times with TBS-T (10 mM Tris, pH 7.5, 150 mM NaCl, 0.05% TWEEN 20), and then blocked for 1 h at room temperature with 3% bovine serum albumin in PBS (pH 7.2). After washing three times with TBS-T, a 100-fold dilution of mouse plasma in TBS-T was added to the wells and incubated at 37° C. for 2.5 h. The wells were washed four times with TBS-T, then TBS-T containing a 1:1,000 dilution of peroxidase conjugated goat anti-mouse IgG (Thermo Fisher Scientific, Waltham, Mass., USA) was added to the wells and incubated at room temperature for 1 h. The wells were washed three times with TBS-T and twice with TBS (10 mM Tris, pH7.5, 150 mM NaCl). Peroxidase substrate (ABTS solution, Invitrogen, Carlsbad, Calif., USA) was added (100 µl per well), and plates were incubated at room temperature for 30 min. The reaction was stopped with the addition of 1% SDS, and the plates read at optical density 410 nm on a Perkin Elmer Victor X4 plate reader (PerkinElmer, Waltham, Mass., USA).

(j) Statistical Analysis

All data were expressed as means and standard deviations (SD). Multiple comparison tests were performed by one-way ANOVA with the Bonferroni's post-hoc test using GraphPad Prism 5.0 (GraphPad Software, San Diego, Calif., USA). The statistical significance of difference was considered as $p<0.05$.

7.4 Example 4. Evaluate the Effect of Prolonged Enzyme Exposure on Bone Pathology The following studies are conducted to evaluate the effect of prolonged enzyme exposure on bone pathology. For this study, AAV8-TBG-hGALNSco is administered into 4-week old MPSIVA KO mice at a dose of $5 \times 10^{13}$ GC/kg body weight. Control groups are untreated MPS IVA KO mice and untreated wild type mice of the same age. Three groups of mice, 6-10 per group, are used in this study. The mice are monitored for either 24 weeks or 48 weeks post injection and blood samples are collected every other week to other week to analyze enzymatic activity and KS levels. Additionally, at necropsy, tissue samples are taken from different organs for enzymatic activity and KS levels as well as knee joints and heart valves for histopathology analysis.

Similarly, AAV8-TBG-hGALNSco is delivered into 4-week old MTOL mice at a dose of $5 \times 10^{13}$ GC/kg body weight. Control groups include untreated MTOL mice, and untreated wild type mice of the same age. Three groups of mice, 6-10 per group, are used in this study. The mice are monitored for either 24 weeks or 48 weeks post injection and blood samples are collected every other week to other week to analyze enzymatic activity and KS levels. Additionally, at necropsy, tissue samples are taken from different organs for enzymatic activity and KS levels as well as knee joints and heart valves for histopathology analysis.

7.5 Example 5. Neonatal Study: Evaluate the Effect of Earlier Intervention on Bone Pathology The following studies are conducted on neonatal mice to evaluate the effect of earlier intervention on bone pathology. For this study, AAV8-TBG-hGALNSco is administered into MPSIVA KO neonatal mice at a dose of $5 \times 10^{13}$ GC/kg body weight. Control groups include untreated MPS IVA KO mice, and untreated wild type mice of the same age. The mice are scarified at 16 weeks of age and blood samples are collected every other week to other week to analyze enzymatic activity and KS levels. Additionally, at necropsy, tissue samples are taken from different organs for enzymatic activity and KS levels as well as knee joints and heart valves for histopathology analysis.

Similarly, we delivered AAV8-TBG-hGALNSco into neonatal MTOL mice at a dose of $5 \times 10^{13}$ GC/kg body weight. Control groups include untreated MTOL mice, and untreated wild type mice of the same age. Three groups of mice, 6 per group, are used in this study The mice are scarified at 16 weeks of age and blood samples are collected every other week to other week to analyze enzymatic activity and KS levels. Additionally, at necropsy, tissue samples are taken from different organs for enzymatic activity and KS levels as well as knee joints and heart valves for histopathology analysis.

7.6 Example 6. New Expression Cassette Evaluation

The following studies are conducted to evaluate optimized promoter constructs for improved efficacy. For this study, AAV8-TBG-hGALNSco, AAV8-CAG-hGALNSco, AAV8-Promoter 1-hGALNSco, AAV8-Promoter 2-hGALNSco, AVV9-Promoter 2-hGALNSco are administered into 4-weeks old MPSIVA KO mice at a dose of $1 \times 10^{13}$ GC/kg body weight (10 mice per group). Control groups include untreated MPS IVA KO mice and untreated wild type mice of the same age. The mice are monitored for either 12 weeks or 48 weeks and blood samples are collected every other week to other week to analyze enzymatic activity and KS levels. Additionally, at necropsy, tissue samples are taken from different organs for enzymatic activity and KS levels as well as knee joints and heart valves for histopathology analysis.

7.7 Example 7. Late Stage AAV Gene Therapy Study

The following studies are conducted to evaluate late-stage AAV gene therapy efficacy. For this study, AAV-TBG-hGALNSco, AAV-CAG-hGALNSco, AAV-Promoter 1-hGALNSco, AAV-Promoter 2-hGALNSco, AVV-Promoter 2-hGALNSco are administered into 8-10 weeks old MPSIVA KO mice (5 mice per group). Untreated MPS IVA KO mice are used as control. The mice are monitored for a period of time and blood samples are collected every other week to other week to analyze enzymatic activity and KS levels. Additionally, at necropsy, tissue samples are taken from different organs for enzymatic activity and KS levels as well as knee joints and heart valves for histopathology analysis.

Similarly, AAV-TBG-hGALNSco, AAV-CAG-hGALNSco, AAV-Promoter 1-hGALNSco, AAV-Promoter 2-hGALNSco, AVV-Promoter 2-hGALNSco are administered into 8-10 weeks old MTOL mice (5 mice per group). Untreated MTOL mice are used as control. The mice are monitored for a period of time and blood samples are collected every other week to other week to analyze enzymatic activity and KS levels. Additionally, at necropsy, tissue samples are taken from different organs for enzymatic activity and KS levels as well as knee joints and heart valves for histopathology analysis.

7.8 Example 8. Comparison Study on the Effect of AAV8-TBG-hGALNS, AAV8-TBG-D8-hGALNS AAV8-CAG-hGALNS, and AAV8-CAG-D8-hGALNS at a High Dose and a Low Dose The following studies were conducted to evaluate the effect of AAV8-TBG-hGALNS, AAV8-TBG-D8-hGALNS, AAV8-CAG-hGALNS, and AAV8-CAG-D8-hGALNS at a high dose and a low dose.

For this study, we intravenously delivered AAV8-TBG-hGALNS and AAV8-TBG-D8-hGALNS into 4 weeks old MPSIVA KO mice (n≥4 per group) at a high dose ($2 \times 10^{14}$ GC/kg body weight), or a low dose ($5 \times 10^{13}$ GC/kg body weight). We also intravenously delivered AAV8-CAG-hGALNS, and AAV8-CAG-D8-hGALNS into 4 weeks old MPSIVA KO mice (n≥4 per group) at a low dose ($5 \times 10^{13}$ GC/kg body weight). Control groups included untreated MPS IVA KO mice and untreated wild type mice of the same age. The mice were monitored for 12 weeks and blood samples (plasma) were collected biweekly to analyze enzymatic activity and KS levels.

Similarly, we intravenously delivered AAV8-TBG-hGALNS and AAV8-TBG-D8-hGALNS into 4 weeks old MTOL mice (n≥4 per group) at a high dose ($2 \times 10^{14}$ GC/kg body weight), or a low dose ($5 \times 10^{13}$ GC/kg body weight). We also intravenously delivered AAV8-CAG-hGALNS, and AAV8-CAG-D8-hGALNS into 4 weeks old MTOL mice (n≥4 per group) at a low dose ($5 \times 10^{13}$ GC/kg body weight). Untreated MTOL mice are used as control. The mice were monitored for 12 weeks and blood samples were collected biweekly to analyze enzymatic activity and KS levels.

7.8.1 Results (a) hGALNS Enzyme Activities in the Plasma of MPS IVA KO Mice Administered with $5 \times 10^{13}$ GC/Kg Body Weight of AAV8-CAG-hGALNS, or AAV8-CAG-D8-hGALNS, as Compared to Untreated Wild Type Mice.

Plasma hGALNS enzyme activities in MPSIVA KO mice administered with $5 \times 10^{13}$ GC/kg body weight of AAV8-CAG-hGALNS, or AAV8-CAG-D8-hGALNS are shown in FIGS. 33-35. Two weeks post-injection, increased plasma hGALNS activities were detected in AAV8-D8-hGALNS mice, as compared to untreated wild type mice. The enzyme activity from AAV8-CAG-D8-hGALNS was higher than that from AAV8-CAG-hGALNS 2 weeks post-injection.

(b) hGALNS Enzyme Activities in the Liver of MPS IVA KO Mice Administered with $5 \times 10^{13}$ GC/Kg Body Weight of AAV8-CAG-hGALNS, or AAV8-CAG-D8-hGALNS, as Compared to Untreated Wild Type Mice.

hGALNS enzyme activities in the liver of MPSIVA KO mice administered with $5 \times 10^{13}$ GC/kg body weight of AAV8-CAG-hGALNS, or AAV8-CAG-D8-hGALNS are shown in FIG. 36. Increased liver hGALNS activities were detected in both AAV8-D8-hGALNS and AAV8-hGALNS treated mice, as compared to untreated wild type mice.

(c) hGALNS Enzyme Activities in the Plasma of MTOL Mice Administered with $5\times10^{13}$ GC/Kg Body Weight of AAV8-CAG-hGALNS, as Compared to Untreated Wild Type Mice.

hGALNS enzyme activities in the plasma of MTOL mice administered with $5\times10^{13}$ GC/kg body weight of AAV8-CAG-hGALNS are shown in FIG. 37.

(d) hGALNS Enzyme Activities in the Liver of MTOL Mice Administered with $5\times10^{13}$ GC/Kg Body Weight of AAV8-CAG-hGALNS, as Compared to Untreated Wild Type Mice.

GALNS enzyme activities in the liver of MTOL mice administered with $5\times10^{13}$ GC/kg body weight of AAV8-CAG-hGALNS are shown in FIG. 38. Increased liver hGALNS activities were detected in AAV8-hGALNS treated mice, as compared to untreated wild type mice.

(e) hGALNS Enzyme Activities in the Plasma of MPS IVA KO Mice Administered with $2\times10^{14}$ GC/Kg Body Weight of AAV8-TBG-hGALNS, or AAV8-TBG-D8-hGALNS, as Compared to Untreated Wild Type Mice.

Plasma hGALNS enzyme activities in MPSIVA KO mice administered with $2\times10^{14}$ GC/kg body weight of AAV8-TBG-hGALNS, or AAV8-TBG-D8-hGALNS are shown in FIGS. 39-40.

(f) hGALNS Enzyme Activities in the Liver of MPS IVA KO Mice Administered with $2\times10^{14}$ GC/Kg Body Weight of AAV8-TBG-hGALNS, or AAV8-TBG-D8-hGALNS, as Compared to Untreated Wild Type Mice hGALNS enzyme activities in the liver of MPSIVA KO mice administered with $2\times10^{14}$ GC/kg body weight of AAV8-TBG-hGALNS, or AAV8-TBG-D8-hGALNS are shown in FIG. 41. Increased liver hGALNS activities were detected in both AAV8-TBG-hGALNS, or AAV8-TBG-D8-hGALNS treated mice, as compared to untreated wild type mice.

8. TABLE OF SEQUENCES

| SEQ ID NO. | DESCRIPTION | SEQUENCE |
|---|---|---|
| 1 | AAV8 capsid protein | MAADGYLPDWLEDNLSEGIREWWALKPGAPKPKAN QQKQDDGRGLVLPGYKYLGPFNGLDKGEPVNAADA AALEHDKAYDQQLQAGDNPYLRYNHADAEFQERLQ EDTSFGGNLGRAVFQAKKRVLEPLGLVEEGAKTAPG KKRPVEPSPQRSPDSSTGIGKKGQQPARKRLNFGQTG DSESVPDPQPLGEPPAAPSGVGPNTMAAGGGAPMAD NNEGADGVGSSSGNWHCDSTWLGDR VITTSTRTWAL PTYNNHLYKQISNGTSGGATNDNTYFGYSTPWGYFD FNRFHCHFSPRDWQRLINNNWGFRPKRLSFKLFNIQV KEVTQNEGTKTIANNLTSTIQVFTDSEYQLPYVLGSA HQGCLPPFPADVFMIPQYGYLTLNNGSQAVGRSSFYC LEYFPSQMLRTGNNFQFTYTFEDVPPHSSYAHSQSLD RLMNPLIDQYLYYLSRTQTTGGTANTQTLGFSQGGPN TMANQAKNWLPGPCYRQQRVSTTTGQNNNSNFAWT AGTKYHLNGRNSLANPGIAMATHKDDEERFFPSNGIL IFGKQNAARDNADYSDVMLTSEEEIKTTNPVATEEYG IVADNLQQQNTAPQIGTVNSQGALPGMVWQNRDVY LQGPIWAKIPHTDGNFHPSPLMGGFGLKHPPPQILIKN TPVPADPPTTFNQSKLNSFITQYSTGQVSVEIEWELQK ENSKRWNPEIQYTSNYYKSTSVDFAVNTEGVYSEPRP IGTRYLTRNL |
| 2 | Human GALNS (hGALNS) | atggcggcggttgtcgcggcgacgaggtggtggcagctgttgctggtgctcagcgc cgcggggatgggggcctcgggcgccccgcagcccccaacatcctgctcctgctc atggacgacatgggatgggtgacctcggggtgtatggagagccctccagagaga ccccgaatttggaccggatggctgcagaagggctgcttttcccaaacttctattctgcc aaccctctgtgctcgccatcgagggcggcactgctcacaggacggctacccatcg caatggcttctacaccaccaacgcccatgccagaaacgcctacacaccgcaggaga ttgtgggcggcatcccagactcggagcagctcctgccggagcttctgaagaaggcc ggctacgtcagcaagattgtcggcaagtggcatctgggtcacaggccccagttcac ccctgaagcacggattgatgagtggtttggatcccccaactgccacttggacctta tgacaacaaggccaggcccaacatccctgtgtacagggactgggagatggttggca gatattatgaagaatttcctattaatctgaagacgggggaagccaacctcacccagat ctacctgcaggaagccctggacttcattaagagacaggcacggcaccaccccttttc ctctactgggctgtcgacgccacgcacgcacccgtctatgcctccaaaccccttcttgg gcaccagtcagcgagggcggtatggagacgccgtccgggagattgatgacagcat tgggaagatactggagctcctccaagacctgcacgtcgcggacaacaccttcgtctt cttcacgtcggacaacggcgctgccctcatttccgccccgaacaaggtggcagca acggccccttctgtgtgggaagcagaccacgtttgaaggagggatgagggagcct gccctcgcatggtggccagggcacgtcactgcaggccaggtgagccaccagctgg gcagcatcatggacctcttcaccaccagcctggcccttgcgggcctgacgccgccc agcgacagggccattgatggcctcaacctcctccccaccctcctgcagggccggct gatggacaggcctatcttctattaccgtggcgacacgctgatggcggccaccctcgg gcagcacaaggctcacttctggacctggaccaactcctgggagaacttcagacagg gcattgatttctgccctgggcagaacgtttcaggggtcacaactcacaatctggaaga ccacacgaagctgccctgatcttccacctgggacgggacccaggggagaggttcc ccctcagctttgccagcgccgagtaccaggaggccctcagcaggatcacctcggtc gtccagcagcaccaggaggccttggtccccgcgcagcccagctcaacgtgtgca actgggcggtcatgaactgggcacctccgggctgtgaaaagttagggaagtgtctg acacctccagaatccattcccaagaagtgcctctggtcccactag |

8. TABLE OF SEQUENCES

| SEQ ID NO. | DESCRIPTION | SEQUENCE |
| --- | --- | --- |
| 3 | hGALNSco (Codon Optimized) | atggctgctgttgttgccgctaccagatggtggcagctgctgctggttctgtctgccgc<br>tggaatgggagcttctggtgctccccagcctcctaacattctgctgctgctcatggacg<br>acatgggctggggcgatctgggagtgtatggcgagcctagcagagagacacccaa<br>cctggatagaatggccgccgagggcctgctgttccccaatttctacagagccaatcct<br>ctgtgcagcccctctagagctgctctgctgacaggcagactgcccatcagaaacggc<br>ttctacaccaccaacgctcacgcccggaatgcctacacaccccaagagatcgttggc<br>ggcatccccgattctgagcagctcctgcctgagctgctgaagaaggccggctacgtc<br>agcaagatcgtcggcaaatggccacctgggcacagaccctcagtttcaccctctgaag<br>cacggcttcgacgagtggttcggcagccccaattgtcacttcggcccctacgacaac<br>aaggccagacctaacatccccgtgtacagagactgggagatggtcggacggtacta<br>cgaggaattccccatcaacctgaaaaccggcgaggccaatctgacccagatctacct<br>gcaagaggccctggacttcatcaagcggcaggccagacaccatccttctttctgtac<br>tgggccgtcgacgccacacacgcccctgtgtatgccagcaagccttttctgggcacc<br>agccagcgtggcagatatggcgacgccgtgcgggaaatcgatgacagcatcggca<br>gatcctggaactgctgcaggatctgcacgtggccgacaacaccttcgtgttcttcac<br>cagcgacaacggcgctgccctgatttctgctcctgagcaaggcggcagcaacggcc<br>catttctgtgtggcaagcagaccacctttgaaggcggcatgagagagcctgctctgg<br>cttggtggcctggacatgtgacagccggacaagtgtctcaccagctgggcagcatc<br>atggacctgtttaccacctctctgccctggccggactgacacctccatctgatagag<br>ccatcgacggcctgaacctgctgcctacactgcttcagggcagactgatggacagac<br>ccatcttctactaccggggcgacaccctgatggccgctacactgggacagcacaag<br>gcccacttttggacctggaccaacagctgggagaacttccggcagggcatcgactt<br>tgccctggccagaatgtgtccggcgtgaccacacacaatctggaagatcacaccaa<br>gctgcccctgatctttcacctgggcagagatcccggcgagagattccctctgtcttttg<br>ccagcgccgagtaccaagaagccctgagcagaatcacctccgtggtgcagcagca<br>ccaagaggctctggttccagctcagccccagctgaacgtgtgtaattgggccgtgat<br>gaactgggcccctcctggatgtgaaaagctgggcaagtgtctgaccccctcctgaga<br>gcatccccaagaaatgcctgtggtcccactga |
| 4 | D8-hGALNS | accgccatgcggggtccgagcggggctctgtggctgctcctggctctgcgcaccgtgctcg<br>gatcagatgatgatgatgatgatgatgatgccgaggcagaaaccggtgccccgcagccccc<br>caacatcctgctcctgctcatggacgacatgggatggggtgacctcggggtgtatggagagc<br>cctccagagagaccccgaatttggaccggatggctgcagaagggctgcttttcccaaacttct<br>attctgccaaccctctgtgctcgccatcgaggggcactgctcacaggacggctacccatc<br>cgcaatggcttctacaccaccaacgccatgccagaaacgcctacacaccgcaggagattgt<br>gggcggcatcccagactcggagcagctcctgccggagcttctgaagaaggccggctacgt<br>cagcaagattgtcggcaagtggcatctgggtcacagccccagttccaccccctgaagcac<br>ggatttgatgagtggtttggatcccccaactgccactttggaccttatgacaacaaggccaggc<br>ccaacatccctgtgtacagggactgggagatggttggcagatattatgaagaatttcctattaat<br>ctgaagacggggaagccaacctcacccagatctacctgcaggaagccctggacttcattaa<br>gagacaggcacggcaccacccccttttcctctactgggctgtcgacgccacgcacgcacccg<br>tctatgcctccaaaccccttcttgggcaccagtcagcgagggcggtatggagacgccgtccgg<br>gagattgatgacagcattgggaagatactggagctcctccaagacctgcacgtcgcggacaa<br>caccttcgtcttcttcacgtcggacaacggcgctgccctcatttccgccccccgaacaaggtgg<br>cagcaacggccccttttctgtgtggaagcagaccacgtttgaaggagggatgagggagcct<br>gccctcgcatggtggccagggcacgtcactgcaggccaggtgagccaccagctgggcagc<br>atcatggacctcttcaccaccagcctggccttgcgggcctgacgccgcccagcgacaggg<br>ccattgatggcctcaacctcctccccaccctcctgcagggccggctgatggacaggcctatct<br>tctattaccgtggcgacacgctgatggcggccaccctcgggcagcacaaggctcacttctgg<br>acctggaccaactcctgggagaacttcagacagggcattgatttctgccctgggcagaacgtt<br>tcaggggtcacaactcacaatctgaagaccacacgaagctgcccctgatcttccacctggg<br>acgggacccaggggagaggttcccccctcagctttgccagcgccgagtaccaggaggccct<br>cagcaggatcacctcggtcgtccagcagcaccaggaggccttggtccccgcgcagccca |
| 5 | D8-GALNSco (codon optimized) | gctcaacgtgtgcaactgggcggtcatgaactgggcacctccgggctgtgaaaagttaggg<br>aagtgtctgacacctccagaatccattcccaagaagtgcctctggtcccactagtcga<br>atgagaggaccatctggtgctctgtggctgctgctggctctgagaacagtgctgggcagcga<br>cgacgatgatgacgatgacgacgaggctgaaacaggtgctcccagcctcctaacatc<br>ctgctgctgctcatggacgatatgggctggggcgatctgggagtgtatggcgagcctagcag<br>agagacacccaacctggatagaatggccgccgagggcctgctgttccccaatttctacagcg<br>ccaatcctctgtgcagcccctctagagctgctctgctgacaggcagactgcccatcagaaac<br>ggcttctacaccaccaacgctcacgcccggaatgcctacacaccccaagagatcgttggcg<br>gcatccccgattctgaacagctgctgcctgagctgctgaagaaggccggctacgtcagcaag<br>atcgtcggcaaatggcacctgggccacagaccctcagtttcaccctctgaagcacggcttcga<br>cgagtggttcggcagccccaattgtcacttcggccctacgacaacaaggccagaccaaac<br>atccccgtgtacagagactgggagatggtcggacggtactacgaggaattccccatcaacct<br>gaaaaccggcgaggccaatctgacccagatctacctgcaagaggccctggacttcatcaag<br>cggcaggccagacaccatccttctttctgtactgggccgtcgacgccacacacgcccctgtg<br>tatgccagcaagccttttctgggcaccagccagcgtggcagatatggcgacgccgtgcggg<br>aaatcgatgacagcatcggcagatcctggaactgctgcaggatctgcacgtggccgacaa<br>caccttcgtgttcttcaccagcgacaacggcgctgccctgatttctgctcctgagcaaggcgg<br>cagcaacggcccatttctgtgtggcaagcagaccacctttgaaggcggcatgagagagcct<br>gctctggcttggtggcctggacatgtgacagccggacaagtgtctcaccagctgggctccat |

8. TABLE OF SEQUENCES

| SEQ ID NO. | DESCRIPTION | SEQUENCE |
|---|---|---|
|  |  | catggacctgtttaccacctctctggccctggccggactgacacctccatctgatagagccatc gacggcctgaacctgctgcctacactgcttcagggcagactgatggacagacccatcttctac taccggggcgacaccctgatggccgctacactgggacagcacaaggcccacttttggacct ggaccaacagctgggagaacttccggcagggcatcgacttttgccctggccagaatgtgtcc ggcgtgaccacacacaatctggaagatcacaccaagctgcccctgatctttcacctgggcag agatcccggcgagagattccctctgtcttttgccagcgccgagtaccaagaagccctgagca gaatcaccagcgtggtgcagcagcaccaagaggctctggttccagctcagccccagctgaa cgtgtgtaattgggccgtgatgaactgggcccctcctggatgtgaaaagctgggcaagtgtct gaccctcctgagagcatcccaagaaatgcctgtggtcccactga |
| 6 | TBG promoter | gggctggaagctacctttgacatcatttcctctgcgaatgcatgtataatttctacagaacctatt agaaaggatcacccagcctctgcttttgtacaactttcccttaaaaaactgccaattccactgct gtttggcccaatagtgagaacttttttcctgctgcctcttggtgcttttgcctatggcccctattctgc ctgctgaagacactcttgccagcatggacttaaaccctccagctctgacaatcctctttctcttt tgttttacatgaaggggtctggcagccaaagcaatcactcaaagttcaaacccttatcattttttgctt tgttcctcttggccttggttttgtacatcagctttgaaaataccatcccagggttaatgctggggtt aatttataactaagagtgctctagttttgcaatacaggacatgctataaaaatggaaagat |
| 7 | 5' ITR | ctgcgcgctcgctcgctcactgaggccgcccgggcaaagcccgggcgtcgggcgacctttggtcgcccgcctcagtgagcgagcgagcgcgcagagagggagtggccaactccatcactagggggttcct |
| 8 | 3' ITR | aggaaccccctagtgatggagttggccactccctctctgcgcgctcgctcgctcactgaggccgggcgaccaaaggtcgcccgacgcccgggctttgcccgggcggcctcagtgagcgagcgagcgcgcag |
| 9 | Rabbit globin poly A | gatcttttccctctgccaaaaattatggggacatcatgaagccccttgagcatctgacttctggctaataaaggaaatttattttcattgcaatagtgtgttggaatttttttgtgtctctcactcg |
| 10 | Intron_1 | gtaagtatcaaggttacaagacaggtttaaggagaccaatagaaactgggcttgtcgagacagagaagactcttgcgtttctgataggcacctattggtcttactgacatccactttgcctttctctccacag |
| 11 | Alpha mic/bik enhancer | aggttaattttaaaaagcagtcaaaagtccaagtggcccttggcagcatttactctctctgtttgctctggttaataatctcaggagcacaaacattcc |
| 12 | GALNS (codon optimized & CpG depleted) | ATGGCTGCTGTGGTGGCTGCTACAAGATGGTGGCAACTG CTGCTGGTGCTGTCTGCAGCTGGAATGGGAGCTTCTGGT GCCCCTCAGCCTCCTAATATCCTGCTGCTGCTGATGGAT GACATGGGCTGGGGAGATCTGGGAGTGTATGGGGAGCC TAGCAGAGAGACACCCAACCTGGATAGAATGGCTGCAG AGGGCCTGCTGTTCCCCAACTTCTACTCTGCCAATCCTCT GTGCAGCCCCTCTAGAGCTGCACTGCTTACAGGCAGACT GCCCATCAGAAATGGCTTCTACACCACAAATGCCCATGC CAGAAATGCCTACACACCCAAGAGATAGTTGGAGGCA TCCCTGACTCTGAACAGCTGCTGCCTGAGCTGCTGAAGA AAGCTGGCTATGTGTCCAAGATAGTTGGCAAGTGGCAC CTGGGCCACAGACCTCAGTTTCACCCTCTGAAACATGGC TTTGATGAGTGGTTTGGCAGCCCCAACTGCCACTTTGGC CCCTATGATAACAAGGCCAGACCTAACATCCCTGTGTAC AGAGACTGGGAGATGGTTGGAAGGTACTATGAAGAGTT CCCCATCAACCTGAAAACAGGGGAAGCCAATCTGACCC AGATCTACCTGCAAGAGGCCCTGGACTTCATCAAGAGA CAGGCCAGACACCATCCTTTCTTTCTGTACTGGGCTGTT GATGCCACACATGCCCCTGTGTATGCCAGCAAGCCTTTT CTGGGCACCAGCCAGAGGGCAGATATGGGGATGCTGT CAGAGAAATTGATGACAGCATTGGCAAGATCCTGGAAC TGCTGCAGGACCTGCATGTGGCTGACAACACCTTTGTGT TCTTCACCTCTGACAATGGGGCAGCCCTGATCTCTGCCC TGAGCAAGGTGGCAGCAATGGCCCATTTCTGTGTGGCA AGCAGACCACCTTTGAAGGTGGCATGAGAGAGCCTGCT CTGGCCTGGTGGCCTGGACATGTTACAGCTGGACAAGTG TCTCACCAGCTGGGCAGCATCATGGACCTGTTTACCACA TCTCTGGCCCTGGCTGGACTGACCCCTCCATCTGATAGA GCCATTGATGGCCTGAACCTGCTGCCTACACTTCTGCAG GGCAGACTGATGGACAGACCCATCTTCTACTACAGAGG TGACACCCTGATGGCTGCCACACTGGGACAGCACAAGG CCCACTTTTGGACCTGGACCAACAGCTGGGAGAACTTCA GACAGGGCATTGATTTCTGCCCTGGCCAGAATGTGTCTG GGGTCACCACTCACAACCTGGAAGATCACACCAAGCTG CCCCTCATCTTCCACCTGGGAAGAGATCCTGGGGAGAG ATTCCCTCTGAGCTTTGCCTCTGCTGAGTACCAAGAAGC CCTGAGCAGAATCACATCTGTGGTGCAGCAGCATCAAG AGGCTCTGGTTCAGCTCAGCCCCAGCTGAATGTGTGCA |

| SEQ ID NO. | DESCRIPTION | SEQUENCE |
|---|---|---|
| | | ACTGGGCAGTGATGAATTGGGCCCCACCTGGCTGTGAA AAGCTGGGCAAATGTCTGACCCCACCTGAGAGCATCCCT AAAAAGTGCCTGTGGTCCCACTGA |
| 13 | LSPX1 Promoter | AGGTTAATTTTTAAAAAGCAGTCAAAAGTCCAAGTGGC CCTTGGCAGCATTTACTCTCTGTTTGCTCTGGTTAATA ATCTCAGGAGCACAAACATTCCAGATCCAGGTTAATTTT TAAAAAGCAGTCAAAAGTCCAAGTGGCCCTTGGCAGCA TTTACTCTCTGTTTGCTCTGGTTAATAATCTCAGGAGC ACAAACATTCCAGATCCGGCGCGCCAGGGCTGGAAGCT ACCTTTGTCTAGAAGGCTCAGAGGCACACAGGAGTTTCT GGGCTCACCCTGCCCCCTTCCAACCCCTCAGTTCCCATC CTCCAGCAGCTGTTTGTGTGCTGCCTCTGAAGTCCACAC TGAACAAACTTCAGCCTACTCATGTCCCTAAAATGGGCA AACATTGCAAGCAGCAAACAGCAAACACACAGCCCTCC CTGCCTGCTGACCTTGGAGCTGGGGCAGAGGTCAGAGA CCTCTCTGGGCCCATGCCACCTCCAACATCCACTCGACC CCTTGGAATTTCGGTGGAGAGGAGCAGAGGTTGTCCTG GCGTGGTTTAGGTAGTGTGAGAGGGGTACCCGGGGATC TTGCTACCAGTGGAACAGCCACTAAGGATTCTGCAGTGA GAGCAGAGGGCCAGCTAAGTGGTACTCTCCCAGAGACT GTCTGACTCACGCCACCCCCTCCACCTTGGACACAGGAC GCTGTGGTTTCTGAGCCAGGTACAATGACTCCTTTCGGT AAGTGCAGTGGAAGCTGTACACTGCCCAGGCAAAGCGT CCGGGCAGCGTAGGCGGGCGACTCAGATCCCAGCCAGT GGACTTAGCCCCTGTTTGCTCCTCCGATAACTGGGGTGA CCTTGGTTAATATTCACCAGCAGCCTCCCCCGTTGCCCC TCTGGATCCACTGCTTAAATACGGACGAGGACAGGGCC CTGTCTCCTCAGCTTCAGGCACCACCACTGACCTGGGAC AGT |
| 14 | LSPX2 Promoter | AGGCTCAGAGGCACACAGGAGTTTCTGGGCTCACCCTG CCCCCTTCCAACCCCTCAGTTCCCATCCTCCAGCAGCTG TTTGTGTGCTGCCTCTGAAGTCCACACTGAACAAACTTC AGCCTACTCATGTCCCTAAAATGGGCAAACATTGCAAGC AGCAAACAGCAAACACACAGCCCTCCCTGCCTGCTGAC CTTGGAGCTGGGGCAGAGGTCAGAGACCTCTCTGGGCC CATGCCACCTCCAACATCCACTCGACCCCTTGGAATTTC GGTGGAGAGGAGCAGAGGTTGTCCTGGCGTGGTTTAGG TAGTGTGAGAGGGTCTAGAAGGCTCAGAGGCACACAGG AGTTTCTGGGCTCACCCTGCCCCCTTCCAACCCCTCAGTT CCCATCCTCCAGCAGCTGTTTGTGTGCTGCCTCTGAAGT CCACACTGAACAAACTTCAGCCTACTCATGTCCCTAAAA TGGGCAAACATTGCAAGCAGCAAACAGCAAACACACAG CCCTCCCTGCCTGCTGACCTTGGAGCTGGGGCAGAGGTC AGAGACCTCTCTGGGCCCATGCCACCTCCAACATCCACT CGACCCCTTGGAATTTCGGTGGAGAGGAGCAGAGGTTG TCCTGGCGTGGTTTAGGTAGTGTGAGAGGGGTACCCGG GGATCTTGCTACCAGTGGAACAGCCACTAAGGATTCTGC AGTGAGAGCAGAGGGCCAGCTAAGTGGTACTCTCCCAG AGACTGTCTGACTCACGCCACCCCCTCCACCTTGGACAC AGGACGCTGTGGTTTCTGAGCCAGGTACAATGACTCCTT TCGGTAAGTGCAGTGGAAGCTGTACACTGCCCAGGCAA AGCGTCCGGGCAGCGTAGGCGGGCGACTCAGATCCCAG CCAGTGGACTTAGCCCCTGTTTGCTCCTCCGATAACTGG GGTGACCTTGGTTAATATTCACCAGCAGCCTCCCCCGTT GCCCCTCTGGATCCACTGCTTAAATACGGACGAGGACA GGGCCCTGTCTCCTCAGCTTCAGGCACCACCACTGACCT GGGACAGT |
| 15 | LTP1 Promoter | AGGTTAATTTTTAAAAAGCAGTCAAAAGTCCAAGTGGC CCTTGGCAGCATTTACTCTCTGTTTGCTCTGGTTAATA ATCTCAGGAGCACAAACATTCCAGATCCAGGTTAATTTT TAAAAAGCAGTCAAAAGTCCAAGTGGCCCTTGGCAGCA TTTACTCTCTGTTTGCTCTGGTTAATAATCTCAGGAGC ACAAACATTCCAGATCCGGCGCGCCAGGGCTGGAAGCT ACCTTTGACATCATTTCCTCTGCGAATGCATGTATAATTT CTACAGAACCTATTAGAAAGGATCACCCAGCCTCTGCTT TTGTACAACTTTCCCTTAAAAAACTGCCAATTCCACTGC TGTTTGGCCCAATAGTGAGAACTTTTTCCTGCTGCCTCTT GGTGCTTTTGCCTATGCCCCTATTCTGCCTGCTGAAGA CACTCTTGCCAGCATGGACTTAAACCCCTCCAGCTCTGA CAATCCTCTTTCTCTTTTGTTTTACATGAAGGGTCTGGCA GCCAAAGCAATCACTCAAAGTTCAAACCTTATCATTTTT |

8. TABLE OF SEQUENCES

| SEQ ID NO. | DESCRIPTION | SEQUENCE |
|---|---|---|
| | | TGCTTTGTTCCTCTTGGCCTTGGTTTTGTACATCAGCTTT<br>GAAAATACCATCCCAGGGTTAATGCTGGGGTTAATTTAT<br>AACTAAGAGTGCTCTAGTTTTGCAATACAGGACATGCTA<br>TAAAAATGGAAAGATGTTGCTTTCTGAGAGGATCTTGCT<br>ACCAGTGGAACAGCCACTAAGGATTCTGCAGTGAGAGC<br>AGAGGGCCAGCTAAGTGGTACTCTCCCAGAGACTGTCT<br>GACTCACGCCACCCCCTCCACCTTGGACACAGGACGCTG<br>TGGTTTCTGAGCCAGGTACAGTGACTCCTTTCGGTAAGT<br>GCAGTGGAAGCTGTACACTGCCCAGGCAAAGCGTCCGG<br>GCAGCGTAGGCGGGCGACTCAGATCCCAGCCAGTGGAC<br>TTAGCCCCTGTTTGCTCCTCCGATAACTGGGGTGACCTT<br>GGTTAATATTCACCAGCAGCCTCCCCGTTGCCCCTCTG<br>GATCCACTGCTTAAATACGGACGAGGACAGGGCCCTGT<br>CTCCTCAGCTTCAGGCACCACCACTGACCTGGGACAGT |
| 16 | LMTP6 Promoter | AGGCTCAGAGGCACACAGGAGTTTCTGGGCTCACCCTG<br>CCCCCTTCCAACCCCTCAGTTCCCATCCTCCAGCAGCTG<br>TTTGTGTGCTGCCTCTGAAGTCCACACTGAACAAACTTC<br>AGCCTACTCATGTCCCTAAAATGGGCAAACATTGCAAGC<br>AGCAAACAGCAAACACACAGCCCTCCCTGCCTGCTGAC<br>CTTGGAGCTGGGGCAGAGGTCAGAGACCTCTCTGGGCC<br>CATGCCACCTCCAACATCCACTCGACCCCTTGGAATTTC<br>GGTGGAGAGGAGCAGAGGTTGTCCTGGCGTGGTTTAGG<br>TAGTGTGAGAGGGCCACTACGGGTTTAGGCTGCCCATGT<br>AAGGAGGCAAGGCCTGGGGACACCCGAGATGCCTGGTT<br>ATAATTAACCCAGACATGTGGCTGCCCCCCCCCCCCCCA<br>ACACCTGCTGCCTCTAAAAATAACCCTGTCCCTGGTGGA<br>TCCCACTACGGGTTTAGGCTGCCCATGTAAGGAGGCAA<br>GGCCTGGGGACACCCGAGATGCCTGGTTATAATTAACCC<br>AGACATGTGGCTGCCCCCCCCCCCCCCAACACCTGCTGC<br>CTCTAAAAATAACCCTGTCCCTGGTGGATCCCACTACGG<br>GTTTAGGCTGCCCATGTAAGGAGGCAAGGCCTGGGGAC<br>ACCCGAGATGCCTGGTTATAATTAACCCAGACATGTGGC<br>TGCCCCCCCCCCCCCCAACACCTGCTGCCTCTAAAAATA<br>ACCCTGTCCCTGGTGGATCCCCTGCATGCGAAGATCTTC<br>GAACAAGGCTGTGGGGGACTGAGGGCAGGCTGTAACAG<br>GCTTGGGGGCCAGGGCTTATACGTGCCTGGGACTCCCAA<br>AGTATTACTGTTCCATGTTCCCGGCGAAGGGCCAGCTGT<br>CCCCCGCCAGCTAGACTCAGCACTTAGTTTAGGAACCAG<br>TGAGCAAGTCAGCCCTTGGGGCAGCCCATACAAGGCCA<br>TGGGGCTGGGCAAGCTGCACGCCTGGGTCCGGGGTGGG<br>CACGGTGCCCGGGCAACGAGCTGAAAGCTCATCTGCTCT<br>CAGGGGCCCCTCCCTGGGGACAGCCCCTCCTGGCTAGTC<br>ACACCCTGTAGGCTCCTCTATATAACCCAGGGGCACAGG<br>GGCTGCCCTCATTCTACCACCACCTCCACAGCACAGACA<br>GACACTCAGGAGCCAGCCAGCGTCGAGATCTTGCTACC<br>AGTGGAACAGCCACTAAGGATTCTGCAGTGAGAGCAGA<br>GGGCCAGCTAAGTGGTACTCTCCCAGAGACTGTCTGACT<br>CACGCCACCCCCTCCACCTTGGACACAGGACGCTGTGGT<br>TTCTGAGCCAGGTACAGTGACTCCTTTCGGTAAGTGCAG<br>TGGAAGCTGTACACTGCCCAGGCAAAGCGTCCGGGCAG<br>CGTAGGCGGGCGACTCAGATCCCAGCCAGTGGACTTAG<br>CCCCTGTTTGCTCCTCCGATAACTGGGGTGACCTTGGTT<br>AATATTCACCAGCAGCCTCCCCGTTGCCCCTCTGGATC<br>CACTGCTTAAATACGGACGAGGACAGGGCCCTGTCTCCT<br>CAGCTTCAGGCACCACCACTGACCTGGGACAGT |

9. EQUIVALENTS AND INCORPORATIONS BY REFERENCE

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

What is claimed is:

1. A recombinant adeno-associated virus (rAAV) comprising:
   (a) an AAV capsid; and
   (b) a recombinant AAV genome comprising a human N-acetylgalactosamine-6-sulfate sulfatase (hGALNS) expression cassette flanked by AAV-inverted terminal repeats (ITRs), the hGALNS expression cassette comprising (1) a nucleotide sequence encoding hGALNS, and (2) a promoter operably linked to the nucleotide sequence encoding hGALNS, wherein the promoter is a liver-specific promoter or a liver- and muscle-specific promoter, and
   (a) comprises a nucleotide sequence that is at least 80% identical to SEQ ID NO: 16; or
   (b) comprises a nucleotide sequence that is at least 85% identical to SEQ ID NO: 16; or
   (c) comprises a nucleotide sequence that is at least 90% identical to SEQ ID NO: 16; or (d) comprises a nucleotide sequence that is at least 95% identical to SEQ ID NO: 16; or
(e) comprises a nucleotide sequence that is at least 98% identical to SEQ ID NO: 16; or
(f) comprises a nucleotide sequence that is 100% identical to SEQ ID NO:16.

2. The rAAV of claim 1, wherein the hGALNS expression cassette encodes a nucleotide sequence encoding a fusion protein that is hGALNS fused to an acidic oligopeptide.

3. The rAAV of claim 1, wherein the AAV is AAV8.

4. The rAAV of claim 1, wherein the AAV is AAV9.

5. The rAAV of claim 1, wherein the nucleotide sequence encoding the transgene is codon-optimized.

6. The rAAV of claim 1, wherein the nucleotide sequence encoding the transgene has CpG sites depleted.

7. A pharmaceutical composition comprising the rAAV of claim 1 and a pharmaceutically acceptable carrier.

8. A method for treating a human subject diagnosed with mucopolysaccharidosis type IVA (MPS IVA), comprising administering to the human subject the rAAV of claim 1.

9. A method for treating a human subject diagnosed with MPS IVA, comprising delivering to the bone, cartilage, ligament, meniscus, growth plate, liver, spleen, lung, kidney, trachea, heart muscle, and/or heart valve of the human subject a therapeutically effective amount of the hGALNS by administering to the human subject the rAAV of claim 1.

10. The method of claim 9, wherein the hGALNS is glycosylated with mannose-6-phosphate by having been produced in and secreted from a liver cell.

11. A method for treating a human subject diagnosed with MPS IVA, comprising delivering to the bone, cartilage, ligament, meniscus, growth plate, liver, spleen, lung, kidney, trachea, heart muscle, and/or heart valve of the human subject a therapeutically effective amount of hGALNS that is produced from an rAAV genome of claim 1, which is glycosylated with mannose-6-phosphate by having been produced in and secreted from a liver cell.

12. The rAAV of claim 2, wherein the acidic oligopeptide is D8.

13. The rAAV of claim 1, wherein the nucleotide sequence encoding the hGALNS comprises the sequence of SEQ ID NO: 3, or has at least 95% identity to SEQ ID NO: 3.

14. The rAAV of claim 2, wherein the nucleotide sequence encoding hGALNS or the hGALNS fusion protein comprises the sequence of SEQ ID NO: 3, or has at least 95% identity to SEQ ID NO: 3.

15. The rAAV of claim 2, wherein the nucleotide sequence encoding the hGALNS fusion protein comprises the sequence of SEQ ID NO: 5, or has at least 95% identity to SEQ ID NO: 5.

16. A recombinant adeno-associated virus (rAAV) of claim 1 comprising:
(a) an AAV capsid; and
(b) a recombinant AAV genome comprising a human N-acetylgalactosamine-6-sulfate sulfatase (hGALNS) expression cassette flanked by AAV-inverted terminal repeats (ITRs), the hGALNS expression cassette comprising (1) a nucleotide sequence encoding hGALNS, and (2) a promoter operably linked to the nucleotide sequence encoding hGALNS, wherein the promoter is a liver-specific promoter or a liver- and muscle-specific promoter,
wherein the hGALNS expression cassette encodes a nucleotide sequence encoding a fusion protein that is hGALNS fused to an acidic oligopeptide, and
wherein the nucleotide sequence encoding hGALNS or the hGALNS portion of the fusion protein comprises the sequence of SEQ ID NO: 3, or has at least 85% identity to SEQ ID NO: 3, or
wherein the nucleotide sequence encoding the hGALNS fusion protein comprises the sequence of SEQ ID NO: 5, or has at least 85% identity to SEQ ID NO: 5.

* * * * *